(12) United States Patent
Schendel et al.

(10) Patent No.: US 11,292,838 B2
(45) Date of Patent: Apr. 5, 2022

(54) METHOD FOR GENERATING ANTIBODIES AGAINST T CELL RECEPTOR

(71) Applicant: MEDIGENE IMMUNOTHERAPIES GMBH, Planegg-Martinsried (DE)

(72) Inventors: Dolores Schendel, Munich (DE); Slavoljub Milosevic, Munich (DE); Tanja Herrmann, Munich (DE); Michaela Kügler, Warthausen (DE)

(73) Assignee: MEDIGENE IMMUNOTHERAPIES GMBH, Planegg-Martinsried (DE)

( * ) Notice: Subject to any disclaimer, the term of this patent is extended or adjusted under 35 U.S.C. 154(b) by 692 days.

(21) Appl. No.: 15/579,110

(22) PCT Filed: Jun. 1, 2016

(86) PCT No.: PCT/EP2016/062367
§ 371 (c)(1),
(2) Date: Dec. 1, 2017

(87) PCT Pub. No.: WO2016/193300
PCT Pub. Date: Dec. 8, 2016

(65) Prior Publication Data
US 2018/0237520 A1 Aug. 23, 2018

(30) Foreign Application Priority Data
Jun. 1, 2015 (EP) ..................... 15170155

(51) Int. Cl.
*C07K 16/28* (2006.01)
*G01N 33/68* (2006.01)
*C07K 16/08* (2006.01)

(52) U.S. Cl.
CPC ........ *C07K 16/2809* (2013.01); *C07K 16/085* (2013.01); *G01N 33/6854* (2013.01); *C07K 2317/14* (2013.01); *C07K 2317/33* (2013.01); *C07K 2317/565* (2013.01); *G01N 2333/7051* (2013.01)

(58) Field of Classification Search
CPC .............. C07K 16/2809; C07K 16/085; C07K 2317/33; C07K 2317/565; C07K 2317/14; G01N 33/6854; G01N 2333/7051
See application file for complete search history.

(56) References Cited

U.S. PATENT DOCUMENTS

| | | | |
|---|---|---|---|
| 4,703,004 A | 10/1987 | Hopp et al. | |
| 4,851,341 A | 7/1989 | Hopp et al. | |
| 5,591,828 A | 1/1997 | Bosslet et al. | |
| 5,616,472 A * | 4/1997 | Choi ................. | C07K 14/7051 435/69.1 |
| 5,766,886 A | 6/1998 | Studnicka et al. | |
| 6,372,716 B1 | 4/2002 | Bush et al. | |
| 6,566,329 B1 | 5/2003 | Meyn et al. | |
| 6,685,940 B2 | 2/2004 | Andya et al. | |
| 2002/0045241 A1 | 4/2002 | Schendel | |
| 2005/0037421 A1 | 2/2005 | Honda et al. | |
| 2005/0042718 A1 | 2/2005 | Bazin et al. | |
| 2005/0112141 A1 | 5/2005 | Terman | |
| 2005/0136049 A1 | 6/2005 | Ledbetter et al. | |
| 2018/0245242 A1 | 8/2018 | Schendel | |
| 2018/0256716 A1 | 8/2018 | Schendel | |

FOREIGN PATENT DOCUMENTS

| | | |
|---|---|---|
| DE | 19625191 A1 | 1/1998 |
| EP | 0451216 A1 | 10/1991 |
| EP | 0404097 B1 | 9/1996 |
| EP | 1910521 A1 | 4/2008 |
| EP | 2700708 A2 | 2/2014 |
| JP | H05-504621 | 7/1993 |
| JP | H06502529 | 3/1994 |
| JP | H06-506362 | 7/1994 |
| JP | H07-502165 | 3/1995 |
| JP | H08-502246 | 3/1996 |
| JP | 2007097580 A | 4/2007 |
| JP | 2004535168 A | 11/2014 |
| WO | WO-9107508 | 5/1991 |
| WO | WO-9202629 | 2/1992 |
| WO | WO-9209305 A1 | 6/1992 |
| WO | WO-9305813 | 4/1993 |
| WO | WO-9311161 A1 | 6/1993 |
| WO | WO 9311794 | 6/1993 |
| WO | WO-9404686 A1 | 3/1994 |
| WO | WO-9405801 | 3/1994 |
| WO | WO-9405801 A1 | 3/1994 |

(Continued)

OTHER PUBLICATIONS

Ahmadi et al, CD3 limits the efficacy of TCR gene therapy in vivo.Blood, Sep. 29, 2011 ,vol. 118, No. 13 (Year: 2011).*

(Continued)

*Primary Examiner* — Amy E Juedes
*Assistant Examiner* — Brian Hartnett
(74) *Attorney, Agent, or Firm* — Clark & Elbing LLP

(57) ABSTRACT

The invention relates to a method for generating an antibody binding to a cell surface protein of interest, the method comprising the following steps:
(a) providing a non-human cell which does not express the endogenous form of the cell surface protein of interest but expresses an exogenous form of the cell surface protein of interest comprising at least one human segment;
(b) immunization of a non-human animal with the cell line provided in step (a);
(c) generation of hybridomas from the immunized non-human animal of step (b);
(d) screening for an antibody that binds to the cell surface protein of interest by contacting the antibodies secreted by the hybridomas of step (c) with human cells which do not express the endogenous form of the cell surface protein of interest but express an exogenous form of the cell surface protein of interest comprising at least one human segment.

Figure 1A:
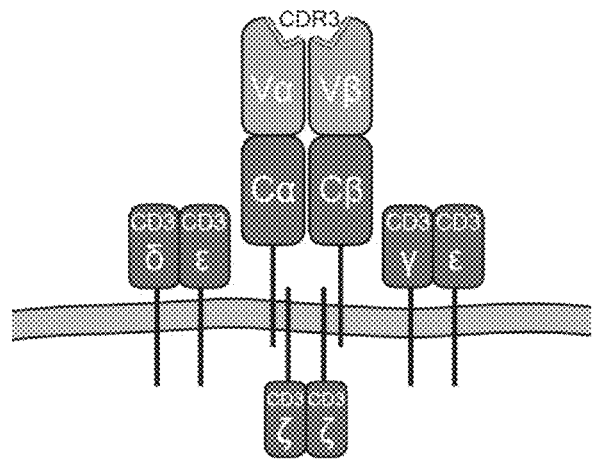

17 Claims, 17 Drawing Sheets
Specification includes a Sequence Listing.

(56) References Cited

FOREIGN PATENT DOCUMENTS

| | | |
|---|---|---|
| WO | WO-0155366 A1 | 8/2001 |
| WO | WO-0162908 A2 | 8/2001 |
| WO | WO-0192291 A2 | 12/2001 |
| WO | WO-2004044004 A2 | 5/2004 |
| WO | WO-2005116074 A2 | 12/2005 |
| WO | WO-2005116646 A1 | 12/2005 |
| WO | WO-2007131092 A2 | 11/2007 |
| WO | WO-2011107409 A1 | 9/2011 |
| WO | WO-2014089335 A2 | 6/2014 |
| WO | WO-2015136072 A1 | 9/2015 |
| WO | WO-2016193299 A1 | 12/2016 |
| WO | WO-2016193300 A1 | 12/2016 |
| WO | WO-2016193301 A1 | 12/2016 |
| WO | WO-2017109109 A1 | 6/2017 |

OTHER PUBLICATIONS

Cohen et al, Enhanced Antitumor Activity of Murine-Human Hybrid T-Cell Receptor (TCR) in Human Lymphocytes Is Associated with Improved Pairing and TCR/CD3 Stability. Cancer Res 2006; 66: (17). Sep. 1, 2006 (Year: 2006).*

Devaux et al, Generation of mAb against soluble human TcR polypeptides. Eur. J. Immunol. 1991. 21: 2111-2119. (Year: 1991).*

Heemskerk et al ,Redirection of anti-leukemic reactivity of peripheral T lymphocytes using gene transfer of minor histocompatibility antigen HA-2-specific T-cell receptor complexes expressing a conserved alpha joining region. Blood, Nov. 15, 2003 vol. 102, No. 10 (Year: 2003).*

Krutzik et al .Fluorescent Cell Barcoding for Multiplex Flow Cytometry Current Protocols in Cytometry 6.31.1-6.31.15, Jan. 2011 (Year: 2011).*

Lu et al. Analysis of T-cell repertoire in hepatitis-associated aplastic anemia.Blood, Jun. 15, 2004 vol. 103, No. 12 (Year: 2004).*

Zumla et al. Use of a Murine T-Cell Hybridoma Expressing Human T-Cell Receptor a- and P-Gene Products as a Tool for the Production of Human T-Cell Receptor-Specific Monoclonal Antibodies Human Immunology 35, 141-148 (1992) (Year: 1992).*

Callan et al. A method for producing monoclonal antibodies to human T-cell-receptor ,Beta-chain variable regions. Proc. Natl. Acad. Sci. USA vol. 90, pp. 10454-10458, Nov. 1993. (Year: 1993).*

Boullart, A.C.I. et al., "Maturation of monocyte-derived dendritic cells with Toll-like receptor 3 and ⅞ ligands combined with prostaglandin E2 results in high interleukin-12 production and cell migration," Cancer Immunol Immunother 57:1589-1597, Springer Publishing Group, United States (2008).

Wehner, C. et al., "Isolation of antigen-specific CD8+ T lymphocytes in vitro and in vivo," J Immother Cancer 1(suppl):P239, BioMed Central, England (2013).

Zerial, M. et al., "The transmembrane segment of the human transferrin receptor functions as a signal peptide," The EMBO Journal 5: 1543-1550, IRL Press, England (1986).

Van Nuffel, A. et al., "Dendritic Cells Loaded with mRNA encoding full-length tumor antigens prime CD4+ and CD8+ T cells in melanoma patients," Mol Ther 20:1063-1074, Cell Press, United States (2012).

Non-Final Office Action dated Sep. 25, 2019, in U.S. Appl. No. 15/579,117, Schendel, D. et al., filed Dec. 1, 2017, 16 pages.

Anonymous: "Immunomic Therapeutics—3D Ammation Script—FINAL," Aug. 31, 2015, XP055266237, Retrieved from the Internet (URL:http://www.immunomix.com/wp-content/uploads/2015/09/IMMUNOMIX_ARKITEK_V4_Script_FINAL_083115.pdf), retrieved on Apr. 18, 2016.

Arruda, L.B., et al., "Dendritic Cell-lysosomal-associated Membrane Protein (LAMP) and LAMP-1-HIV-1 Gag Chimeras Have Distinct Cellular Trafficking Pathways and Prime T and B Cell Responses to a Diverse Repertoire of Epitopes," Journal of Immunology 177(4):2265-2275, American Association of Immunologists, United States (Aug. 2006).

Becker, C., et al., "Adoptive Tumor Therapy With T Lymphocytes Enriched Through an IFN-gamma Capture Assay," Nature Medicine 7(10):1159-1162, Nature Publishing Company, United States (Oct. 2001).

Burdek, M., et al., "Three-day Dendritic Cells for Vaccine Development: Antigen Uptake, Processing and Presentation," Journal of Translational Medicine 8:90, BioMed Central, England (Sep. 2010).

Bonehill A. et al., "Messenger RNA-electroporated dendritic cells presenting MAGE-A3 simultaneously in HLA class I and class II molecules," J Immunol 172(11):6649-6657, The American Association of Immunologists, United States (2004).

Chu, T.H. et al., "Highly Efficient Eukaryotic Gene Expression vectors for Peptide Secretion," Biotechniques Pept Res 8:101-7, Future Science Group, England, (1995).

Ellinger, C., et al., "MHC Class-II Expression Targeting (CrossTAg) for the Generation of Tumor-Antigen-Specific CD4+ T Lymphocytes," Abstract—CIMT Cancer Immunotherapy Annual Meeting, Mainz, Germany (2013), XP055266213, accessed at https://www.medigene.com/fileadmin/download/abstracts/12_ellinger_-_mhc_class-ii_expression_targeting_crosstag_-cimt_2013.pdf, accessed Nov. 8, 2018.

Ellinger, Christian: "Gezielte MHC-Klasse-II—Kreuzprasentation fur die Generierung und Isolierung Tumor/Testis—Antigenspezifischer CD4 + T—Lymphozyten—Dissertation," Jul. 16, 2013 (Jul. 16, 2013). XP55358711, Retrieved from the Internet: URL:https://edoc.ub.uni-muenchen.de/19870/1/Ellinger Christian.pdf, [retrieved-on Mar. 24, 2017], 155 pages.

Engels, B., et al., "Relapse or Eradication of Cancer Is Predicted by Peptide-major Histocompatibility Complex Affinity," Cancer Cell 23(4):516-526, Cell Press, United States (Apr. 2013).

Extended European Search Report for EP Application No. EP15202329, Munich, Germany, dated Aug. 29, 2016, 12 pages.

Frentsch, M., et al., "Direct Access to CD4+ T Cells Specific for Defined Antigens According to CD 154 Expression," Nature Medicine 11(10):1118-1124, Nature Publishing Company, United States (2005).

GenBank, "Homo sapiens MAGE family member A4 (MAGEA4), transcript variant 4, mRNA," Accession No. NM_001011550.1, accessed at https://www.ncbi.nlm.nih.gov/nuccore/NM_001011550, accessed on Jun. 23, 2018.

GenBank, "Homo sapiens mRNA for NY-ESO-1 protein," Accession No. AJ003149.1, accessed at https://www.ncbi.nlm.nih.gov/nuccore/AJ003149, accessed on Oct. 7, 2008.

GenBank, "Homo sapiens SSX4 (SSX4) mRNA, complete cds," Accession No. U90841.1, accessed at https://www.ncbi.nlm.nih.gov/nuccore/U90841, accessed on Mar. 18, 1998.

GenBank, "Homo sapiens XAGE-1 mRNA, complete cds," Accession No. AF251237.1, accessed at https://www.ncbi.nlm.nih.gov/nuccore/AF251237, accessed on Aug. 23, 2000.

GenBank, "Human GAGE-1 protein mRNA, complete cds," Accession No. U19142.1, accessed at https://www.ncbi.nlm.nih.gov/nuccore/U19142, accessed on Dec. 4, 1995.

Genbank, "Lysosome-associated membrane glycoprotein 1 precursor," Accession No. NP_005552, accessed at https://www.ncbi.nlm.nih.gov/protein/NP_005552, accessed on Jun. 23, 2018.

GenBank, "Lysosome-associated Membrane Glycoprotein 3 Precursor," Accession No. NP_055213, accessed at https://www.ncbi.nlm.nih.gov/protein/NP_055213.2, accessed on Jun. 11, 2018.

Harlow, et al. (Eds), Antibodies A Laboratory Manual, Cold Spring Harbor Laboratory, Chapter 6, NY (1988).

Hinrichs, C.S. and Rosenberg, S.A., "Exploiting the Curative Potential of Adoptive T-cell Therapy for Cancer," Immunological Reviews 257(1):56-71, Blackwell, England (Jan. 2014).

IMGT Repertoire (IG and TR) IGMT Web Resources, "Reagents monoclonal antibodies: anti-mouse TRAV," accessed at http://www.imgt.org/IMGTrepertoire/index.php?section=Regulation&repertoire=antibodies&species=mouse&group=TRAV.

International Preliminary Report on Patentability for Application No. PCT/EP2016/082443, European Patent Office, Rijswijk, dated Jun. 26, 2018, 9 pages.

International Preliminary Report on Patentability for Application No. PCT/EP2016/082445, dated Jun. 26, 2018, 8 pages.

(56) References Cited

OTHER PUBLICATIONS

International Search Report and Written Opinion for Application No. PCT/EP2016/082445, dated Apr. 12, 2017, 13 pages.
International Search Report and Written Opinion for International Application No. PCT/EP2016/082443, European Patent Office, Rijswijk, dated May 23, 2017, 16 pages.
Javorovic, M., et al., "Inhibitory Effect of RNA Pool Complexity on Stimulatory Capacity of RNA-pulsed Dendritic Cells," Journal of immunotherapy 31(1):52-62, Lippincott Williams & Wilkins, United States (Jan. 2008).
Kavanagh, D.G., et al., "Expansion of HIV-specific CD4+ and CD8+ T Cells by Dendritic Cells Transfected With mRNA Encoding Cytoplasm-or Lysosome-Targeted Nef," Blood 107(5):1963-1969, American Society of Hematology, United States (Mar. 2006).
Kempkes, B., et al., "Immortalization of Human B Lymphocytes by a Plasmid Containing 71 Kilobase Pairs of Epstein-barr Virus DNA," Journal of Virology 69(1):231-238, American Society for Microbiology, United States (Jan. 1995).
Knabel, M., et al., "Reversible MHC Multimer Staining for Functional Isolation of T-cell Populations and Effective Adoptive Transfer," Nature Medicine 8(6):631-637, Nature Publishing Company, United States (Jun. 2002).
Kontermann, "Dual targeting strategies with bispecific antibodies," mAbs 4(2):182-197, Taylor & Francis, England (2012).
Milosevic, S., et al., "Identification of Major Histocompatibility Complex Class II-restricted Antigens and Epitopes of the Epstein-barr Virus by a Novel Bacterial Expression Cloning Approach," Journal of Virology 80(21):10357-10364, American Society for Microbiology, United States (Nov. 2006).
Moosmann, A., et al., "B Cells Immortalized by a Mini-Epstein-Barr Virus Encoding a Foreign Antigen Efficiently Reactivate Specific Cytotoxic T Cells," Blood 100(5):1755-1764, American Society of Hematology, United States (Sep. 2002).
Mortenson, E.D., et al., "Effective Anti-neu-initiated Antitumor Responses Require the Complex Role of CD4+ T Cells, "Clinical Cancer Research, 19(6):1476-1486, The Association, United States (Mar. 2013).
RecName: Full=Lysosome-associated membrane glycoprotein 3; (LAMP-3),UniprotAC:Q9UQV4 (LAMP3_Human), Nov. 11, 2015, <URL: https://www.uniprot.org/uniprot/09UQV4.txt?version=101>.
RecName: Full=Lysosome-associated membrane glycoprotein 1, Uniprot AC:P11279 (LAMP1_Human), Dec. 9, 2015, <URL: https://www.uniprot.org/uniprot/P11279. txt?version= 155>.
Regn, S., et al., "Ex Vivo Generation of Cytotoxic T Lymphocytes Specific for One or Two Distinct Viruses for the Prophylaxis of Patients Receiving an Allogeneic Bone Marrow Transplant," Bone Marrow Transplantation 27(1):53-64, Nature Publishing Group, England (Jan. 2001).
Rosenberg, S.A., et al., "Cancer Immunotherapy: Moving Beyond Current Vaccines," Nature Medicine 10(9):909-915, Nature Publishing Company, United States (2004).
Schendel, D.J., et al., "Human CD8+ T lymphocytes," in: The Immunology Methods Manual, Lefkovits, Ed, pp. 670-690, 1997.
Schoenbrunn, A., et al., "A Converse 4-1BB and CD40 Ligand Expression Pattern Delineates Activated Regulatory T Cells (Treg) and Conventional T Cells Enabling Direct Isolation of Alloantigen-reactive Natural Foxp3+ Treg," Journal of Immunology 189(12):5985-5994, American Association of Immunologists, United States (Dec. 2012).
Shultz, L.D., et al., "Humanized Mice in Translational Biomedical Research," Nature Reviews Immunology, 7(2):118-130, Nature Publishing Group, England (Feb. 2007).
Spranger S. et al., "Generation of Th1-polarizing dendritic cells using the TLR7/8 agonist CL075," J Immunol 185(1):738-747, The American Association of Immunologists, United States (2010).
Spranger, S., et al., "NOD/Scid Il-2rg(Null) Mice: a Preclinical Model System to Evaluate Human Dendritic Cell-based Vaccine Strategies in Vivo," Journal of Translational Medicine, 10:30, BioMed Central, England (Feb. 2012).
Steinle, A., et al., "In Vivo Expansion of HLA-B35 Alloreactive T Cells Sharing Homologous T Cell Receptors: Evidence for Maintenance of an Oligoclonally Dominated Allospecificity by Persistent Stimulation With an Autologous MHC/peptide Complex," The Journal of Experimental Medicine 181(2):503-513, Rockefeller University Press, United States (Feb. 1995).
Su, Z., et al., "Antigen Presenting Cells Transfected With LMP2a Rna Induce CD4+ LMP2a-specific Cytotoxic T Lymphocytes Which Kill via a Fas-independent Mechanism," Leukemia & Lymphoma 43(8):1651-1662, Informa Healthcare, England (Aug. 2002).
Wehner, C., et al., "Generation of Tumor Antigen-specific CD4+ and CD8+ T Cells by Simultaneous MHC-I and -II Epitope Presentation in Vitro and in Vivo," Journal for Immunotherapy of Cancer 2 (Suppl 3):P65, BioMed Central, England (2014).
Wehner C., Induktion Tumorantigen-spezifischer CD8+ T-Lymphozyten in vitro und in vivo, Doctoral dissertation, Jul. 1, 2013, <URL: https://edoc.ub.uni-muenchen.de/20384/1/Wehner Carina.pdf>, 177 pages.
Wilde, S., et al., "Dendritic Cells Pulsed With RNA Encoding Allogeneic MHC and Antigen Induce T Cells With Superior Antitumor Activity and Higher TCR Functional Avidity," Blood 114(10):2131-2139, American Society of Hematology, United States (Sep. 2009).
Wu, T.C., et al., "Engineering an Intracellular Pathway for Major Histocompatibility Complex Class II Presentation of Antigens," Proceedings of the National Academy of Sciences of the United States of America 92(25):11671-11675, National Academy of Sciences, United States (Dec. 1995).
Yu, X., et al., "Antigen-armed Antibodies Targeting B Lymphoma Cells Effectively Activate Antigen-specific CD4+ T Cells," Blood 125(10):1601-1610, American Society of Hematology, United States (Mar. 2015).
Office Action for Japanese Application No. JP2017-563246, dated Dec. 11, 2018, The Japan Patent Office, Tokyo, Japan, 6 pages.
Office Action for Japanese Application No. JP2017-563247, dated Dec. 11, 2018, The Japan Patent Office, Tokyo, Japan, 6 pages.
Abraham, R.T., et al., "Jurkat T cells and development of the T-cell receptor signaling paradigm," Immunology Nature Reviews 4:301, Nature Publishing Group, England (2004).
Dreyer, A.M., et al., "An efficient system to generate monoclonal antibodies against membrane-associated proteins by immunization with antigen-expressing mammalian cells," BMC Technology 10:87, Bio Med Central, England (2010).
Letourneur, F., et al., "Derivation of a T cell hybridoma variant deprived of functional T cell receptor alpha and beta chain transcripts reveals a nonfunctional a-mRNA of BW5147 origin," Eur. J. Immunol. 19:2269-2274, VCH Verlagsgesellshaft mbH, Germany (1989).
Ahlgren, K.M., et al., "T Cell Receptor-Vbeta Repertoires in Lung and Blood CD4+ and CD8+ T Cells of Pulmonary Sarcoidosis Patients," BMC Pulmonary Medicine 14(1):50, BioMed Central, England (Mar. 2014).
De Alboran, I.M., et al., "Attenuation of autoimmune disease and lymphocyte accumulation in MRL//pr mice by treatment with anti-$V_\beta$ antibodies*," Eur. J. Immunol. 22:2153-2158, Wiley-VCH, Germany ( Apr. 1992).
Balow, J.P. and Kerase, K.P., "Isolation of Newly Expressed Surface T Cell Antigen Receptor Complexes by Serial Precipitation with Anti-TCR Antibodies and Immobilized Streptavidin," Journal of Immunological Methods 189(2):251-258, Elsevier, Netherlands (Feb. 1996).
Brewer, J.L. and Ericson, S.G., "An Improved Methodology to Detect Human T Cell Receptor beta Variable Family Gene Expression Patterns," Journal of Immunological Methods 302(1-2):54-67, Elsevier, Netherlands (Jul. 2005).
Busch, D.H., et al., "Evolution of a Complex T Cell Receptor Repertoire During Primary and Recall Bacterial Infection," The Journal of Experimental Medicine 188(1):61-70, Rockefeller University Press, United States (Jul. 1998).
Chiocchia, G., et al., "Therapy against murine collagen-induced arthritis with T cell receptor $V_\beta$-specific antibodies*," Eur. J. Immunol. 21:2899-2905, Wiley-VCH, Germany (1991).

(56) References Cited

OTHER PUBLICATIONS

Coren, L., et al., "Production of Retroviral constructs for effective transfer and expression of T-cell receptor genes using Golden Gate Cloning," Biotechniques 58(3):135-139, Future Medicine, United States (Mar. 2015).

IOTest Beta Mark, "25 T-Cell Repertoire assays," IOTest® Beta Mark PN IM3497 TCR Vβ Repertoire Kit, accessed at https://www.bccytometry.com/PDF/DataSheet/IM3497DS.pdf, last accessed Jun. 20, 2007, 20 pages.

IMGT Repertoire (IG and TR), IGMT Web Resources, "Reagents Monoclonal antibodies: anti-human TRBV," accessed at http://www.imgt.org/IMGTrepertoire/Regulation/antibodies/human/TRB/TRBV/Hu_TRBVMab.html, last accessed Jul. 9, 2018, 3 pages (2003).

IMGT Repertoire (IG and TR), "Reagents monoclonal antibodies: anti-mouse TRBV," accessed at http://www.imgt.org/IMGTrepertoire/index.php?section=Regulation&repertoire=antibodies&species=mouse&group=TRBV, last accessed Jul. 9, 2018, 2 pages (2011).

International Search Report and Written Opinion for International Application No. PCT/EP2016/062366, European Patent Office, Rijswijk, dated Aug. 31, 2016, 17 pages.

International Search Report and Written Opinion for International Application No. PCT/EP2016/062370, European Patent Office, Rijswijk, dated Jul. 8, 2016, 12 pages.

Kessels, H.W.H.G., et al., "Changing T Cell Specificity by Retroviral T Cell Receptor Display," Proceedings of the National Academy of Sciences of the United States of America 97(26):14578-14583, National Academy of Sciences, United States (Dec. 2000).

Lu, J., et al., "Analysis of T-cell Repertoire in Hepatitis-associated Aplastic Anemia," Blood 103(12):4588-4593, American Society of Hematology, United States (Jun. 2004).

Maeda, T., et al., "Amelioration of Acute Graft-Versus-Host Disease and Re-Establishment of Tolerance by Short-Term Treatment With an Anti-TCR Antibody," Journal of Immunology 153(9):4311-4320, American Association of Immunologists, United States (Nov. 1994).

Olsson, T., et al., "Depletion of Vβ5.2/5.3 T cells with a humanized antibody in patients with multiple sclerosis," European Journal of Neurology 9:153-164, Wiley Blackwell, United States (2002).

Pilch, H., et al., "Improved Assessment of T-cell Receptor (TCR) VB Repertoire in Clinical Specimens: Combination of TCR-CDR3 Spectratyping With Flow Cytometry-based TCR VB Frequency Analysis," Clinical and Diagnostic Laboratory Immunology 9(2):257-266, American Society for Microbiology, United States (Mar. 2002).

Zumla, et al., "Use of a Murine T-Cell Hybridoma Expressing Human T-Cell Receptor alpha and beta Products as a tool for the production of Human T-Cell Receptor-Specific Monoclonal Antibodies," Human Immunology 35(3):141-148, American Society for Histocompatibility and Immunogenetics, United States (1992).

Office Action for New Zealand Patent IP No. 737851, dated Aug. 16, 2018, New Zealand Intellectual Property Office, New Zealand, 6 pages.

Office Action for New Zealand Patent IP No. 737400, dated Sep. 3, 2018, New Zealand Intellectual Property Office, New Zealand, 7 pages.

Office Action for New Zealand Patent IP No. 737423, dated Aug. 2, 2018, New Zealand Intellectual Property Office, New Zealand, 6 pages.

Abraham, R.T. and Weiss, A., "Jurkat T Cells and Development of the T-cell Receptor Signaling Paradigm," Nature Reviews. Immunology 4(4):301-308, Nature Pub. Group, England (Apr. 2004).

Altschul, S.F., et al., "Basic Local Alignment Search Tool," Journal of Molecular Biology 215(3):403-410, Elsevier, England (Oct. 1990).

Arbabi Ghahroudi, M., et al., "Selection and Identification of Single Domain Antibody Fragments from Camel Heavy-chain Antibodies," FEBS Letters 414(3):521-526, John Wiley & Sons Ltd., England (Sep. 1997).

Bernett, M.J., et al., "Engineering Fully Human Monoclonal Antibodies from Murine Variable Regions," Journal of Molecular Biology 396(5):1474-1490, Elsevier, England (Mar. 2010).

Bird, R.E., et al., "Single-chain Antigen-binding Proteins," Science 242(4877):423-426, Association for the Advancement of Science, United States (Oct. 1988).

Brennan, M., et al., "Preparation of Bispecific Antibodies by Chemical Recombination of Monoclonal Immunoglobulin G1 Fragments," Science 229(4708):81-83, American Association for the Advancement of Science, United States (Jul. 1985).

Byers, V.S. and Baldwin, R.W., "Rationale for Clinical Use of Immunotoxins in Cancer and Autoimmune Disease," Seminars in Cell Biology 2(1):59-70, Academic Press, England (Feb. 1991).

Call, M.E. and Wucherpfennig, K.W., "The T Cell Receptor: Critical Role of the Membrane Environment in Receptor Assembly and Function," Annual Review of Immunology 23:101-125, Annual Reviews Inc., United States (2005).

Cohen, C.J., et al.," Enhanced Antitumor Activity of T Cells Engineered to Express T-cell Receptors with a Second Disulfide Bond," Cancer Research 67(8):3898-3903, American Association for Cancer Research, United States (Apr. 2007).

Cohen, C.J., et al., "Enhanced Antitumor Activity of Murine-human Hybrid T-cell Receptor (TCR) in Human Lymphocytes is Associated with Improved Pairing and TCR/CD3 Stability," Cancer Research 66(17):8878-8886, American Association for Cancer Research, United States (Sep. 2006).

Conrath, K.E., et al., "Beta-lactamase Inhibitors Derived From Single-domain Antibody Fragments Elicited in the Camelidae," Antimicrobial Agents and Chemotherapy 45(10):2807-2812, American Society for Microbiology, United States (Oct. 2001).

Cortez-Retamozo, V., et al., "Efficient Cancer Therapy with a Nanobody-based Conjugate," Cancer Research 64(8):2853-2857, American Association for Cancer Research, United States (Apr. 2004).

Delobel, A., et al., "Therapeutic Antibody Glycosylation Analysis: a Contract Research Organization Perspective in the Frame of Batch Release or Comparability Support," Methods in Molecular Biology 988:115-143, Humana Press, United States (2013).

Desmet, J., et al., Chapter 22, "Humanization by Resurfacing," in Antibody Engineering, vol. 1, second edition, Kontermann, R, and Dubel, S., eds., pp. 341-342, Springer-Verlag Berlin Heidelberg, Germany (2010).

Desmyter, A., et al., "Antigen Specificity and High Affinity Binding Provided by One Single Loop of a Camel Single-domain Antibody," The Journal of Biological Chemistry 276(28):26285-26290, American Society for Biochemistry and Molecular Biology, United States (Jul. 2001).

Diener, E., et al., "Specific Immunosuppression by Immunotoxins Containing Daunomycin," Science 231(4734):148-150, American Association for the Advancement of Science, United States (Jan. 1986).

Fanger, M.W., et al., "Bispecific Antibodies and Targeted Cellular Cytotoxicity," Immunology Today 12(2):51-54, Elsevier Science Publishers, England (Feb. 1991).

Fanger, M.W., et al., "Bispecific Antibodies," Critical Reviews in Immunology 12(3-4):101-24, Begell House, United States (1992).

Fanger, M.W., et al., "Use of Bispecific Antibodies in the Therapy of Tumors," in Immunoconjugate Therapy of Hematologic Malignancies, Chapter 10, Rosen, S., ed., pp. 181-194, Springer US, United States (1991).

Folch, G. and Lefranc, M.P., "The Human T Cell Receptor Beta Variable (TRBV) Genes," Experimental and Clinical Immunogenetics 17(1):42-54, Karger, Switzerland (2000).

Greenberg, A.S., et al., "A New Antigen Receptor Gene Family that Undergoes Rearrangement and Extensive Somatic Diversification in Sharks," Nature 374(6518):168-173, Nature Publishing Group, England (Mar. 1995).

Gruber, M., et al., "Efficient Tumor Cell Lysis Mediated by a Bispecific Single Chain Antibody Expressed in *Escherichia coli*," The Journal of Immunology 152(11):5368-5374, The American Association of Immunologists, Inc., United States (1994).

Hamers-Casterman, C., et al., "Naturally Occurring Antibodies Devoid of Light Chains," Nature 363(6428):446-448, Nature Publishing Group, England (Jun. 1993).

(56) References Cited

OTHER PUBLICATIONS

Higgins, P.J., et al., "In Vitro Inhibition of a Variety of Human Immunodeficiency Virus Isolates by a Broadly Reactive, V3-directed Heteroconjugate Antibody In Vitro Inhibition of a Variety of Human Immunodeficiency Virus Isolates by a Broadly Reactive, V3-directed Heteroconjugate Antibody," The Journal of Infectious Diseases 166(1):198-202, Oxford University Press, United States (Jul. 1992).

Hildinger, M., et al., "Design of 5' Untranslated Sequences in Retroviral Vectors Developed for Medical Use," Journal of Virology 73(5):4083-4089, American Society for Microbiology, United States (May 1999).

Holliger, P., et al., "Diabodies: Small Bivalent and Bispecific Antibody Fragments," Proceedings of the National Academy of Sciences USA 90(14):6444-6448, National Academy of Sciences, United States (Jul. 1993).

Huston, J.S., et al., "Protein Engineering of Antibody Binding Sites: Recovery of Specific Activity in an Anti-digoxin Single-chain Fv Analogue Produced in *Escherichia coli*," Proceedings of the National Academy of Sciences USA 85(16):5879-5883, National Academy of Sciences, United States (Aug. 1988).

International Search Report and Written Opinion for International Application No. PCT/EP2016/062367, European Patent Office, Rijswijk, dated Aug. 2, 2016, 16 pages.

Irving, R.A., et al., "Ribosome Display and Affinity Maturation: From Antibodies to Single V-domains and Steps Towards Cancer Therapeutics," Journal of Immunological Methods 248(1-2):31-45, Elsevier Science Publishers, Netherlands (Feb. 2001).

Karlin, S. and Altschul, S.F., "Applications and Statistics for Multiple High-Scoring Segments in Molecular Sequences," Proceedings of the National Academy of Sciences of the United States of America 90(12):5873-5877, National Academy of Sciences, United States (Jun. 1993).

Kipriyanov, S.M., et al., "Single-chain Antibody Streptavidin Fusions: Tetrameric Bifunctional Scfv-complexes With Biotin Binding Activity and Enhanced Affinity to Antigen," Human Antibodies and Hybridomas 6(3):93-101, Butterworth-Heinemann, United States (1995).

Kipriyanov, S.M., et al., "Recombinant Single-chain Fv Fragments Carrying C-terminal Cysteine Residues: Production of Bivalent and Biotinylated Miniantibodies," Molecular Immunology 31(14):1047-1058, Pergamon Press, England (1994).

Kohler, G. and Milstein, C., "Continuous Cultures of Fused Cells Secreting Antibody of Predefined Specificity," Nature 256(5517):495-497, Macmillan Journals Ltd., England (Aug. 1975).

Lee, N.E. and Davis, M.M., "T Cell Receptor beta-chain Genes in BW5147 and Other AKR Tumors. Deletion Order of Murine V beta Gene Segments and Possible 5' Regulatory Regions," Journal of Immunology 140(5):1665-1675, American Association of Immunologists, United States (Mar. 1988).

Lefranc, M.P., et al., "IMGT, the International ImMunoGeneTics Information System," Nucleic Acids Research 33:D593-D597, Oxford University Press, England (Jan. 2005).

Lefranc, M.P., et al., "IMGT Unique Numbering for Immunoglobulin and T Cell Receptor Variable Domains and Ig Superfamily V-like Domains," Developmental and Comparative Immunology 27(1):55-77, Elsevier Science, United States (Jan. 2003).

Letourneur, F. and Malissen, B., "Derivation of a T Cell Hybridoma Variant Deprived of Functional T Cell Receptor alpha and beta Chain Transcripts Reveals a Nonfunctional alpha-mRNA of BW5147 Origin," European Journal of Immunology 19(12):2269-2274, Wiley-VCH, Germany (Dec. 1989).

Mamedov, I.Z., et al., "Preparing Unbiased T-Cell Receptor and Antibody cDNA Libraries for the Deep Next Generation Sequencing Profiling," Frontiers in Immunology 4:456, Frontiers Research Foundation, Switzerland (2013).

Milstein, C. and Cuello, A.C., "Hybrid Hybridomas and their Use in Immunohistochemistry," Nature 305(5934):537-540, Nature Publishing Group, England (Oct. 1983).

Muyldermans, S. and Lauwereys, M., "Unique Single-Domain Antigen Binding Fragments Derived From Naturally Occurring Camel Heavy-Chain Antibodies," Journal of Molecular Recognition 12(2):131-140, John Wiley & Sons, England (Mar.-Apr. 1999).

Muyldermans, S., "Single Domain Camel Antibodies: Current Status," Reviews in Molecular Biotechnology 74(4):277-302, Elsevier Science Publishers, Netherlands (2001).

Nguyen, V.K., et al., "Functional Heavy-Chain Antibodies in Camelidae," Advances in Immunology 79:261-296, Academic Press, United States (2001).

Nguyen, V.K., et al., "Heavy-Chain Antibodies in Camelidae; a Case of Evolutionary Innovation," Immunogenetics 54(1):39-47, Springer Verlag, United States (Apr. 2002).

Nguyen, V.K., et al., "Loss of Splice Consensus Signal is Responsible for the Removal of the Entire C(H)1 Domain of the Functional Camel IGG2A Heavy-Chain Antibodies," Molecular Immunology 36(8):515-524, Pergamon Press, England (Jun. 1999).

Nguyen, V.K., et al., "The Specific Variable Domain of Camel Heavy-chain Antibodies is Encoded in the Germline," Journal of Molecular Biology 275(3):413-418, Elsevier, England (Jan. 1998).

Nuttall, S.D., et al., "Isolation of the New Antigen Receptor From Wobbegong Sharks, and Use as a Scaffold for the Display of Protein Loop Libraries," Molecular Immunology 38(4):313-326, Pergamon Press, England (Aug. 2001).

Poljak, R.J., "Production and Structure of Diabodies," Structure 2(12):1121-1123, Cell Press, United States (1994).

Riechmann, L. and Muyldermans, S., "Single Domain Antibodies: Comparison of Camel VH and Camelised Human VH Domains," Journal of Immunological Methods 231(1-2):25-38, Elsevier, Netherlands (Dec. 1999).

Roux, K.H., et al., "Structural Analysis of the Nurse Shark (New) Antigen Receptor (NAR): Molecular Convergence of NAR and Unusual Mammalian Immunoglobulins," Proceedings of the National Academy of Sciences of the United States of America 95(20):11804-11809, National Academy of Sciences, United States (Sep. 1998).

Schambach, A., et al., "Context Dependence of Different Modules for Posttranscriptional Enhancement of Gene Expression From Retroviral Vectors," Molecular Therapy 2(5):435-445, Cell Press, United States (Nov. 2000).

Shevach, E.M., Current Protocols in Immunology, Chapter 13 Complement, pp. 13.0.1-13.0.4, Jun. 2005.

Sommermeyer, D. and Uckert, W., "Minimal Amino Acid Exchange in Human TCR Constant Regions Fosters Improved Function of TCR Gene-Modified T Cells," Journal of Immunology 184(11):6223-6231, American Association of Immunologists, United States (Jun. 2010).

Hirsch, T., et al., "Effects of In Vivo Administration of anti-T3 Monoclonal Antibody on T cell Function in Mice—I. Immunosuppression of transplantation responses," Journal of Immunology 140(11): 3766-3772, American Association of Immunologists, United States (1988).

Penaranda, C., et al., "Anti-CD3 Therapy Promotes Tolerance by Selectively Depleting Pathogenic Cells While Preserving Regulatory T cells," Journal of Immunology 187(4):2015-2022, The American Association of Immunologists, United States (2011).

Su, C., et al., "Evolutionary Dynamics of the T-Cell Receptor VB Gene Family as Inferred from the Human and Mouse Genomic Sequences," Molecular Biology and Evolution 18(4):503-513, Oxford Academic, England (2001).

Traunecker, A., et al., "Janusin: New Molecular Design for Bispecific Reagents," International Journal of Cancer 7:51-52, Alan R. Liss, Inc., United States (1992).

Urlaub, G. and Chasin, L.A., "Isolation of Chinese Hamster Cell Mutants Deficient in Dihydrofolate Reductase Activity," Proceedings of the National Academy of Sciences USA 77(7):4216-4220, National Academy of Sciences, United States (Jul. 1980).

Van Der Linden, R.H., et al., "Improved Production and Function of Llama Heavy Chain Antibody Fragments by Molecular Evolution," Journal of Biotechnology 80(3):261-270, Elsevier Science Publishers, Netherlands (Jul. 2000).

(56) References Cited

OTHER PUBLICATIONS

Ward, E.S., et al., "Binding Activities of a Repertoire of Single Immunoglobulin Variable Domains Secreted from *Escherichia coli*," Nature 341 (6242):544-546, Nature Publishing Group, England (Oct. 1989).

Woolven, B.P., et al., "The Structure of the Llama Heavy Chain Constant Genes Reveals a Mechanism for Heavy-chain Antibody Formation," Immunogenetics 50(1-2):98-101, Springer Verlag, United States (Oct. 1999).

\* cited by examiner

Figure12A

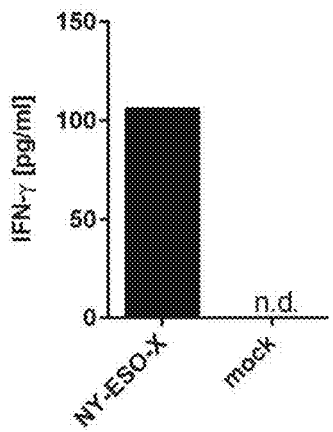

Figure12D

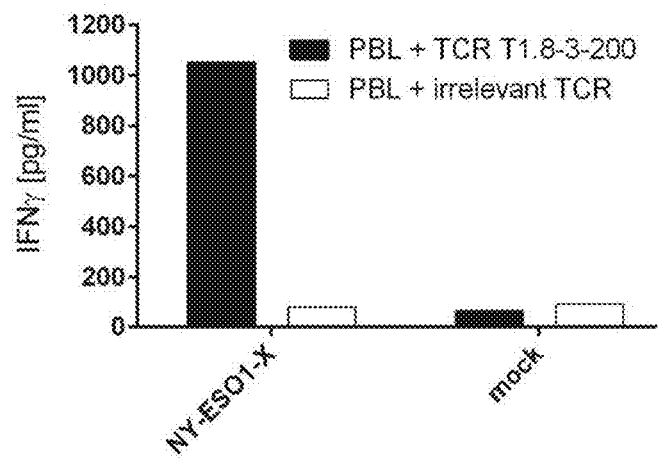

Figure 12B: F12 TCRα Sequence

| Result summary: | Productive TRA rearranged sequence | |
|---|---|---|
| V-GENE and allele | Homsap TRAV14/DV4*01 F | identity = 100.00% (276/276 nt) |
| J-GENE and allele | Homsap TRAJ49*01 F | identity = 100.00% (56/56 nt) |

| | 104 | 105 | 106 | 107 | 108 | 109 | 113 | 114 | 115 | 116 | 117 | 118 | Frame | CDR3-IMGT length |
|---|---|---|---|---|---|---|---|---|---|---|---|---|---|---|
| CDR3 region | C | A | I | S | N | T | G | N | Q | F | Y | F | | |
| | tgt | gca | att | tcg | aac | acc | ggt | aac | cag | ttc | tat | ttt | + | 10 |

Figure 12C: F12 TCRβ Sequence

| Result summary: | Productive TRB rearranged sequence | |
|---|---|---|
| V-GENE and allele | Homsap TRBV27*01 F | identity = 100.00% (273/273 nt) |
| J-GENE and allele | Homsap TRBJ2-1*01 F | identity = 100.00% (50/50 nt) |
| D-GENE and allele by IMGT/JunctionAnalysis | Homsap TRBD2*01 F | |

| | 104 | 105 | 106 | 107 | 108 | 109 | 110 | 112 | 113 | 114 | 115 | 116 | 117 | 118 | Frame | CDR3-IMGT length |
|---|---|---|---|---|---|---|---|---|---|---|---|---|---|---|---|---|
| CDR3 region | C | A | S | N | N | L | A | S | Y | N | E | Q | F | F | | |
| | tgt | gcc | agc | aat | aac | tta | gcc | tcc | tac | aat | gag | cag | ttc | ttc | + | 12 |

METHOD FOR GENERATING ANTIBODIES AGAINST T CELL RECEPTOR

REFERENCE TO SEQUENCE LISTING SUBMITTED ELECTRONICALLY

The content of the electronically submitted substitute sequence listing, file name 41140030001_Sequencelisting_ST25.txt; size 343,674 bytes; and date of creation May 11, 2018, filed herewith, is incorporated herein by reference in its entirety.

FIELD OF THE INVENTION

The present invention relates to a method for generating antibodies binding to cell surface proteins. In particular, the present invention provides methods for generation and screening of antibodies binding to T cell receptors (TCRs). More particularly, the invention refers to methods for generating and screening of antibodies binding to at least one variable chain of a TCR.

BACKGROUND OF THE INVENTION

The generation of antibodies against cell surface proteins is problematic as the cell surface proteins typically need their natural environment of the cell membrane in order to fold correctly.

Therefore, the generation of antibodies and screening of antibodies against cell surface proteins remains difficult and there is a need for a method to effectively produce antibodies against cell surface proteins.

OBJECTIVES AND SUMMARY OF THE INVENTION

To meet these needs, it is one objective of the invention to provide a method for generating antibodies binding to cell surface proteins. In particular, it is an objective of the present invention to provide methods for generation and screening of antibodies binding to T cell receptors (TCRs). More particularly, the invention is concerned with the provision of methods for generating and screening of antibodies binding to at least one variable chain of a TCR.

Accordingly, a first aspect of the present invention relates to a method for generating an antibody binding to a cell surface protein of interest, the method comprising the following steps:
(a) providing a non-human cell which does not express the endogenous form of the surface protein of interest but expresses an exogenous form of the protein of interest comprising at least one human segment;
(b) immunization of a non-human animal with the cell line provided in step (a);
(c) generation of hybridomas from the immunized non-human animal of step (b);
(d) screening for an antibody that binds to the surface molecule of interest by contacting the antibodies secreted by the hybridomas of step (c) with human cells which do not express the endogenous form of the surface protein of interest but expresse an exogenous form of the protein of interest comprising at least one human segment.

In certain embodiments, in step (d) the antibodies secreted by the hybridomas of step (c) are contacted with a mixture of human cells which does not express the endogenous form of the surface protein of interest comprising:
(i) a first proportion of the mixture of human cells which expresses the functional surface molecule of interest; and
(ii) a second proportion of the mixture of human cells which does not express a functional surface molecule of interest and which comprises a selection marker.

In specific embodiments, in step (d) the antibodies secreted by the hybridomas of step (c) are contacted with a mixture of human cells which does not express the endogenous form of the cell surface protein of interest comprising:
(i) a first proportion of the mixture of human cells which expresses the functional cell surface molecule of interest; and
(ii) a second proportion of the mixture of human cells which does not express a functional cell surface molecule of interest and which comprises a selection marker, wherein the selection marker is preferably a fluorescent marker;
wherein binding to (i) and not to (ii) indicates that the antibody is specifically binding to the cell surface protein of interest.

Typically, the selection marker is a fluorescent marker such as GFP. For example, the screening may be carried out by FACS.

In some embodiments, the non-human animal that is immunized in step (b) is of another species than the non-human cell line provided in step (a). Preferably, the non-human animal that is immunized in step (b) is a rat and the non-human cell line provided in step (a) is a mouse cell line.

In specific embodiments, the surface molecule of interest is at least one TCR receptor of interest. Accordingly, in some embodiments the cell provided in step (a) does neither express an endogenous TCR α chain nor an endogenous TCR β chain.

In preferred embodiments, the exogenous TCR comprises a variable human TCR α chain and a variable human TCR β chain.

In other embodiments, the exogenous TCR comprises a constant mouse TCR α chain and a constant mouse TCR β chain.

In some embodiments, the antibody binds to at least one T cell receptor variable alpha (TCR Vα) chain or binds to at least one T cell receptor variable beta (TCR Vβ) chain, the method comprising the following steps:
(a) providing a non-human cell which does neither express the endogenous TCR α chain nor the endogenous TCR β chain but expresses an exogenous TCR α chain and an exogenous TCR β chain comprising a variable human TCR V a chain and a variable human TCR β chain;
(b) immunization of a non-human animal with the cell line provided in step (a);
(c) generation of hybridomas from the immunized non-human animal of step (b);
(d) screening for an antibody that binds to the TCR of interest by contacting the antibodies secreted by the hybridomas of step (c) with a mixture of human cells which does neither express the endogenous TCR α chain nor the endogenous TCR β chain comprising:
  (i) a first proportion of the mixture of human cells which comprises the TCR having the TCR chains that are expressed by the non-human cell provided in step (a),
  (ii) a second proportion of the mixture of human cells which does not comprise a functional TCR but comprises a selection marker;
wherein binding to (i) and not to (ii) indicates that the antibody binds to at least one TCR Vα chain or binds to at least one TCR Vβ chain.

Certain embodiments refer to a method for generating an antibody that binds to at least one T cell receptor variable alpha (TCR Vα) chain or binds to at least one T cell receptor variable beta (TCR Vβ) chain, the method comprising the following steps:
(a) providing a non-human cell which does neither express the endogenous TCR α chain nor the endogenous TCR β chain but expresses an exogenous TCR α chain and an exogenous TCR β chain comprising a variable human TCR V a chain and variable human TCR β chain;
(b) immunization of a non-human animal with the cell line provided in step (a);
(c) generation of hybridomas from the immunized non-human animal of step (b);
(d) screening for an antibody that binds to the TCR of interest by contacting the antibodies secreted by the hybridomas of step (c) with a mixture of human cells which does neither express the endogenous TCR α chain nor the endogenous TCR β chain comprising:
  (i) a first defined proportion of the mixture of human cells which comprises the TCR having the TCR chains that are expressed by the non-human cell provided in step (a),
  (ii) a second defined proportion of the mixture of human cells which does not comprise a TCR having TCR chains that are different to the TCR chains expressed by the non-human cell provided in step (a) but comprises a TCR having TCR chains that are different to the TCR chains expressed by the non-human cell provided in step (a), and
  (iii) a third defined proportion of the mixture of human cells which does not comprise a functional TCR but comprises a selection marker.

In some embodiments the exogenous TCR comprises constant mouse TCR Ca and TCR chains.

In particular embodiments, the antibody binds to a fraction of TCR Vα chains comprising at least two different TCR Vα chains but less than all TCR Vα chains or that binds to a fraction of TCR Vβ chains comprising at least two different TCR Vβ chains but less than all TCR Vβ chains, the method comprising the following steps:
(a) providing a non-human cell which does neither express the endogenous TCR α chain nor the endogenous TCR β chain but expresses an exogenous TCR α chain comprising a variable human TCR V a chain and an exogenous TCR β chain comprising a variable human TCR β chain;
(b) immunization of a non-human animal with the cell line provided in step (a);
(c) generation of hybridomas from the immunized non-human animal of step (b);
(d) screening for an antibody that binds to at least one TCR Vα chain or binds to at least one TCR Vβ chain by contacting the antibodies secreted by the hybridomas of step (c) with a mixture of human cells which express neither the endogenous TCR α chain nor the endogenous TCR β chain comprising:
  (i) a first defined proportion of the mixture of human cells which comprises the TCR having the TCR chains that are expressed by the non-human cell provided in step (a),
  (ii) a second defined proportion of the mixture of human cells which does not comprise a TCR having TCR chains that are expressed by the non-human cell line provided in step (a) but comprises a TCR having TCR chains that are different to the TCR chains expressed by the non-human cell provided in step (a), and
  (iii) a third defined proportion of the mixture of human cells which does not comprise a functional TCR but comprises a selection marker;
wherein the non-human animal is mouse or rat and the non-human cell provided in step (a) is a mouse cell line.
wherein binding to (i) and/or (ii) and binding not to (iii) identifies the antibody to bind to at least one TCR Vα chain to bind to at least one TCR Vβ chain;
(e) identifying an antibody that binds to a fraction of TCR Vα chains comprising at least two different TCR Vα chains but less than all TCR Vα chains or that binds to a fraction of TCR chains comprising at least two different TCR Vβ chains but less than all TCR Vβ chains, comprising the following steps:
  (i) incubating human peripheral blood lymphocytes (PBL) with the antibody identified in step (d) as binding to at least one TCR Vα chain or binding to at least one TCR chain;
  (ii) screening for cells that bind to the antibody by FACS sorting;
  (iii) analysis of the TCR Vα chain repertoire or TCR Vβ chain repertoire of the cells that bind to the antibody of step (ii);
wherein a TCR Vα chain repertoire or TCR Vβ chain repertoire comprising different TCR Vα chains but less than all TCR Vα chains or at least two different TCR Vβ chains but less than all TCR Vβ chains indicates that the antibody binds to a fraction of TCR Vα chains comprising at least two different TCR Vα chains but less than all TCR Vα chains or that binds to a fraction of TCR Vβ chains comprising at least two different TCR Vβ chains but less than all TCR chains.

In more specific embodiments, the antibody binds to a fraction of TCR Vα chains comprising at least two different TCR Vα chains but less than all TCR Vα chains or that binds to a fraction of TCR Vβ chains comprising at least two different TCR Vβ chains but less than all TCR chains, the method comprising the following steps:
(a) providing a non-human cell which does neither express the endogenous TCR α chain nor the endogenous TCR β chain but expresses an exogenous TCR α chain comprising a variable human TCR V a chain and an exogenous TCR β chain comprising a variable human TCR β chain;
(b) immunization of a non-human animal with the cell line provided in step (a);
(c) generation of hybridomas from the immunized non-human animal of step (b);
(d) screening for an antibody that binds to at least one TCR Vα chain or binds to at least one TCR Vβ chain by contacting the antibodies secreted by the hybridomas of step (c) with a mixture of human cells which express neither the endogenous TCR α chain nor the endogenous TCR β chain comprising:
  (i) a first defined proportion of the mixture of human cells which comprises the TCR having the TCR chains that are expressed by the non-human cell provided in step (a),
  (ii) a second defined proportion of the mixture of human cells which does not comprise a TCR having TCR chains that are expressed by the non-human cell line provided in step (a) but comprises a TCR having TCR chains that are different to the TCR chains expressed by the non-human cell provided in step (a), and
  (iii) a third defined proportion of the mixture of human cells which does not comprise a functional TCR but comprises a selection marker;
wherein the non-human animal is mouse or rat and the non-human cell provided in step (a) is a mouse cell line.
wherein binding to (i) and to (ii) and not binding to (iii) identifies the antibody to bind to at least two TCR Vα chains or to bind to at least two TCR Vβ chains;

(e) identifying an antibody that binds to a fraction of TCR Vα chains comprising at least two different TCR Vα chains but less than all TCR Vα chains or that binds to a fraction of TCR chains comprising at least two different TCR Vβ chains but less than all TCR Vβ chains, comprising the following steps:
  (i) incubating human peripheral blood lymphocytes (PBL) with the antibody identified in step (d) as binding to at least two TCR Vα chains or binding to at least two TCR chains;
  (ii) screening for cells that bind to the antibody by FACS sorting;
  (iii) analysis of the TCR Vα chain repertoire or TCR Vβ chain repertoire of the cells that bind to the antibody of step (ii);
  wherein a TCR Vα chain repertoire or TCR Vβ chain repertoire comprising different TCR Vα chains but less than all TCR Vα chains or at least two different TCR Vβ chains but less than all TCR Vβ chains indicates that the antibody binds to a fraction of TCR Vα chains comprising at least two different TCR Vα chains but less than all TCR Vα chains or that binds to a fraction of TCR Vβ chains comprising at least two different TCR Vβ chains but less than all TCR Vβ chains.

FIGURE LEGENDS

FIG. 1:

FIG. 1A: Schematic depiction of the TCR complex on the cell surface containing the TCR α and β chains as well as the CD3 complex (chains ε, γ, and δ). The TCR is composed of two different protein chains, a and (3, which in turn consist of variable (V) and constant (C) regions. The variable regions of both the TCRα and the β chain contain hypervariable regions (CDR, complementarity determining regions), among which the CDR3 region determines the specific epitope recognition.

Figure 1B:
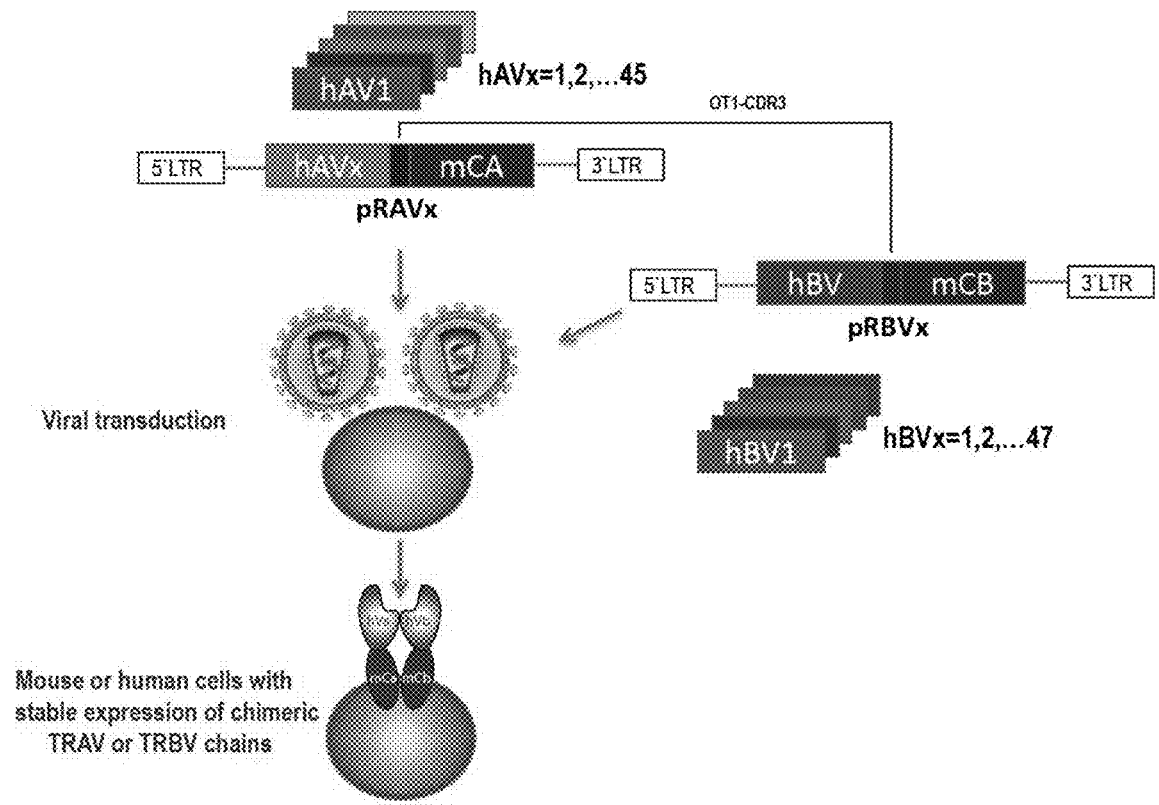

FIG. 1B: Modular retroviral TCR expression vector system. The pRAVx (pRBVx) vector system is based on the pMP71 backbone (Schambach A, Wodrich H, Hildinger M, Bohne J, Krausslich H G, Baum C., Mol Ther. 2000 November; 2(5):435-45; Hildinger M, Abel K L, Ostertag W, Baum C., J Virol. 1999 May; 73(5):4083-9.). Each vector contains the murine constant alpha (mCA) or beta constant (mCB) region and one of 45 human AV or 47 human BV regions (hAVx and hBVx). Each vector contains an identical CDR3 region derived from the OT-1-specific T cell clone. The 45 pRAVx are used successively to produce retroviruses (RV). One AV-specific RV is used to transduce recipient T cells, in combination with a second RV encoding a TRBV chain, containing a murine constant beta and human BV region. Likewise, cells expressing a selected human BV region are produced using pRAV encoding a TRAV, containing a murine constant alpha and human AV region with successive pRBVx vectors. 5'LTR, 3'LTR designates the 5' and 3' retroviral long terminal repeats.

Figure 2:
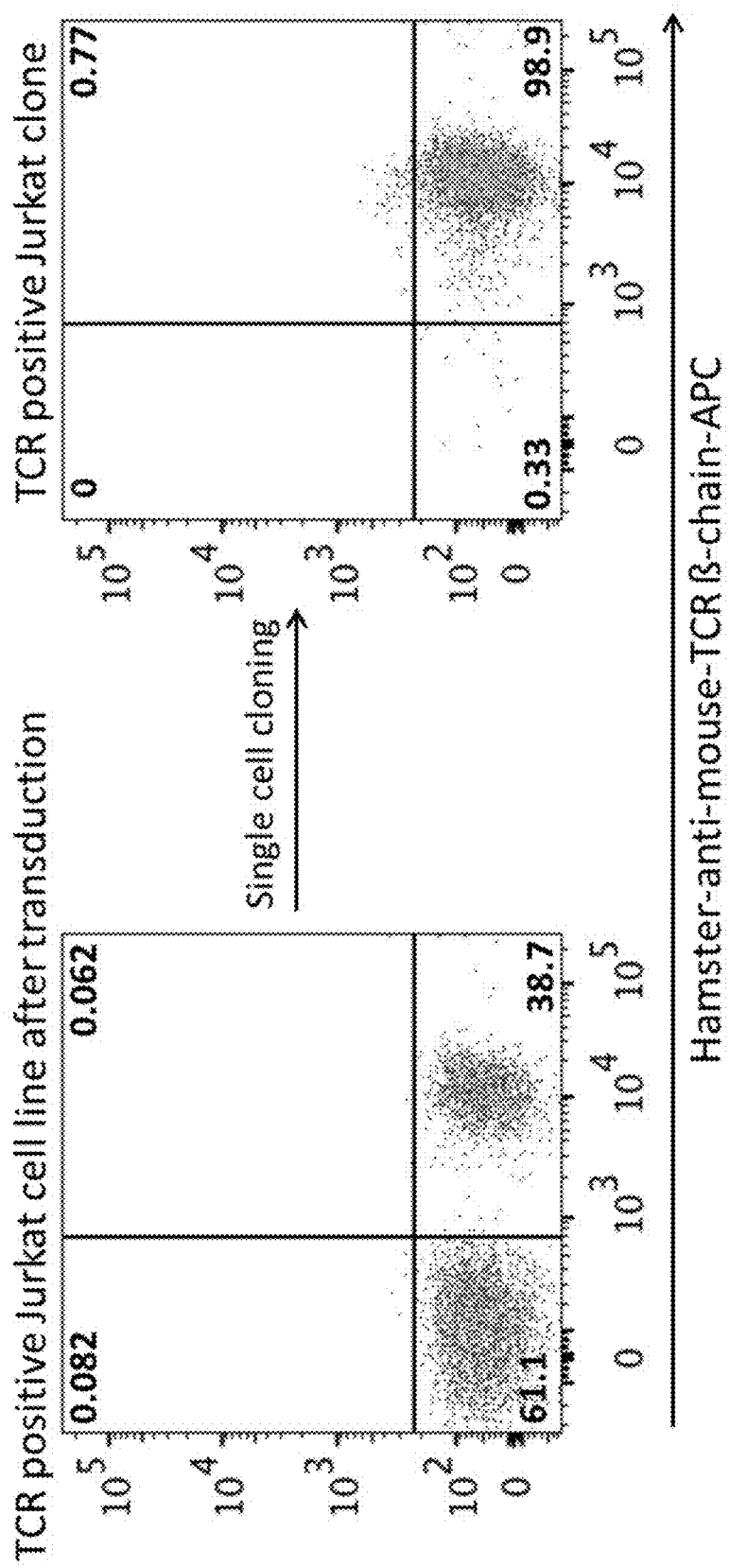

FIG. 2: Surface TCR expression on the transduced Jurkat cell line and a selected clone. The Jurkat cells were retrovirally transduced and stained for murine beta chain constant region (mCB) surface expression. TCR positive cells were either directly sorted using the FACS Aria cell sorter or manually subcloned by limiting dilution.

Figure 3:
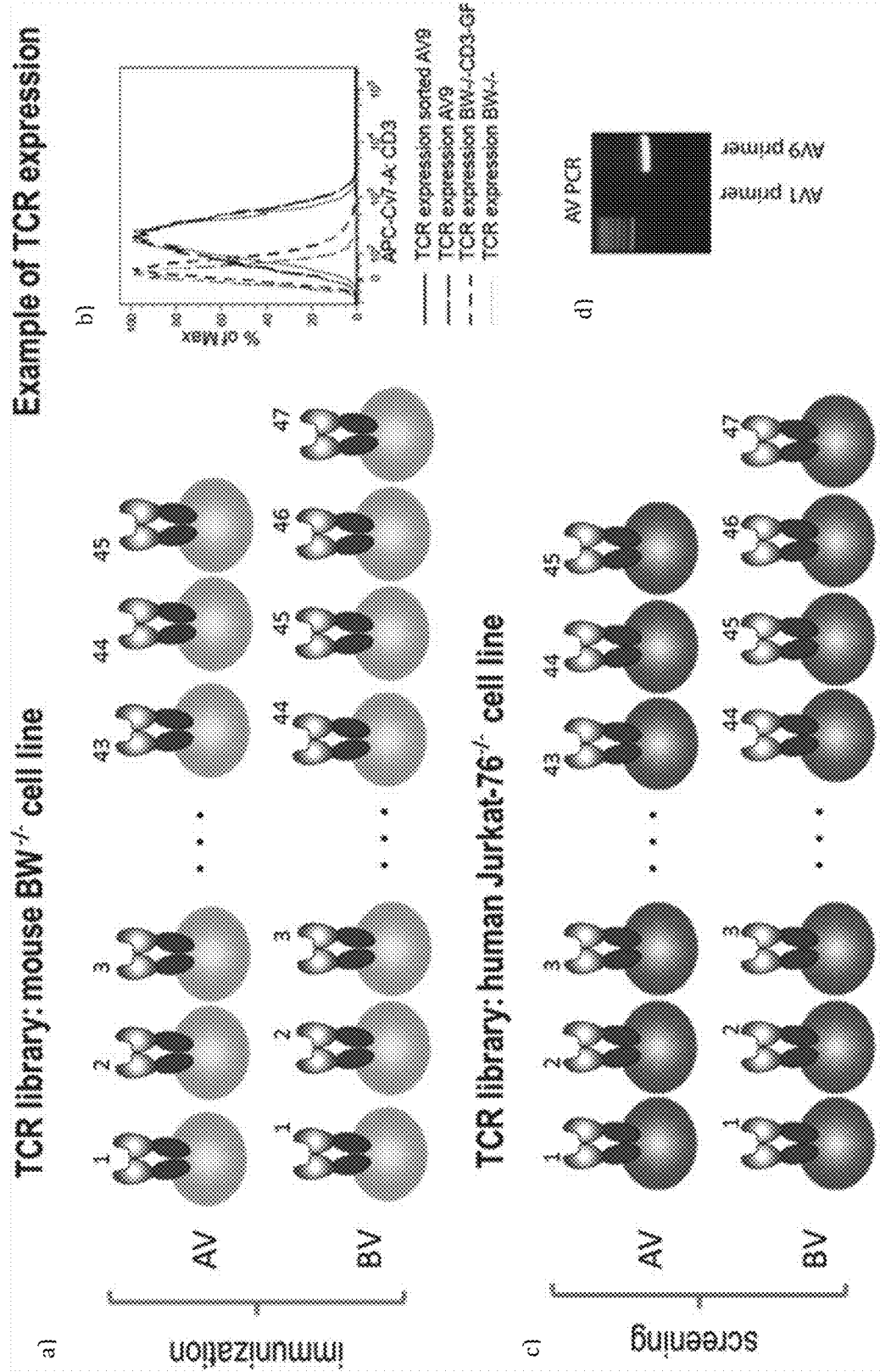

FIG. 3: TCR cell libraries. a) The murine BW–/– TCR library upon completion will express 45 different human AV and 47 different human BV TCR regions as shown in light grey (gradient) to represent the human sequence. All other regions of the TCR are shown in dark grey to indicate their mouse origin. The murine cell library is used for immunization. b) Upon retroviral transduction with selected RVs, cells were stained with anti-mCB-specific antibodies. Positive cells were sorted and TCR expression was compared on BW–/– parental cells, recipient BW–/– cells prior to transduction, AV9-transduced BW cells (BW-AV9 cell line) before sorting and the sorted BW-AV9 cell line. c) The complete Jurkat TCR library will express 45 different human AV and 47 different human BV TCR regions. This human Jurkat library will be used for screening. d) Specific primers for the TRAV9 variable region and control primers specific for TRAV1 region were used for PCR amplification using cDNA from the transduced and sorted BW-AV9 cell line. Subsequently, the amplified DNA band was cut out, sequenced and AV9 sequences confirmed by alignment with the AV9 sequence in IMGT database.

Figure 4:
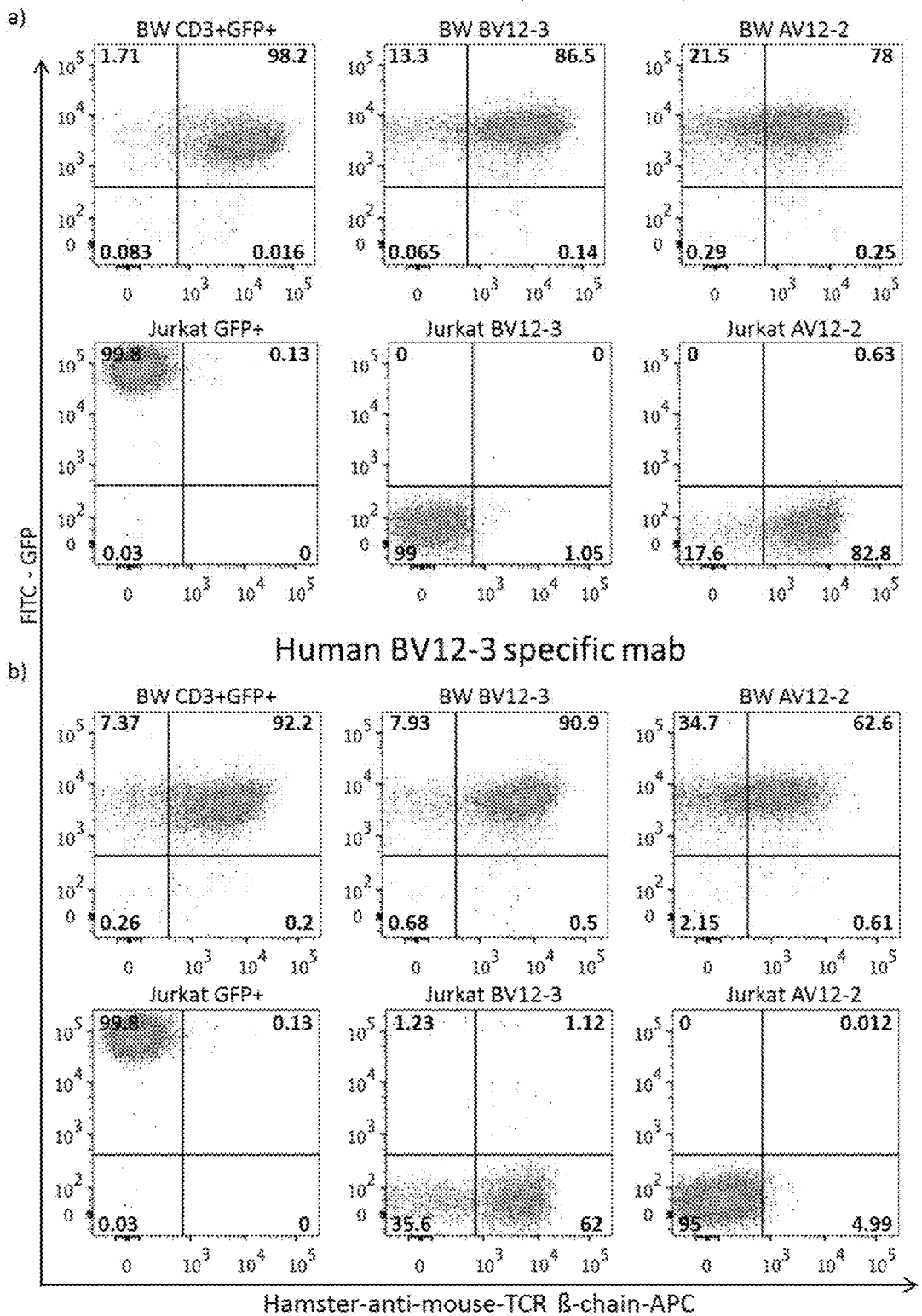

FIG. 4: Cross-species screening using BW$^{-/-}$ and Jurkat$^{-/-}$ cells. BW-TCR transduced cells were used for immunization, however these cells could not be used for hybridoma screening since they bind mouse or rat Ig non-specifically as shown here for the anti-human AV12-2-specific hybridoma supernatant, as well as for the anti-human BV12-3-specific supernatant. Both hybridoma supernatants stain BW$^{-/-}$ cells irrespective of their TCR expression (first row in a and b). In contrast, the same supernatants stain Jurkat$^{-/-}$ cells only when they express the specific AV or BV TCR chain (second row a and b). TCR-transduced BW$^{-/-}$ cells are stably transduced also with CD3-GFP in order to allow TCR expression, accounting for their moderate level of GFP. To distinguish between non-specific and specific TCR binding on TCR-transduced Jurkat$^{-/-}$ cells, a stable Jurkat$^{-/-}$ cell clone transduced to express high levels of GFP and used as a control during hybridoma supernatant screening. The location in the upper left corner of the histogram indicates the very high GFP signal which allows distinction from the lower level of GFP in BW$^{-/-}$ cells. As shown, Jurkat-GFP cells remain unlabeled when tested with supernatant containing either AV- or BV-specific mabs (second row a and b). This is seen by their failure to shift to the left in the presence of supernatant containing AV- or BV-specific mabs.

Figure 5A:
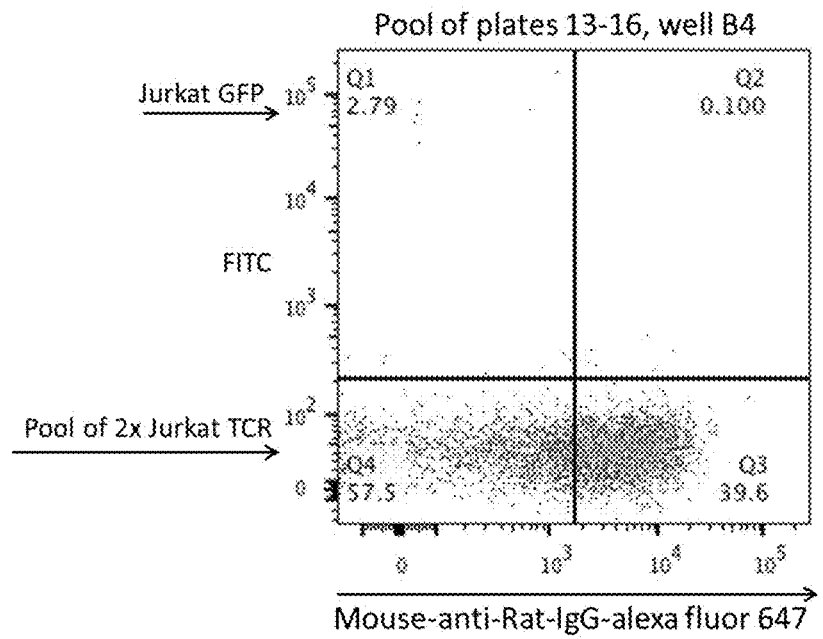
Figure 5B:
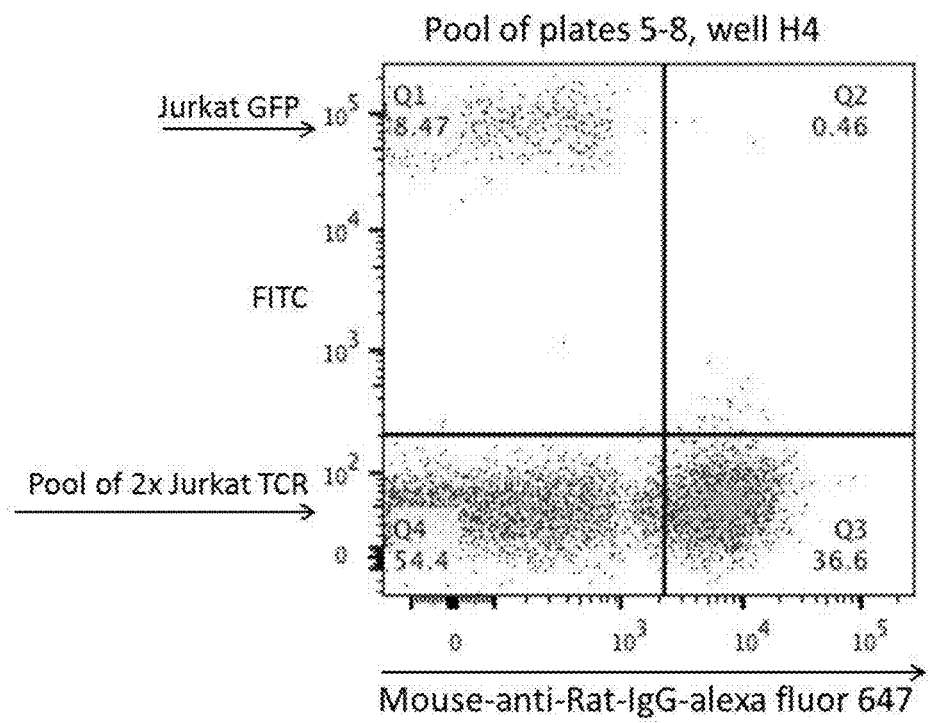

FIG. 5: Primary screening of pooled hybridoma supernatants including hybridoma clone 15B4 (FIG. 5A) and 5H4 (FIG. 5B). Pooled hybridoma supernatants were screened using a pool of Jurkat cells expressing four different TCRs and 10% GFP-expressing negative control cells. It is expected that about 45% of cells are shifted toward alexa fluor 647 in the TCR-expressing cells, but not in the Jurkat-GFP fraction if a mab specific for an individual BV region is present in the pooled supernatant.

Figure 6A:
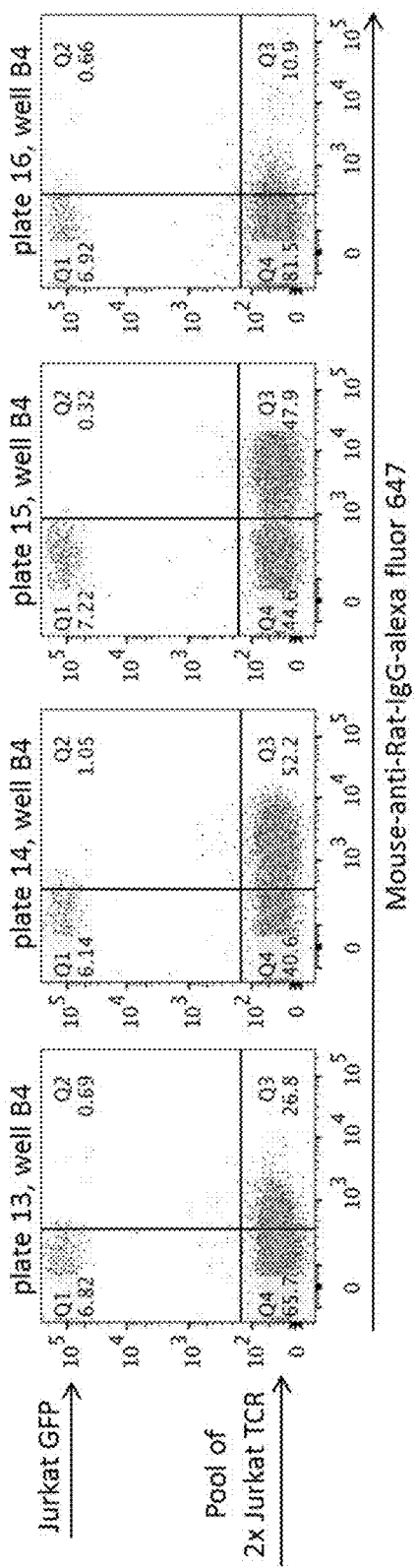
Figure 6B:
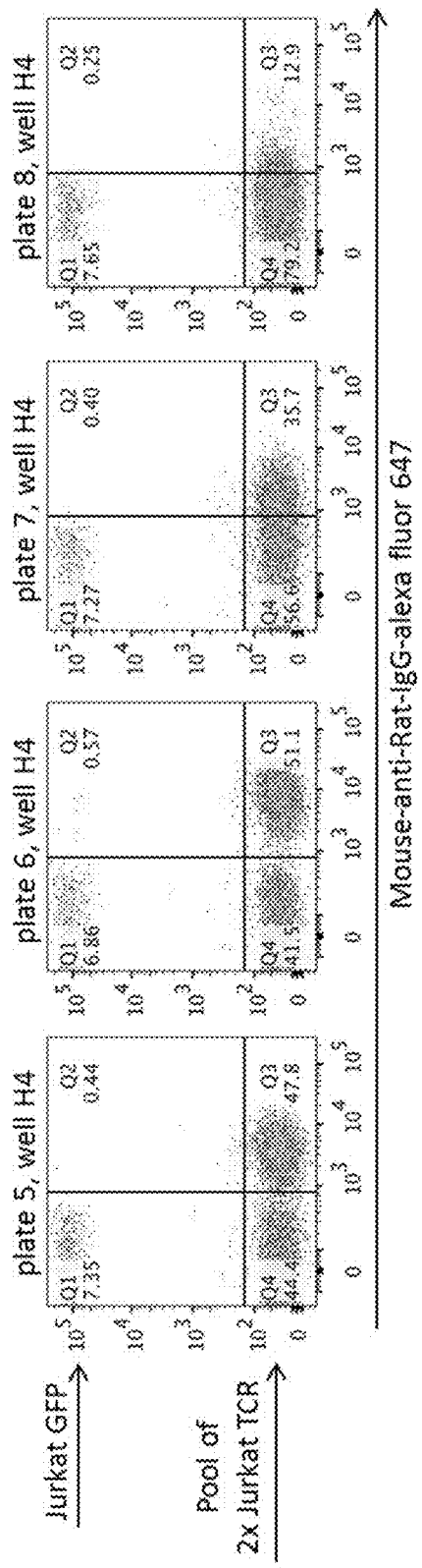

FIG. 6: Secondary screening of single hybridoma supernatants. Hybridoma supernatants of the single plates were screened using a pool of Jurkat cells expressing four different TCRs and 10% GFP-expressing negative control cells. Secondary screening including 15B4 is shown in FIG. 6A. Secondary screening including 5B4 is shown in FIG. 6B.

Figure 7:
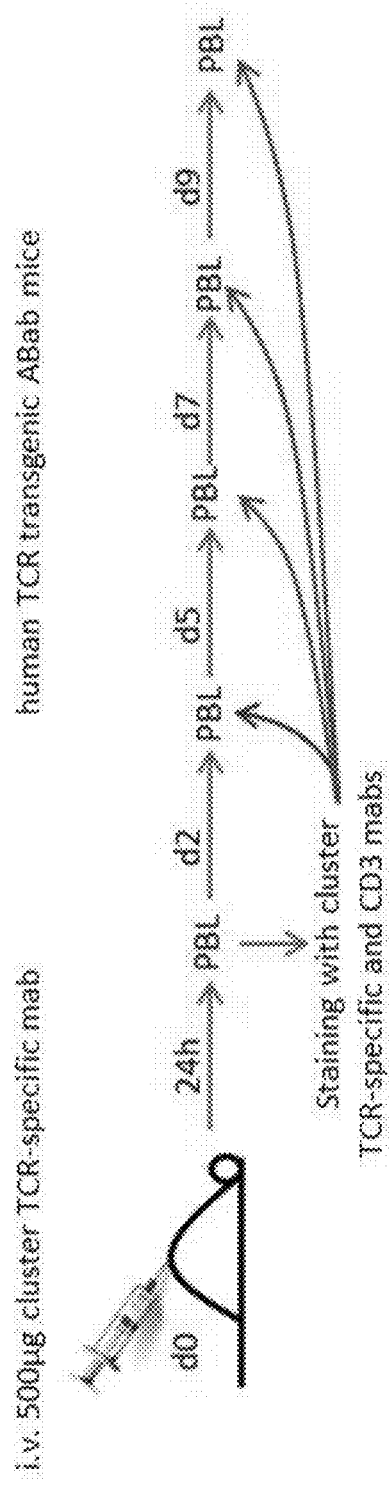

FIG. 7: Experimental set-up for in vivo depletion of BV-cluster expressing T cells in human ABab TCR transgenic mice with a cluster TCR-specific mab.

Figure 8:
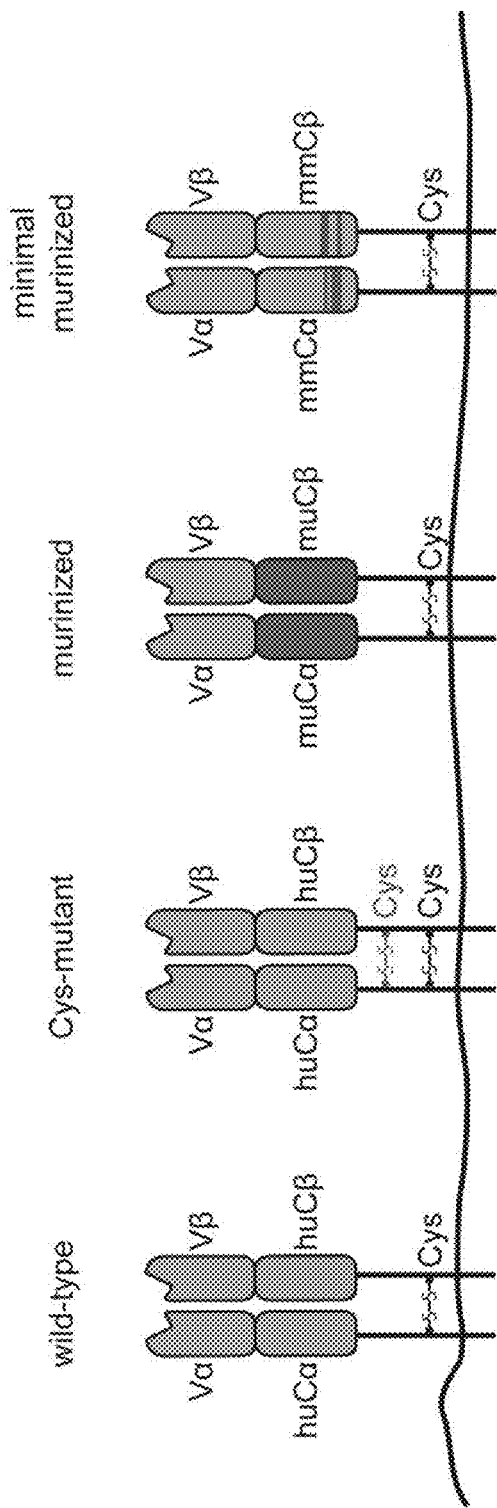

FIG. 8: Structures of different TCR constructs to reduce TCR mispairing in transgenic settings. Wild-type TCRs comprise the human constant regions (huCα, huCβ) and one disulfide bond linking the two TCR chains via two cysteine residues (Cys). Cys-mutants comprise an additional disulfide bond, therefore increasing the linkage between modified TCR chains. In murinized constructs the human constant regions are replaced by murine constant regions (muCα) to enhance stable surface expression and preferable pairing. To reduce possible immunogenicity due to foreign mouse segments, the minimal murinized constructs comprise only critical murine amino acids required for improved surface expression and pairing.

FIG. 9: Modular vector system.

Figure 9A:
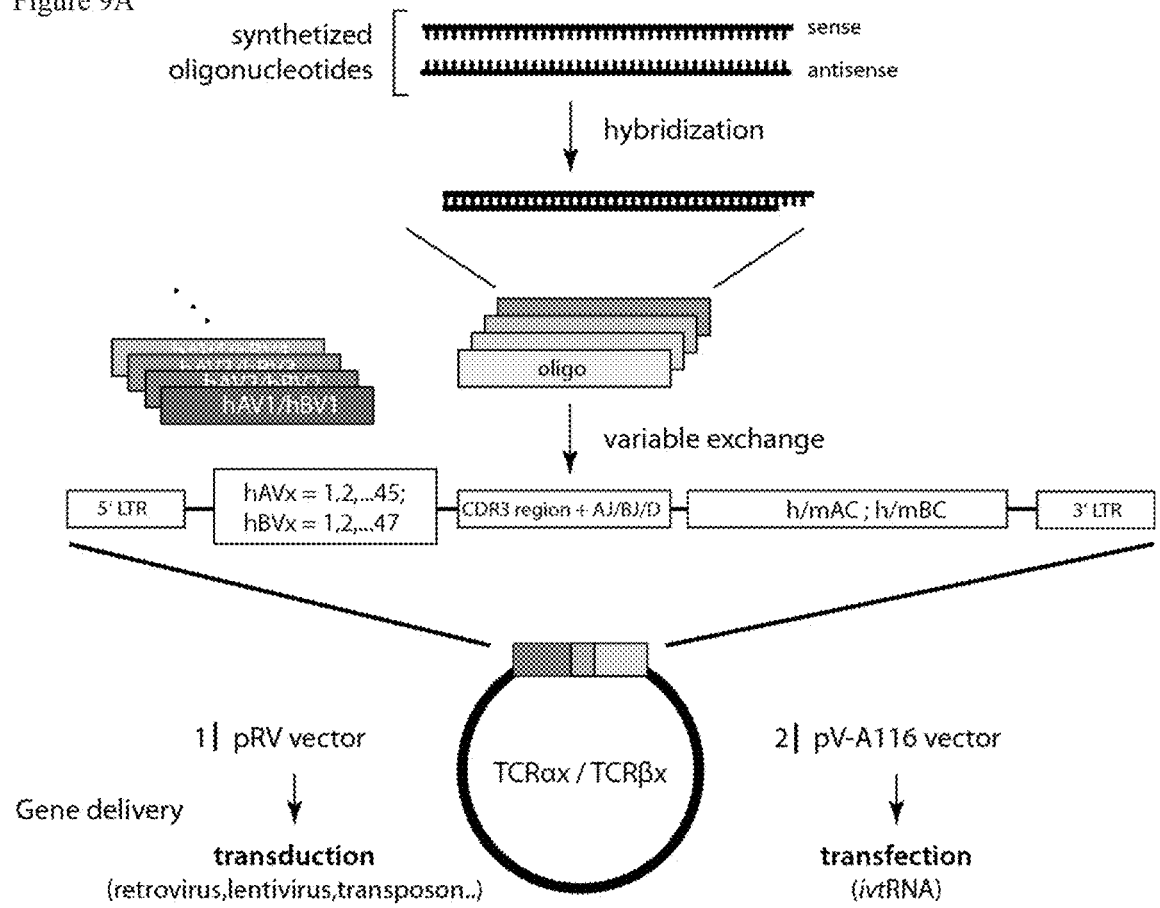
Figure 9B:
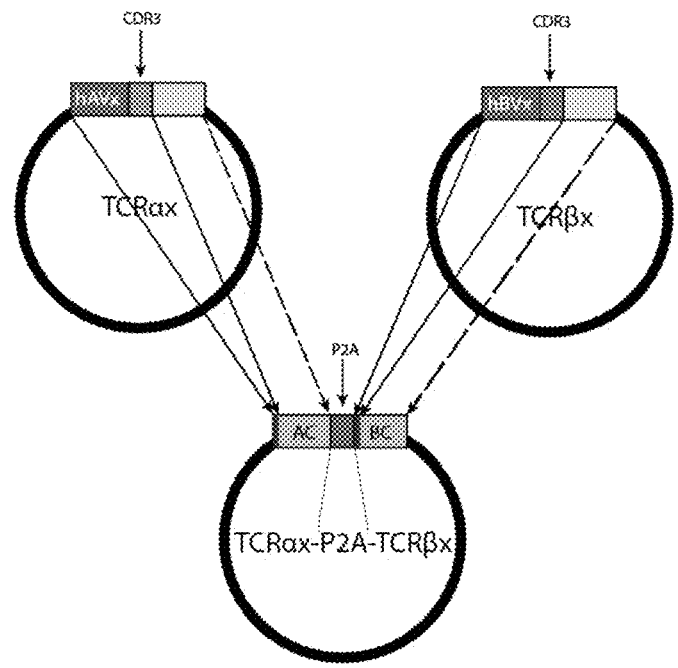

FIG. 9A: The TCR constructs are constructed in such a way that each segment or segment variation (variable region, linker sequence comprising CDR3 region and constant C region) as well as any vector backbone (e.g. retro-, lenti-, transposon,-ivtRNA.) can be easily exchanged in a single step procedure. Thereby any type of TCR chain can be generated by exchange of the variable region. The specificity can be switched by the introduction of a desired CDR3 region which can be introduced for example by hybridized oligonucleotides. Moreover, the segments can also be switched between different species versions and modified versions (such as human, murine, cysteine-engineered). FIG. 9B: reconstituted TRAV and TRBV chains can be introduced in the same vector as whole genes divided by P2A sequence. Alternatively, AV-CDR3-J and BV-CDR3-J/D can be introduced in front of a mouse or human constant region that is already incorporated in the vector backbone.

Figure 10A:
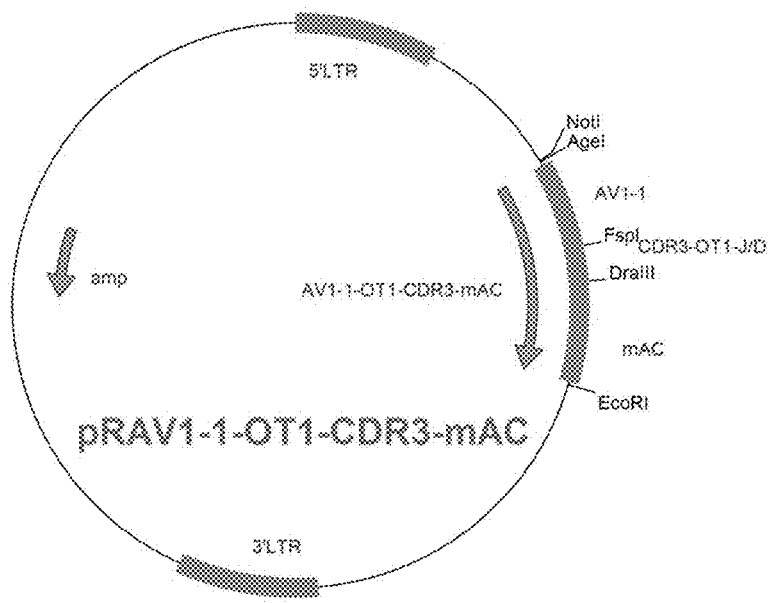
Figure 10B:
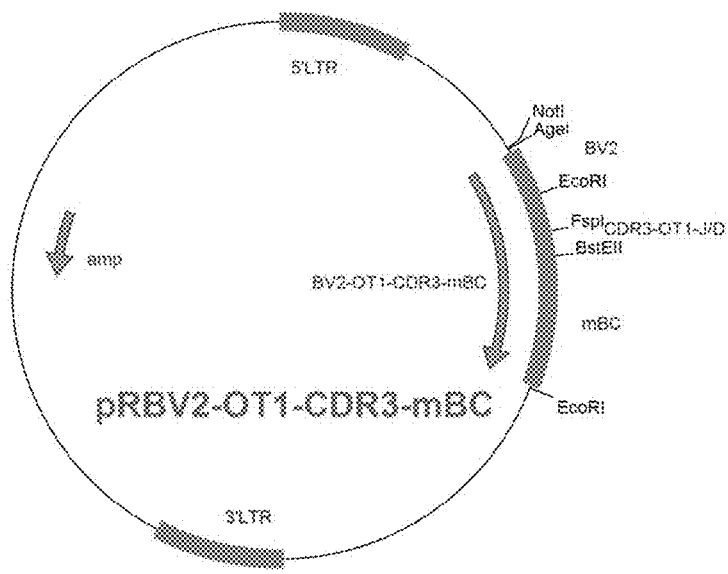

FIG. 10: Vector maps of example vectors having a mouse constant segment. FIG. 10A shows an example of retroviral vector carrying TCR α chain composed of human AV1-1, CDR3 derived for OT1 TCR α chain and mouse alpha constant region. The sequence of this vector is set forth in SEQ ID NO: 204. FIG. 10B shows an example of retroviral vector carrying TCR β chain composed of human BV2, CDR3 derived for OT1 TCR β chain and mouse constant β region. The sequence of this vector is set forth in SEQ ID NO: 205.

FIG. 11: Vector maps of example vectors comprising a human constant region.

Figure 11A:
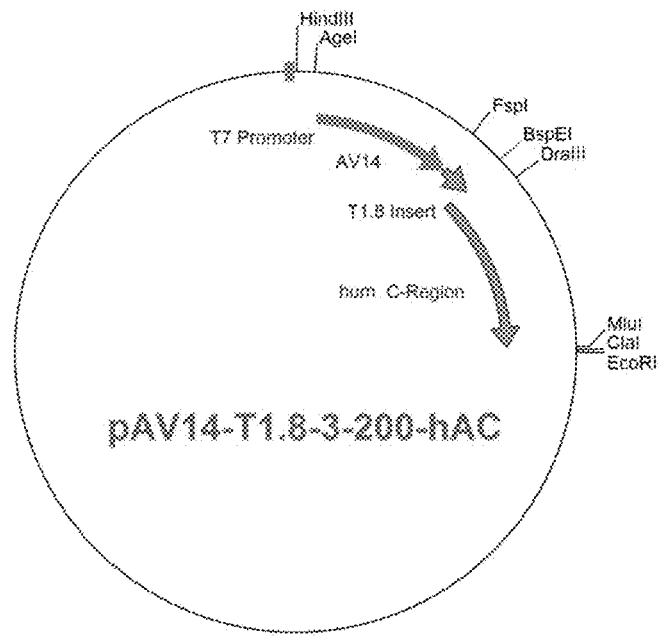
Figure 11B:
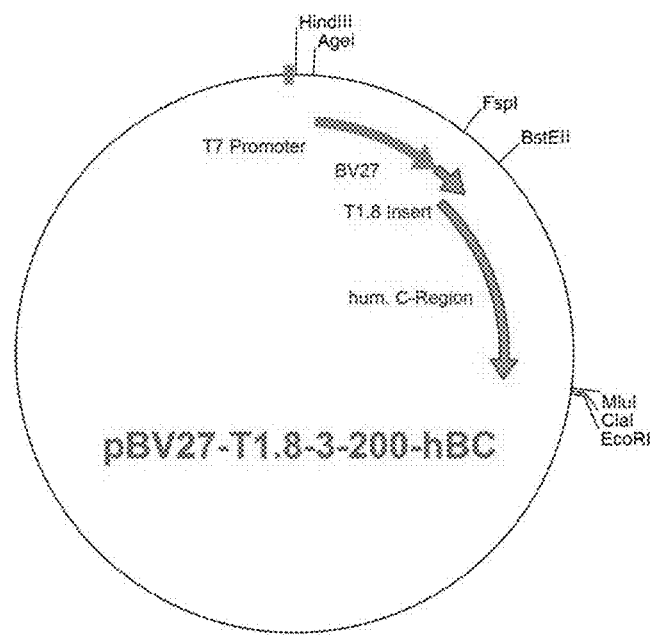

FIG. 11A shows an example of a retroviral vector carrying TCR α chain composed of human AV14, CDR3 derived from T1.8 TCR α chain and mouse human constant region. The sequence of this vector is set forth in SEQ ID NO: 208. FIG. 11B shows an example of a retroviral vector carrying TCR β chain composed of human BV27, CDR3 derived from T1.8 TCR β chain and mouse constant β region. The sequence of this vector is set forth in SEQ ID NO: 209.

FIG. 12: Reengineering of an isolated TCR

FIG. 12A: Functional analysis of isolated T cell clone T1.8-3-200. Interferon-gamma (IFN-γ) measurements of co-culture of T cell clone T1.8-3-200 with HLA-matched NY-ESO1-X-(human NY-ESO1 antigen fused to a signal peptide)-loaded APC. FIG. 12B: IMGT sequence analysis of T1.8-3-200 TCRα chain. FIG. 12C: IMGT sequence analysis of T1.8-3-200 TCRβ chain. FIG. 12D: Transgenic function analysis of TCR T1.8-3-200. IFN-γ measurements of co-culture of the T1.8-3-200 TCR-transfected PBL with HLA-matched NY-ESO1-X-loaded APC.

Figure 13:
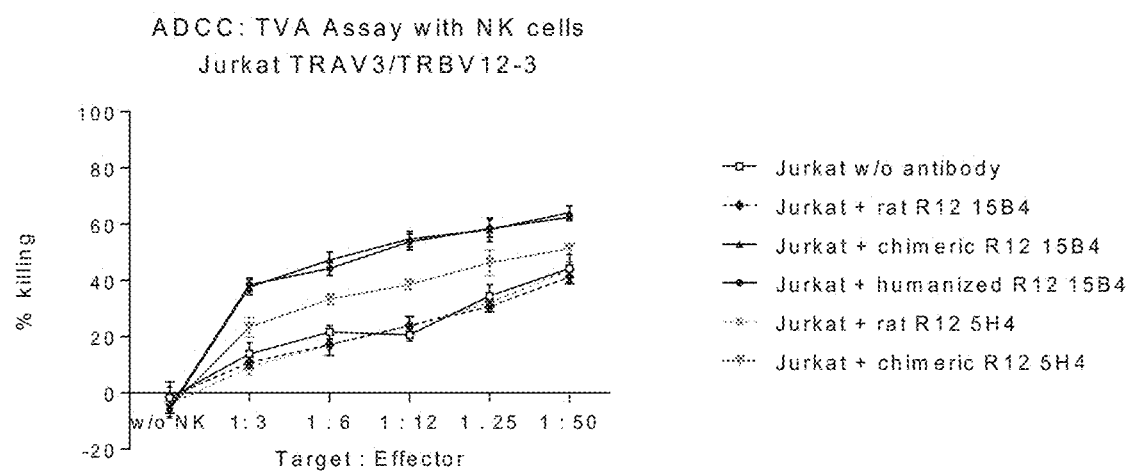
Figure 13:
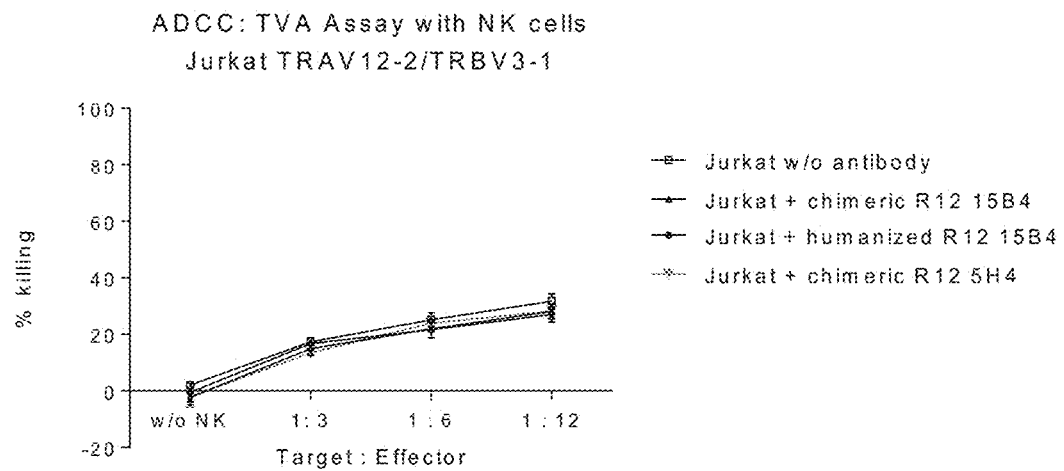

FIG. 13: FIG. 13 A: Induction of ADCC in BV12-3 expressing human leukemia cells by candidate antibodies. Antibodies were incubated at 33.5-66.7 nM with human leukemia cells (Jurkat) expressing the human TCR variable alpha chain 3 and beta chain 12-3 (recognized by the isolated antibodies) and NK cells at different target-to-effector ratios for 6 hrs. FIG. 13 B: Induction of ADCC in BV3-1-expressing human leukemia cells by candidate antibodies. Antibodies were incubated at 33.5-66.7 nM with human leukemia cells (Jurkat) expressing the human TCR variable alpha chain 12-2 and beta chain 3-1 (not recognized by the isolated antibodies) and NK cells at different target-to-effector ratios for 6 hrs.

Figure 14:
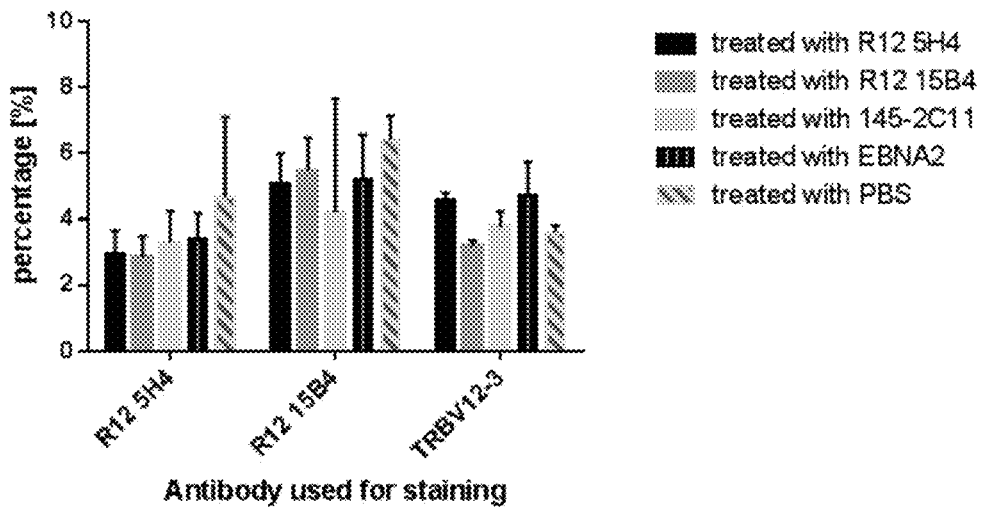
Figure 14:
Figure 14:
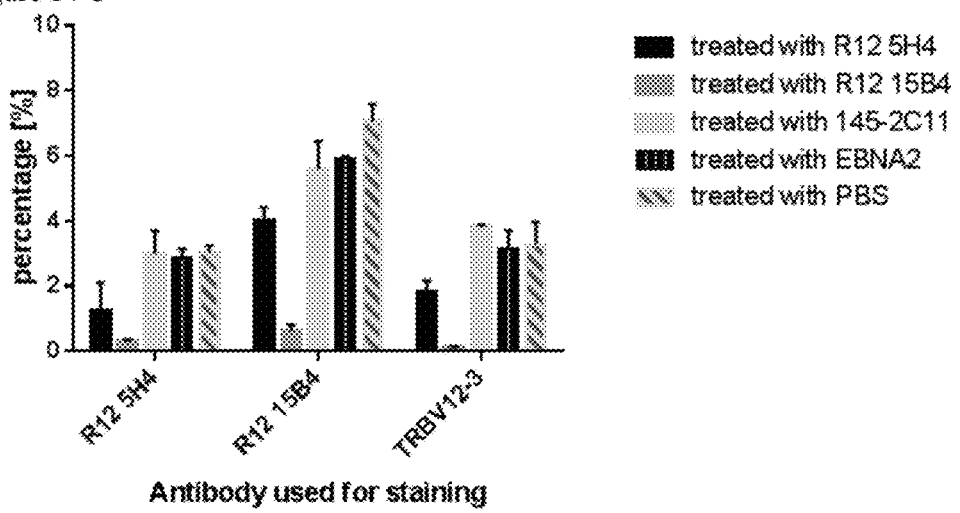

FIG. 14: In vivo depletion of T cells expressing BV12-3-related TCRs in a humanized TCR mouse model. FIG. 14 A: CD3+ positive PBL of blood samples before treatment. FIG.14B: FIG. 14 B: CD3+ positive PBL of blood samples on day 4 after treatment; FIG. 14 C: CD3+ positive PBL of blood samples on day 21 after treatment. Antibodies used for staining and depletion treatment are indicated in the legend.

Figure 15:
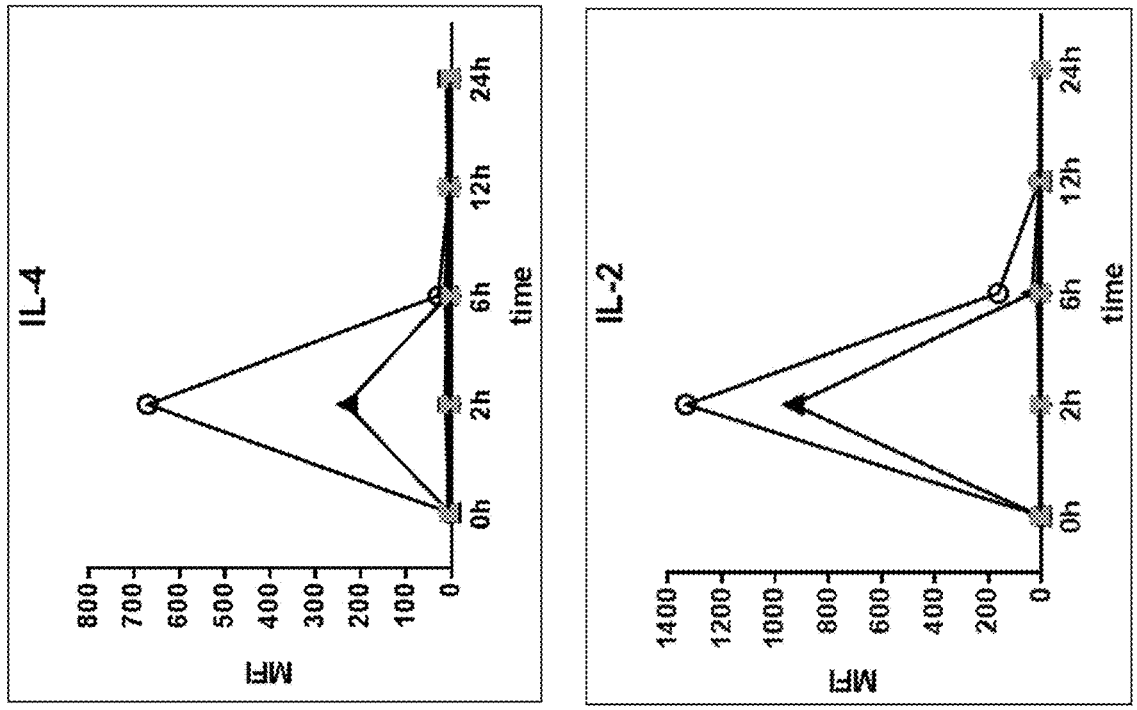

FIG. 15: Measurement of IL-2 and IL-4 during in vivo depletion. Serum concentration of IL-2 and IL-4 0, 2, 6, 12 and 24 hours after antibody treatment. Application of aCD3-AB to mouse #6077 was unsuccessful, therefore no reaction was expected.

Figure 16:
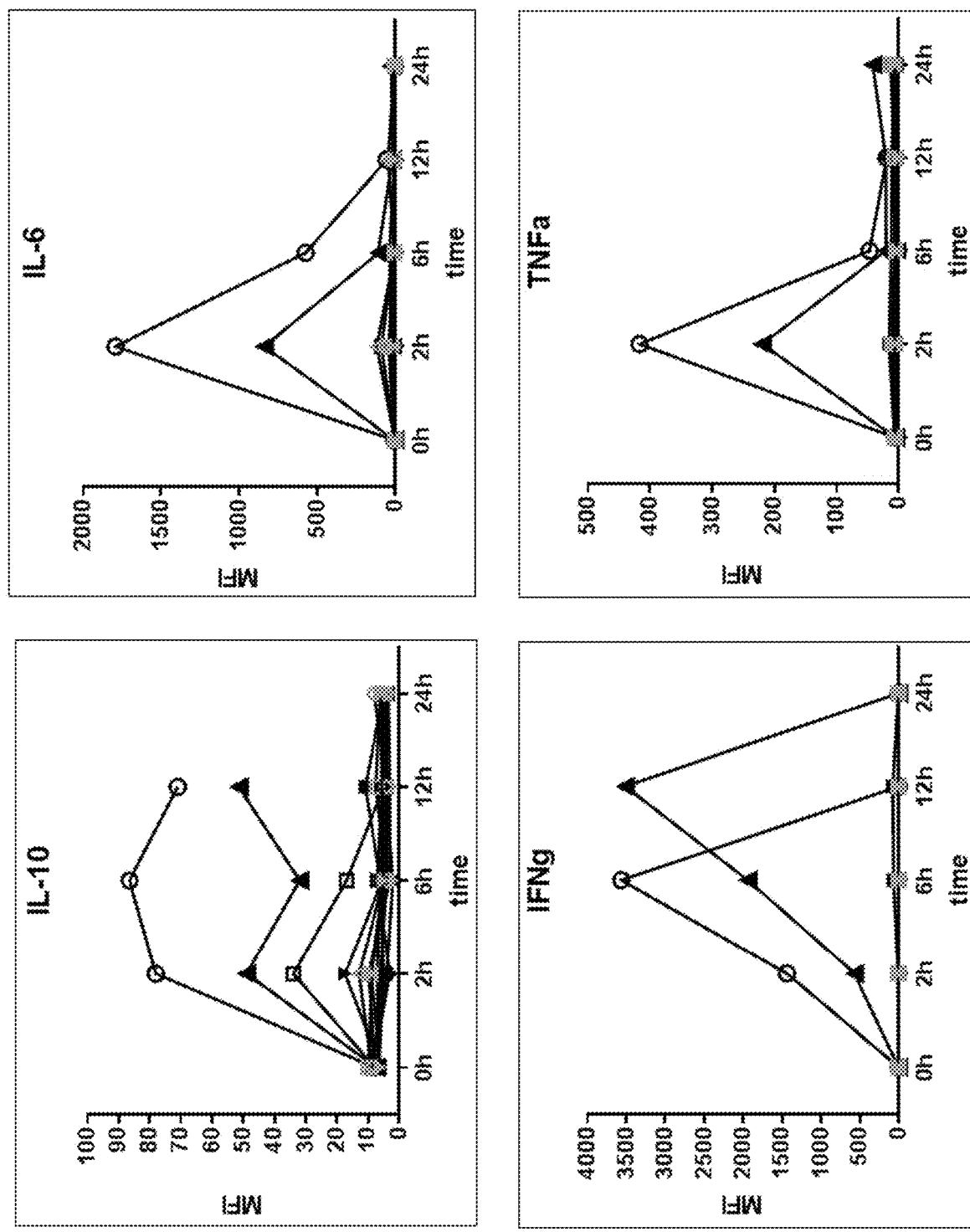

FIG. 16: Measurement of IL-10, IL-6, INFγ and TNFα during in vivo depletion. Serum concentration of IL-2 and IL-4 0, 2, 6, 12 and 24 hours after antibody treatment. The legend is shown in FIG. 15. Application of αCD3-AB to mouse #6077 was unsuccessful, therefore no reaction was expected.

Figure 17:
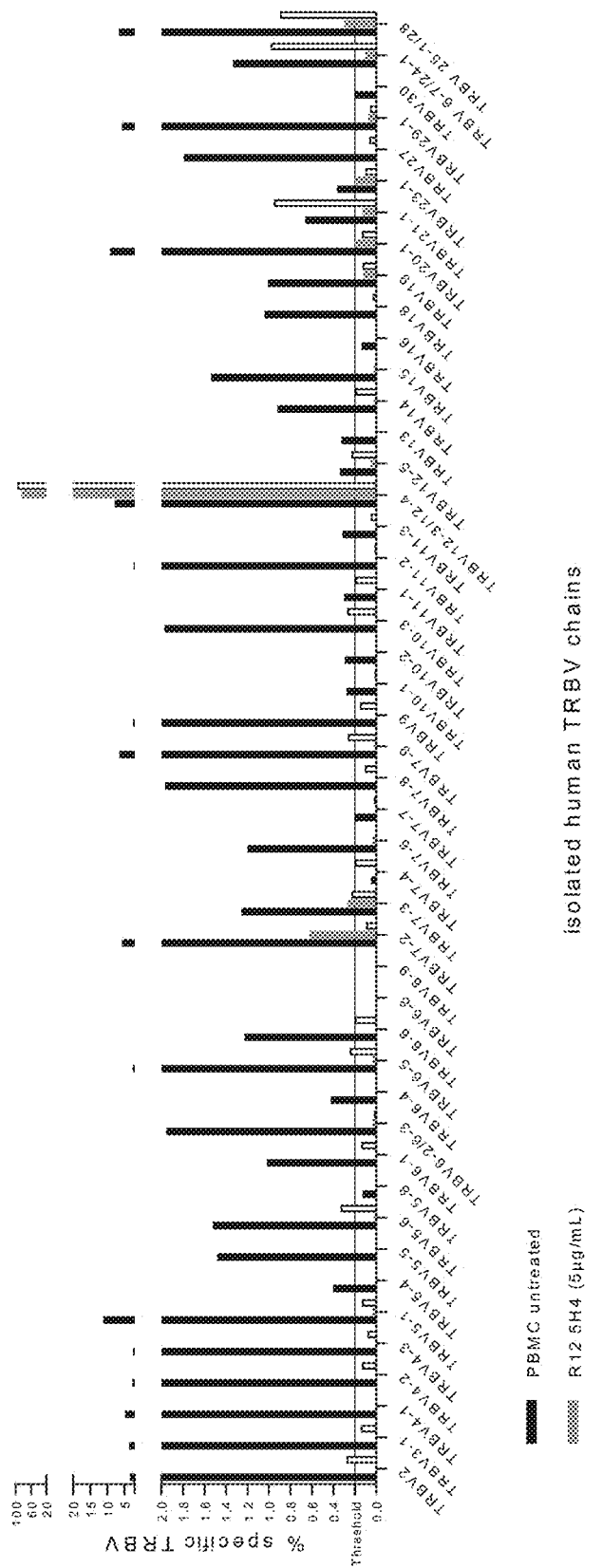

FIG. 17: TRBV chains isolated by cluster specific R12 5H4 and R12 15B4 antibodies determined by next generation sequencing. The lymphocytes sorted after staining with R12 5H4 and R12 15B4 were NGS sequenced and BV repertoire analyzed. The identified BV sequences are presented as a percentage of specific TRBV chains. Thus the bars indicate the percentage of the specific TRBV chain with respect to the total amount of TRBV chains within the respective sample (5H4 sorted, 115B4 sorted or whole PBMC respectively). Upon staining with R12 5H4 the sorted population contained TRBV7-2, TRBV7-3, TRBV12-3/TRBV12-4* and TRBV 25-1/TRBV28* (gray bars). The isolated BV repertoire using R12 15B4 is composed of TRBV2, TRBV5-6, TRBV6-5, TRBV7-3, TRBV7-9, TRBV10-3, TRBV12-3/TRBV12-4*, TRBV12-5, TRBV21-1, TRBV6-7/TRBV24-1* and TRBV 25-1/TRBV28* (white bars). These results indicate that these antibodies recognize small similar but distinct clusters. The sequencing of unsorted whole PBMC repertoire served as internal control (black bars). Due to a high sequence homology the chains pairs marked with "*" were recognized as a group.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

For the purposes of the present invention, the term "obtained" is considered to be a preferred embodiment of the term "obtainable". If hereinafter e.g. an antibody is defined to be obtainable from a specific source, this is also to be understood to disclose an antibody which is obtained from this source.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±10%, and preferably of ±5%.

Technical terms are used by their common sense. If a specific meaning is conveyed to certain terms, definitions of terms will be given in the following in the context of which the terms are used.

One aspect of the invention refers to an antibody or binding fragment thereof that binds to a fraction of T cell receptor variable alpha (TCR Vα) chains comprising at least two different TCR Vα chains but less than all TCR Vα chains or that binds to a fraction of T cell receptor variable beta (TCR Vβ) chains comprising at least two different TCR Vβ chains but less than all TCR chains.

The terms "fraction", "fraction of TCR Vα chains" or "fraction of TCR Vβ chains" as used herein means the specific group of TCR Vα chains or TCR Vβ chains to which the antibody is binding which is smaller than the group of all TCR Vα chains or all TCR Vβ chains, but larger than just one specific TCR Vα chain or TCR Vβ chain.

In other words, an antibody or binding fragment according to the invention does not bind to only to one TCR Vα chain, i.e. type of TCR Vα chain or one TCR Vβ chain, i.e. type of TCR chain, but binds to several TCR Vα chains, i.e. type of TCR Vα chains or TCR Vβ chains, i.e. type of TCR Vβ chains.

The antibodies or binding fragments of the invention bind to a fraction of TCR Vα chains that is smaller than all functional TCR Vα chains or binds to a fraction of TCR Vβ chains which is smaller than all functional TCR Vβ chains. In other words the antibodies of the invention are not pan-specific antibodies that recognize all TCR Vα chains and/or all TCR Vβ chains, in particular all functional TCR Vα chains or functional TCR Vβ chains.

The terms "functional TCR Vα chains" or "functional TCR Vβ chains" or "functional TCR variable chains" relate to TCR variable chains that are expressed on T cells. That means that this term does not include TCR variable chains that are not expressed, such as pseudogenes, i.e. genes with frameshift mutations or defects in the recombination signal. The annotation whether a TCR variable chain is functional or rather a pseudogene can be found for example in Folch ("The Human T cell Receptor Beta Variable (TRBV) Genes", Folch Géraldibem Lefranc Maire-Paule, Exp Clin Immunogenet 2000; 17:42-54) or Su et al. (Chen Su and Masatoshi Nei, Mol.-Biol. Evol. 2001; 18(4):505-513). Correspondingly, the term "functional TCR types" refers to TCRs that are composed of TCR variable chains that are expressed on T cells.

In one embodiment, the antibody or binding fragment thereof binds a fraction of TCR Vβ chains comprising at least 3, at least 4, at least 5, at least 6, at least 7, at least 8, at least 9, at least 10, at least 15 or at least 20 different TCR Vβ chains. The invention thus contemplates an antibody or binding fragment thereof which binds to a fraction of TCR Vβ chains comprising at least 3, 4, 5, 6, 7, 8, 9 10, 11, 12, 13, 14, 15, 20, 21, 22, 23, 24, 25, 26, 27, 28, 29, 30, 31, 32, 33, 34, 35, 36, 37, 38, 39 or 40 different TCR Vβ chains. Antibodies or binding fragments thereof which bind larger numbers of different TCR Vβ chains (e.g. 20 different Vβ chains compared to 2 different Vβ chains) are in general of particular interest as these antibodies may e.g. be more broadly usable for TCR-related diseases such as TCL in different patients.

In a specific embodiment, the antibody or binding fragment thereof binds to a fraction of TCR Vβ chains consisting of 3, 4, 5, 6, 7, 8, 9 10, 11, 12, 13, 14, 15, 16, 17, 18, 19, 20, 21, 22, 23, 24, 25, 26, 27, 28, 29 or 30 different TCR Vβ chains selected from the group consisting of TCR Vβ chains of Table 1.

In another embodiment the antibody or binding fragment thereof binds a fraction of TCR Vα chains comprising at least 3, at least 4, at least 5, at least 6, at least 7, at least 8, at least 9, at least 10, at least 15 or at least 20 different TCR Vα chains. The invention thus contemplates an antibody or binding fragment thereof which binds to a fraction of TCR Vα chains comprising at least 3, 4, 5, 6, 7, 8, 9 10, 11, 12, 3, 14, 15, 20, 21, 22, 23, 24, 25, 26, 27, 28, 29, 30, 31, 32, 33, 34, 35, 36, 37, 38, 39 or 40 different TCR Vα chains. Antibodies or binding fragments thereof which bind larger numbers of different TCR Vα chains (e.g. 20 different Vα chains compared to 2 different Vα chains) are in general of particular interest as these antibodies may e.g. be more broadly usable for TCR related diseases such as TCL in different patients.

In a specific embodiment the antibody or binding fragment thereof binds to a fraction of TCR Vα chains consisting of 3, 4, 5, 6, 7, 8, 9 10, 11, 12, 13, 14, 15, 16, 17, 18, 19, 20, 21, 22, 23, 24, 25, 26, 27, 28, 29 or 30 different TCR Vα chains selected from the group consisting of TCR Vα chains of Table 1.

TABLE 1

Table 1 - known functional TCR Vα chains and TCR Vβ chains. AV stands for variable α chain and BV stands for variable β chain.

| TCR V class | TCR V type |
|---|---|
| TCR Vβ chains | BV2, BV3-1, BV4-1, BV4-2, BV4-3, BV5-1, BV5-4, BV5-5, BV5-6, BV5-8, BV6-1, BV6-2, BV6-4, BV6-5, BV6-6, BV6-8, BV6-9, BV7-2, BV7-3, BV7-4, BV7-6, BV 7-7, BV 7-8, BV7-9, BV9, BV10-1, BV10-2, BV10-3, BV11-1, BV11-2, BV11-3, BV12-3, BV12-4, BV12-5, BV13, BV14, BV15, BV16, BV18, BV19, BV20-1, BV 24-1, BV25-1, BV27, BV28, BV29-1, BV30 |
| TCR Vα chains | AV1-1, AV1-2, AV2, AV3, AV4, AV5, AV6, AV7, AV8-1, AV8-2, AV8-3, AV8-4, AV8-6, AV9-1, AV9-2, AV10, AV12-1, AV12-2, AV12-3, AV13-1, AV13-2, AV14/DV4, AV16, AV17, AV18, AV19, AV20, AV21, AV22, AV23/DV6, AV24, AV25, AV26-1, AV26-2, AV27, AV29/DV5, AV30, AV34, AV35, AV36/DV7, AV38-1, AV38-2/DV8, AV39, AV40, AV41 |

TABLE 2

TCR Vα chains and TCR Vβ chains with identifiers for their nucleic acid sequences and amino acid sequences.

| Identifier | TCR V type | nucleic acid sequence | amino acid sequence |
|---|---|---|---|
| AVseg1 | AV1-1 | SEQ ID NO: 8 | SEQ ID NO: 100 |
| AVseg2 | AV1-2 | SEQ ID NO: 9 | SEQ ID NO: 101 |
| AVseg3 | AV2 | SEQ ID NO: 10 | SEQ ID NO: 102 |
| AVseg4 | AV3 | SEQ ID NO: 11 | SEQ ID NO: 103 |

TABLE 2-continued

TCR Vα chains and TCR Vβ chains with identifiers for their nucleic acid sequences and amino acid sequences.

| Identifier | TCR V type | nucleic acid sequence | amino acid sequence |
|---|---|---|---|
| AVseg5 | AV4 | SEQ ID NO: 12 | SEQ ID NO: 104 |
| AVseg6 | AV5 | SEQ ID NO: 13 | SEQ ID NO: 105 |
| AVseg7 | AV6 | SEQ ID NO: 14 | SEQ ID NO: 106 |
| AVseg8 | AV7 | SEQ ID NO: 15 | SEQ ID NO: 107 |
| AVseg9 | AV8-1 | SEQ ID NO: 16 | SEQ ID NO: 108 |
| AVseg10 | AV8-2 | SEQ ID NO: 17 | SEQ ID NO: 109 |
| AVseg11 | AV8-3 | SEQ ID NO: 18 | SEQ ID NO: 110 |
| AVseg12 | AV8-4 | SEQ ID NO: 19 | SEQ ID NO: 111 |
| AVseg13 | AV8-6 | SEQ ID NO: 20 | SEQ ID NO: 112 |
| AVseg14 | AV9-1 | SEQ ID NO: 21 | SEQ ID NO: 113 |
| AVseg15 | AV9-2 | SEQ ID NO: 22 | SEQ ID NO: 114 |
| AVseg16 | AV10-1 | SEQ ID NO: 23 | SEQ ID NO: 115 |
| AVseg17 | AV12-1 | SEQ ID NO: 24 | SEQ ID NO: 116 |
| AVseg18 | AV12-2 | SEQ ID NO: 25 | SEQ ID NO: 117 |
| AVseg19 | AV12-3 | SEQ ID NO: 26 | SEQ ID NO: 118 |
| AVseg20 | AV13-1 | SEQ ID NO: 27 | SEQ ID NO: 119 |
| AVseg21 | AV13-2 | SEQ ID NO: 28 | SEQ ID NO: 120 |
| AVseg22 | AV14/DV4 | SEQ ID NO: 29 | SEQ ID NO: 121 |
| AVseg23 | AV16 | SEQ ID NO: 30 | SEQ ID NO: 122 |
| AVseg24 | AV17 | SEQ ID NO: 31 | SEQ ID NO: 123 |
| AVseg25 | AV18 | SEQ ID NO: 32 | SEQ ID NO: 124 |
| AVseg26 | AV19 | SEQ ID NO: 33 | SEQ ID NO: 125 |
| AVseg27 | AV20 | SEQ ID NO: 34 | SEQ ID NO: 126 |
| AVseg28 | AV21 | SEQ ID NO: 35 | SEQ ID NO: 127 |
| AVseg29 | AV22 | SEQ ID NO: 36 | SEQ ID NO: 128 |
| AVseg30 | AV23/DV6 | SEQ ID NO: 37 | SEQ ID NO: 129 |
| AVseg31 | AV24 | SEQ ID NO: 38 | SEQ ID NO: 130 |
| AVseg32 | AV25 | SEQ ID NO: 39 | SEQ ID NO: 131 |
| AVseg33 | AV26-1 | SEQ ID NO: 40 | SEQ ID NO: 132 |
| AVseg34 | AV26-2 | SEQ ID NO: 41 | SEQ ID NO: 133 |
| AVseg35 | AV27 | SEQ ID NO: 42 | SEQ ID NO: 134 |
| AVseg36 | AV29/DV5 | SEQ ID NO: 43 | SEQ ID NO: 135 |
| AVseg37 | AV30 | SEQ ID NO: 44 | SEQ ID NO: 136 |
| AVseg38 | AV34 | SEQ ID NO: 45 | SEQ ID NO: 137 |
| AVseg39 | AV35 | SEQ ID NO: 46 | SEQ ID NO: 138 |
| AVseg40 | AV36/DV7 | SEQ ID NO: 47 | SEQ ID NO: 139 |
| AVseg41 | AV38-1 | SEQ ID NO: 48 | SEQ ID NO: 140 |
| AVseg42 | AV38-2/DV8 | SEQ ID NO: 49 | SEQ ID NO: 141 |
| AVseg43 | AV39 | SEQ ID NO: 50 | SEQ ID NO: 142 |
| AVseg44 | AV40 | SEQ ID NO: 51 | SEQ ID NO: 143 |
| AVseg45 | AV41 | SEQ ID NO: 52 | SEQ ID NO: 144 |
| BVseg1 | BV2 | SEQ ID NO: 53 | SEQ ID NO: 145 |
| BVseg2 | BV3-1 | SEQ ID NO: 54 | SEQ ID NO: 146 |
| BVseg3 | BV4-1 | SEQ ID NO: 55 | SEQ ID NO: 147 |
| BVseg4 | BV4-2 | SEQ ID NO: 56 | SEQ ID NO: 148 |
| BVseg5 | BV4-3 | SEQ ID NO: 57 | SEQ ID NO: 149 |
| BVseg6 | BV5-1 | SEQ ID NO: 58 | SEQ ID NO: 150 |
| BVseg7 | BV5-4 | SEQ ID NO: 59 | SEQ ID NO: 151 |
| BVseg8 | BV5-5 | SEQ ID NO: 60 | SEQ ID NO: 152 |
| BVseg9 | BV5-6 | SEQ ID NO: 61 | SEQ ID NO: 153 |
| BVseg10 | BV5-8 | SEQ ID NO: 62 | SEQ ID NO: 154 |
| BVseg11 | BV6-1 | SEQ ID NO: 63 | SEQ ID NO: 155 |
| BVseg12 | BV6-2 | SEQ ID NO: 64 | SEQ ID NO: 156 |
| BVseg13 | BV6-4 | SEQ ID NO: 65 | SEQ ID NO: 157 |
| BVseg14 | BV6-5 | SEQ ID NO: 66 | SEQ ID NO: 158 |
| BVseg15 | BV6-6 | SEQ ID NO: 67 | SEQ ID NO: 159 |
| BVseg16 | BV6-8 | SEQ ID NO: 68 | SEQ ID NO: 160 |
| BVseg17 | BV6-9 | SEQ ID NO: 69 | SEQ ID NO: 161 |
| BVseg18 | BV7-2 | SEQ ID NO: 70 | SEQ ID NO: 162 |
| BVseg19 | BV7-3 | SEQ ID NO: 71 | SEQ ID NO: 163 |
| BVseg20 | BV7-4 | SEQ ID NO: 72 | SEQ ID NO: 164 |
| BVseg21 | BV7-6 | SEQ ID NO: 73 | SEQ ID NO: 165 |
| BVseg22 | BV7-7 | SEQ ID NO: 74 | SEQ ID NO: 166 |
| BVseg23 | BV7-8 | SEQ ID NO: 75 | SEQ ID NO: 167 |
| BVseg24 | BV7-9 | SEQ ID NO: 76 | SEQ ID NO: 168 |
| BVseg25 | BV9 | SEQ ID NO: 77 | SEQ ID NO: 169 |
| BVseg26 | BV10-1 | SEQ ID NO: 78 | SEQ ID NO: 170 |
| BVseg27 | BV10-2 | SEQ ID NO: 79 | SEQ ID NO: 171 |
| BVseg28 | BV10-3 | SEQ ID NO: 80 | SEQ ID NO: 172 |
| BVseg29 | BV11-1 | SEQ ID NO: 81 | SEQ ID NO: 173 |
| BVseg30 | BV11-2 | SEQ ID NO: 82 | SEQ ID NO: 174 |
| BVseg31 | BV11-3 | SEQ ID NO: 83 | SEQ ID NO: 175 |
| BVseg32 | BV12-3 | SEQ ID NO: 84 | SEQ ID NO: 176 |
| BVseg33 | BV12-4 | SEQ ID NO: 85 | SEQ ID NO: 177 |
| BVseg34 | BV12-5 | SEQ ID NO: 86 | SEQ ID NO: 178 |
| BVseg35 | BV13 | SEQ ID NO: 87 | SEQ ID NO: 179 |
| BVseg36 | BV14 | SEQ ID NO: 88 | SEQ ID NO: 180 |
| BVseg37 | BV15 | SEQ ID NO: 89 | SEQ ID NO: 181 |
| BVseg38 | BV16 | SEQ ID NO: 90 | SEQ ID NO: 182 |
| BVseg39 | BV18 | SEQ ID NO: 91 | SEQ ID NO: 183 |
| BVseg40 | BV19 | SEQ ID NO: 92 | SEQ ID NO: 184 |
| BVseg41 | BV20-1 | SEQ ID NO: 93 | SEQ ID NO: 185 |
| BVseg42 | BV24-1 | SEQ ID NO: 94 | SEQ ID NO: 186 |
| BVseg43 | BV25-1 | SEQ ID NO: 95 | SEQ ID NO: 187 |
| BVseg44 | BV27 | SEQ ID NO: 96 | SEQ ID NO: 188 |
| BVseg45 | BV28 | SEQ ID NO: 97 | SEQ ID NO: 189 |
| BVseg46 | BV29-1 | SEQ ID NO: 98 | SEQ ID NO: 190 |
| BVseg47 | BV30 | SEQ ID NO: 99 | SEQ ID NO: 191 |

The nucleotide sequences coding for the variable region of the TCR α and the TCR β chains include leader sequences. During maturation the leader sequence is cleaved off, which means that the protein sequence of the variable region of the TCR α and the TCR β chain is devoid of the leader sequence. The amino acid sequences of the variable regions of the TCR α and the TCR β chains disclosed herein therefore do not contain the leader sequence.

The variable region of the TCR α chain AV1-1 is encoded by the AV segment AVseg1 (SEQ ID No. 8) and has an amino acid sequence of SEQ ID No. 100.

In certain embodiments, the variable AV segments AVseg1 to AVseg45 code for variable TCR α chain regions which are at least 80% identical to the sequences set forth in SEQ ID NO: 100 to SEQ ID NO: 144 and wherein the variable BV segments BVseg 1 to BVseg 47 code for variable TCR β chain regions which are least 80% identical to the sequences set forth in SEQ ID NO: 145 to SEQ ID NO: 191.

In certain embodiments, the variable AV segments AVseg1 to AVseg45 code for variable TCR α chain region which are at least 70%, 75%, 80%, 85%, 90%, 95%, 96%, 97%, 98%, 99% identical to the sequences set forth in SEQ ID NO: 100 to SEQ ID NO: 144 and wherein the variable BV segments BVseg1 to BVseg 47 code for variable TCR β chain regions which are least 70%, 75%, 80%, 85%, 90%, 95%, 96%, 97%, 98%, 99% identical to the sequences set forth in SEQ ID NO: 145 to SEQ ID NO: 199.

In certain embodiments, the variable AV segments AVseg1 to AVseg45 code for variable TCR α chain regions which have sequences set forth in SEQ ID NO: 100 to SEQ ID NO: 144 and wherein the variable BV segments BVseg1 to BVseg47 code for variable TCR β chain regions which have sequences set forth in SEQ ID NO: 145 to SEQ ID NO: 199.

In certain embodiments, the variable AV segments AVseg1 to AVseg45 have sequences which are at 80 identical to the sequences set forth in SEQ ID NO: 8 to SEQ ID NO: 52 and the variable BV segments BVseg1 to BVseg47 segments have sequences which are at least 80% identical to the sequences set forth in SEQ ID NO: 53 to SEQ ID NO: 99.

In certain embodiments, the variable AV segments AVseg1 to AVseg45 have sequences which are at least 70%, 75%, 80%, 85%, 90%, 95%, 96%, 97%, 98%, 99% identical to the sequences set forth in SEQ ID NO: 8 to SEQ ID NO: 52 and the variable BV segments BVseg1 to BVseg47 segments have sequences which are at least 70%, 75%, 80%, 85%, 90%, 95%, 96%, 97%, 98%, 99% identical to the sequences set forth in SEQ ID NO: 53 to SEQ ID NO: 99.

In certain embodiments, the variable AV segments AVseg1 to AVseg45 segments have sequences which are set forth in SEQ ID NO: 8 to SEQ ID NO: 52 and the variable BV segments BVseg1 to BVseg47 segments have sequences which are set forth in SEQ ID NO: 53 to SEQ ID NO: 99.

In one embodiment of the invention the fraction of TCR Vα chains comprises at least two different TCR Vα chains that belong to two different TCR Vα chain subfamilies or wherein the fraction TCR Vβ chains comprises least two different TCR Vβ chains that belong to two different TCR Vβ chain subfamilies.

The term subfamily as used herein refers to conventional gene notation for VB genes. In the nomenclature each gene is denoted by two numbers. The first number represents the subfamily to which the gene belongs; the second indicates the order of discovery of the genes in each subfamily. For example, the variable chains BV6-1, BV6-2, BV6-4, BV6-5, BV6-6, BV6-8, BV6-9 belong to one subfamily.

TCR Vα chains can thus be grouped into 34 subfamilies as shown in Table 3.

TABLE 3

Table 3 - TCR Vα chains grouped into subfamilies, AV stands for variable a chain.

| Identifier | TCR Vα Subfamily | TCR Vα type |
| --- | --- | --- |
| M1 | FAV1 | AV1-1, AV1-2 |
| M2 | FAV2 | AV2 |
| M3 | FAV3 | AV3 |
| M4 | FAV4 | AV4 |
| M5 | FAV5 | AV5 |
| M6 | FAV6 | AV6 |
| M7 | FAV7 | AV7 |
| M8 | FAV8 | AV8-1, AV8-2, AV8-3, AV8-4, AV8-6 |
| M9 | FAV9 | AV9-1, AV9-2 |
| M10 | FAV10 | AV10-1 |
| M11 | FAV12 | AV12-1, AV12-2, AV12-3 |
| M12 | FAV13 | AV13-1,13-2 |
| M13 | FAV14 | AV14/DV4 |
| M14 | FAV16 | AV16 |
| M15 | FAV17 | AV17 |
| M16 | FAV18 | AV18 |
| M17 | FAV19 | AV19 |
| M18 | FAV20 | AV20 |
| M19 | FAV21 | AV21 |
| M20 | FAV22 | AV22 |
| M21 | FAV23 | AV23/DV6 |
| M22 | FAV24 | AV24 |
| M23 | FAV25 | AV25 |
| M24 | FAV26 | AV26-1, AV26-2 |
| M25 | FAV27 | AV27 |
| M26 | FAV29 | AV29/DV5 |
| M27 | FAV30 | AV30 |
| M28 | FAV34 | AV34 |
| M29 | FAV35 | AV35 |
| M30 | FAV36 | AV36/DV7 |
| M31 | FAV38 | AV38-1, AV38-2/DV8 |
| M32 | FAV39 | AV39 |
| M33 | FAV40 | AV40 |
| M34 | FAV41 | AV41 |

TCR Vβ chains can be grouped into 23 subfamilies as shown in Table 4:

TABLE 4

TCR Vβ chains grouped into subfamilies. BV stands for variable β chain

| Identifier | TCR Vβ Subfamily | TCR Vβ type |
| --- | --- | --- |
| N1 | FBV2 | BV2 |
| N2 | FBV3 | BV3-1 |
| N3 | FBV4 | BV4-1, BV4-2, BV4-3 |
| N4 | FBV5 | BV5-1, BV5-4, BV5-5, BV5-6, BV5-8 |
| N5 | FBV6 | BV6-1, BV6-2, BV6-4, BV6-5, BV6-6, BV6-8, BV6-9 |
| N6 | FBV7 | BV7-2, BV7-3, BV7-4, BV7-6, BV7-7, BV7-8, BV7-9, |
| N7 | FBV9 | BV9 |
| N8 | FBV10 | BV10-1, BV10-2, BV10-3, |
| N9 | FBV11 | BV11-1, BV11-2, BV11-3 |
| N10 | FBV12 | BV12-3, BV12-4, BV12-5 |
| N11 | FBV13 | BV13 |
| N12 | FBV14 | BV14 |
| N13 | FBV15 | BV15 |
| N14 | FBV16 | BV16 |
| N15 | FBV18 | BV18 |
| N16 | FBV19 | BV19 |
| N17 | FBV20 | BV20-1 |
| N18 | FBV24 | BV24-1 |
| N19 | FBV25 | BV25-1 |
| N20 | FBV27 | BV27 |
| N21 | FBV28 | BV28 |
| N22 | FBV29 | BV29-1 |
| N23 | FBV30 | BV30-1 |

The invention thus contemplates that the fraction of TCR Vα chains comprises at least 3, at least 4, at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, or at least 25 different TCR Vα chains that belong to at least 2 different TCR Vα chain subfamilies. The at least 3, at least 4, at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, or at least 25 different TCR Vα chains can of course belong also to more than at least 2, such as at least 3, at least 4, at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, or at least 24 different TCR Vα chain subfamilies. Antibodies or binding fragments that recognize TCR Vα chains from larger numbers of different TCR Vα chain subfamilies are in general of particular interest as these antibodies may e.g. be more broadly usable for TCR related diseases such as TCL in different patients. Such antibodies or binding fragments thereof may have even broader application than TCR specific antibodies or binding fragments thereof that recognize different TCR Vα chains which all belong to the same subfamily.

The invention correspondingly contemplates that the fraction of TCR Vα chains comprises at least 3, at least 4, at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, or at least 25 different TCR Vα chains that belong to at least 2 different TCR Vα chain subfamilies.

The invention thus contemplates that the fraction of TCR Vα chains comprises at least 3, at least 4, at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, at least 25 different TCR Vα chains that belong to at least 3 different TCR Vα chain subfamilies.

The invention also contemplates that the fraction of TCR Vα chains comprises at least 4, at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, at least 25 different TCR Vα chains that belong to at least 4 different TCR Vα chain subfamilies.

The invention also contemplates that the fraction of TCR Vα chains comprises at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, at least 25 different TCR Vα chains that belong to at least 5 different TCR Vα chain subfamilies.

The invention also contemplates that the fraction of TCR Vα chains comprises at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, at least 25 different TCR Vα chains that belong to at least 6 different TCR Vα chain subfamilies.

The invention also contemplates that the fraction of TCR Vα chains comprises at least 7, at least 8, at least 9, at least 10, at least 11, at least 12, at least 13, at least 14, at least 15, at least 16, at least 17, at least 18, at least 20, at least 21, at least 22, at least 23, at least 24, at least 25 different TCR Vα chains that belong to at least 7 different TCR Vα chain subfamilies.

The invention also contemplates that the fraction of TCR Vα chains comprises at least 8, at least 9, at least 10, at least 11, at least 12, at least 13, at least 14, at least 15, at least 16, at least 17, at least 18, at least 20, at least 21, at least 22, at least 23, at least 24, at least 25 different TCR Vα chains that belong to at least 8 different TCR Vα chain subfamilies.

The invention also contemplates that the invention the fraction of TCR Vα chains comprises at least 9, at least 10, at least 11, at least 12, at least 13, at least 14, at least 15, at least 16, at least 17, at least 18, at least 20, at least 21, at least 22, at least 23, at least 24, at least 25 different TCR Vα chains that belong to at least 9 different TCR Vα chain subfamilies.

The invention also contemplates that the fraction of TCR Vα chains comprises at least 10, at least 11, at least 12, at least 13, at least 14, at least 15, at least 16, at least 17, at least 18, at least 20, at least 21, at least 22, at least 23, at least 24, at least 25 different TCR Vα chains that belong to at least 10 different TCR Vα chain subfamilies.

The invention also contemplates that the fraction of TCR Vα chains comprises at least 11, at least 12, at least 13, at least 14, at least 15, at least 16, at least 17, at least 18, at least 20, at least 21, at least 22, at least 23, at least 24, at least 25 different TCR Vα chains that belong to at least 11 different TCR Vα chain subfamilies.

The invention also contemplates that the fraction of TCR Vα chains comprises at least 12, at least 13, at least 14, at least 15, at least 16, at least 17, at least 18, at least 20, at least 21, at least 22, at least 23, at least 24, at least 25, at least 30, at least 35 different TCR Vα chains that belong to at least 12 different TCR Vα chain subfamilies.

The invention also contemplates that the fraction of TCR Vα chains comprises at least 12, at least 13, at least 14, at least 15, at least 16, at least 17, at least 18, at least 20, at least 21, at least 22, at least 23, at least 24, at least 25, at least 30, at least 35 different TCR Vα chains that belong to at least 15 different TCR Vα chain subfamilies.

The invention also contemplates that the fraction of TCR Vα chains comprises at least 12, at least 13, at least 14, at least 15, at least 16, at least 17, at least 18, at least 20, at least 21, at least 22, at least 23, at least 24, at least 25, at least 30, at least 35 different TCR Vα chains that belong to at least 20 different TCR Vα chain subfamilies.

The invention also contemplates that the fraction of TCR Vα chains comprises at least 12, at least 13, at least 14, at least 15, at least 16, at least 17, at least 18, at least 20, at least 21, at least 22, at least 23, at least 24, at least 25, at least 30, at least 35 different TCR Vα chains that belong to at least 25 different TCR Vα chain subfamilies.

The invention also contemplates that the fraction of TCR Vα chains comprises at least 12, at least 13, at least 14, at least 15, at least 16, at least 17, at least 18, at least 20, at least 21, at least 22, at least 23, at least 24, at least 25, at least 30, at least 35 different TCR Vα chains that belong to at least 30 different TCR Vα chain subfamilies.

The invention thus contemplates that the fraction of TCR Vβ chains comprises at least 3, at least 4, at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, or at least 25 different TCR Vβ chains that belong to at least 2 different TCR VP chain subfamilies. The least 3, at least 4, at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, or at least 25 different TCR Vβ chains can of course belong also to more than at least 2, such as at least 3, at least 4, at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, or at least 24 different TCR Vβ chain subfamilies. Antibodies or binding fragments that recognize TCR Vβ chains from larger numbers of different TCR Vβ chain subfamilies are in general of particular interest as these antibodies may e.g. be more broadly usable for TCR-related diseases such as TCL in different patients. Such antibodies or binding fragments thereof may have even broader application than cluster TCR-specific antibodies or binding fragments thereof that recognize different TCR Vβ chains which all belong to the same subfamily.

The invention correspondingly contemplates that the fraction of TCR Vβ chains comprises at least 3, at least 4, at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, at least 25 different TCR Vβ chains that belong to at least 2 different TCR Vβ chain subfamilies.

The invention thus contemplates that the fraction of TCR Vβ chains comprises at least 3, at least 4, at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, at least 25 different TCR Vβ chains that belong to at least 3 different TCR VP chain subfamilies.

The invention also contemplates that the fraction of TCR Vβ chains comprises at least 4, at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, at least 25 different TCR Vβ chains that belong to at least 4 different TCR Vβ chain subfamilies.

The invention also contemplates that the fraction of TCR Vβ chains comprises at least 5, at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, at least 25 different TCR Vβ chains that belong to at least 5 different TCR Vβ chain subfamilies.

The invention also contemplates that the fraction of TCR Vβ chains comprises at least 6, at least 7, at least 8, at least 9, at least 10, at least 11, at least 12, at least 13, at least 14, at least 15, at least 16, at least 17, at least 18, at least 20, at least 21, at least 22, at least 23, at least 24, at least 25 different TCR Vβ chains that belong to at least 6 different TCR Vβ chain subfamilies.

The invention also contemplates that the fraction of TCR Vβ chains comprises at least 7, at least 8, at least 9, at least 10, at least 11, at least 12, at least 13, at least 14, at least 15, at least 16, at least 17, at least 18, at least 20, at least 21, at least 22, at least 23, at least 24, at least 25 different TCR Vβ chains that belong to at least 7 different TCR Vβ chain subfamilies.

The invention also contemplates that the fraction of TCR Vβ chains comprises at least 8, at least 9, at least 10, at least 11, at least 12, at least 13, at least 14, at least 15, at least 16, at least 17, at least 18, at least 20, at least 21, at least 22, at least 23, at least 24, at least 25 different TCR chains that belong to at least 8 different TCR Vβ chain subfamilies.

The invention also contemplates that the invention the fraction of TCR Vβ chains comprises at least 9, at least 10, at least 11, at least 12, at least 13, at least 14, at least 15, at least 16, at least 17, at least 18, at least 20, at least 21, at least 22, at least 23, at least 24, at least 25 different TCR VP chains that belong to at least 9 different TCR Vβ chain subfamilies.

The invention also contemplates that the fraction of TCR Vβ chains comprises at least 10, at least 11, at least 12, at least 13, at least 14, at least 15, at least 16, at least 17, at least 18, at least 20, at least 21, at least 22, at least 23, at least 24, at least 25 different TCR Vβ chains that belong to at least 10 different TCR Vβ chain subfamilies.

The invention also contemplates that the fraction of TCR Vβ chains comprises at least 11, at least 12, at least 13, at least 14, at least 15, at least 16, at least 17, at least 18, at least 20, at least 21, at least 22, at least 23, at least 24, at least 25 different TCR Vβ chains that belong to at least 11 different TCR Vβ chain subfamilies.

The invention also contemplates that the fraction of TCR Vβ chains comprises at least 12, at least 13, at least 14, at least 15, at least 16, at least 17, at least 18, at least 20, at least 21, at least 22, at least 23, at least 24, at least 25 different TCR Vβ chains that belong to at least 12 different TCR Vβ chain subfamilies.

The invention also contemplates that the fraction of TCR Vβ chains comprises at least 12, at least 13, at least 14, at least 15, at least 16, at least 17, at least 18, at least 20, at least 21, at least 22, at least 23, at least 24, at least 25 different TCR Vβ chains that belong to at least 15 different TCR Vβ chain subfamilies.

The invention also contemplates that the fraction of TCR Vβ chains comprises at least 12, at least 13, at least 14, at least 15, at least 16, at least 17, at least 18, at least 20, at least 21, at least 22, at least 23, at least 24, at least 25 different TCR Vβ chains that belong to at least 18 different TCR Vβ chain subfamilies.

The invention also contemplates that the fraction of TCR Vβ chains comprises at least 12, at least 13, at least 14, at least 15, at least 16, at least 17, at least 18, at least 20, at least 21, at least 22, at least 23, at least 24, at least 25 different TCR Vβ chains that belong to at least 21 different TCR Vβ chain subfamilies.

Table 5 shows which groups of different TCR Vβ chains may be recognized by cluster TCR-specific antibodies or binding fragments thereof

TABLE 5

TCR Vβ chain types groups recognized by antibodies according to the invention

| TCR Vβ type group no. | TCR Vβ type |
|---|---|
| T-1 | BV6-2, BV6-3, BV6-4, BV6-5, BV6-6, BV12-3, BV12-5, BV14, BV18, BV20-1, BV21-1, BV24-1, BV29-1 |
| T-2 | BV6-4, BV6-5, BV6-6, BV12-3, BV12-5, BV14, BV18, BV20-1, BV21-1, BV24-1, BV29-1 |
| T-3 | BV6-4, BV6-5, BV6-5, BV12-3, BV14, BV24-1, BV29-1, |
| T-4 | BV12-3, BV12-5, BV14, BV24-1, BV29-1 |
| T-5 | BV12-3, BV12-5, BV14, BV18, BV24-1, BV29-1 |
| T-6 | BV12-3, BV14, BV18, BV24-1, BV29-1 |
| T-7 | BV5-6, BV12-3, BV12-5, BV13, BV14, BV15, BV18, BV19, BV24-1, BV25-1 BV29-1 |
| T-8 | BV12-3, BV12-5, BV14, BV18 |
| T-9 | BV6-1, BV6-2, BV6-3, BV6-4, BV6-5, BV6-6, BV6-8, BV6-9, BV10-1, BV10-2, BV10-3, BV19, BV25-1, BV27, BV24-1, BV28, BV29-1 |
| T-10 | BV6.1, BV6.2, BV6.3, BV6.5, BV10.3, BV19, BV27, BV28, BV29-1 |
| T-11 | BV6-1, BV19, BV27, BV28, BV29-1 |
| T-12 | BV11-1, BV11-2, BV11-3, BV12-3, BV12-4, BV12-5, BV14, BV2, BV4-1, BV4-2, BV4-3, BV7-2, BV7-3, BV7-4, BV7-6, BV7-7, BV7-8, BV7-9, BV5-1, BV5-4, BV5-5, BV5-6, BV5-8, BV13, BV16, BV18, BV20-1, BV9-1, BV3-1, BV15, BV30 |
| T-13 | BV12-3, BV4-2, BV7-3, BV7-6, BV5-1, BV20-1, BV9, BV3-1, BV2- |
| T-14 | BV12-3, BV2, BV4-2, BV5-1, BV20-1, BV9, BV3-1 |
| T-15 | BV12-3, BV2, BV5-1, BV20-1, BV9 |
| T-16 | BV19, BV29-1, BV5-1, BV20-1 |
| T-17 | BV12-3, BV14, BV24-1, BV29-1 |
| T-18 | BV12-3, BV14-, BV24-1 |
| T-19 | BV6-1, BV19, BV29-1 |
| T-20 | BV19, BV29-1 |
| T-21 | BV5-1, BV20-1 |
| T-22 | BV2, BV5-6, BV6-5, BV7-3, BV7-9, BV10-3, BV12-3, BV12-4, BV12-5, BV21-1, BV 6-7, BV 24-1, BV 25-1, BV28 |
| T-23 | BV12-3, BV12-4, BV21-1, BV6-7, BV24-1, BV25-1, BV28 |
| T24 | BV7-2, BV7-3, BV12-3, BV12-4, BV25-1, BV28 |
| T25 | BV7-2, BV12-3, BV12-4 |

The invention thus contemplates that the fraction of TCR Vβ chains comprises at least two different TCR Vβ chains selected from one of the groups defined in lines T-1 to T-25 of Table 5.

The invention further contemplates that the fraction of TCR Vβ chains comprises at least 3 different TCR Vβ chains selected from one of the groups defined in lines T1 to T-19 and T-22 to T-25 of Table 5.

The invention further contemplates that the fraction of TCR Vβ chains comprises at least 4 different TCR Vβ chains selected from one of the groups defined in lines T-1 to T-17 and T22 to T24 of Table 5.

The invention further contemplates that the fraction of TCR Vβ chains comprises at least 5 different TCR Vβ chains selected from one of the groups defined in lines T-1 to T-15 and T22 to T24 of Table 5.

The invention further contemplates that the fraction of TCR Vβ chains comprises at least two different TCR Vβ chains selected from one of the groups as defined in lines T-1 to T-25 of Table 5 that belong to at least 2 different TCR Vβ chain subfamilies.

The invention further contemplates that the fraction of TCR Vβ chains comprises at least 3 different TCR Vβ chains selected from one of the groups as defined in lines T-1 to T-19 and T22 to T24 of Table 5 that belong to at least 2 different TCR Vβ chain subfamilies.

The invention further contemplates that the fraction of TCR Vβ chains comprises at least 4 different TCR Vβ chains selected from one of the groups defined in lines T-1 to T-17 and T22 to T24 of Table 5 that belong to at least 2 different TCR Vβ chain subfamilies.

The invention further contemplates that the fraction of TCR Vβ chains comprises at least 5 different TCR Vβ chains selected from one of the groups defined in lines T-1 to T-15 and T22 to T24 of Table 5 that belong to at least 2 different TCR Vβ chain subfamilies.

The invention further contemplates that the fraction of TCR Vβ chains comprises at least 3 different TCR Vβ chains selected from one of the groups as defined in lines T-1 to T-19 of Table 5 that belong to at least 3 different TCR Vβ chain subfamilies.

The invention further contemplates that the fraction of TCR Vβ chains comprises at least 4 different TCR Vβ chains selected from one of the groups defined in lines T-1 to T-17 of Table 5 that belong to at least 3 different TCR Vβ chain subfamilies.

The invention further contemplates that the fraction of TCR Vβ chains comprises at least 5 different TCR Vβ chains selected from one of the groups defined in lines T-1 to T-15 of Table 5 that belong to at least 3 different TCR Vβ chain subfamilies.

The invention further contemplates that the fraction of TCR Vβ chains comprises at least 4 different TCR Vβ chains selected from one of the groups defined in lines T-1 to T-17 of Table 5 that belong to at least 4 different TCR Vβ chain subfamilies.

The invention further contemplates that the fraction of TCR Vβ chains comprises at least 5 different TCR Vβ chains selected from one of the groups defined in lines T-1 to T-15 of Table 5 that belong to at least 5 different TCR Vβ chain subfamilies.

Table 6 shows to which groups of subfamilies the TCR Vβ chains may belong, that are recognized by cluster TCR-specific antibodies or binding fragments thereof.

TABLE 6

TCR Vβ chain subfamily groups recognized by antibodies according to the invention

| TCR Vβ subfamily group no. | TCR Vβ subfamily |
|---|---|
| F-1 | FBV6, FBV12, FBV14, FBV18, FBV20, FBV21, FBV24, FBV29 |
| F-2 | FBV6, FBV12, FBV14, FBV24, FBV29, |
| F-3 | FBV12, FBV14, FBV24, FBV29 |
| F-4 | FBV12, FBV14, FBV18, FBV20, FBV24, FBV29 |
| F-5 | FBV12, FBV14, FBV18, FBV24, FBV29 |
| F-6 | FBV5, FBV12, FBV13, FBV14, FBV15, FBV18, FBV19, FBV23, FBV24, FBV25, FBV29 |
| F-7 | FBV6, FBV10, FBV19, FBV25, FBV24, FBV27, FBV28, FBV29 |
| F-8 | FBV6, FBV10, FBV19, FBV27, FBV28, FBV29 |
| F-9 | FBV6, FBV19, FBV27, FBV28, FBV29 |
| F-10 | FBV2, FBV3, FBV4, FBV5, FBV7, FBV9, FBV11, FBV12, FBV14, FBV13, FBV15, FBV16, FBV18, FBV20, FBV30 |
| F-11 | FBV2, FBV3, FBV4, FBV5, FBV7, FBV9, FBV12, FBV20 |
| F-12 | FBV2, FBV3, FBV4, FBV5, FBV9, FBV12, FBV20 |
| F-13 | FBV2, FBV5, FBV9, FBV12, FBV20 |
| F-14 | FBV5, FBV19, FBV20, FBV29, |
| F-15 | FBV12, FBV14, FBV24, FBV29 |
| F-16 | FBV12, FBV14, FBV24 |
| F-17 | FBV6, FBV19, FBV29 |
| F-18 | FBV12, FBV14, FBV18 |
| F-19 | FBV19, FBV29 |
| F-20 | FBV5, FBV20 |
| F-21 | FBV2, FBV5, FBV6, FBV7, FBV10, FBV12, FBV21, FBV24, FBV25, FBV 28 |
| F-22 | FBV6, FBV12, FBV21, FBV24, FBV25, FBV28 |
| F-23 | FBV 7, FBV12, FBV 15 |
| F-24 | FBV2, FBV5, FBV6, FBV7, FBV10, FBV12, FBV21, FBV24, FBV25, FBV 28 |
| F-25 | FBV12, FBV21, FBV6, FBV24, FBV25, FBV28 |
| F-26 | FBV12, FBV 7, FBV 15 |

The invention thus contemplates that the fraction of TCR Vβ chains comprises at least two different TCR Vβ chains that belong to at least two different TCR Vβ chain subfamilies as defined in lines F-1 to F-26 of Table 6.

The invention further contemplates that the fraction of TCR Vβ chains comprises at least 3 different TCR Vβ chains that belong to at least 3 different TCR Vβ chain subfamilies as defined in lines F-1 to F-18 and lines F-21 to 26 of Table 6.

The invention further contemplates that the fraction of TCR Vβ chains comprises at least 4 different TCR Vβ chains that belong to at least 4 different TCR Vβ chain subfamilies as defined in lines F-1 to F-15 of Table 6.

The invention further contemplates that the fraction of TCR Vβ chains comprises at least 5 different TCR Vβ chains that belong to at least 5 different TCR Vβ chain subfamilies as defined in lines F-1 to F-13 of Table 6.

The invention further contemplates that the fraction of TCR Vβ chains comprises at least 5, at least 6, at least 7, at least 8, at least 9, at least 10 different TCR Vβ chains that belong to at least 5 different TCR Vβ chain subfamilies as defined in lines F-1 to F-13 of Table 6.

In a specific embodiment of the invention the fraction of TCR Vβ chains comprises at least two different TCR Vβ chains that belong to at least two different TCR Vβ chain subfamilies as defined in lines F-21 to F-26 of Table 6.

If it is stated that an antibody or fragment thereof binds to a variable TCR Vα chains or TCR Vβ chains, this means that the antibody or fragments thereof binds specifically to said variable chains, i.e. binds the variable chain with greater affinity than other variable chains.

For example, an antibody or fragment is specific for its cognate antigen when the variable regions of the antibody or fragment recognize and bind the cognate antigen with a detectable preference distinguishing the antigen from other known polypeptides of similar but not identical sequence by virtue of measurable differences in binding affinity. It will be understood that specific antibodies and fragments may also interact with other proteins (for example, *S. aureus* protein A or other antibodies in ELISA techniques) through interactions with sequences outside the variable region of the antibodies, and in particular, in the constant region of the antibody or fragment. Screening assays to determine binding specificity of an antibody are well known and routinely practiced in the art. For a comprehensive discussion of such assays (see e.g. 4. Harlow et al. (Eds), Antibodies A Laboratory Manual; Cold Spring Harbor Laboratory; Cold Spring Harbor, N.Y. (1988), Chapter 6).

The antibodies and binding fragments thereof as they are used in the context of the present invention may be preferably monoclonal and more preferably monoclonal chimeric, humanized or human antibodies. A particularly preferred aspect which applies to all embodiments described herein relates to monoclonal humanized antibodies or binding fragments thereof.

The antibodies can be of different subtypes such as of the IgG or IgM class. Antibodies of the IgG class are of particular interest.

Antibodies or binding fragments as described herein are capable to deplete subpopulations of T cells. This means that only a subpopulation of T cells is depleted while the remaining populations are still present after the depletion.

In particular antibodies or binding fragments as described herein are capable to deplete a specific subpopulation of T cells. This means that the antibodies of the present invention deplete a subpopulation of T cells that expresses at least two different TCR Vα chains to which the antibody is binding or deplete a subpopulation of T cells that express at least two different TCR Vβ chains to which the antibody is binding. The remaining T cells do not express the at least two different TCR Vα chains to which the antibody is binding or do not express the at least two different TCR Vβ chains to which the antibody is binding. By binding not only one but several different types of TCR Vα chains or several different types of TCR Vβ permits the specific depletion of different T cells in a larger population of T cells with a single antibody.

These properties of the antibodies or binding fragments described herein may thus allow specifically depleting a subpopulation of T cells which contains aberrant T cells while the remaining T cells not containing aberrant T cells stay intact. The antibodies or binding fragments as described herein may therefore be used as a therapeutic agent, in particular for T-cell related malignancies such as TCL.

Given that the antibodies or binding fragments as described herein can recognize fractions of TCRs from e.g. different subfamilies, this may allow for different malignancies involving aberrant T cells being cured with a limited set of antibodies or binding fragments thereof or even with a single antibody or binding fragment thereof.

Moreover, in conditions that are linked to the aberration of several different T cell types antibodies or binding fragments as described herein can target the different T cell types at once and it is not necessary to target each individual T cell type with a separate specific antibody or binding fragment. Dependent on the combination of the aberrant T cell types, e.g. only one or a combination of e.g. two or three different antibodies is necessary in order to deplete a population of aberrant T cells that comprises a larger number of different T cell types, such as 3 to 20 different T cell types.

Moreover, antibody or binding fragments as described herein may not induce the release of proinflammartory cytokines in the form of a cytokine storm when being used for therapeutic purposes.

The present invention therefore also relates to antibodies or binding fragments thereof as described herein for use as a medicament.

In particular the application relates to the provision of an antibody or binding fragment thereof according to the invention for use in the treatment of T cell leukemia.

Correspondingly, the application relates to methods of treating T cell leukemia in a human or animal being by administering antibodies and binding fragments thereof according to the invention.

Further, the application relates to an antibody or binding fragment thereof according to the invention in the manufacture of a medicament for the treatment of T cell leukemia.

Turning to more specific aspects a preferred embodiment relates to antibodies or binding fragments thereof which bind to a fraction comprising at least two different TCR VD chains. In an even more preferred embodiment the fraction comprises at least two different TCR VD chains that belong to different TCR VD chain subfamilies. Such antibodies or binding fragments may be used to deplete a subpopulation of T cells expressing at least two different TCR VD chains to which the antibody is binding.

Such antibodies or binding fragments thereof may comprise a variable heavy chain and/or a variable light chain of the exemplary antibody 15B4 a variable heavy chain and/or a variable light chain having at least 80% sequence identity with the variable heavy chain and/or variable light chain of the exemplary antibody 15B4. 15B4 is an antibody that was identified in the experimental sections as binding to the human BV12. This sequence may therefore be used to obtain antibodies with similar properties as 15B4 by changing this sequence.

Other contemplated exemplary antibodies or binding fragments thereof may thus comprise the complementarity determining regions (CDRs) of the exemplary antibody 15B4 within their variable heavy chain and/or variable light chain. Such antibodies may also comprise CDRs within their variable heavy chain and/or variable light chain having at least 80% sequence identity with the CDRs of the exemplary antibody 15B4.

The heavy chain of 15B4 is e.g. encoded by SEQ ID No. 223. The light chain of 15B4 is e.g. encoded by SEQ ID No. 222. The heavy chain of 15B4 has thus the amino acid sequence as set out in SEQ ID No: 221. The light chain of 15B4 has thus the amino acid sequence as set out in SEQ ID No: 220.

The variable heavy chain of 15B4 has an amino acid sequence of SEQ ID No.219. The variable light chain of 15B4 has an amino acid sequence of SEQ ID No. 218. As regards the variable heavy chain of 15B4, the CDR1 has an amino acid sequence of SEQ ID No. 215, the CDR2 has an amino acid sequence of SEQ ID No. 216 and the CDR3 has an amino acid sequence of SEQ ID No. 217 As regards the variable light chain of 15B4, the CDR1 has an amino acid sequence of SEQ ID No. 212, the CDR2 has the amino acid sequence "RAS" and the CDR3 has an amino acid sequence of SEQ ID No. 214.

One embodiment refers to the humanized version of 15B4:

The heavy chain of the humanized version of 15B4 is e.g. encoded by SEQ ID No. 304. The light chain of the humanized version of 15B4 is e.g. encoded by SEQ ID No. 303. The heavy chain of the humanized version of 15B4 thus has an amino acid sequence of SEQ ID No. 300. The light chain of the humanized version of 15B4 thus has an amino acid sequence of SEQ ID No. 299. The heavy chain of the humanized version of 15B4 including the signal peptide (which is cleaved of in the mature protein) has an amino acid sequence of SEQ ID No. 302. The light chain of the humanized version of 15B4 including the signal peptide (which is cleaved of in the mature protein) has an amino acid sequence of SEQ ID No. 301.

The variable heavy chain of the humanized version of 15B4 has an amino acid sequence of SEQ ID No. 298. The variable light chain of the humanized version of 15B4 has an amino acid sequence of SEQ ID No. 297. As regards the variable heavy chain of the humanized version of 15B4, the CDR1 has an amino acid sequence of SEQ ID No. 294, the CDR2 has the amino acid sequence of SEQ ID No. 295 and the CDR3 has an amino acid sequence of SEQ ID No. 296. As regards the variable light chain of the humanized version of 15B4, the CDR1 has an amino acid sequence of SEQ ID No. 292, the CDR2 has the amino acid sequence "RAS" and the CDR3 has an amino acid sequence of SEQ ID No. 293.

Another embodiment refers to the chimeric version of 15B4:

The heavy chain of the chimeric version of 15B4 is e.g. encoded by SEQ ID No. 291. The light chain of the chimeric version of 15B4 is e.g. encoded by SEQ ID No. 290. The heavy chain of the chimeric version of 15B4 thus has an amino acid sequence of SEQ ID No. 287. The light chain of the chimeric version of 15B4 thus has an amino acid sequence of SEQ ID No. 286. The heavy chain of the chimeric version of 15B4 including the signal peptide (which is cleaved off in the mature protein) has an amino acid sequence of SEQ ID No. 289. The light chain of the chimeric version of 15B4 including the signal peptide (which is cleaved off in the mature protein) has an amino acid sequence of SEQ ID No. 288.

The variable heavy chain of the chimeric version of 15B4 has an amino acid sequence of SEQ ID No. 285. The variable light chain of the chimeric version of 15B4 has an amino acid sequence of SEQ ID No. 284. As regards the variable heavy chain of the chimeric version of 15B4, the CDR1 has an amino acid sequence of SEQ ID No. 281, the CDR2 has an amino acid sequence of SEQ ID No. 282 and the CDR3 has an amino acid sequence of SEQ ID No. 283. As regards the variable light chain of the chimeric version of 15B4, the CDR1 has an amino acid sequence of SEQ ID No. 279, the CDR2 has the amino acid sequence "RAS" and the CDR3 has an amino acid sequence of SEQ ID No. 280.

Such antibodies or binding fragments thereof may comprise a variable heavy chain and/or a variable light chain of the exemplary antibody 5H4, a variable heavy chain and/or a variable light chain having at least 80% sequence identity with the variable heavy chain and/or variable light chain of the exemplary antibody 5H4. 5H4 is an antibody that was identified in the experimental sections as binding to the human BV12. This sequence may therefore be used to obtain antibodies with similar properties as 5H4 by changing this sequence.

Other contemplated exemplary antibodies or binding fragments thereof may thus comprise the complementarity determining regions (CDRs) of the exemplary antibody 5H4 within their variable heavy chain and/or variable light chain. Such antibodies may also comprise CDRs within their variable heavy chain and/or variable light chain having at least 80% sequence identity with the CDRs of the exemplary antibody 5H4.

The heavy chain of 5H4 is e.g. encoded by SEQ ID No. 237. The light chain of 5H4 is e.g. encoded by SEQ ID No. 236. The heavy chain of 5H4 thus has an amino acid sequence of SEQ ID No. 235. The light chain of 5H4 thus has an amino acid sequence of SEQ ID No. 234.

The variable heavy chain of 5H4 has an amino acid sequence of SEQ ID No. 233. The variable light chain of 5H4 has an amino acid sequence of SEQ ID No. 232. As regards the variable heavy chain of 5H4, the CDR1 has an amino acid sequence of SEQ ID No. 229, the CDR2 has an amino acid sequence of SEQ ID No. 230 and the CDR3 has an amino acid sequence of SEQ ID No. 231. As regards the variable light chain of 5H4, the CDR1 has an amino acid sequence of SEQ ID No. 226, the CDR2 has the amino acid sequence "RAS" and the CDR3 has an amino acid sequence of SEQ ID No. 228.

One embodiment refers to the humanized version of 5H4:

The heavy chain of the humanized version of 5H4 is e.g. encoded by SEQ ID No. 265. The light chain of the humanized version of 5H4 is e.g. encoded by SEQ ID No. 264. The heavy chain of the humanized version of 5H4 thus has an amino acid sequence of SEQ ID No. 261. The light chain of the humanized version of 5H4 thus has an amino acid sequence of SEQ ID No. 260. The heavy chain of the humanized version of 5H4 including the signal peptide (which is cleaved off in the mature protein) has an amino acid sequence of SEQ ID No. 263. The light chain of the humanized version of 5H4 including the signal peptide (which is cleaved off in the mature protein) has an amino acid sequence of SEQ ID No. 262.

The variable heavy chain of the humanized version of 5H4 has an amino acid sequence of SEQ ID No. 259. The variable light chain of the humanized version of 5H4 has an amino acid sequence of SEQ ID No. 258. As regards the variable heavy chain of the humanized version of 5H4, the CDR1 has an amino acid sequence of SEQ ID No. 255, the CDR2 has an amino acid sequence of SEQ ID No. 256 and the CDR3 has an amino acid sequence of SEQ ID No. 257. As regards the variable light chain of the humanized version of 5H4, the CDR1 has an amino acid sequence of SEQ ID No. 253, the CDR2 has the amino acid sequence "RAS" and the CDR3 has an amino acid sequence of SEQ ID No. 254.

One embodiment refers to the chimeric version of 5H4:

The heavy chain of the chimeric version of 5H4 is e.g. encoded by SEQ ID No. 278. The light chain of the chimeric version of 5H4 is e.g. encoded by SEQ ID No. 277. The heavy chain of the chimeric version of 5H4 thus has an amino acid sequence of SEQ ID No. 274. The light chain of the chimeric version of 5H4 thus has an amino acid sequence of SEQ ID No. 273. The heavy chain of the chimeric version of 5H4 including the signal peptide (which is cleaved off in the mature protein) has an amino acid sequence of SEQ ID No. 276. The light chain of the chimeric version of 5H4 including the signal peptide (which is cleaved off in the mature protein) has an amino acid sequence of SEQ ID No. 275.

The variable heavy chain of the chimeric version of 5H4 has an amino acid sequence of SEQ ID No. 272. The variable light chain of the chimeric version of 5H4 has an amino acid sequence of SEQ ID No. 271. As regards the variable heavy chain of the chimeric version of 5H4, the CDR1 has an amino acid sequence of SEQ ID No. 268, the CDR2 has an amino acid sequence of SEQ ID No. 269 and the CDR3 has an amino acid sequence of SEQ ID No. 270. As regards the variable light chain of the chimeric version of 5H4, the CDR1 has an amino acid sequence of SEQ ID No. 266, the CDR2 has the amino acid sequence "RAS" and the CDR3 has an amino acid sequence of SEQ ID No. 267.

Such antibodies or binding fragments thereof may comprise a variable heavy chain and/or a variable light chain of the humanized or chimeric antibody 5H4, a variable heavy chain and/or a variable light chain having at least 80% sequence identity with the variable heavy chain and/or variable light chain of the humanized or chimeric antibody 5H4.

Other contemplated exemplary antibodies or binding fragments thereof may thus comprise the complementarity determining regions (CDRs) of the humanized version of 5H4 within their variable heavy chain and/or variable light chain. Such antibodies may also comprise CDRs within their variable heavy chain and/or variable light chain having at least 80% sequence identity with the CDRs of the humanized version of 5H4.

Further contemplated exemplary antibodies or binding fragments thereof may thus comprise the complementarity determining regions (CDRs) of the chimeric version of 5H4 within their variable heavy chain and/or variable light chain. Such antibodies may also comprise CDRs within their variable heavy chain and/or variable light chain having at least 80% sequence identity with the CDRs of the chimeric version of 5H4.

Preferably, in all these embodiments the sequence identity is at least about 85%, more preferably at least about 90%, even more preferably at least about 95% and most preferably at least about 98% or about 99%. Sequence identity may be determined over the whole length of the respective sequences.

The determination of percent identity between two sequences is preferably accomplished using the mathematical algorithm of Karlin and Altschul (1993) *Proc. Natl. Acad. Sci USA* 90: 5873-5877. Such an algorithm is incorporated into the BLASTn and BLASTp programs of Altschul et al. (1990) *J. Mol. Biol.*, 215: 403-410 (see references) available at NCBI (http://www.ncbi.nlm.nih.gov/blast/Blast.cge).

The determination of percent identity is performed with the standard parameters of the BLASTn and BLASTp programs.

BLAST polynucleotide searches are performed with the BLASTn program.

For the general parameters, the "Max Target Sequences" box may be set to 100, the "Short queries" box may be ticked, the "Expect threshold" box may be set to 10 and the "Word Size" box may be set to 28. For the scoring parameters the "Match/mismatch Scores" may be set to 1, −2 and the "Gap Costs" box may be set to linear. For the Filters and Masking parameters, the "Low complexity regions" box may not be ticked, the "Species-specific repeats" box may not be ticked, the "Mask for lookup table only" box may be ticked, the "Mask lower case letters" box may not be ticked.

BLAST protein searches are performed with the BLASTp program. For the general parameters, the "Max Target Sequences" box may be set to 100, the "Short queries" box may be ticked, the "Expect threshold" box may be set to 10 and the "Word Size" box may be set to "3". For the scoring parameters the "Matrix" box may be set to "BLOSUM62", the "Gap Costs" Box may be set to "Existence: 11 Extension:1", the "Compositional adjustments" box may be set to "Conditional compositional score matrix adjustment". For the Filters and Masking parameters the "Low complexity regions" box may not be ticked, the "Mask for lookup table only" box may not be ticked and the "Mask lower case letters" box may not be ticked.

The term "CDR" refers to the complementarity determining region or hypervariable region amino acid residues of an antibody that participate in or are responsible for antigen-binding. The CDRs as described herein are defined according to the international ImMunoGeneTics information System® (LaFranc, et al. 2005. Nucl Acids Res. 33:D593-D597) and as described in (Lefranc et al. Dev. Comparat. Immunol. 27:55-77, 2003).

The above-mentioned CDRs of a light and heavy chain variable region may be embedded in human sequences of framework and constant regions derived from other human antibodies, particularly if such sequences have been shown to be effective in antibody dependent cell mediated cytotoxicity (ADCC). In this context, one may e.g. use the human constant and framework sequences of humanized therapeutic antibodies that have been successfully used for therapeutic applications. The above-mentioned CDRs of a light and heavy chain variable region are preferably incorporated into the framework and constant regions of such humanized antibodies of the human IgG class.

Further, the above-mentioned CDRs of a light and heavy chain variable region may be embedded in essentially human sequences for framework and constant regions. However, particularly the framework regions, but also the constant regions may comprise amino acids as they are e.g. typically found in mouse antibodies which are known to enhance antigen binding and/or e.g. ADCC (see e.g. European patent application EP 0 451 216). Preferably these antibodies are of the IgG class.

In the following several methodologies are described which have been developed for reduction of immunogenicity of non-human derived antibodies, like chimerization or humanization. These approaches may also be applied to other antibodies that can be identified using e.g. the immunization and screening approaches which are described in the experiments hereinafter. They may thus be applied to antibodies and binding fragments thereof that recognize other human Vβ chains than human BV12 or that recognize human Vα chains.

During humanization, all amino acids which are not essential for proper antibody folding or antigen recognition are exchanged with amino acids from the human antibody counterpart. Several methods for mab humanization are developed including traditional CDR grafting or more novel approaches which involve computer modeling and bioinformatics analysis. Humanization of the heavy and light chains of CL 1 was performed using the CDR grafting method (see e.g. Desmet et al. in Kontermann and Dube' (eds.) Antibody Engineering Vol. 1, p. 341ff; Bernett et al. J. Mol. Biol. (2010) 396, 1474-1490). The heavy and light chain variable framework regions can be derived from the same or different human antibody sequences. The human antibody sequences can be the sequences of naturally occurring human antibodies. Human heavy and light chain variable framework regions are listed e.g. in Lefranc, M.-P., Current Protocols in Immunology (2000)—Appendix IP A.1P.1-A.1P.37 and are accessible via IMGT, the international ImMunoGeneTics information System® (http://imgt.cines.fr). A humanized BV cluster mab IGK chain sequence of 15B4 can be prepared based on human IGKV7-3*01(P), IGKV3-11*01, IGKV3-NL5*01, IGKV3D-7*01, IGKV3-NL1*01 and rat 15B4 IGVK chain as indicated in SEQ ID NO: 224.

A humanized BV cluster mab IGH chain sequence of 15B4 may thus be prepared based on human IGHV1-f*0, IGHV1-24*01, IGHJ6*01, IGHD3-10*01 and rat 15B4 IGVH chain as indicated in SEQ ID NO: 225.

It is therefore to be understood that 15B4 and 5H4 serve not only as an example of antibodies or binding fragments thereof which recognize human Vβ chains other than human VB12 but also as an example of antibodies or binding fragments thereof, which recognize a fraction of TCR Vα chains comprising at least two different two different TCR Vα chains but less than all TCR Vα chains or which recognize a fraction of TCR Vβ chains comprising at least two different two different TCR Vβ chains but less than all TCR Vβ chains.

The invention therefore also contemplates using TCR Vα chain antibodies and binding fragments thereof or TCR Vβ chain antibodies and binding fragments thereof binding substantially to the same epitope or parts of the same epitope as do the TCR Vα binding antibodies and binding fragments or TCR Vβ chain antibodies and binding fragments thereof as described above. Thus the invention relates TCR Vβ chain antibodies and binding fragments thereof binding substantially to the same epitope or parts of the same epitope as 15B4 or 5H4. The invention relates to antibodies and binding fragments thereof binding substantially to the same epitope or parts of the same epitope as 15B4 or 5H4.

Further, the invention considers using TCR Vα chain antibodies and binding fragments thereof or TCR Vβ chain antibodies and binding fragments thereof competing with TCR Vα chain antibodies and binding fragments thereof or TCR Vβ chain antibodies and binding fragments thereof as described above. Thus the invention relates to TCR Vα chain antibodies and binding fragments thereof or TCR Vβ chain antibodies and binding fragments thereof antibodies and binding fragments thereof competing with 15B4 or 5H4.

Epitope mapping may be undertaken by producing different fragments of the antigen such as the TCR Vα chain or the TCR Vβ chain and to then test these fragments for binding to antibodies or the binding fragments thereof. Binding may be measured using a Biacore® interaction analysis. One may also use commercially available peptide arrays such as PepSpot™ from JPT Peptide Technologies GmbH (Berlin, Germany), or proteomics-based mass spectrometry methods. Competition for binding to a particular antigen or epitope can be determined using assays known in the art. For example one may label an antibody in accordance with the invention and test for its binding to TCR Vα chain or TCR Vβ chain. Subsequently, one adds unlabeled 15B4 (or any other TCR Vα chain or TCR Vβ chain antibody) and determines whether it affects binding of the labeled antibody, or binding of the labeled antibody is studied in presence or absence of various concentrations of such unlabeled TCR Vα chain or TCR Vβ chain binding antibody. Such label could be radioactive or fluorescent or other kinds of detectable label.

Competition for binding to a particular antigen or epitope is determined by a reduction in binding to antigen or epitope of at least about 50%, or at least about 70%, or at least about 80%, or at least about 90%, or at least about 95%, or at least about 99% or about 100% for the antibody in accordance with the invention. Binding may be measured using Biacore® equipment, various fluorescence detection technologies (e.g. fluorescence correlation spectroscopy, fluorescence cross-correlation, fluorescence lifetime measurements etc.) or various types of radioimmunoassays or other assays used to follow antibody binding to a target molecule.

As mentioned above, the present invention considers cluster-specific TCR Vα chain or TCR chain antibodies or binding fragments thereof. A full-length antibody includes a constant domain and a variable domain. The constant region need not be present in an antigen binding fragment of an antibody.

Binding fragments may thus include portions of an intact full length antibody, such as an antigen binding or variable region of the complete antibody. Examples of antibody fragments include Fab, F(ab')$_2$, Id and Fv fragments; diabodies; linear antibodies; single-chain antibody molecules (e.g., scFv); multispecific antibody fragments such as bispecific, trispecific, and multispecific antibodies (e.g., diabodies, triabodies, tetrabodies); minibodies; chelating recombinant antibodies; tribodies or bibodies; intrabodies; nanobodies; small modular immunopharmaceuticals (SMIP), binding-domain immunoglobulin fusion proteins; camelized antibodies; VHH containing antibodies; chimeric antigen receptor (CAR); and any other polypeptides formed from antibody fragments. The skilled person is aware that the antigen-binding function of an antibody can be performed by fragments of a full-length antibody.

A Fab fragment consists of the VL, VH, CL and CH1 domains. An F(ab')$^2$ fragment comprises two Fab fragments linked by a disulfide bridge at the hinge region. An Fd is the VH and CH1 domains of a single arm of an antibody. An Fv fragment is the VL and VH domains of a single arm of an antibody.

Binding fragments also encompass monovalent or multivalent, or monomeric or multimeric (e.g. tetrameric), CDR-derived binding domains.

A bispecific antibody comprises two different binding specificities and thus binds to two different antigens. In one embodiment, the bispecific antibody comprises a first antigen recognition domain that binds to a first antigen and a second antigen recognition domain that binds to a second antigen. In one embodiment, the first antigen recognition domain binds to a fraction of T cell TCR Vα chains as defined herein and the second antigen recognition region binds to a fraction of T cell TCR Vα chains as defined herein which comprises at least one different TCR Vα chain as the fraction of T cell TCR Vα chains that is recognized by the first antigen recognition domain. In one embodiment, the first antigen recognition domain binds to a fraction of T cell TCR Vβ chains as defined herein and the second antigen recognition region binds to a fraction of T cell TCR Vβ chains as defined herein which comprises at least one different TCR Vβ chain as the fraction of T cell TCR Vβ chains that is recognized by the first antigen recognition domain.

In some instances, a bispecific antibody that recognizes a T cell antigen is referred to as a Bispecific T Cell Engager (BiTE). The present invention is not limited by the use of any particular bispecific antibody. Rather, any bispecific antibody or BiTE can be used. One of the scFvs binds to T cells via the CD3 receptor, and the other to the antigen to be targeted via an antigen specific molecule. This causes T cells to exert cytotoxic activity on cells expressing the targeted antigen by producing proteins like perforin and granzymes, independently of the presence of MHC I or co-stimulatory molecules. Examples of TCR Vα chains or TCR Vβ chains are described elsewhere herein, all of which may be targeted by the bispecific antibody. In one embodiment, the bispecific antibody comprises a human antibody, a humanized antibody, or fragments thereof.

In one embodiment, the first antigen recognition domain binds to a fraction of T cell TCR chains and the second antigen recognition region binds to an antigen recognition region binds to CD3 on T cells. Methods for making bispecific antibodies are known to the skilled person in the art. Bispecific antibodies can be produced recombinantly using the co-expression of two immunoglobulin heavy chain/light chain pairs, as for example described in Milstein et al. (1983; Nature 305:537). Alternatively, bispecific antibodies can be prepared using chemical linkage (see, e.g., Brennan et al. (1985)). Bispecific antibodies include bispecific antibody fragments (see, e.g., Holliger et al. (1993) Proc. Natl. Acad. Sci. U.S.A. 90:6444-48, Gruber et al. (1994) J. Immunol. 152:5368.)

A chimeric antigen receptor CAR comprises an antigen binding domain derived from a bispecific antibody, a transmembrane domain, and a CD3 zeta signaling domain.

More specifically the term "chimeric antigen receptors (CARs)," as used herein, refers for example to chimeric T-cell receptors, artificial T-cell receptors, or chimeric immunoreceptors. CARs may be used for mediating the specificity of a monoclonal antibody onto a T cell. In specific embodiments of the invention, CARs direct specificity of the cell to TCR Vα chains or TCR Vβ chains, for example. In some embodiments, CARs comprise an intracellular activation domain, a transmembrane domain, and an extracellular domain comprising a binding region directed to TCR Vα chains or TCR Vβ chains. In particular aspects, CARs comprise fusions of single-chain variable fragments (scFv) derived from monoclonal antibodies, fused to CD3-zeta a transmembrane domain and endodomain. In certain cases, the spacing of the antigen-recognition domain can be modified to reduce activation-induced cell death. In certain cases, CARs comprise domains for additional co-stimulatory signaling, such as CD3-zeta, FcR, CD27, CD28, CD137, DAP10, and/or OX40. It is contemplated by the invention that a CAR could be used for enhancing the effect of the antibody or fragment of the invention. For example, if an antibody that binds to a fraction of T cell receptor variable alpha (TCR Vα) chains comprising at least two different TCR Vα chains but less than all TCR Vα chains or that binds to a fraction of T cell receptor variable beta (TCR Vβ) chains comprising at least two different TCR Vβ chains but less than all TCR Vβ chains shows no or only little activity of T cell depletion, its binding domain can be integrated into a CAR in order to elicit or enhance its T cell depletion capability. It is also envisioned that the activity of an antibody of the invention that is considerably effective, for example in depleting specific T cells, is further enhanced by the integration of its binding domain or fragments and/or variations thereof into a CAR.

The TCR variable chain binding antibodies and binding fragments thereof may also encompass variants of the exemplary antibodies, binding fragments and sequences disclosed herein. Variants include peptides and polypeptides comprising one or more amino acid sequence substitutions, deletions, and/or additions that have the same or substantially the same affinity and specificity of epitope binding as one or more of the exemplary antibodies, fragments and sequences disclosed herein. Thus, variants include peptides and polypeptides comprising one or more amino acid sequence substitutions, deletions, and/or additions to the exemplary antibodies, fragments and sequences disclosed herein where such substitutions, deletions and/or additions do not cause substantial changes in affinity and specificity of epitope binding. For example, a variant of an antibody or fragment may result from one or more changes to an antibody or fragment comprising one or more of amino acid sequence of SEQ ID NOs: 218, 219 or 232, 233 or where the changed antibody or fragment has the same or substantially the same affinity and specificity of epitope binding as the starting sequence.

Antibodies or binding fragments thereof as far as they are generally referred to in the context of the present invention may also be part of larger immunoadhesion molecules, formed by covalent or non-covalent association of the antibody or antibody portion with e.g. one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibodies and fragments comprising immunoadhesion molecules can be obtained using standard recombinant DNA techniques, as described herein. Preferred antigen binding portions are complete domains or pairs of complete domains.

The binding antibodies and binding fragments of the present invention may also encompass domain antibody (dAb) fragments (Ward et al., *Nature* 341:544-546, 1989) which consist of a $V_H$ domain. The antibodies and binding fragments of the present invention also encompass diabodies are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., *Proc. Natl. Acad. Sci. USA* 90:6444-6448, 1993, and Poljak et al., *Structure* 2:1121-1123, 1994). Diabodies can be bispecific or monospecific.

As mentioned the antibodies and binding fragments of the present invention also encompass single-chain antibody fragments (scFv). An scFv comprises an antibody heavy chain variable region ($V_H$) operably linked to an antibody light chain variable region ($V_L$) wherein the heavy chain variable region and the light chain variable region, together or individually, form a binding site. A scFv may comprise a $V_H$ region at the amino-terminal end and a $V_L$ region at the carboxy-terminal end. Alternatively, scFv may comprise a $V_L$ region at the amino-terminal end and a $V_H$ region at the carboxy-terminal end. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883).

A scFv may optionally further comprise a polypeptide linker between the heavy chain variable region and the light chain variable region. Such polypeptide linkers generally comprise between 1 and 50 amino acids, alternatively between 3 and 12 amino acids, alternatively 2 amino acids. An example of a linker peptide for linking heavy and light chains in a scFv comprises the 5 amino acid sequence Gly-Gly-Gly-Gly-Ser (SEQ ID NO: 238). Other examples comprise one or more tandem repeats of this sequence (for example, a polypeptide comprising two to four repeats of Gly-Gly-Gly-Gly-Ser (SEQ ID NO: 238) to create linkers.

The antibodies and binding fragments of the present invention also encompass heavy chain antibodies (HCAb). Exceptions to the $H_2L_2$ structure of conventional antibodies occur in some isotypes of the immunoglobulins found in camelids (camels, dromedaries and llamas; Hamers-Casterman et al., 1993 *Nature* 363: 446; Nguyen et al., 1998 *J. Mol. Biol.* 275: 413), wobbegong sharks (Nuttall et al., *Mol Immunol.* 38:313-26, 2001), nurse sharks (Greenberg et al., *Nature* 374:168-73, 1995; Roux et al., 1998 *Proc. Nat. Acad. Sci. USA* 95: 11804), and in the spotted ratfish (Nguyen, et al., "Heavy-chain antibodies in Camelidae; a case of evolutionary innovation," 2002 *Immunogenetics* 54(1): 39-47). These antibodies can apparently form antigen-binding regions using only heavy chain variable region, in that these functional antibodies are dimers of heavy chains only (referred to as "heavy-chain antibodies" or "HCAbs"). Accordingly, some embodiments of the present antibodies and binding fragments may be heavy chain antibodies (HCAb) that specifically bind to the TCR. For example, heavy chain antibodies that are a class of IgG and devoid of light chains are produced by animals of the genus Camelidae which includes camels, dromedaries and llamas (Hamers-Casterman et al., Nature 363:446-448 (1993)). HCAbs have a molecular weight of about 95 kDa instead of the about 160 kDa molecular weight of conventional IgG antibodies. Their binding domains consist only of the heavy-chain variable domains, often referred to as $V_{HH}$ to distinguish them from conventional $V_H$, Muyldermans et al., J. Mol. Recognit. 12:131-140 (1999). The variable domain of the heavy-chain antibodies is sometimes referred to as a nanobody (Cortez-Retamozo et al., Cancer Research 64:2853-57, 2004). A nanobody library may be generated from an immunized dromedary as described in Conrath et al., (Antimicrob Agents Chemother 45: 2807-12, 2001) or using recombinant methods.

Since the first constant domain ($C_{H1}$) is absent (spliced out during mRNA processing due to loss of a splice consensus signal), the variable domain ($V_{HH}$) is immediately followed by the hinge region, the $C_{H2}$ and the $C_{H3}$ domains (Nguyen et al., Mol. Immunol. 36:515-524 (1999); Woolven et al., Immunogenetics 50:98-101 (1999)). Camelid $V_{HH}$ reportedly recombines with IgG2 and IgG3 constant regions that contain hinge, CH2, and CH3 domains and lack a CH1 domain (Hamers-Casterman et al., supra). For example, llama IgG1 is a conventional ($H_2L_2$) antibody isotype in which $V_H$ recombines with a constant region that contains hinge, CH1, CH2 and CH3 domains, whereas the llama IgG2 and IgG3 are heavy chain-only isotypes that lack CH1 domains and that contain no light chains.

Although the HCAbs are devoid of light chains, they have an antigen-binding repertoire. The genetic generation mechanism of HCAbs is reviewed in Nguyen et al. Adv. Immunol 79:261-296 (2001) and Nguyen et al., Immunogenetics 54:39-47 (2002). Sharks, including the nurse shark, display similar antigen receptor-containing single monomeric V-domains. Irving et al., J. Immunol. Methods 248: 31-45 (2001); Roux et al., Proc. Natl. Acad. Sci. USA 95:11804 (1998).

$V_{HH}$s comprise small intact antigen-binding fragments (for example, fragments that are about 15 kDa, 118-136 residues). Camelid $V_{HH}$ domains have been found to bind to antigen with high affinity (Desmyter et al., J. Biol. Chem. 276:26285-90, 2001), with $V_{HH}$ affinities typically in the nanomolar range and comparable with those of Fab and scFv fragments. $V_{HH}$s are highly soluble and more stable than the corresponding derivatives of scFv and Fab fragments. $V_H$ fragments have been relatively difficult to produce in soluble form, but improvements in solubility and specific binding can be obtained when framework residues are altered to be more $V_{HH}$-like (see, for example, Reichman et al., J Immunol Methods 1999, 231:25-38). $V_{HH}$s carry amino acid substitutions that make them more hydrophilic and prevent prolonged interaction with BiP (Immunoglobulin heavy-chain binding protein), which normally binds to the H-chain in the Endoplasmic Reticulum (ER) during folding and assembly, until it is displaced by the L-chain. Because of the $V_{HG}$s' increased hydrophilicity, secretion from the ER is improved.

Functional $V_{HH}$s may be obtained by proteolytic cleavage of HCAb of an immunized camelid, by direct cloning of $V_{HH}$ genes from B-cells of an immunized camelid resulting in recombinant $V_{HH}$s, or from naive or synthetic libraries. $V_{HH}$s with desired antigen specificity may also be obtained through phage display methodology. Using $V_{HH}$s in phage display is much simpler and more efficient compared to Fabs or scFvs, since only one domain needs to be cloned and expressed to obtain a functional antigen-binding fragment. Muyldermans, Biotechnol. 74:277-302 (2001); Ghahroudi et al., FEBS Lett. 414:521-526 (1997); and van der Linden et al., J. Biotechnol. 80:261-270 (2000). Methods for generating antibodies having camelid heavy chains are also described in U.S. Patent Publication Nos. 20050136049 and 20050037421.

The binding antibodies and binding fragments thereof may also encompass any of the e.g. foregoing specifically mentioned amino acid sequences of the light or heavy chains with one or more conservative substitutions (e.g., 1, 2, 3, 4, 5, 6, 7, 8, 9, 10, 11, 12, 13, 14, or 15 conservative substitutions). One can determine the positions of an amino acid sequence that are candidates for conservative substitutions, and one can select synthetic and naturally-occurring amino acids that effect conservative substitutions for any particular amino acids. Consideration for selecting conservative substitutions include the context in which any particular amino acid substitution is made, the hydrophobicity or polarity of the side-chain, the general size of the side chain, and the pK value of side-chains with acidic or basic character under physiological conditions. For example, lysine, arginine, and histidine are often suitably substituted for each other. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. Other groups of amino acids frequently suitably substituted for each other include, but are not limited to, the group consisting of glutamic and aspartic acids; the group consisting of phenylalanine, tyrosine, and tryptophan; and the group consisting of serine, threonine, and, optionally, tyrosine.

By making conservative modifications to the amino acid sequence or corresponding modifications to the encoding nucleotides, one can produce antibodies or binding fragments thereof having functional and chemical characteristics similar to those of the exemplary antibodies and fragments disclosed herein.

The binding antibodies and binding fragments thereof as they are mentioned in the context of the present invention may encompass derivatives of the exemplary antibodies, fragments and sequences disclosed herein. Derivatives include polypeptides or peptides, or variants, fragments or derivatives thereof, which have been chemically modified. Examples include covalent attachment of one or more polymers, such as water soluble polymers, N-linked, or O-linked carbohydrates, sugars, phosphates, and/or other such molecules such as detectable labels such as fluorophores.

Labeling agents may be coupled either directly or indirectly to the antibodies or antigens of the invention. One example of indirect coupling is by use of a spacer moiety. Furthermore, the antibodies of the present invention can comprise a further domain, said domain being linked by covalent or noncovalent bonds. The linkage can be based on genetic fusion according to the methods known in the art and described above or can be performed by, e.g., chemical cross-linking as described in, e.g., international application WO 94/04686. The additional domain present in the fusion protein comprising the antibody of the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the antibody of the invention or vice versa. The therapeutically or diagnostically active agent can be coupled to the antibody of the invention or an antigen-binding fragment thereof by various means. This includes, for example, single-chain fusion proteins comprising the variable regions of the antibody of the invention coupled by covalent methods, such as peptide linkages, to the therapeutically or diagnostically active agent. Further examples include molecules which comprise at least an antigen-binding fragment coupled to additional molecules covalently or non-covalently include those in the following non-limiting illustrative list. Traunecker et al., *Int. J. Cancer Surp. SuDP* 7 (1992), 51-52, describe the bispecific reagent janusin in which the Fv region directed to CD3 is coupled to soluble CD4 or to other ligands such as OVCA and IL-7. Similarly an Fv region directed to TCR Vα chains or TCR Vβ chains may be coupled to portions of e.g. an anti-CD40 agonistic antibody and/or portions of an anti-CTLA4 antagonistic antibody. Similarly, the variable regions of the antibody of the invention can be constructed into Fv molecules and coupled to alternative ligands such as those illustrated in the cited article. Higgins et al., *J. Infect Disease* 166 (1992), 198-202, described a hetero-conjugated antibody composed of OKT3 cross-linked to an antibody directed to a specific sequence in the V3 region of GP120. Such hetero-conjugate antibodies can also be constructed using at least the variable regions contained in the antibody of the invention methods. Additional examples of specific antibodies include those described by Fanger et al., *Cancer Treat. Res.* 68 (1993), 181-194 and by Fanger et al., *Crit. Rev. Immunol.* 12 (1992), 101-124. Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers et al., *Seminars Cell. Biol.* 2 (1991), 59-70 and by Fanger et al., *Immunol.* Today 12 (1991), 51-54.

The above described fusion proteins may further comprise a cleavable linker or cleavage site for proteases. These spacer moieties, in turn, can be either insoluble or soluble (Diener et al., *Science* 231 (1986), 148) and can be selected to enable drug release from the antigen at the target site.

Examples of therapeutic agents which can be coupled to the antibodies and antigens of the present invention for immunotherapy are drugs, radioisotopes, lectins, and toxins. The drugs with which can be conjugated to the antibodies and antigens of the present invention include compounds which are classically referred to as drugs such as mitomycin C, daunorubicin, and vinblastine. In using radioisotopically conjugated antibodies or antigens of the invention for, e.g., tumor immunotherapy, certain isotopes may be more preferable than others depending on such factors as leukocyte distribution as well as stability and emission.

Some emitters may be preferable to others. In general, alpha and beta particle emitting radioisotopes are preferred in immunotherapy. Preferred are short range high energy a emitters such as $^{212}$Bi. Examples of radioisotopes which can be bound to the antibodies or antigens of the invention for therapeutic purposes are $^{125}$I, $^{131}$I, $^{90}$Y, $^{67}$Cu, $^{212}$Bi, $^{212}$At, $^{211}$Pb, $^{47}$Sc, $^{109}$Pd and $^{188}$Re. Other therapeutic agents which can be coupled to the antibody or antigen of the invention, as well as ex vivo and in vivo therapeutic protocols, are known, or can be easily ascertained, by those of ordinary skill in the art.

As mentioned, the invention also relates in some embodiment to nucleic acid molecules encoding antibodies and binding fragments thereof, vectors comprising such nucleic acid molecules and host cells comprising such nucleic acid sequences and vectors.

The antibodies and binding fragments thereof may be encoded by a single nucleic acid (e.g., a single nucleic acid comprising nucleotide sequences that encode the light and heavy chain polypeptides of the antibody), or by two or more separate nucleic acids, each of which encode a different part of the antibody or antibody fragment. In this regard, the invention provides one or more nucleic acids that encode any of the forgoing antibodies, or binding fragments. The nucleic acid molecules may be DNA, cDNA, RNA and the like.

According to one aspect of the invention, the invention provides a nucleic acid that encodes a heavy chain region of an antibody or a portion thereof. Exemplary nucleic acid sequences are provided in SEQ ID Nos: 223 and 237. The invention also provides a nucleic acid that encodes a light chain variable region of an antibody or a portion thereof. Exemplary nucleic acid sequences are provided in SEQ ID Nos.:222 and 236.

Also encompassed by the invention are nucleic acids encoding any of the foregoing amino acid sequences of the light or heavy chains that comprise one or more conservative substitutions (e.g., 1, 2, 3, 4, 5, 6, 7, 8, 9, 10, 11, 12, 13, 14, or 15 conservative substitutions), as discussed with respect to the antibody and antibody fragment of the invention, where the antibody or fragment comprising the substitution has the same or substantially the same affinity and specificity of epitope binding as one or more of the exemplary antibodies, fragments and sequences disclosed herein.

Preferably, the polynucleotide of the invention is operatively linked to expression control sequences allowing expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally associated or heterologous promoter regions.

The nucleic acids described herein can be inserted into vectors, e.g., nucleic acid expression vectors and/or targeting vectors. Such vectors can be used in various ways, e.g., for the expression of an antibody or a binding fragment in a cell or transgenic animal. Accordingly, the invention provides a vector comprising any one or more of the nucleic acids of the invention. A "vector" is any molecule or composition that has the ability to carry a nucleic acid sequence into a suitable host cell where synthesis of the encoded polypeptide can take place. Typically and preferably, a vector is a nucleic acid that has been engineered, using recombinant DNA techniques that are known in the art, to incorporate a desired nucleic acid sequence (e.g., a nucleic acid of the invention). Desirably, the vector is comprised of DNA. However, vectors that are not based on nucleic acids, such as liposomes, are also known in the art and can be used in connection with the invention. The inventive vector can be based on a single type of nucleic acid (e.g., a plasmid) or non-nucleic acid molecule (e.g., a lipid or a polymer). Alternatively, the vector can be a combination of a nucleic acid and a non-nucleic acid (i.e., a "chimeric" vector). For example, a plasmid harboring the nucleic acid can be formulated with a lipid or a polymer as a delivery vehicle. Such a vector is referred to herein as a "plasmid-lipid complex" and a "plasmid-polymer" complex, respectively. The inventive gene transfer vector can be integrated into the host cell genome or can be present in the host cell in the form of an episome.

Vectors are typically selected to be functional in the host cell in which the vector will be used (the vector is compatible with the host cell machinery such that amplification of the gene and/or expression of the gene can occur). A nucleic acid molecule encoding an antibody or binding fragment thereof may be amplified/expressed in prokaryotic, yeast, insect (baculovirus systems) and/or eukaryotic host cells. Selection of the host cell will depend in part on whether the antibody or fragment is to be post-transitionally modified (e.g., glycosylated and/or phosphorylated). If so, yeast, insect, or mammalian host cells are preferable.

Expression vectors typically contain one or more of the following components (if they are not already provided by the nucleic acid molecules): a promoter, one or more enhancer sequences, an origin of replication, a transcriptional termination sequence, a complete intron sequence containing a donor and acceptor splice site, a leader sequence for secretion, a ribosome binding site, a polyadenylation sequence, a polylinker region for inserting the nucleic acid encoding the polypeptide to be expressed, and a selectable marker element.

The invention in some aspects further provides a cell (e.g., an isolated or purified cell) comprising a nucleic acid or vector of the invention. The cell can be any type of cell capable of being transformed with the nucleic acid or vector of the invention so as to produce a polypeptide encoded thereby. The cell is preferably the cell of a mammal, such as a human, and is more preferably a hybridoma cell, an embryonic stem cell, or a fertilized egg. The embryonic stem cell or fertilized egg may not be a human embryonic stem cell or a human fertilized egg.

The host cells may be prokaryotic host cells (such as *E. coli*) or eukaryotic host cells (such as a yeast cell, an insect cell, or a vertebrate cell). The host cell, when cultured under appropriate conditions, expresses an antibody or binding fragment which can subsequently be collected from the culture medium (if the host cell secretes it into the medium) or directly from the host cell producing it (if it is not secreted). Selection of an appropriate host cell will depend upon various factors, such as desired expression levels, polypeptide modifications that are desirable or necessary for activity, such as glycosylation or phosphorylation, and ease of folding into a biologically active molecule. A number of suitable host cells are known in the art and many are available from the American Type Culture Collection (ATCC), Manassas, Va. Examples include mammalian cells, such as Chinese hamster ovary cells (CHO) (ATCC No. CCL61) CHO DHFR-cells (Urlaub et al. Proc. Natl. Acad. Sci. USA 97, 4216-4220 (1980)), human embryonic kidney (HEK) 293 or 293T cells (ATCC No. CRL1573), 3T3 cells (ATCC No. CCL92), or PER.C6 cells.

The cell comprising the nucleic acid or vector of the invention can be used to produce the antibody or binding fragment thereof, or a portion thereof (e.g., a heavy chain sequence, or a light chain sequence encoded by the nucleic acid or vector). After introducing the nucleic acid or vector of the invention into the cell, the cell is cultured under conditions suitable for expression of the encoded sequence. The antibody, antigen binding fragment, or portion of the antibody then can be isolated from the cell.

Another aspect of the invention relates to the use of an antibody or binding fragment thereof according to any one of the preceding claims for depleting a subpopulation of T cells expressing a fraction of TCR Vα chains comprising at least two different TCR Vα chains or for depleting a subpopulation of T cells expressing a fraction of TCR Vβ chains comprising at least two different TCR Vβ chains.

Another aspect of the invention relates to the use of an antibody or binding fragment thereof according to any one of the preceding claims for ex vivo depleting a subpopulation of T cells expressing a fraction of TCR Vα chains comprising at least two different TCR Vα chains or for depleting a subpopulation of T cells expressing a fraction of TCR Vβ chains comprising at least two different TCR Vβ chains.

A further aspect of the invention relates to an antibody or binding fragment thereof as described herein for use as a medicament.

A specific embodiment relates to an antibody or binding fragment thereof according to any one of the preceding claims for use in the treatment of T cell leukemia.

The binding data showing that CL 1 binds to Jurkat cells, which are T cell leukemia cells and hence are an established model for T-cell leukemia, show that the antibody or binding fragments according to the invention are targeting T cell leukemia cells. Therefore, the antibodies or binding fragments of the invention can be used for the treatment of T cell mediated diseases such as T cell leukemia.

In vivo depletion experiments in mouse are suitable to prove that it is feasible to deplete specific T cell populations, such as aberrant T cells causing T cell leukemia, in vivo.

Further the ADCC assay monitors the capability of the antibody of the invention to trigger the ADCC, i.e. the active lysis of a target cells, e.g. malignant T cells.

The TCR variable chain binding antibodies or binding fragments thereof can be formulated in compositions, especially pharmaceutical compositions. Such compositions comprise a therapeutically or prophylactically effective amount of an antibody or binding fragment thereof in admixture with a suitable carrier, e.g., a pharmaceutically acceptable agent.

Pharmaceutically acceptable agents for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

The composition can be in liquid form or in a lyophilized or freeze-dried form and may include one or more lyoprotectants, excipients, surfactants, high molecular weight structural additives and/or bulking agents (see for example U.S. Pat. Nos. 6,685,940, 6,566,329, and 6,372,716).

Compositions can be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, antioxidants, chelating agents, inert gases and the like. See generally, Remington's Pharmaceutical Science, 16th Ed., Mack Eds., 1980, which is incorporated herein by reference.

Pharmaceutical compositions described herein can be formulated for controlled or sustained delivery in a manner that provides local concentration of the product (e.g., bolus, depot effect) and/or increased stability or half-life in a particular local environment. The compositions can include the formulation of antibodies, binding fragments, nucleic acids, or vectors of the invention with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection.

Both biodegradable and non-biodegradable polymeric matrices can be used to deliver compositions of the present invention, and such polymeric matrices may comprise natural or synthetic polymers. Biodegradable matrices are preferred. The period of time over which release occurs is based on selection of the polymer. Typically, release over a period ranging from between a few hours and three to twelve months is most desirable.

Alternatively or additionally, the compositions can be administered locally via implantation into the affected area of a membrane, sponge, or other appropriate material on to which an antibody, binding fragment, nucleic acid, or vector of the invention has been absorbed or encapsulated. Where an implantation device is used, the device can be implanted into any suitable tissue or organ, and delivery of an antibody, binding fragment, nucleic acid, or vector of the invention can be directly through the device via bolus, or via continuous administration, or via catheter using continuous infusion.

A pharmaceutical composition comprising a binding antibody or binding fragment thereof can be formulated for inhalation, such as for example, as a dry powder. Inhalation solutions also can be formulated in a liquefied propellant for aerosol delivery. In yet another formulation, solutions may be nebulized.

Certain formulations containing antibodies or binding fragments thereof can be administered orally. Formulations administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of a selective binding agent. Diluents, flavorings, low melting point waxes, vegetable oils, lubricants, suspending agents, tablet disintegrating agents, and binders also can be employed.

Antibody or binding fragment thereof that binds to a fraction of TCR Vβ chains comprising at least two different TCR Vβ chains but less than all TCR Vβ chains has an $EC_{50}$ of about 0.08 nm to about 1000 nM, preferably of about 0.1 to about 900 nM, more preferably of about 0.4 to about 800 nM, such as about 0.4 to about 400 nM, about 0.08 nM to about 0.8 nM, or about 0.1 nM to about 0.6 nM. The EC50 values of the rat antibodies may vary from the chimeric or humanized antibody version. The EC50 value of the chimeric or humanized antibodies according to the invention may be of about 0.4 to about 800 nM, preferably 100 to about 500 nM, more preferably of about 150 nM to 350 nM.

The invention is now described with respect to some examples which are however not be construed as limiting.

ADCC refers to antibody-dependent cellular cytotoxicity. In order to determine whether an antibody is in principle capable of mediating ADCC, ADCC may be measured in vitro by a luciferase assay monitoring the activation of gene transcription through the NFAT (nuclear factor of activated T-cells) pathway in the effector cell. For example, the ADCC Reporter Bioassay (Promega) uses engineered Jurkat cells stably expressing the FcγRIIIa receptor, V158 (high affinity) variant, and an NFAT response element driving expression of firefly luciferasease effector cells. The biological activity of the antibody in ADCC MOA is quantified through the luciferase produced as a result of NFAT pathway activation;

In addition ADCC could be measured by so-called $Cr^{51}$, Eu, $S^{35}$, and Calcein-release assays. A target cell displaying the antigen of interest on its surface may be labeled with these compounds. After binding of the therapeutic antibody, the cells are washed and effector cells expressing Fc receptors such as FcγRIII are co incubated with the antibody-labeled target cells and lysis of the target cells can be monitored by release of the labels. Another approach uses the so-called aCella TOX™ assay.

CDC refers to complement-dependent cellular cytotoxicity. In order to determine whether an antibody is in principle capable of mediating CDC, CDC may be measured in vitro as described e.g. in Delobel A et al, *Methods Mol Biol.* (2013); 988:115-43 or Current Protocols in Immunology, Chapter 13 Complement (Print ISSN: 1934-3671).

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

The above-mentioned CDRs of a light and heavy chain variable region are preferably embedded in the framework and constant region of a human-derived antibody, i.e. in the sequences as determined for antibodies obtained from human patients as described herein. Preferably these antibodies are of the IgG class.

However, the above-mentioned CDRs of a light and heavy chain variable region may also be embedded in human sequences of framework and constant regions derived from other human antibodies, particularly if such sequences have been shown to be effective in antibody dependent cell mediated cytotoxicity (ADCC). In this context, one may e.g. use the human constant and framework sequences of humanized therapeutic antibodies that have been successfully used for therapeutic applications. The above-mentioned CDRs of a light and heavy chain variable region are preferably incorporated into the framework and constant regions of such humanized antibodies of the human IgG class.

Further, the above-mentioned CDRs of a light and heavy chain variable region may be embedded in essentially human sequences for framework and constant regions. However, particularly the framework regions, but also the constant regions may comprise amino acids as they are e.g. typically found in mouse antibodies which are known to enhance antigen binding and/or e.g. ADCC (see e.g. European patent application EP 0 451 216). Preferably these antibodies are of the IgG class.

The antibody may trigger antibody dependent cytotoxicity (ADCC) and/or CDC complement dependent cytotoxicity and/or antibody dependent cellular phagocytosis (ADCP) phagocytosis. In a specific embodiment of the present application the antibody triggers ADCC.

Method for Generating an Antibody

A further aspect of the invention refers to a method for generating an antibody binding to a cell surface protein of interest, the method comprising the following steps:
(a) providing a non-human cell which does not express the endogenous form of the cell surface protein of interest but expresses an exogenous form of the cell surface protein of interest comprising at least one human segment;
(b) immunization of a non-human animal with the cell line provided in step (a);
(c) generation of hybridomas from the immunized non-human animal of step (b);
(d) screening for an antibody that binds to the surface protein of interest by contacting the antibodies secreted by the hybridomas of step (c) with human cells which do not express the endogenous form of the cell surface protein of interest but express an exogenous form of the cell surface protein of interest comprising at least one human segment.

Providing a non-human cell which does not express the endogenous form of the cell surface protein of interest means that the non-human cell is substantially incapable of producing the endogenous form of the protein but is capable of producing an exogenous form of the cell surface protein of interest. The skilled person is aware of different methods to inhibit the expression of the endogenous form of the protein. Also isolated cell lines, not expressing the endogenous form of the surface protein of interest that arose spontaneously can be used. Typically, in the non-human cell line the gene locus/loci of the surface protein of interest has/have been disabled.

The term "at least one human segment" as used herein refers to at least one part or region of the protein. This means that both completely human cell surface proteins and cell surface proteins that are not completely human are envisaged by the invention. Accordingly, the cell surface protein may comprise in addition to the at least one human segment, segments of another origin. For example, the intracellular domain and transmembrane domain of cell surface protein may be of mouse origin and the extracellular domain may be of human origin. For example, the constant regions of a TCR may be of mouse origin, while the variable domains may be of human origin. The term "segment" as used herein refers to parts of a protein such as, without limitation, domains or sequence stretches.

The term "cell surface protein of interest" refers to any protein that is known by the skilled person as a cell surface protein. "Cell surface protein" as used herein is a protein of which at least one part is exposed to the extracellular environment. The protein may be embedded in the lipid layer of the cell membrane or may bind to a molecule which is integrated in the lipid layer. The cell surface protein of interest may be a dimer, preferably a heterodimer, such as the TCR. An exemplary embodiment of the cell surface protein is the TCR. In a specific embodiment the cell surface protein is not CD5.

The exogenous form of the cell surface protein of interest can be expressed transiently or permanently. The skilled person is familiar with techniques of permanent or transient expression of genes.

The preparation of the monoclonal antibodies may be carried out based on known methods (C. Milstein, G. Köhler, Nature 256 (1975) 495). As immunogen a non-human cell which does not express the endogenous form of the cell surface protein of interest but expresses an exogenous form of the cell surface protein of interest comprising at least one human segment is used.

The term "non-human cell line" as used herein refers to any non-human cell line that is known to the skilled in the art which is suitable for immunization of a non-human animal. For example mouse or rat cell lines may be used.

Examples for non-human animals that may be immunized are cattle, sheep, goat, lama, pig, horse, mouse, rat, fowl, monkey, rabbit and the like. In a preferred embodiment, rat, mouse, rabbit or lama may be immunized. In a more preferred embodiment a rat may be immunized. In the rat a high number of spleen cells, in particular a higher number of spleen cells compared to a mouse, can be obtained.

In one embodiment, the non-human animal that is immunized in step (b) is of another species than the non-human cell line provided in step (a). For example the immunization of rats with a mouse cell line has the advantage that a strong immune response is triggered in the rat by the mouse cell line.

In a particular embodiment, the non-human animal to be immunized is a rat and the non-human cell line used for immunization is a mouse cell line. Also other combinations of non-human animals to be immunized and non-human cell lines can be used.

Screening for an antibody that binds to the surface protein of interest may be carried out by the use flow cytometry in particular, by FACS. The antibody is secreted by the hybridomas of step (c) is thereby contacted with a human cell line. The non-human cell line used for immunization is not used for screening, since this cell line also binds antibodies which are not specific for the cell surface protein of interest. A human cell line expressing the cell surface protein of interest which is used in the screening step is advantageous since antibodies specific for the human cell surface protein of interest bind to this cell line, but antibodies not specific for the human cell surface protein of interest bind substantially not to this human cell line. Hence, using the human cell line in the screening step allows differentiating between antibodies which bind specifically to the cell surface protein of interest and antibodies which bind non-specifically.

In order to make the screening step more efficient, supernatants of several plates can be pooled and be analyzed in a single step. For example the supernatant of 2, of 3, of 4, of 5, of 6, of 7, of 8, of 9, of 10 or more wells can be pooled. Preferably the supernatants of 4 wells can be pooled and analyzed in a primary screening step. If a supernatant pooled from several wells shows binding of an antibody, the supernatants of the single wells may be analyzed individually in a secondary screening step.

The antibodies secreted by the hybridomas of step (c) may be contacted with a mixture of human cells which do not express the endogenous form of the cell surface protein of interest comprising:
(i) a first defined proportion of the mixture of human cells which expresses the functional cell surface protein of interest; and
(ii) a second defined proportion of the mixture of human cells which does not express a functional cell surface protein of interest and which comprises a selection marker.

The term "selection marker" as used herein may refer to a marker that can be used in flow cytometry, in particular in FACS. For FACS typically fluorescent markers are used. The skilled person is aware of different fluorescent markers that are useful for FACS, for example and without limitation fluorescent proteins expressed in the cell line, such as, without limitation, GFP, YFP or DsRed or derivatives thereof. In some embodiments, the first defined proportion of cells and the second defined proportion of may comprise the selection marker but the level of the selection marker may be different in the two proportions which allow distinguishing both proportions. For example, the selection marker may be present at moderate levels in the first defined proportion and may be present at high levels at the second defined proportion.

One aspect of the invention refers to a method for generating an antibody binding to a cell surface protein of interest, the method comprising the following steps:
(a) providing a mouse cell which does not express the endogenous form of the cell surface protein of interest but expresses an exogenous form of the cell surface protein of interest comprising at least one human segment;
(b) immunization of a non-human animal with the mouse cell line provided in step (a);
(c) generation of hybridomas from the immunized non-human animal of step (b);
(d) screening for an antibody that binds to the cell surface protein of interest by contacting the antibodies secreted by the hybridomas of step (c) with a mixture of human cells which does not express the endogenous form of the cell surface protein of interest comprising:
(i) a first defined proportion of the mixture of human cells which expresses the functional cell surface protein of interest; and
(ii) a second defined proportion of the mixture of human cells which does not express a functional cell surface protein of interest and which comprises a selection marker.
wherein the non-human animal is either a mouse or a rat.

One aspect of the invention refers to a method for generating an antibody binding to a cell surface protein of interest, the method comprising the following steps:
(a) providing a mouse cell which does not express the endogenous form of the cell surface protein of interest but expresses an exogenous form of the cell surface protein of interest comprising at least one human segment;
(b) immunization of a rat with the mouse cell line provided in step (a);
(c) generation of hybridomas from the immunized rat of step (b);
(d) screening for an antibody that binds to the cell surface protein of interest by contacting the antibodies secreted by the hybridomas of step (c) with a mixture of human cells which does not express the endogenous form of the cell surface protein of interest comprising:
(i) a first defined proportion of the mixture of human cells which expresses the functional cell surface protein of interest; and
(ii) a second defined proportion of the mixture of human cells which does not express a functional cell surface protein of interest and which comprises a selection marker.

Another aspect of the invention refers to a method for generating an antibody binding to a cell surface protein of interest, the method comprising the following steps:
(a) providing a mouse cell which does not express the endogenous form of the cell surface protein of interest but expresses an exogenous form of the cell surface protein of interest comprising at least one human segment;
(b) immunization of a non-human animal with the mouse cell line provided in step (a);
(c) generation of hybridomas from the immunized non-human animal of step (b);
(d) screening for an antibody that binds to the cell surface protein of interest by contacting the antibodies secreted by the hybridomas of step (c) with human cells which do not express the endogenous form of the cell surface protein of interest but express an exogenous form of the cell surface protein of interest comprising at least one human segment;
wherein the non-human animal is either a mouse or a rat.

As a non-limiting example, the generation of antibodies binding to a TCRs is shown.

Therefore, one embodiment relates to a method for generating an antibody binding to a TCR of interest, the method comprising the following steps:
(a) providing a non-human cell which does not express the endogenous form of the TCR of interest but expresses an exogenous form of the TCR of interest comprising at least one human segment;
(b) immunization of a non-human animal with the cell line provided in step (a);
(c) generation of hybridomas from the immunized non-human animal of step (b);
(d) screening for an antibody that binds to the surface protein of interest by contacting the antibodies secreted by the hybridomas of step (c) with human cells which do not express the endogenous form of the TCR of interest but express an exogenous form of the TCR of interest comprising at least one human segment.

The cell line provided in step (a) may be a mouse $BW^{-/-}$ cell line.

The term "$BW^{-/-}$ cell line" refers to a BW cell line, which was derived from the parental BW5147 thymoma that arose spontaneously in an AKR mouse (Lee N E and Davis M M., J Immunol. 1988 Mar. 1; 140(5):1665-75; Letourneur F., Malissen B., Eur J Immunol. 1989; 19(12):2269-2274) and does neither express the endogenous TCR α chain nor the endogenous TCR β chain. Since the surface expression of a TCR heterodimer is dependent on association with the CD3 protein complex the $BW^{-/-}$ cell line was stably transduced to co-express human CD3 with GFP ($BW^{-/-}$-CD3-GFP; herein referred to simply as $BW^{-/-}$), enabling transduced cells to be easily identified. The presence of human CD3 allows these cells to express any human or mouse transgenic TCR at the cell surface.

The human cell line of step (d) may be a Jurkat cell$^{-/-}$ line.

The terms "Jurkat$^{-/-}$" and "Jurkat76$^{-/-}$" refer to a human Jurkat76$^{-/-}$ cell line which is a variant of the original human TCL line that does not express human Vα and Vβ chains (Abraham R T, Weiss A., Nat Rev Immunol. 2004 April; 4(4):301-8). It has all remaining TCR-associated CD3 components necessary for transgenic TCR surface expression.

Another embodiment relates to a method for generating an antibody binding to a TCR of interest, the method comprising the following steps:

(a) providing a mouse BW cell line which expresses an exogenous form of the TCR of interest comprising at least one human segment;
(b) immunization of a non-human animal with the cell line provided in step (a);
(c) generation of hybridomas from the immunized non-human animal of step (b);
(d) screening for an antibody that binds to the surface protein of interest by contacting the antibodies secreted by the hybridomas of step (c) with Jurkat$^{-/-}$ cells which do not express the endogenous form of the TCR of interest but express an exogenous form of the TCR of interest comprising at least one human segment.

A further embodiment relates to a method for generating an antibody binding to a TCR of interest, the method comprising the following steps:
(a) providing a mouse BW$^{-/-}$ cell line which expresses an exogenous form of the TCR of interest comprising at least one human segment;
(b) immunization of a non-human animal with the cell line provided in step (a);
(c) generation of hybridomas from the immunized non-human animal of step (b);
(d) screening for an antibody that binds to the TCR of interest by contacting the antibodies secreted by the hybridomas of step (c) with a mixture of Jurkat$^{-/-}$ cells which do not express the endogenous form of the TCR of interest comprising:
(i) a first defined proportion of the mixture of Jurkat$^{-/-}$ cells which expresses the TCR of interest; and
(ii) a second defined proportion of the mixture of Jurkat$^{-/-}$ cells which does not express a functional TCR of interest and which comprises a selection marker.

An additional embodiment relates to a method for generating an antibody binding to a TCR of interest, the method comprising the following steps:
(a) providing a mouse BW$^{-/-}$ cell line which expresses an exogenous form of the TCR of interest comprising at least one human segment;
(b) immunization of a rat with the cell line provided in step (a);
(c) generation of hybridomas from the rat of step (b);
(d) screening for an antibody that binds to the TCR of interest by contacting the antibodies secreted by the hybridomas of step (c) with a mixture of Jurkat$^{-/-}$ cells which do not express the endogenous form of the TCR of interest comprising:
(i) a first defined proportion of the mixture of Jurkat$^{-/-}$ cells which expresses the TCR of interest; and
(ii) a second defined proportion of the mixture of Jurkat$^{-/-}$ cells which does not express a TCR of interest and which comprises a selection marker.

An additional embodiment relates to a method for generating an antibody binding to a TCR of interest, the method comprising the following steps:
(a) providing a mouse cell which does not express the endogenous form of the TCR of interest but expresses an exogenous form of the TCR of interest comprising at least one human segment;
(b) immunization of a rat with the cell line provided in step (a);
(c) generation of hybridomas from the rat of step (b);
(d) screening for an antibody that binds to the surface protein of interest by contacting the antibodies secreted by the hybridomas of step (c) with a mixture with human cells which do not express the endogenous form of the TCR of interest comprising:
(i) a first defined proportion of the mixture of human cells which expresses the TCR of interest; and
(ii) a second defined proportion of the mixture of human cells which does not express TCR of interest and which comprises a selection marker.

In a specific embodiment the invention refers to a method for generating an antibody that binds to at least one TCR Vα chain or binds to at least one TCR Vβ chain, the method comprising the following steps:
(a) providing a non-human cell which does neither express the endogenous TCR α chain nor the endogenous TCR β chain and expresses an exogenous TCR α chain and an exogenous TCR β chain comprising a variable human TCR V a chain and variable human TCR β chain;
(b) immunization of a non-human animal with the cell line provided in step (a);
(c) generation of hybridomas from the immunized non-human animal of step (b);
(d) screening for an antibody that binds to at least one TCR Vα chain or binds to at least one TCR Vβ chain by contacting the antibodies secreted by the hybridomas of step (c) with a mixture of human cells which express neither the endogenous TCR α chain nor the endogenous TCR β chain comprising:
  (i) a first defined proportion of the mixture of human cells which comprises the TCR having the TCR chains that are expressed by the non-human cell provided in step (a),
  (ii) a second defined proportion of the mixture of human cells which does not comprise a TCR having TCR chains that are expressed by the non-human cell line provided in step (a) but comprises a TCR having TCR chains that are different to the TCR chains expressed by the non-human cell provided in step (a), and
  (iii) a third defined proportion of the mixture of human cells which does not comprise a functional TCR but comprises a selection marker.

In a specific embodiment the invention refers to a method for generating an antibody that binds to at least one T cell receptor variable alpha (TCR Vα) chain or binds to at least one T cell receptor variable beta (TCR Vβ) chain, the method comprising the following steps:
(a) providing a non-human cell which does neither express the endogenous TCR α chain nor the endogenous TCR β chain and expresses an exogenous TCR α chain and an exogenous TCR β chain comprising a variable human TCR V a chain and variable human TCR β chain;
(b) immunization of a non-human animal with the cell line provided in step (a);
(c) generation of hybridomas from the immunized non-human animal of step (b);
(d) screening for an antibody that binds to at least one TCR Vα chain or binds to at least one TCR Vβ chain by contacting the antibodies secreted by the hybridomas of step (c) with a mixture of human cells which express neither the endogenous TCR α chain nor the endogenous TCR β chain comprising:
  (i) a first defined proportion of the mixture of human cells which comprises the TCR having the TCR chains that are expressed by the non-human cell provided in step (a),
  (ii) a second defined proportion of the mixture of human cells which does not comprise a TCR having TCR chains that are expressed by the non-human cell line provided in step (a) but comprises a TCR having TCR chains that are different to the TCR chains expressed by the non-human cell provided in step (a), and (iii) a third defined proportion of the mixture of human cells which does not comprise a functional TCR but comprises a selection marker;

wherein the non-human animal is mouse or rat and the non-human cell provided in step (a) is a mouse cell line.

Certain embodiments comprise a step of identifying an antibody that binds to a fraction of TCR Vα chains comprising at least two different TCR Vα chains but less than all TCR Vα chains or that binds to a fraction of TCR Vβ chains comprising at least two different TCR Vβ chains but less than all TCR Vβ chains, comprising the following steps:
(i) incubating human peripheral blood lymphocytes (PBL) with the antibody identified in step (d) as binding to at least one TCR Vα chain or binding to at least one TCR Vβ chain;
(ii) screening for cells that bind to the antibody by FACS sorting;
(iii) analysis of the TCR Vα chain repertoire or TCR Vβ chain repertoire of the cells that bind to the antibody of step (ii);
wherein a TCR Vα chain repertoire or TCR Vβ chain repertoire comprising at least two different TCR Vα chains but less than all TCR Vα chains or at least two different TCR Vβ chains but less than all TCR Vβ chains indicates that the antibody binds to a fraction of TCR Vα chains comprising at least two different TCR Vα chains but less than all TCR Vα chains or that binds to a fraction of TCR Vβ chains comprising at least two different TCR Vβ chains but less than all TCR Vβ chains.

For example, one embodiment the invention refers to a method for generating an antibody that binds to a fraction of TCR Vα chains comprising at least two different TCR Vα chains but less than all TCR Vα chains or that binds to a fraction of TCR Vβ chains comprising at least two different TCR Vβ chains but less than all TCR Vβ chains, the method comprising the following steps:
(a) providing a non-human cell which does neither express the endogenous TCR α chain nor the endogenous TCR β chain but expresses an exogenous TCR α chain comprising a variable human TCR V a chain and an exogenous TCR β chain comprising a variable human TCR β chain;
(b) immunization of a non-human animal with the cell line provided in step (a);
(c) generation of hybridomas from the immunized non-human animal of step (b);
(d) screening for an antibody that binds to at least one TCR Vα chain or binds to at least one TCR Vβ chain by contacting the antibodies secreted by the hybridomas of step (c) with a mixture of human cells which express neither the endogenous TCR α chain nor the endogenous TCR β chain comprising:
(i) a first defined proportion of the mixture of human cells which comprises the TCR having the TCR chains that are expressed by the non-human cell provided in step (a),
(ii) a second defined proportion of the mixture of human cells which does not comprise a TCR having TCR chains that are expressed by the non-human cell line provided in step (a) but comprises a TCR having TCR chains that are different to the TCR chains expressed by the non-human cell provided in step (a), and
(iii) a third defined proportion of the mixture of human cells which does not comprise a functional TCR but comprises a selection marker;
wherein the non-human animal is mouse or rat and the non-human cell provided in step (a) is a mouse cell line.
(e) identifying an antibody that binds to a fraction of TCR Vα chains comprising at least two different TCR Vα chains but less than all TCR Vα chains or that binds to a fraction of TCR chains comprising at least two different TCR Vβ chains but less than all TCR Vβ chains, comprising the following steps:
(i) incubating human peripheral blood lymphocytes (PBL) with the antibody identified in step (d) as binding to at least one TCR Vα chain or binding to at least one TCR chain;
(ii) screening for cells that bind to the antibody by FACS sorting;
(iii) analysis of the TCR Vα chain repertoire or TCR Vβ chain repertoire of the cells that bind to the antibody of step (ii);
wherein a TCR Vα chain repertoire or TCR Vβ chain repertoire comprising different TCR Vα chains but less than all TCR Vα chains or at least two different TCR chains but less than all TCR Vβ chains indicates that the antibody binds to a fraction of TCR Vα chains comprising at least two different TCR Vα chains but less than all TCR Vα chains or that binds to a fraction of TCR Vβ chains comprising at least two different TCR Vβ chains but less than all TCR Vβ chains.

Another embodiment of the invention refers to a method for generating an antibody that binds to a fraction of TCR Vα chains comprising at least two different TCR Vα chains but less than all TCR Vα chains or that binds to a fraction of TCR Vβ chains comprising at least two different TCR Vβ chains but less than all TCR Vβ chains, the method comprising the following steps:
(a) providing a mouse cell which does neither express the endogenous TCR α chain nor the endogenous TCR β chain but expresses an exogenous TCR α chain comprising a variable human TCR V a chain and an exogenous TCR β chain comprising a variable human TCR β chain;
(b) immunization of a rat with the cell line provided in step (a);
(c) generation of hybridomas from the immunized rat of step (b);
(d) screening for an antibody that binds to at least one TCR Vα chain or binds to at least one TCR Vβ chain by contacting the antibodies secreted by the hybridomas of step (c) with a mixture of human cells which express neither the endogenous TCR α chain nor the endogenous TCR β chain comprising:
(i) a first defined proportion of the mixture of human cells which comprises the TCR having the TCR chains that are expressed by the non-human cell provided in step (a),
(ii) a second defined proportion of the mixture of human cells which does not comprise a TCR having TCR chains that are expressed by the non-human cell line provided in step (a) but comprises a TCR having TCR chains that are different to the TCR chains expressed by the non-human cell provided in step (a), and
(iii) a third defined proportion of the mixture of human cells which does not comprise a functional TCR but comprises a selection marker;
wherein the non-human animal is mouse or rat and the non-human cell provided in step (a) is a mouse cell line.
(e) identifying an antibody that binds to a fraction of TCR Vα chains comprising at least two different TCR Vα chains but less than all TCR Vα chains or that binds to a fraction of TCR chains comprising at least two different TCR Vβ chains but less than all TCR Vβ chains, comprising the following steps:

(i) incubating human peripheral blood lymphocytes (PBL) with the antibody identified in step (d) as binding to at least one TCR Vα chain or binding to at least one TCR chain;
(ii) screening for cells that bind to the antibody by FACS sorting;
(iii) analysis of the TCR Vα chain repertoire or TCR Vβ chain repertoire of the cells that bind to the antibody of step (ii);
wherein a TCR Vα chain repertoire or TCR Vβ chain repertoire comprising different TCR Vα chains but less than all TCR Vα chains or at least two different TCR chains but less than all TCR Vβ chains indicates that the antibody binds to a fraction of TCR Vα chains comprising at least two different TCR Vα chains but less than all TCR Vα chains or that binds to a fraction of TCR Vβ chains comprising at least two different TCR Vβ chains but less than all TCR Vβ chains.

The analysis of the TCR Vα chain repertoire or TCR Vβ chain repertoire may be carried out for example by PCR or by next generation sequencing methods. Methods for identifying the sequence of a nucleic acid are well known to those skilled in the art.

TCR Library

In a further aspect the present application is concerned with a library for the expression of all functional TCR types comprising 45 TCR constructs each encoding one of the 45 different TCR α chains and 47 TCR constructs each encoding one of the 47 different TCR β chains, wherein each of the 45 TCR constructs encoding one of 45 different TCR α chain comprises the following building blocks:
one of the variable AV1 to AV45 segments, and
a constant AC segment; and
wherein each of the 47 TCR constructs encoding one of 47 different TCR β chains comprises the following building blocks:
one of the variable BV1 to BV47 segments, and
a constant BC segment.

Certain embodiments refer to a library for the expression of all functional TCR types comprising 45 TCR constructs each encoding one of the 45 different TCR α chains and 47 TCR constructs each encoding one of the 47 different TCR β chains, wherein each of the 45 TCR constructs encoding one of 45 different TCR α chain comprises the following building blocks:
(i) one of the variable AV1 to AV45 segments;
(ii) a linker sequence specific for the A segment; and
(iii) a constant AC segment; and
wherein each of the 47 TCR constructs encoding one of 47 different TCR β chains comprises:
(i) one of the variable BV1 to BV47 segments,
(ii) a linker sequence specific for the B segment, and
(iii) a constant BC segment.

The term "functional TCR types" refers to TCRs that are composed of TCR variable chains that are expressed on T cells. A "TCR receptor construct" refers to a nucleic acid sequence that encodes a TCR α chain or a TCR β chain.

The term "building block" as used herein refers to the elements of the TCR library and the expression system for expressing TCRs, such as the variable AV and AB segments, the constant AC and BC segments, the linker sequences and the backbone vectors.

The linker sequence specific for the A segment may be any sequence that will be considered by the skilled person in the art as useful for linking a variable AV segment with the constant AC segment. The linker may contain sequences that are useful for the recombination, such as, without limitation, one or several restriction sites or may contain sequences useful for modifying the TCR construct via cloning. Further, the linker may contain any AJ and or CDR3 sequence, so that the construct consisting of the (i) one variable AV segment, (ii) a linker sequence specific for the A segment and (iii) a constant AC segment encodes a functional TCR α chain. In a specific embodiment the linker sequence has a sequence which is at least 90% identical to the sequence set forth in SEQ ID No: 192 or which is at least 90% identical to the sequence set forth in SEQ ID No: 194. In a more specific embodiment the linker sequence has a sequence which set forth in SEQ ID No: 192 and in SEQ ID No: 194.

The linker sequence specific for the B segment may be any sequence that will be considered by the skilled person in the art as useful for linking a variable BV segment with the constant BC segment. The linker may contain one or several restriction sites or may contain sequences useful for modifying the TCR construct via cloning. Further, the linker may contain any BD, BJ and/or
CDR3 sequence, so that the construct consisting of the (i) one variable BV segment, (ii) a linker sequence specific for the B segment and (iii) a constant BC segment encodes a functional TCR β chain. In a specific embodiment the linker sequence has a sequence which is at least 90% identical to the sequence set forth in SEQ ID No: 193 or which is at least 90% identical to the sequence set forth in SEQ ID No: 195. In a more specific embodiment the linker sequence has a sequence which set forth in SEQ ID No: 193 and in SEQ ID No: 195.

The AC segment and the BC segment may be murine, minimal-murinized, cysteine-engineered or wild-type human or a combination thereof.

These modifications may improve pairing of the TCR α and TCR β chain. "cysteine-engineered" AC and BC segments encode for mutations of single amino acids to cysteines in each TCR chain and lead to formation of an additional disulfide bond connecting the C regions of the TCR α and TCR β chain (Cohen, C. J., Li, Y. F., El-Gamil, M., Robbins, P. F., Rosenberg, S. a, & Morgan, R. a. (2007), *Cancer Research,* 67(8), 3898-903.). This reduces mixed TCR pairing and enhances the functionality of TCR gene-modified T cells. Therefore, human TCRs are equipped with murine C regions lead to a more stable expression of the TCRs, this so called "murinization" increases the cell surface expression of these hybrid TCRs compared with wild-type (wt) human TCRs and results in a higher functional avidity of T cells modified with different TCRs (Cohen, C. J., Zhao, Y., Zheng, Z., Rosenberg, S. a, & Morgan, R. a. (2006). Cancer Research, 66(17), 8878-86). Alternatively the AC and the BC segments can be minimal-murinized, i.e. the critical amino acids within the C regions of the murine TCR α and β chain that ensure TCR cell surface expression comparable to full replacement of human C regions are exchanged (Sommermeyer, D., & Uckert, W. (2010); *Journal of Immunology* (Baltimore, Md.: 1950), 184(11), 6223-31.). See also FIG. 8. In a preferred embodiment, the AC segment and the BC segment are murine or human.

In another embodiment the variable AV segments and variable BV segments are human or murine. In a preferred embodiment the variable AV segments and variable BV segments are human. In an even more preferred embodiment the AC segment and the BC segment are murine and the variable AV segments and variable BV segments are human.

In particular, if the TCRs are used for non-therapeutic use, such as the generation of TCR specific antibodies, it is advantageous that the AC segment and the BC segment be murine and the variable AV segments and variable BV segments be human.

In another preferred embodiment the AC segment and the BC segment are human and the variable AV segments and the variable BV segments are human.

In particular, if the TCRs that are produced by the library as described herein are used for therapy, it is advantageous that the AC segment and the BC segment be human and the variable AV segments and the variable BV segments be human.

The sequence of the TCR constructs may be modified, e.g., without limitation, it may be codon optimized or further restriction sites may be inserted for example by exchange of nucleotides. In preferred embodiments, the sequence of the TCR constructs is codon optimized for the expression in mammalian cells, preferably in human cells. Alternatively the sequence of the TCR construct may not be modified.

For example, SEQ ID No: 1 is a modified version of nucleotide sequence SEQ ID No: 2 encoding the human constant α region, since SEQ ID No: 1 further contains a DraIII restriction site. Another example is SEQ ID No: 4 which is a modified version of nucleotide sequence SEQ ID No: 5 encoding the human constant β region, as it further contains a BstEII restriction site.

The building blocks of the TCR construct are constructed so that they can be easily exchanged, e.g. by a single cloning step. That means that the elements contain combination sites that are compatible, i.e. all AV segments comprise combination sites at the 5'-end that can be combined with the combination sites of the 3'-end of the backbone vectors and further comprise combination sites at their 3'-end that can be combined with the linker sequence specific for the A segment. In addition, all AC segments comprise combination sites at their 5'-end that can be combined with the linker sequence specific for the A segment and further comprise combination sites at their 3'-end that can be combined with the 5'-end of the backbone vector. Thus, the linker sequences specific for the A segment comprise combination sites at their 5'-end that can be combined with the combination site of the 3'-end of the AV segments and further comprise combination sites at their 3'-end that can be combined with the combination site of the 5'-end of the AC segments. Further, all BV segments comprise combination sites at the 5'-end that can be combined with the combination site of the 3'-end of the backbone vectors and further comprise combination sites at their 3'-end that can be combined with the linker sequence specific for the B segment. In addition, all BC segments comprise combination sites at their 5'-end that can be combined with the linker sequence specific for the B segment and further comprise combination sites at their 3'-end that can be combined with the 5'-end of the backbone vector. Thus, the linker sequences specific for the B segment comprise combination sites at their 5'-end that can be combined with the combination site of the 3'-end of the BV segments and further comprise combination sites at their 3'-end that can be combined with the combination site of the 5'-end of the BC segments.

The term "combination site" as used herein refers to any sequence that is useful for cloning in order to exchange sequences in a vector, such as, without limitation, restriction sites, recombination sequences or homology regions for seamless cloning techniques.

For example, all AV segments comprise restriction sites at the 5'-end that can be combined with the restriction site of the 3'-end of the backbone vectors and further comprise restriction sites at their 3'-end that can be combined with the linker sequence specific for the A segment. In addition, all AC segments comprise restriction sites at their 5'-end that can be combined with the linker sequence specific for the A segment and further comprise restriction sites at their 3'-end that can be combined with the 5'-end of the backbone vector. Thus, the linker sequences specific for the A segment comprise restriction sites at their 5'-end that can be combined with the restriction site of the 3'-end of the AV segments and further comprise restriction sites at their 3'-end that can be combined with the restriction site of the 5'-end of the AC segments.

Further, all BV segments comprise restriction sites at the 5'-end that can be combined with the restriction site of the 3'-end of the backbone vectors and further comprise restriction sites at their 3'-end that can be combined with the linker sequence specific for the B segment. In addition, all BC segments comprise restriction sites at their 5'-end that can be combined with the linker sequence specific for the B segment and further comprise restriction sites at their 3'-end that can be combined with the 5'-end of the backbone vector. Thus, the linker sequences specific for the B segment comprise restriction sites at their 5'-end that can be combined with the restriction site of the 3'-end of the BV segments and further comprise restriction sites at their 3'-end that can be combined with the restriction site of the 5'-end of the BC segments.

In certain embodiments the library may contain AV segments of different types, such as murine, minimal-murinized, cysteine-engineered or wild-type human, which comprise the same restriction sites at their 3'-end and their 5'-end, so that they can be easily exchanged. Accordingly, the library may contain BV segments of different types, such as murine, minimal-murinized, cysteine-engineered or wild-type human which comprise the same restriction sites at their 3'-end and their 5'-end, so that they can be easily exchanged.

In certain embodiments the library may contain AC segments of different types, such as murine, minimal-murinized, cysteine-engineered or wild-type human, which comprise the same restriction sites at their 3'-end and their 5'-end, so that they can be easily exchanged. Accordingly, the library may contain BC segments of different types, such as murine, minimal-murinized, cysteine-engineered or wild-type human which comprise the same restriction sites at their 3'-end and their 5'-end, so that they can be easily exchanged.

In certain embodiments, the variable AV segment is preceded by a NotI and/or AgeI restriction site and followed by a FspI restriction site.

In certain embodiments, the linker sequence specific for the A segment is preceded by a FspI restriction site and followed by a DraIII restriction site. In certain embodiments, the linker sequence specific for the A segment is preceded by a FspI restriction site and followed by a BspEI and/or a DraIII restriction site.

In certain embodiments, the linker sequence specific for the A segment is preceded by a FspI restriction site and followed by a BspEI restriction site.

In certain embodiments, the constant AC segment is preceded by a BspEI and/or DraIII restriction site and followed by MluI and/or ClaI and/or EcoRI restriction site.

In certain embodiments, the constant AC segment is preceded by a BspEI restriction site and followed by MluI and/or ClaI and/or EcoRI restriction site.

In specific embodiments, the variable AV segment is preceded by a NotI and/or AgeI restriction site and followed by a FspI restriction site. The linker sequence specific for the A segment is preceded by a FspI restriction site and followed by a BspEI and/or a DraIII restriction site. The constant AC segment is preceded by a BspEI and/or DraIII restriction site and followed by MluI and/or ClaI and/or EcoRI restriction site.

In certain embodiments, the variable BV segment is preceded by a NotI and/or AgeI restriction site and followed by a FspI restriction site.

In certain embodiments, the linker sequence specific for the B segment is preceded by a FspI restriction site and followed by a BstEII restriction site.

In certain embodiments, the constant BC segment is preceded by a BspEII restriction site and followed by MluI, ClaI and EcoRI restriction site.

In certain embodiments, the constant BC segment is preceded by a BspEII restriction site and followed by a EcoRI restriction site.

In specific embodiments, the variable BV segment is preceded by a NotI and/or AgeI restriction site and followed by a FspI restriction site. The linker sequence specific for the B segment is preceded by a FspI restriction site and followed by a BstEII restriction site. The constant BC segment is preceded by a BspEII restriction site and followed by MluI, ClaI and EcoRI restriction site.

Therefore, the variable segment, the linker sequence and the C segment can be replaced in a single cloning step. In addition the unique design of the restriction sites of the TCR constructs and the backbone vectors allows not only efficient exchange of the variable and the constant chains of the TCR and its CDR3 regions but also facilitates easy switching between the vectors for ivtRNA production and/or viral transfection.

A specific embodiment thus relates to a library for the expression of all functional TCR types comprising 45 TCR constructs, each encoding one of the 45 different TCR α chains and 47 TCR constructs each encoding one of the 47 different TCR β chains, wherein each of the 45 TCR constructs, encoding one of 45 different TCR α chain comprises:
  (i) one of the variable AV1 to AV45 segments comprising a NotI and/or AgeI restriction site at the 5'-end and a FspI restriction site at the 3'-end
  (ii) a linker sequence specific for the A segment comprising a FspI restriction site at the 5'-end a BspEI restriction site at the 3' end, and
  (iii) a constant AC segment comprising a BspEI and/or a DraIII restriction site at the 5'-end and a MluI and/or ClaI and/or EcoRI restriction site at the 3'-end; and
wherein each of the 47 TCR constructs encoding one of 47 different TCR β chains comprises:
  (i) one of the variable BV1 to BV47 segments comprising a NotI and/or AgeI restriction site at the 5'-end and a FspI-restriction site at the 3'-end,
  (ii) a linker sequence specific for the B segment comprising a FspI restriction site at the 5'-end and a BstEII restriction site at the 3'-end, and
  (iii) a constant BC segment comprising a BspEII restriction site at the 5'-end and followed by MluI, ClaI and EcoRI restriction site at the 3' end.

Accordingly in the expression systems for the expression of TCRs described herein the backbone vectors comprise compatible combination sites for the introduction of the library constructs. In a specific embodiment, the expression systems for the expression of TCRs described herein the backbone vectors comprise compatible restriction sites for the introduction of the library constructs.

For example, the AC segment may have a sequence which is at least 90% identical to the sequences set forth in SEQ ID NOs: 1, 2 or 6 and the BC segment may have a sequence which is at least 90% identical to the sequences set forth in SEQ ID NOs: 3, 4, 5 or 7. Particularly, the AC segment may have a sequence which is set forth in SEQ ID Nos: 1, 2 or 6 and the BC segment may have a sequence which is set forth in SEQ ID Nos: 3, 4, 5 or 7.

The variable AV segments AVseg1 to AVseg45 may have sequences which are at least 90% identical to the sequences set forth in SEQ ID No: 8 to SEQ ID No: 52 and the variable BV segments BV1 to BV47 segments may have sequences which are at least 90% identical to the sequences set forth in SEQ ID No: 53 to SEQ ID No: 99. In particular, the variable AV1 to AV45 segments may have sequences which are set forth in SEQ ID No: 8 to SEQ ID No: 52 and the variable BV1 to BV47 segments may have sequences which are set forth in SEQ ID No: 53 to SEQ ID No: 99.

The TCR constructs are integrated into at least one backbone vector.

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome. Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. The backbone vector may be a circular or linear nucleic acid molecule to which an insert sequence can be integrated so as to bring about replication of the insert sequence. The vector may comprise any of a number of vector elements, such as those described below. The vector may be produced using a combination of in vitro and in vivo methods such as those described in Sambrook, J., et al., "Molecular Cloning: A Laboratory Manual," which is incorporated herein by reference. Representative examples of vectors include, but are not limited to, in vitro transcription mRNA (ivtRNA) backbone vectors, transposon vectors (e.g. sleeping beauty transposon system), adenoviral backbone vectors, retroviral backbone vectors, lentiviral backbone vectors including next generation SIN retroviral or lentiviral vectors.

The vector may also comprise an insert site, which may be used to clone a nucleic acid. The insert site may be the recognition site of an endonuclease such as a Type I, II or III restriction enzyme, a homing endonuclease, or a nicking enzyme. The insert site may also be a specific site for homologous recombination. The insert site may be present in the vector only at the insert site. In certain circumstances, it may be desirable to remove other insert sites from the vector. For example, when the insert site is the recognition site for a restriction enzyme, it may be desirable to remove other such recognition sites from the chromosome.

Representative examples of Type I restriction enzymes include, but are not limited to, CfrAI, Eco377I, Eco394I, Eco585I, Eco646I, Eco777I, Eco826I, Eco851I, Eco912I, EcoAI, EcoBI, EcoDI, EcoDR2, EcoDR3, EcoDXXI, EcoEI, EcoKI, EcoprrI, EcoR124I, EcoR124II, EcoRD2, EcoRD3, HindI, KpnAI, KpnBI, NgoAV, StyLTIII, StySBLI, StySEAI, StySGI, StySJI, StySKI, StySPI and StySQI. Representative examples of Type III restriction enzymes include, but are not limited to, EcoP15I, EcoPI, HinfIII and StyLTI. Representative examples of Type II restriction enzymes include, but are not limited to, AarI, AatII, AccI, AceIII, AciI, AclI, AcyI, AflII, AflIII, AgeI, AhaIII, AjuI, AlfI, AloI, AluI, AlwFI, AlwNI, ApaBI, ApaI, ApaLI, ApoI, AscI, AspCNI, AsuI, AsuII, AvaI, AvaiI, AvaIII, AvrII, BaeI, BalI, BamHI, BbvCI, BbvI, BbvII, BccI, Bce83I, BcefI, BcgI, BciVI, BelI, BdaI, BetI, BfiI, BglI, BglII, BinI, BmgI, BplI, Bpul0I, BsaAI, BsaBI, BsaXI, BsbI, BscGI, BseMII, BsePI, BseRI, BseSI, BseYI, BsgI, BsiI, BsiYI, BsmAI, BsmI, Bsp14071, Bsp24I, BspGI, BspHI, BspLU11I, BspMI, BspMII, BspNCI, BsrBI, BsrDI, BsrI, BstEII, BstXI, BtgZI, BtrI, BtsI, Cac8I, CauII, CdiI, Cfr10I, CfrI, CjeI, CjeNII, CjePI, ClaI, CspCI, CstMI, CviJI, CviRI, DdeI, DpnI, DraII, DraIII, DrdI, DrdII, DsaI, Eam1105I, EciI, Eco31I, Eco47III, Eco57I, Eco57MI, EcoNI, EcoRI, EcoRII, EcoRV, Esp3I, EspI, FalI, FauI, FinI, Fnu4HI, FnuDII, FokI, FseI, FspI, GdiII, GsuI, HaeI, HaeII, HaeIII, HaeIV, HgaI, HgiAI, HgiCI, HgiEII, HgiJII, HhaI, Hin4I, Hin4II, HindII, HindIII, HinfI, HpaI, HpaII, HphI, Hpyl78III, Hpyl88I, Hpy99I, KpnI, Ksp632I, MaeI, MaeII, MaeIII, MboI, MboII, McrI, MfeI, MjaIV, MluI, MmeI, MnlI, MseI, Ms1I, MstI, MwoI, NaeI, NarI, NcoI, NdeI, NheI, NlaIII, NlaIV, NotI, NruI, NspBII, NspI, OliI, Pad, PasI, Pfl1108I, PflMI, PfoI, PleI, PmaCI, PmeI, PpiI, PpuMI, PshAI, PsiI, PspXI, PsrI, PstI, PvuI, PvuII, RleAI, RsaI, RsrII, SacI, SacII, SalI, SanDI, SapI, SauI, Scd, ScrFI, SduI, SecI, SexAI, SfaNI, SfeI, SfiI, SgfI, SgrAI, SgrDI, SimI, SmaI, SmlI, SnaBI, SnaI, SpeI, SphI, SplI, SrfI, Sse232I, Sse8387I, Sse8647I, SsmI, SspI, Sth132I, StuI, StyI, SwaI, TaqI, TaqII, TatI, TauI, TfiI, TseI, TsoI, Tsp45I, Tsp4CI, TspDTI, TspEI, TspGWI, TspRI, TssI, TstI, TsuI, Tth111I, Tth111II, UbaF10I, UbaF9I, UbaPI, VspI, XbaI, XcmI, XhoI, XhoII, XmaIII and XmnI. Representative examples of homing endonucleases include, but are not limited to, F-SceI, F-SceII, F-SuvI, F-TevI, F-TevII, F-TflI, F-TflIII, F-TflIV (also known as HegA), H-DreI, I-AmaI, I-AniI, I-BasI, I-BmoI, I-CeuI, I-CeuAIIP, I-ChuI, I-CmoeI, I-CpaI, I-CpaII, I-CreI, I-CrepsbIP, I-CrepsbIIP, I-CrepsbIIIP, I-CrepsbIVP, I-CsmI, I-CvuI, I-CvuAIP, I-DdiI, I-DirI, I-DmoI, I-HmuI, I-HspNIP, I-LlaI, I-MsoI, I-NaaI, I-NanI, I-NclIP, I-NgrIP, I-NitI, I-NjaI, I-Nsp236IP, I-PakI, I-PbolP, I-PculP, I-PcuAI, I-PcuVI, I-PgrIP, I-PobIP, I-PogI, I-PorI, I-PorIIP, I-PpbIP, I-PpoI, I-ScaI, I-SceI, I-SceII, I-SceIII, I-SceIV, I-SceV, I-SceVI, I-SceVII, I-SneIP, I-SpomI, I-SquIP, I-Ssp6803I, I-SthPhiJP, I-SthPhiST3P, I-SthPhiS3bP, I-TevI, I-TevII, I-TevIII, I-Tsp061I, I-TwoI, I-UarHGPA1P, I-VinIP, I-ZbiIP, PI-MgaI, PI-MtuI, PI-MtuHIP, PI-MtuHIIP, PI-PabI, PI-PabII, PI-PfuI, PI-PfuII, PI-PkoI, PI-PkoII, PI-PspI, PI-Rma43812IP, PI-ScaI, PI-SceI, PI-TfuI, PI-TfuII, PI-ThyI, PI-TliI, PI-TliII and PI-ZbaI. Other possible types of endonucleases are enzymes characterized by the complexity of their recognition sites. A representative example of such an enzyme is FseI.

The vector may comprise a plurality of insert sites and the insert sites may be clustered as part of a multiple cloning site. The vector may also comprise more than one multiple cloning sites, which may be identical.

The constructs may be integrated into the backbone vectors by the cloning techniques known to the skilled person. These include use of Type I, Type II, Type IIS and Type IIG restriction enzyme based cloning approaches, use of recombination based cloning approaches such as Gateway® cloning (Life technologies, ThermoFisher), use of homology based cloning approaches such as Gibson Assembly® (NEB), GeneArt® (Life technologies, ThermoFisher) or In-Fusion® system (Clonetech) seamless cloning.

In a particular embodiment the backbone is an ivtRNA backbone vector or retroviral backbone vector.

The term "ivtRNA backbone vector" refers to any vector that can be used for in vitro transcription of RNA. ivtRNA backbone vectors contemplated for use in the invention include those comprising at a T7, a T3 and/or a sp6 promotor. Such vectors are well known to ordinary skill in the art. In one embodiment the ivtRNA backbone vector comprises a T7 and/or a sp6 promotor. Further the ivtRNA backbone vector may comprise at least one RNA stabilizing sequence, such as, without limitation a poly-adenine tail. The poly-adenine tails may comprise at least 40 adenines, at least 60 adenines, at least 80 adenines, at least 90 adenines, at least 100 adenines, at least 110 adenines.

As used herein, the term "retroviral backbone vector" refers to any vector that can be used for integration of a desired DNA construct into the host genome of a eukaryotic cell. The skilled person is aware of such vectors. A non-limiting example of a vector contemplated for use in the present invention is the MP71 retroviral backbone vector (Schambach A, Wodrich H, Hildinger M, Bohne J, Krausslich H G, Baum C., Mol Ther. 2000 November; 2(5):435-45; Hildinger M, Abel K L, Ostertag W, Baum C., J Virol. 1999 May; 73(5):4083-9). Receiver plasmids (pR) containing candidate DNA constructs are used for virus production. Retroviruses carrying the transgenes are subsequently utilized for transduction of target cells. Transduced cells permanently expressing the transgenic protein can easily be produced in large numbers. The skilled person is aware that a retroviral backbone vector may comprise elements such as long terminal repeat (LTR) sequences. The design of retroviral backbone vectors is known to those of ordinary skill in the art and is described in the pertinent texts and literature (e.g. "Retroviruses", Coffin J M, et al. eds.; 1997).

Preferably, the replacement of the linker sequence specific for the A segment by a CDR3A sequence and AJ sequence results in a construct encoding a functional TCR α chain and replacement of the linker sequence specific for the A segment by a CDR3B sequence, a BD and BJ region results in a construct encoding a functional TCR β chain.

In a preferred embodiment, the CDR3A sequence and the AJ sequences, the CDR3 sequence, the BD and BJ region are contained in an oligonucleotide. Thereby, the library described herein allows the efficient generation of TCRs of any specificity by the insertion of any CDR3 region via an oligonucleotide.

In certain embodiments, the ivtRNA backbone vector has a sequence which is at least 90% identical to the sequence set forth in SEQ ID No: 196. In particular embodiments, the ivtRNA backbone vector has a sequence which is set forth in SEQ ID No: 196. In other embodiments, the retroviral backbone vector has a sequence which is at least 90% identical to the sequence set forth in SEQ ID No: 200. In particular embodiments, the retroviral backbone vector has a sequence which is set forth in SEQ ID No: 200.

Preferably, in the TCR construct encoding one TCR α chain and one TCR β chain, the sequence encoding one TCR α chain and the sequence encoding one TCR β chain are linked by elements that allow the expression of more than one protein from a vector. Such exemplary elements include without limitation internal ribosome entry sites (IRES) or ribosomal skipping elements. The ribosomal skipping element allows the stoichiometric production of the proteins that are encoded by the sequences flanking the element. The sequence prevents the ribosome form covalently linking a new inserted amino acid and let the ribosome continue translation resulting in a co-translational cleavage of the polyprotein. A preferred ribosomal skipping element is the P2A element.

Another aspect of the invention refers to an expression system for the expression of TCRs comprising
- a library comprising 45 TCR constructs each encoding one of the 45 different variable TCR α chains and 47 TCR constructs each encoding one of the 47 different variable TCR β chains,
- wherein each 45 TCR constructs encoding one of 45 different variable TCR α chain comprises:
  - (i) one of the variable AV segments AVseg1 to AVseg45;
  - (ii) a linker sequence specific for the A segment;
- wherein each 47 TCR constructs encoding one of 47 different variable TCR β chain comprises:
  - (i) one of the variable BV segments BVseg1 to BVseg47;
  - (ii) a linker sequence specific for the B segment; and
- at least one ivtRNA backbone vector selected from the group consisting of:
  - (i) ivtRNA backbone vector comprising a AC segment
  - (ii) ivtRNA backbone vector comprising a BC segment
  - (iii) ivtRNA backbone vector comprising a AC and a BC segment; and/or
- at least one retroviral backbone vector selected from the group consisting of:
  - (iv) retroviral backbone vector comprising a AC segment
  - (v) retroviral backbone vector comprising a BC segment
  - (vi) retroviral backbone vector comprising a AC and a BC segment.

In certain embodiments of the invention, the expression system as described above, further comprises at least one lentiviral backbone vector selected from the group consisting of:
- (vii) lentiviral backbone vector comprising a AC segment
- (viii) lentiviral backbone vector comprising a BC segment
- (ix) lentiviral backbone vector comprising a AC and a BC segment.

In certain embodiments, the ivtRNA backbone vector comprising a AC segment has a sequence which is at least 90% identical to the sequence set forth in SEQ ID NO: 197 and/or the ivtRNA backbone vector comprising a BC segment has a sequence which is at least 90% identical to the sequence set forth in SEQ ID NO: 198 and/or the ivtRNA backbone vector comprising a AC and a BC segment has a sequence which is at least 90% identical to the sequence set forth in SEQ ID NO: 199. In particular embodiments, the ivtRNA backbone vector comprising a AC segment has a sequence which is set forth in SEQ ID NO: 197 and/or the ivtRNA backbone vector comprising a BC segment has a sequence which is set forth in SEQ ID NO: 198 and/or the ivtRNA backbone vector comprising a AC and a BC segment has a sequence set forth in SEQ ID NO: 199.

In other embodiments, the retroviral backbone vector comprising a AC segment has a sequence which is at least 90% identical to the sequence set forth in SEQ ID No: 201 and/or the retroviral backbone vector comprising a BC segment has a sequence which is at least 90% identical to the sequence set forth in SEQ ID No: 202 and/or the retroviral backbone vector comprising a AC and a BC segment has a sequence which is at least 90% identical to the sequence set forth in SEQ ID No: 203. In particular embodiments, the retroviral backbone vector comprising a AC segment has a sequence which is set forth in SEQ ID No: 201 and/or the retroviral backbone vector comprising a BC segment has a sequence which is set forth in SEQ ID No: 202 and/or the retroviral backbone vector comprising a AC and a BC segment has a sequence set forth in SEQ ID No: 203.

An additional aspect of the invention refers to an expression system for the expression of TCRs comprising
- a library comprising 45 TCR constructs each encoding one of the 45 different variable TCR α chains and 47 TCR constructs each encoding one of the 47 different variable TCR β chains,
- wherein each of the 45 TCR constructs encoding one of 45 different variable TCR α chain comprises one of the variable AV segments AVseg 1 to AVseg 45;
- wherein each of the 47 TCR constructs encoding one of 47 different variable TCR β chain comprises one of the variable BV segments BVseg 1 to BVseg 47; and
- at least one ivtRNA backbone vector selected from the group consisting of:
  - (i) ivtRNA backbone vector comprising a AC segment and a linker sequence specific for the A segment,
  - (ii) ivtRNA backbone vector comprising a BC segment and a linker sequence specific for the B segment,
  - (iii) ivtRNA backbone vector comprising a AC segment, a linker sequence specific for the A segment, a BC segment and a linker sequence specific for the B segment, and/or
- at least one retroviral backbone vector selected from the group consisting of:
  - (iv) retroviral backbone vector comprising a AC segment and linker sequence specific for the A segment,
  - (v) retroviral backbone vector comprising a BC segment and linker sequence specific for the B segment,
  - (vi) retroviral backbone vector comprising a AC segment, a linker sequence specific for the A segment, a BC segment and a linker sequence specific for the B segment.

In one embodiment this expression system further comprises at least one lentiviral backbone vector selected from the group consisting of:
- (vii) lentiviral backbone vector comprising a AC segment,
- (viii) lentiviral backbone vector comprising a BC segment,
- (ix) lentiviral backbone vector comprising a AC and a BC segment.

The skilled person understands that the invention also contemplates expression systems as described above which comprise ivtRNA backbone vectors (i) to (iii) and retroviral backbone vectors (iv) to (vi). Further, it is clear that the above described expression systems may comprise ivtRNA backbone vectors (i) to (iii), retroviral backbone vectors (iv) to (vi) and lentiviral backbone vectors (vii) to (ix).

A further aspect relates to a library of cell clones expressing TCRs comprising a population of cell clones expressing 45 different TCR α chains and a population of cell clones expressing 47 different TCR β chains,
wherein each of the cell clones expressing different TCR α chains comprises one of the 45 TCR constructs encoding one of 45 different TCR α chains as described herein and one TCR construct encoding a TCR β chain; and
wherein each of the cell clones expressing different TCR β chains comprises one of the 47 TCR constructs encoding one of 47 different TCR β chains as described herein and one TCR construct encoding a TCR α chain.

Certain embodiments relate to a library of cell clones expressing TCRs comprising a population of cell clones expressing 45 different TCR α chains and a population of cell clones expressing 47 different TCR β chains, wherein each of the cell clones expressing different TCR α chains comprises one of the 45 TCR constructs encoding one of 45 different TCR α chains according to claim 1 and one TCR construct encoding a TCR β chain; and wherein each of the cell clones expressing different TCR β chains comprises one of the 47 TCR constructs encoding one of 47 different TCR β chains according to claim 1 and one TCR construct encoding a TCR α chain;

wherein the cell clones do neither express the endogenous TCR α chain nor the endogenous TCR β chain.

In certain embodiments the cell clones are of the BW$^{-/-}$ cell line and/or the Jurkat$^{-/-}$ cell line.

The term "BW$^{-/-}$ cell line" refers to a BW cell line, which was derived from the parental BW5147 thymoma that arose spontaneously in an AKR mouse (Lee N E and Davis M M., J Immunol. 1988 Mar. 1; 140(5):1665-75; Letourneur F., Malissen B., Eur J Immunol. 1989; 19(12):2269-2274) and does neither express the endogenous TCR α chain nor the endogenous TCR β chain. Since the surface expression of a TCR heterodimer is dependent on association with the CD3 protein complex the BW$^{-/-}$ cell line was stably transduced to co-express human CD3 with GFP (BW$^{-/-}$-CD3-GFP) (hereafter referred to simply as BW$^{-/-}$), enabling transduced cells to be easily identified. The presence of human CD3 allows these cells to express any human or mouse transgenic TCR at the cell surface after successful co-transduction with selected AV- and BV-encoding RVs.

The terms "Jurkat$^{-/-}$" and "Jurkat76$^{-/+}$" refer to a human Jurkat76$^{-/-}$ cell line which is a variant of the original human TCL line that does not express human Vα and Vβ chains (Abraham R T, Weiss A., Nat Rev Immunol. 2004 April; 4(4):301-8). It has all remaining TCR-associated CD3 components necessary for transgenic TCR surface expression, after transduction with appropriate RVs of choice.

A further aspect of the invention relates to a library of TCR proteins comprising a population of TCR proteins comprising 45 different TCR α chains and a population of TCR proteins 47 comprising 47 different TCR β chains, wherein each of the TCR proteins comprising different TCR α chains comprises one of the 45 different TCR α chains encoded by the TCR constructs according to claim 1 and a TCR β chains; and wherein each of the TCR proteins comprising different TCR β chains comprises one of the 47 different TCR β chains encoded by the TCR constructs according to claim 1 and a TCR α chains.

As already described, the TCR library can be used for the immunization of animals in order to generate polyclonal and monoclonal, preferably monoclonal antibodies. The TCR library can be used for the generation of pan-specific, cluster-specific and mono-specific antibodies. In a preferred embodiment, the TCR library can be used for the generation of cluster-specific antibodies. In particular, the library may be used for the immunization of animals for antibody production and the selection of TCR specific antibodies.

The library is constructed in a way that it can be specifically adapted to the needs of its application:

In particular, if the library is used for the generation of TCR-specific antibodies, a TCR construct coding for a TCR having mouse constant region, human variable regions and linker sequence may be used. More particular, if the library is used for the generation of TCR-specific antibodies, a TCR construct coding for a TCR having mouse constant region, human variable regions and a mouse linker sequence may be used. Preferably, the TCR construct is integrated into a retroviral backbone vector. Exemplary vectors that may be used for the generation of TCR-specific antibodies are shown in FIG. 10. FIG. 10A depicts a vector that may be used for the generation of an antibody specific for the human AV1-1 region. The sequence of this vector is set forth in SEQ ID NO: 204. An exemplary vector that may be used for the generation of an antibody specific for the human BV2 chain is shown in FIG. 10B and its sequence is set forth in SEQ ID NO: 205.

On the other hand, if the library is used for the construction of therapeutic TCRs, the TCR construct coding for a TCR having human constant regions and human variable regions is used and a CDR3 having the desired specificity is introduced by an oligonucleotide.

More specifically, for the production of the therapeutic TCR, the sequence of a candidate TCR is identified as described in detail in the section "Reengineering of an isolated TCR" for clone T1.8. Therefore, the specific sequence of the CDR3 region is sequenced. Further, the type of the variable region of the TCR α chain and of the variable region of the TCR β chain of the desired TCR is identified, either by PCR using primers specific for the variable TCR α chain and variable TCR β chain types, or by sequencing (For illustration, the sequence coding for the TCR α chain of the isolated T1.8 clone is set forth in SEQ ID No: 210 and the sequence coding for the TCR β chain of isolated clone T1.8 is depicted in SEQ ID No: 211). The TCR is then rebuilt by combining the AV and BV segments corresponding to the variable α chains and variable β chains identified for the desired TCR with the constant CA and CB segments respectively and replacing the linker sequence by the desired CDR 3 sequence using a synthesized oligonucleotide having this sequence. The sequences of the reengineered TCR are shown in FIG. 11. The vector map of the reengineered TCR α chain is shown in FIG. 11A and its sequence is depicted in SEQ ID No: 208. The vector map of the reengineered TCR β chain is shown in FIG. 11B and its sequence is depicted in SEQ ID No: 209.

The building blocks of the TCR library can also be generated by DNA synthesis. DNA synthesis methods are well known to skilled person in the art.

Further, the library as described herein can be used for synthetic display screens in order to generate antibodies such as phage display, yeast display, ribosomal display or cellular display screens. The skilled person in the art is aware of the diverse display screening techniques which include naive, immunized library and synthetic library.

The library as described herein can be used for the transient or stable expression of TCRs for their characterization and/or their use in therapy.

Another aspect of the application refers to a TCR receptor comprising a TCR α chain having a amino acid sequence which is at least 50%, at least 60%, at least 70%, at least 80%, at least 85%, at least 90%, at least 95%, at least 96%, at least 97%, at least 98%, at least 99% identical to SEQ ID No: 249 and a TCR β chain having an amino acid sequence which is at least 50%, at least 60%, at least 70%, at least 80%, at least 85%, at least 90%, at least 95%, at least 96%, at least 97%, at least 98%, at least 99% identical to SEQ ID No: 250.

Certain embodiments relate to a TCR receptor comprising a TCR α chain having the amino acid sequence of SEQ ID No: 249 and a TCR β chain comprising the amino acid sequence of SEQ ID No: 250.

Further, the application is related to a TCR receptor comprising a TCR α chain and a TCR β chain, wherein
- the TCR α chain comprises a amino acid sequence which is at least 80% identical to SEQ ID No: 249 and comprises a CDR3 having the sequence of SEQ ID No: 245;
- the TCR β chain comprises a amino acid sequence which is at least 80% identical to SEQ ID No: 250 and comprises a CDR3 having the sequence of SEQ ID No: 246.

Certain embodiments relate to a TCR receptor comprising TCR α chain and a TCR β chain, wherein
- the TCR α chain comprises a amino acid sequence which is at least 50%, at least 60%, at least 70%, at least 80%, at least 85%, at least 90%, at least 95%, at least 96%, at least 97%, at least 98%, at least 99% identical to SEQ ID No: 249 and comprises a CDR3 having the sequence of SEQ ID No: 245;
- the TCR β chain comprises amino acid sequence which is at least 50%, at least 60%, at least 70%, at least 80%, at least 85%, at least 90%, at least 95%, at least 96%, at least 97%, at least 98%, at least 99% identical to SEQ ID No: 250 and comprises a CDR3 having the sequence of SEQ ID No: 246.

Certain embodiments refer to a TCR receptor comprising a TCR α chain encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 247 and a TCR β chain encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 248.

Certain embodiments relate to a TCR receptor comprising a TCR α chain encoded by the nucleotide sequence SEQ ID No: 247 and a TCR β chain encoded by the nucleotide sequence SEQ ID No: 248.

Further, the application is related to a TCR receptor comprising a TCR α chain and a TCR β chain, wherein
- the TCR α chain is encoded by a nucleotide sequence which is at least 80% identical to SEQ ID No: 247 and comprises a CDR3 region encoded by the nucleotide sequence set out in SEQ ID No: 243;
- the TCR β chain is encoded by a nucleotide sequence which is at least 80% identical to SEQ ID No: 248 and comprises a CDR3 region encoded by the nucleotide sequence set out SEQ ID No: 244.

Certain embodiments relate to a TCR receptor comprising TCR α chain and a TCR β chain, wherein
- the TCR α chain is encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 247 and comprises a CDR3 region encoded by the nucleotide sequence set out in SEQ ID No: 243;
- the TCR β chain is encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 248 and comprises a CDR3 region encoded by the nucleotide sequence set out in SEQ ID No: 244.

It is clear to the skilled person that the present application also relates to nucleotide acid molecules coding for the TCRs as defined above.

Another aspect of the application relates to the TCRs as defined above for use as a medicament. Thus, the present application also contemplates a pharmaceutical composition comprising the TCRs as defined above and a pharmaceutically acceptable carrier. Certain embodiments refer to the TCRs as defined above for use in treating a disease involving malignant cells expressing NY-ESO1. Thus, the application also refers to the TCRs as defined above for use in the treatment of cancer.

EXPERIMENTS

Generation of TCR-Specific Immunogens

As heterodimeric proteins expressed in association with CD3, the native TCR is a highly conformation-dependent structure. This complex structure impacts strongly on the exposure of epitopes that can be used to distinguish different V regions.

In a first step each and every TCR Vα and Vβ chain in its native configuration are expressed on the surface of recipient cells. These cells serve as immunogens and as primary screening cells. The cellular immunogens are developed in three steps. First, vector libraries that encode all 45 AV gene segments and all 47 BV gene segments in the human TCR repertoire are generated. Next, vectors are selected from this library as needed to create retroviruses (RV) to transduce TCR-negative cell lines (Jurkat-76$^{-/-}$), to thereby generate cell lines with individually defined VαVβ heterodimers. Third, these TCR-transgenic cell lines are selected by flow cytometry for TCR surface expression and individual T cell clones showing stable, high surface expression are obtained. These T cell clones become part of a master cell library after expansion, validation of their specific AV and BV regions by PCR, and cyro conservation.

TCR Vector Library

The modular TCR vector library was developed using the MP71 retroviral vector backbone (Schambach, 2000; Hildinger, 1999; FIG. 1B). The complete TCR vector library is composed of 92 different vectors, each containing one of the 45 separate AV or 47 separate BV variable regions. The vectors were designed in order to allow expression of different TCRs in the correct native conformation. A common CDR3 region was used in all vectors. This was derived from the OT-1 mouse T cell clone, which is specific for ovalbumin protein. Second, the human variable regions were combined with the respective mouse constant regions (mCA or mCB). The murine constant regions foster better pairing of human Vα and Vβ protein chains because they contain several charged amino acids, not present in human constant regions, which allow improved reciprocal protein interactions and better TCR heterodimer pairing and higher surface expression.

Retrovirus Production and Cell Transduction

Individual pRAVx or pRBVx vectors are used to make corresponding RVs. An example demonstrating the capacity of chimeric human-mouse TCR chains encoded by these vectors to form heterodimers, with the appropriate confirmation at the cell surface, is shown in FIG. 1. Here a T cell line was transduced with a selected combination of pRAVx and pRBVx retroviruses. Surface expression of the transgenic TCR was assessed in flow cytometry using a hamster anti-mouse antibody specific for mCB. Surface expression of any TCR requires the fully correct formation of the α/β heterodimer and association with CD3. Thus, a TCR will only show surface expression if the heterodimer folds and pairs in a proper configuration. As seen in this case, a subpopulation of around 40% of cells expressed surface TCR after simultaneous transduction with two RVs. Upon selection of an individual clone, uniform stable expression was found on all T cells. In a similar manner, several other TCR heterodimers are expressed for which corresponding commercial Vβ-specific mabs are available. These were found to bind the mabs, demonstrating that the conformation was equivalent to that of human T cells for the epitopes recognized by the tested mabs (data not shown).

Development of TCR Cell Libraries Expressing Chimeric TCRs

Two TCR cell libraries are developed using the respective AV and BV retroviral vector libraries. Upon retroviral transduction with selected RVs, cells were stained with an antibody that is useful for detecting the expression of a functional TCR and positive cells were sorted. For the generation of a TCR cell library expressing TCR with a mouse constant region an anti-mCB-specific antibody was used. For the generation of a TCR cell library expressing TCR with a human constant region an anti-CD3 antibody was used. The cell libraries are generated using transformed TCR-negative T cells in order to efficiently produce cellular reagents with uniform TCR expression specific for the AV or BV region of choice. Further, these cells have unlimited capacity for proliferation in vitro. One cell library is developed using murine TCR-negative cells ($BW^{-/-}$) and the second library is developed using TCR-negative human Jurkat T cells (FIG. 3).

The $BW^{-/-}$ TCR cellular library was used for immunization. For this purpose, mice were immunized with chimeric TCR-expressing $BW^{-/-}$ cells, which minimize the differences seen during immunization with whole cell immunogens. Despite this minimization of TCR immunogenicity to selected V regions, mice were still able to produce antibodies against other surface proteins expressed by $BW^{-/-}$ cells. These included responses to allogeneic MHC molecules, dependent upon the immunized strains of mice. Furthermore, undefined surface proteins expressed by $BW^{-/-}$ cells, associated with cellular transformation or viral transduction also served as immunogenic epitopes. Lastly, $BW^{-/-}$ cells were found to bind mouse or rat Ig non-specifically.

In order to avoid that mabs were identified which do not react with TCR structures in primary screens the corresponding Jurkat$^{-/-}$ library is used for screening ("cross-species screening"). Since Jurkat$^{-/-}$ cells differ for MHC and other cell surface proteins from $BW^{-/-}$ cells, they will not bind mabs specific for these molecules raised using $BW^{-/-}$ cellular immunogens. Furthermore, Jurkat$^{-/-}$ cells do not show non-specific binding of mouse or rat Ig.

An example of cross-species screening is illustrated in FIG. 4, with two supernatants with putative specificity for human TCR AV12-2 and BV12-3 regions. As seen, all three $BW^{-/-}$ cell lines bind both supernatants, irrespective of specific TCR expression, due to their property of non-specific Ig binding. In contrast, the Jurkat$^{-/-}$ GFP control cells remain negative with both supernatants and each supernatant binds only to the TCR-transduced Jurkat$^{-/-}$ cell line with the appropriate TCR.

Mouse $BW^{-/-}$ Cell Library Expressing Chimeric TCRs

The mouse cell library is based on the $BW^{-/-}$ cell line, which was derived from the parental BW5147 thymoma that arose spontaneously in an AKR mouse (Lee N E and Davis M M., J Immunol. 1988 Mar. 1; 140(5):1665-75; Letourneur F., Malissen B., Eur J Immunol. 1989; 19(12):2269-2274). As described above, surface expression of a TCR heterodimer is dependent on association with the CD3 protein complex. Therefore, the $BW^{-/-}$ cell line was stably transduced to co-express human CD3 with GFP ($BW^{-/-}$-CD3-GFP) (hereafter referred to simply as $BW^{-/-}$), enabling transduced cells to be easily identified. The presence of human CD3 allows these cells to express any human or mouse transgenic TCR at the cell surface after successful co-transduction with selected AV- and BV-encoding RVs. Surface expression can be monitored via binding of antibody specific for human CD3, or with antibody against the murine constant region, as shown in FIG. 2.

Human Jurkat Cell Library Expressing Chimeric TCR

The second cell library is constructed using the human Jurkat TCL. The human Jurkat76$^{-/-}$ cell line (hereafter Jurkat$^{-/-}$) is a variant of the original human TCL line that does not express human Vα and Vβ chains (Abraham R T, Weiss A., Nat Rev Immunol. 2004 April; 4(4):301-8). It has all remaining TCR-associated CD3 components necessary for transgenic TCR surface expression, after transduction with appropriate RVs of choice. As a negative control, Jurkat$^{-/-}$ cells were made which express very high levels of GFP, but do not express TCR proteins.

Cross-Species Screening Using $BW^{-/-}$ and Jurkat$^{-/-}$ Cells.

BW-TCR transduced cells were used for immunization, however these cells could not be used for hybridoma screening since they bind mouse or rat Ig non-specifically as shown here for the anti-human AV12-2-specific hybridoma supernatant, as well as for the anti-human BV12-3-specific supernatant. Both hybridoma supernatants stain $BW^{-/-}$ cells irrespective of their TCR expression (FIG. 4, first row in a and b). In contrast, the same supernatants stain Jurkat$^{-/-}$ cells only when they express the specific AV or BV TCR chain (FIG. 4, second row a and b). As previously mentioned, TCR-transduced $BW^{-/-}$ cells are stably transduced also with CD3-GFP in order to allow TCR expression, accounting for their intermediate level of GFP. To distinguish between non-specific and specific TCR binding on TCR-transduced Jurkat$^{-/-}$ cells, a stably transduced GFP Jurkat$^{-/-}$ cell clone was established and used as a control during hybridoma supernatant screening. As shown, Jurkat-GFP cells remain unlabeled when tested with supernatant containing either AV- or BV-specific mabs (FIG. 4, second row a and b).

Lewis Rats Immunization

Lewis rats with were immunized with $BW^{-/-}$ cells expressing hAV/hBV heterodimers containing mouse constant regions in combination or as single TCRs. The spleen cells of these rats were harvested and were fused to with myeloma cell line P3X63Ag8 and plated in twenty-four 96 well-plates. Two weeks later, an average of three hybridoma clones per well were observed throughout all plates, yielding approximately 6,900 hybridomas to be assessed.

Primary Screening

For the first screening, supernatants from four 96-well-plates were pooled in one collecting plate for screening in flow cytometry. This reduced the sample number for the primary flow cytometry screen from twenty-four to six 96-well-plates.

In order to distinguish whether positive supernatants show mono-, cluster- or pan-TCR specificity during the primary screen, a pool of Jurkat cell clones, comprising a population expressing hAV3/hBV12-3 (45%), a population expressing Jurkat hAV8-2/hBV24 (45%) and one population of non TCR-transduced Jurkat-GFP cells (10%) were analyzed to identify non-TCR-specific mabs.

During the primary cross-species screen, for example one pooled supernatant of different antibody clones was found that bound around 40% of the screening pool (FIG. 5). This mab shows a TCR-associated binding pattern since Jurkat-GFP (TCR-negative) control cells did not show any shift in binding; Results of primary screening including clone 15B4 is shown in FIG. 5A. Results of primary screening including clone 5H4 is shown in FIG. 5B.

Secondary Screening

In order to identify the individual hybridoma responsible for the primary screening activity, the supernatants from location identified in the primary screen as having TCR associated binding pattern in the pooled supernatant of the primary screening were tested individually on the same pool of screening cells. One supernatant for example was found to reproduce the expected binding pattern, this hybridoma clone is indicated herein as 15B4 (FIG. 6A). Another supernatant for example was also found to reproduce the expected binding pattern, this hybridoma clone is indicated herein as 5H4 (FIG. 6B). These experiments establish that 15B4 as well as 5H4 recognize at least BV12-3. In the following, experiments are described which can be used to establish that 15B4 is a cluster TCR-specific mab.

PBL Sorting

To differentiate whether a candidate antibody is monospecific or cluster-specific (i.e. reacting with multiple BV chains that share amino acid homologies), PBL of a single human donor are stained with the candidate mab. The positive fraction of cells is sorted by flow cytometry and a full human TCR AV and BV PCR repertoire analysis is performed on the sorted cells.

From the PBL sorted PBL mRNA is extracted and cDNA prepared. The full human TCR AV and BV repertoire is analyzed by a standard PCR protocol (denaturation: 94° C. for 2 min; annealing: 35 cycles of: 94° C. for 30 sec, 55° C. for 30 sec, 72° C. for 1 min; extension: 72° C. for 1 min) using primer-pairs specific for each specific BV chain. Amplified bands are extracted and sequenced. Samples that show several amplicons of different TCR Vα or TCR Vβ chains will indicate that the candidate antibody is specific for a cluster of TCR Vα or TCR Vβ chains.

Sequence Analysis of Sorted Cells

For antibodies binding to several TCR Vα or TCR Vβ chains, cells expressing BV chains for which the antibody is specific would be included in the sorted population. However, some contaminating cells might also be included in the sorted population, yielding a positive PCR amplicon due to the high sensitivity of the PCR method. In order to exclude amplicons due to contamination, all amplicon bands detected with BV-specific primers are sequenced. When the sequences are analyzed, the chromatopherograms as well as the density of the amplified bands were taken into account.

The previously described analysis of sequences obtained after sorting and Sanger sequencing of PCR amplicons generated from isolated lymphocyte population recognized by potential cluster antibodies indicated that these antibodies recognize a small cluster of BV chains. In order to more precisely determine the size and diversity of the clusters, the human PBMC were stained with R12 5H4 or R12 15B4 antibodies and positive populations sorted by FACS Aria sorting. The sorted cells are then used for preparation of library for next generation sequencing as published in Mamedov et al., (Front. Immunol. 2013; 4: 1-10). Briefly, the sorted lymphocytes were lysed and mRNA isolated using magnetic beads. This mRNA is then used for reverse transcription of cDNA coding for AV and BV TCR chains using smart cDNA synthesis technology. The AV and BV cDNA from each sample were then amplified in first PCR using universal primers specific for AV and BV chains. During this procedure ethe samples were labeled with unique barcodes on their 3' and 5' ends so that multi-sample NGS library can be sequenced and subsequently data analyzed and assigned for each specific sample. The illumina adaptor sequences needed for sequencing on MiSeq instrument by using illumina MiSeq Reagent Kits v2 chemistry were added during second PCR. The expected 600 base pair DNA band obtained after amplification of AV and BV chains containing respective adaptor sequences were extracted after classical DNA gel electrophoresis and NGS library for sequencing on MiSeq instrument prepared by illumina protocol. Upon sequencing, bioinformatic data analysis was performed and data presented in FIG. 17. The sequencing of whole PBMC repertoire by the same procedure was used as internal control.

ADCC Reporter Bioassay (Promega)

ADCC is measured using ADCC Reporter Bioassay (Promega) according to the manufacturer's protocol. In short, the activation of gene transcription through the NFAT (nuclear factor of activated T-cells) pathway in the effector cell is monitored by the luciferase activity in the effector cell which is quantified with luminescence readout. The ADCC Reporter Bioassay uses engineered Jurkat cells stably expressing the FcγRIIIa-receptor, V158 (high affinity) variant, and an NFAT response element driving expression of firefly luciferasease effector cells. The biological activity of the antibody in ADCC MOA is quantified through the luciferase produced as a result of NFAT pathway activation;

ADDC Assay: Human Natural Killer Target Cell Visualization Assay (TVA™)

A preferred assay for the measuring ADCC is the Human Natural Killer Target Cell Visualization Assay (TVA™; C.T.L., Cell Technology Limited). The capacity of the identified antibodies to induce ADCC (antibody-dependent cellular cytotoxicity) was assessed using this non-radioactive target cell visualization assay.

The TVA™ utilizes direct imaging of fluorescence-labeled target cells and was performed according to the instructions of the manufacturer. Shortly, 5E+03 labeled Jurkat cells expressing either the TCR variable beta chain 12-3 (recognized by the antibody candidates) or BV3-1 (not recognized by the antibodies) were co-incubated with IL-2 stimulated NK cells, isolated from the blood of healthy donors. The cells were co-cultured for 4-6 hours at varying target-to-effector ratios in combination with the antibody candidates. Following NK-mediated lysis, target cells lose their fluorescent signal. The direct visualization of remaining viable target cells at the end of an assay period determines the percentage of cytotoxicity for each T:E ratio. % cytotoxicity was assessed using following formula: % killing sample=100−((100×sample)/target cells only).

In Vivo Depletion of T Cells Expressing BV12-3-Related TCRs in a Humanized TCR Mouse Model ABab mice expressing human AV and BV (hAV/hBV) TCR chains were treated with the antibodies 5H4 and 15B4 (500 μg/mouse). Each antibody was applicated to three mice/group. Also included in the experimental setting were three control groups with 3 animals each. One group was treated with antibody 145-2C11 (anti-mouse CD3) as a positive control, since this antibody depletes all T-cells and induces a severe cytokine storm. One group was treated with an isotype control antibody (anti-EBNA2), which should not lead to any depletion since its recognized epitope is not present in mice. The last control group was left untreated (PBS) serving as a naive control. The PBL acquired by tail bleeds were analyzed before treatment (d0) and after treatment on day 4 and 21 (alternatively also bleeds for example at days 2, 5, 7 and 9 can be used) by staining with anti-CD3-PE and candidate anti-TCR variable chain mab in combination with mouse anti-rat-IgG secondary antibody (see also FIGS. 7 and 14).

The population of CD3+ T cells identified by the anti-TCR variable chain antibodies should remain stable in both groups treated with EBNA2 or the naive group throughout the whole experimental time course. In contrast, T cells expressing the respective TCR variable chains disappeared in the groups treated with the anti-TCR variable chain antibodies within 21 days (FIG. 14 C; also shown 4 days: FIG. 14 B; without treatment: FIG. 14 A). The remaining T cells, represented as a CD3+ and TCR variable chain antibody negative population should remained stable at the same level during the experiment. In the positive control group, all CD3+ T cells should disappear within 4 days.

In order to examine in detail the in vivo effects of the candidate TCR V chain mab, the size of the T cell population to the candidate antibody is assessed in comparison with the size of the T cell population detected using a commercial mab that is mono-specific for a TCR Vα chain or a TCR Vβ chain. This comparison is made before and after in vivo depletion studies. The experiments include mab staining of PBL of human TCR transgenic (ABab) mice and wild type C57BL/6 mice on day 0 and 48 hrs later.

To determine which BV chains are targeted by the candidate mab, a complete TCR BV repertoire analysis is prepared by using individual BV chain-specific primers. The PBL from human TCR transgenic mice (ABab) depleted with the candidate antibody (500 µg) are collected and the complete BV repertoire is determined using individual BV-specific primers.

Cytokine Measurement During In Vivo Depletion

Many mab that target T cell structures, including those specific for CD3 (145-2C11 control antibody in this experiment) or CD28 receptors, induce rapid systemic release of many cytokines from T cells that are involved in immune responses. Mabs recognizing a structural region of the TCR that is not directly involved in recognition of the antigen-MHC complex and is not involved in TCR signaling should be safe and only pathogenic T cells should be depleted, without evoking a toxic cytokine storm.

In order to measure cytokine release in mice during in vivo T cell depletion, serum concentrations of IL-2, IL-4, IL-6, IL-10, IFN-gamma and TNF-alpha were measured 0, 2, 6, 12, and 24 hours after mab application using a bead based flow cytometry assay (alternatively ELISA could be used). The same groups as descripted in section "In vivo depletion of T cells expressing BV12-3-related TCRs in a humanized TCR mouse model") were analyzed: Each mouse receives 500 µg of purified mab. Besides the antibodies 5H4 and 15B4, 3 controls were included: The first control group is treated with isotype control mab of the rat IgG2a isotype. This mab recognizes the Epstein-Barr-Virus antigen EBNA2. This mab should not show any effect in treated mice. The second control is a hamster anti-mouse CD3 mab (IgG1 anti-mouse CD3 zeta, clone 145-2C11), which is known to induce cytokine storm in treated animals (Hirsch, 1988; Penaranda, 2011). The last control group was left untreated serving as a naïve control.

Treatment with anti-EBNA2 mab shows no effect on cytokine production. In contrast treatment with anti-CD3 mab induced a cytokine storm, including the release of IL-2, IL-4, IL-6 and IFN-γ about 2 hrs after application. However, the candidate mabs did not increase cytokine levels in serum of the treated animals. Increased levels of IL-10 and TNF-α may be detected at later time points (e.g. 12 hrs) indicating that an inflammatory response may be occurring in vivo, perhaps involving macrophage activation through phagocytosis of targeted T cells due to the time delay. However, also these effects could not be detected with the antibodies 5H4 and 15B4 (FIGS. 15 and 16).

Assembled Library

A library is constructed comprising the following TCR constructs:

TABLE 8 constructed TCR library

| TCR construct | C segment | SEQ ID NO: | V segment | SEQ ID No: | linker sequence | SEQ ID No: |
|---|---|---|---|---|---|---|
| TCRA1 | AC | 6 | AVseg1 | 8 | linker specific for A | 192 |
| TCRA2 | AC | 6 | AVseg2 | 9 | linker specific for A | 192 |
| TCRA3 | AC | 6 | AVseg3 | 10 | linker specific for A | 192 |
| TCRA4 | AC | 6 | AVseg4 | 11 | linker specific for A | 192 |
| TCRA5 | AC | 6 | AVseg5 | 12 | linker specific for A | 192 |
| TCRA6 | AC | 6 | AVseg6 | 13 | linker specific for A | 192 |
| TCRA7 | AC | 6 | AVseg7 | 14 | linker specific for A | 192 |
| TCRA8 | AC | 6 | AVseg8 | 15 | linker specific for A | 192 |
| TCRA9 | AC | 6 | AVseg9 | 16 | linker specific for A | 192 |
| TCRA10 | AC | 6 | AVseg10 | 17 | linker specific for A | 192 |
| TCRA11 | AC | 6 | AVseg11 | 18 | linker specific for A | 192 |
| TCRA12 | AC | 6 | AVseg12 | 19 | linker specific for A | 192 |
| TCRA13 | AC | 6 | AVseg13 | 20 | linker specific for A | 192 |
| TCRA14 | AC | 6 | AVseg14 | 21 | linker specific for A | 192 |
| TCRA15 | AC | 6 | AVseg15 | 22 | linker specific for A | 192 |
| TCRA16 | AC | 6 | AVseg16 | 23 | linker specific for A | 192 |
| TCRA17 | AC | 6 | AVseg17 | 24 | linker specific for A | 192 |
| TCRA18 | AC | 6 | AVseg18 | 25 | linker specific for A | 192 |
| TCRA19 | AC | 6 | AVseg19 | 26 | linker specific for A | 192 |
| TCRA20 | AC | 6 | AVseg20 | 27 | linker specific for A | 192 |
| TCRA21 | AC | 6 | AVseg21 | 28 | linker specific for A | 192 |
| TCRA22 | AC | 6 | AVseg22 | 29 | linker specific for A | 192 |
| TCRA23 | AC | 6 | AVseg23 | 30 | linker specific for A | 192 |
| TCRA24 | AC | 6 | AVseg24 | 31 | linker specific for A | 192 |
| TCRA25 | AC | 6 | AVseg25 | 32 | linker specific for A | 192 |
| TCRA26 | AC | 6 | AVseg26 | 33 | linker specific for A | 192 |
| TCRA27 | AC | 6 | AVseg27 | 34 | linker specific for A | 192 |
| TCRA28 | AC | 6 | AVseg28 | 35 | linker specific for A | 192 |
| TCRA29 | AC | 6 | AVseg29 | 36 | linker specific for A | 192 |
| TCRA30 | AC | 6 | AVseg30 | 37 | linker specific for A | 192 |

TABLE 8-continued constructed TCR library

| TCR construct | C segment | SEQ ID NO: | V segment | SEQ ID No: | linker sequence | SEQ ID No: |
|---|---|---|---|---|---|---|
| TCRA31 | AC | 6 | AVseg31 | 38 | linker specific for A | 192 |
| TCRA32 | AC | 6 | AVseg32 | 39 | linker specific for A | 192 |
| TCRA33 | AC | 6 | AVseg33 | 40 | linker specific for A | 192 |
| TCRA34 | AC | 6 | AVseg34 | 41 | linker specific for A | 192 |
| TCRA35 | AC | 6 | AVseg35 | 42 | linker specific for A | 192 |
| TCRA36 | AC | 6 | AVseg36 | 43 | linker specific for A | 192 |
| TCRA37 | AC | 6 | AVseg37 | 44 | linker specific for A | 192 |
| TCRA38 | AC | 6 | AVseg38 | 45 | linker specific for A | 192 |
| TCRA39 | AC | 6 | AVseg39 | 46 | linker specific for A | 192 |
| TCRA40 | AC | 6 | AVseg40 | 47 | linker specific for A | 192 |
| TCRA41 | AC | 6 | AVseg41 | 48 | linker specific for A | 192 |
| TCRA42 | AC | 6 | AVseg42 | 49 | linker specific for A | 192 |
| TCRA43 | AC | 6 | AVseg43 | 50 | linker specific for A | 192 |
| TCRA44 | AC | 6 | AVseg44 | 51 | linker specific for A | 192 |
| TCRA45 | AC | 6 | AVseg45 | 52 | linker specific for A | 192 |
| TCRB1 | BC1 | 7 | BVseg1 | 53 | linker specific for B | 193 |
| TCRB2 | BC1 | 7 | BVseg2 | 54 | linker specific for B | 193 |
| TCRB3 | BC1 | 7 | BVseg3 | 55 | linker specific for B | 193 |
| TCRB4 | BC1 | 7 | BVseg4 | 56 | linker specific for B | 193 |
| TCRB5 | BC1 | 7 | BVseg5 | 57 | linker specific for B | 193 |
| TCRB6 | BC1 | 7 | BVseg6 | 58 | linker specific for B | 193 |
| TCRB7 | BC1 | 7 | BVseg7 | 59 | linker specific for B | 193 |
| TCRB8 | BC1 | 7 | BVseg8 | 60 | linker specific for B | 193 |
| TCRB9 | BC1 | 7 | BVseg9 | 61 | linker specific for B | 193 |
| TCRB10 | BC1 | 7 | BVseg10 | 62 | linker specific for B | 193 |
| TCRB11 | BC1 | 7 | BVseg11 | 63 | linker specific for B | 193 |
| TCRB12 | BC1 | 7 | BVseg12 | 64 | linker specific for B | 193 |
| TCRB13 | BC1 | 7 | BVseg13 | 65 | linker specific for B | 193 |
| TCRB14 | BC1 | 7 | BVseg14 | 66 | linker specific for B | 193 |
| TCRB15 | BC1 | 7 | BVseg15 | 67 | linker specific for B | 193 |
| TCRB16 | BC1 | 7 | BVseg16 | 68 | linker specific for B | 193 |
| TCRB17 | BC1 | 7 | BVseg17 | 69 | linker specific for B | 193 |
| TCRB18 | BC1 | 7 | BVseg18 | 70 | linker specific for B | 193 |
| TCRB19 | BC1 | 7 | BVseg19 | 71 | linker specific for B | 193 |
| TCRB20 | BC1 | 7 | BVseg20 | 72 | linker specific for B | 193 |
| TCRB21 | BC1 | 7 | BVseg21 | 73 | linker specific for B | 193 |
| TCRB22 | BC1 | 7 | BVseg22 | 74 | linker specific for B | 193 |
| TCRB23 | BC1 | 7 | BVseg23 | 75 | linker specific for B | 193 |
| TCRB24 | BC1 | 7 | BVseg24 | 76 | linker specific for B | 193 |
| TCRB25 | BC1 | 7 | BVseg25 | 77 | linker specific for B | 193 |
| TCRB26 | BC1 | 7 | BVseg26 | 78 | linker specific for B | 193 |
| TCRB27 | BC1 | 7 | BVseg27 | 79 | linker specific for B | 193 |
| TCRB28 | BC1 | 7 | BVseg28 | 80 | linker specific for B | 193 |
| TCRB29 | BC1 | 7 | BVseg29 | 81 | linker specific for B | 193 |
| TCRB30 | BC1 | 7 | BVseg30 | 82 | linker specific for B | 193 |
| TCRB31 | BC1 | 7 | BVseg31 | 83 | linker specific for B | 193 |
| TCRB32 | BC1 | 7 | BVseg32 | 84 | linker specific for B | 193 |
| TCRB33 | BC1 | 7 | BVseg33 | 85 | linker specific for B | 193 |
| TCRB34 | BC1 | 7 | BVseg34 | 86 | linker specific for B | 193 |
| TCRB35 | BC1 | 7 | BVseg35 | 87 | linker specific for B | 193 |
| TCRB36 | BC1 | 7 | BVseg36 | 88 | linker specific for B | 193 |
| TCRB37 | BC1 | 7 | BVseg37 | 89 | linker specific for B | 193 |
| TCRB38 | BC1 | 7 | BVseg38 | 90 | linker specific for B | 193 |
| TCRB39 | BC1 | 7 | BVseg39 | 91 | linker specific for B | 193 |
| TCRB40 | BC1 | 7 | BVseg40 | 92 | linker specific for B | 193 |
| TCRB41 | BC1 | 7 | BVseg41 | 93 | linker specific for B | 193 |
| TCRB42 | BC1 | 7 | BVseg42 | 94 | linker specific for B | 193 |
| TCRB43 | BC1 | 7 | BVseg43 | 95 | linker specific for B | 193 |
| TCRB44 | BC1 | 7 | BVseg44 | 96 | linker specific for B | 193 |
| TCRB45 | BC1 | 7 | BVseg45 | 97 | linker specific for B | 193 |
| TCRB46 | BC1 | 7 | BVseg46 | 98 | linker specific for B | 193 |
| TCRB47 | BC1 | 7 | BVseg47 | 99 | linker specific for B | 193 |

An additional library is constructed which comprises TCRA1 to TCRA45 constructs which correspond to the TCRA1 to TCRA45 constructs identified Table 8, except that they contain a human constant a AC segment (SEQ ID No:1) instead of mouse constant AC segment (SEQ ID No: 6) and which further comprises TCRB1 to TCRB47 construct which correspond to the TCRB1 to TCRB47 construct identified in Table 8, except that they contain a human constant BC segment (SEQ ID No:4) instead of mouse constant BC segment (SEQ ID No: 7).

The TCR constructs TCRA1 to TCRA45 and the TCRB1 to TCRB47 have been integrated into the ivtRNA backbone vector SEQ ID No: 196.

The TCR constructs TCRA1 to TCRA45 and the TCRB1 to TCRB47 have been integrated into the retroviral backbone vector SEQ ID No: 200.

The constructs TCRA1 and TCRB12 have been integrated into the ivtRNA backbone AC-P2A-BC (SEQ ID No: 199).

The constructs TCRA11 and TCRB12 have been integrated into the retroviral backbone vector AC-P2A-BC (SEQ ID No: 203).

Reengineering of an Isolated TCR
Functional Analysis of T Cell Clone T1.8-3-200

Co-culture of T cell clone T1.8-3-200 with HLA-matched NY-ESO1-X-(human NY-ESO1 antigen fused to a signal peptide)-loaded APC demonstrated the specificity and function of clone T1.8-3-200 (n.d., not detectable; FIG. 12A).

TCR Analysis of Original T Cell Clone T1.8-3-200

Rearranged TCR DNA sequences of T cell clone T1.8-3-200 were amplified by 5'RACE PCR. For this, whole RNA was isolated from T1.8-3-200 (recognizing human NY-ESO1 antigen fused to a signal peptide; NY-ESO1-X) T cells and reverse transcribed to complementary DNA (cDNA). The rearranged TCRα and β sequences were subsequently amplified by 5'RACE amplification. Using TOPO cloning, the amplified DNA fragments were cloned into an adequate recipient vector to allow the isolation of individual TCR DNA sequences after bacterial transformation.

DNA Sequencing

TCR sequence inserts from vectors that were isolated from single bacterial colonies were analyzed by DNA nucleotide sequencing.

```
T1.8-3-200 TCRα sequencing result (SEQ ID No: 210):
atgtcactactagcctgctgaaggtggtcacagcttcactgtggctagga cctggcattgcccagaagataactcaaacccaaccaggaatgttcgtgca ggaaaaggaggctgtgactctggactgcacatatgacaccagtgatccaa gttatggtctattctggtacaagcagcccagcagtggggaaatgattttt cttatttatcaggggtcttatgaccagcaaaatgcaacagaaggtcgcta ctcattgaatttccagaaggcaagaaaatccgccaaccttgtcatctccg cttcacaactgggggactcagcaatgtacttctgtgcaatttcgaacacc ggtaaccagttctattttgggacagggacaagtttgacggtcattccaaa tatccagaaccctgaccctgccgtgtaccagctgagagactctaaatcca gtgacaagtctgtctgcctattcaccgattttgattctcaaacaaatgtg tcacaaagtaaggattctgatgtgtatatcacagacaaaactgtgctaga catagtcagg T1.8-3-200 TCRβ sequencing result (SEQ ID No: 211):
atgggccccagctccttggctatgtggtcctttgccttctaggagcagg cccccctggaagcccaagtgacccagaacccaagatacctcatcacagtga ctggaaagaagttaacagtgacttgttctcagaatatgaaccatgagtat atgtcctggtatcgacaagacccagggctgggcttaaggcagatctacta ttcaatgaatgttgaggtgactgataagggagatgttcctgaagggtaca aagtctctcgaaagagaagaggaatttcccctgatcctggagtcgccc agccccaaccagacctctctgtacttctgtgccagcaataacttagcctc ctacaatgagcagttcttcgggccagggacacggctcaccgtgctagagg acctgaaaacgtgttcccacccgaggtcgctgtgtttgagccatcagaa gcagagatctcccacacccaaaaggccacactggtgtgcctggcacagg cttctaccccgaccacgtggagctgagctggtgggtgaatgggaaggagg tgcacagtggggtcagcacagaccccgcagcccctcaagagcagcgctt
```

IMGT Sequence Analysis

The TCR specificity-defining parameters (rearranged TCR V-(D)-Jα/β segments, sequence of CDR3 region and employed Cα/β region) were analyzed from the retrieved DNA sequences using the IMGT/V-QUEST search platform (www.imgt.org); The results for the TCR α and the TCRβ chain are shown in FIG. 12B and FIG. 12C respectively.

Identified T1.8-3-200 TCRα CDR3 sequences:
DNA Sequence:
(SEQ ID No: 243)
gcaatttcgaacaccggtaaccagttctat Protein Sequence:
(SEQ ID No: 245)
AISNTGNQFY IdentifiedT1.8-3-200 TCRβ CDR3 Sequences:
DNA Sequence:
(SEQ ID No: 244)
gccagcaataacttagcctcctacaatgagcagttc Protein Sequence:
(SEQ ID No: 246)
ASNNLASYNEQ Reconstruction in TCR Vector Library Appropriate vectors from the pGEM-based TCR vector library with human constant regions were used to reconstruct the T1.8-3-200 TCRα/β chains by exchanging the generic CDR3 linker with annealed DNA oligonucleotides coding for the respective T1.8-3-200 TCRα/β CDR3+J region (restriction sites: FspIxBspEI (TCRα chain; AV14 vector); FspIxBstEII (TCRβ chain; BV27 vector)).

```
T1.8-3-200 TCRα oligonucleotide Sense 5'→3'
(SEQ ID No: 239):
GCAATCAGCAACACCGGCAACCAGTTCTACTTCGGCACCGGCACCAGCCT
GACCGTGATCCCCAACATCCAGAAT T1.8-3-200 TCRα oligonucleotide Antisense 5'→3'
(SEQ ID No: 240):
CCGGATTCTGGATGTTGGGGATCACGGTCAGGCTGGTGCCGGTGCCGAAG
TAGAACTGGTTGCCGGTGTTGCTGATTGC T1.8-3-200 TCRβ oligonucleotide Sense 5'→3'
(SEQ ID No: 241):
GCAAGCAACAACCTGGCCAGCTACAACGAGCAGTTCTTCGGCCCTGGCAC
CCGGCTGACCGTGCTGGAAGATCTGAAGAACGTGTTCCCCCCAGAG T1.8-3-200 TCRβ oligonucleotide Antisense 5'→3'
(SEQ ID No: 242):
GTCACCTCTGGGGGGAACACGTTCTTCAGATCTTCCAGCACGGTCAG
CCGGGTGCCAGGGCCGAAGAACTGCTCGTTGTAGCTGGCCAGGTTGT
TGCTTGC
```

The sequences of the reconstructed T1.8-3-200 TCRα plasmids are set out in SEQ ID No: 208 (pMP71 based retroviral vector) and SEQ ID No: 251(ivtRNA vector). The sequences of reconstructed T1.8-3-200 TCRβ plasmids are set out in SEQ ID No: 209 (retroviral vector) and SEQ ID No: 252 (pGEM based ivtRNA vector). The nucleotide sequence of the reconstructed TCR α chain is set out in SEQ ID No: 247, the corresponding amino acid sequence is set out in SEQ ID No: 249. The nucleotide sequence of the reconstructed TCR β chain is set out in SEQ ID No: 248, the corresponding amino acid sequence is set out in SEQ ID No: 250.

Transgenic Function Analysis of TCR T1.8-3-200

RNA coding for T1.8-3-200 TCRα/β chains was produced from the generated pAV/BV-T1.8-3-200-ivtRNA vector constructs and used for transfection of peripheral blood lymphocyts (PBL). Co-culture of the T1.8-3-200 TCR-transfected PBL with HLA-matched NY-ESO1-X-loaded APC demonstrated the restoration of the previously defined T1.8-3-200 TCR specificity and function in the recipient T cells (FIG. 12D).

The application further comprises the following embodiments:

Embodiment 1

Method for generating an antibody binding to a cell surface protein of interest, the method comprising the following steps:
(a) providing a non-human cell which does not express the endogenous form of the cell surface protein of interest but expresses an exogenous form of the cell surface protein of interest comprising at least one human segment;
(b) immunization of a non-human animal with the cell line provided in step (a);
(c) generation of hybridomas from the immunized non-human animal of step (b);
(d) screening for an antibody that binds to the cell surface protein of interest by contacting the antibodies secreted by the hybridomas of step (c) with human cells which do not express the endogenous form of the cell surface protein of interest but express an exogenous form of the cell surface protein of interest comprising at least one human segment.

Embodiment 2

Method according to embodiment 1, wherein in step (d) the antibodies secreted by the hybridomas of step (c) are contacted with a mixture of human cells which does not express the endogenous form of the cell surface protein of interest comprising:
(i) a first defined proportion of the mixture of human cells which expresses the functional cell surface molecule of interest; and
(ii) a second defined proportion of the mixture of human cells which does not express a functional cell surface molecule of interest and which comprises a selection marker.

Embodiment 3

Method according to embodiment 2, wherein the selection marker is a fluorescent marker.

Embodiment 4

Method according to embodiment 3, wherein the selection marker is a fluorescent protein, preferably GFP.

Embodiment 5

Method according to any one of the preceding embodiments, wherein the screening is carried out by FACS.

Embodiment 6

Method according to any one of the preceding embodiments, wherein the non-human animal that is immunized in step (b) is of another species than the non-human cell line provided in step (a).

Embodiment 7

Method according to any one of the preceding embodiments, wherein the non-human animal that is immunized in step (b) is a rat and the non-human cell line provided in step (a) is a mouse cell line.

Embodiment 8

Method according to any one of the preceding embodiments, wherein the cell surface protein of interest is at least one TCR receptor of interest.

Embodiment 9

Method according to embodiment 8, wherein the cell provided in step (a) does neither express an endogenous TCR α chain nor an endogenous TCR β chain.

Embodiment 10

Method according to embodiment 9, wherein the cell provided in step (a) is the BW$^{-/-}$ cell line.

Embodiment 11

Method according to embodiment 10, wherein the human cell line of step
(d) is a Jurkat cell line deficient of a functional TCR.

Embodiment 12

Method according to embodiment 11, wherein the exogenous TCR comprises a variable human TCR α chain and a variable human TCR β chain.

Embodiment 13

Method according to embodiment 12, wherein the exogenous TCR comprises a constant mouse TCR α chain and a constant mouse TCR β chain.

Embodiment 14

Method according to embodiment 9, wherein the antibody binds to at least one T cell receptor variable alpha (TCR Vα) chain or binds to at least one T cell receptor variable beta (TCR Vβ) chain, the method comprising the following steps:
(a) providing a non-human cell which does neither express the endogenous TCR α chain nor the endogenous TCR β chain but expresses an exogenous TCR α chain and an exogenous TCR β chain comprising a variable human TCR V a chain and variable human TCR β chain;
(b) immunization of a non-human animal with the cell line provided in step (a);
(c) generation of hybridomas from the immunized non-human animal of step (b);
(d) screening for an antibody that binds to the TCR of interest by contacting the antibodies secreted by the hybridomas of step (c) with a mixture of human cells which does neither express the endogenous TCR α chain nor the endogenous TCR β chain comprising the following steps:
(i) a first defined proportion of the mixture of human cells which comprises the TCR having the TCR chains that are expressed by the non-human cell provided in step (a), (ii) a second defined proportion of the mixture of human cells which does not comprise a TCR having TCR chains that are different to the TCR chains expressed by the non-human cell provided in step(a), and
(iii) a third defined proportion of the mixture of human cells which does not comprise a functional TCR but comprises a selection marker.

Embodiment 15

Method according to embodiment 14, wherein the mouse cell line is the BW$^{-/-}$ cell line.

Embodiment 16

Method according to embodiment 14 or 15, wherein the human cell line of step (d) is a Jurkat cell line deficient of a functional TCR.

Embodiment 17

Method according to embodiments 14 to 16, wherein the exogenous TCR comprises constant mouse TCR Cα and TCR Cβ chains.

Embodiment 18

Method according to embodiment 14, wherein the antibody binds to a fraction of TCR Vα chains comprising at least two different TCR Vα chains but less than all TCR Vα chains or that binds to a fraction of TCR Vβ chains comprising at least two different TCR Vβ chains but less than all TCR Vβ chains, the method comprising the following steps:
(a) providing a non-human cell which does neither express the endogenous TCR α chain nor the endogenous TCR β chain but expresses an exogenous TCR α chain comprising a variable human TCR V a chain and an exogenous TCR β chain comprising a variable human TCR β chain;
(b) immunization of a non-human animal with the cell line provided in step (a);
(c) generation of hybridomas from the immunized non-human animal of step (b);
(d) screening for an antibody that binds to at least one TCR Vα chain or binds to at least one TCR Vβ chain by contacting the antibodies secreted by the hybridomas of step (c) with a mixture of human cells which express neither the endogenous TCR α chain nor the endogenous TCR β chain comprising:
(i) a first defined proportion of the mixture of human cells which comprises the TCR having the TCR chains that are expressed by the non-human cell provided in step (a),
(ii) a second defined proportion of the mixture of human cells which does not comprise a TCR having TCR chains that are expressed by the non-human cell line provided in step (a) but comprises a TCR having TCR chains that are different to the TCR chains expressed by the non-human cell provided in step (a), and
(iii) a third defined proportion of the mixture of human cells which does not comprise a functional TCR but comprises a selection marker;
wherein the non-human animal is mouse or rat and the non-human cell provided in step (a) is a mouse cell line.
(e) identifying an antibody that binds to a fraction of TCR Vα chains comprising at least two different TCR Vα chains but less than all TCR Vα chains or that binds to a fraction of TCR chains comprising at least two different TCR Vβ chains but less than all TCR Vβ chains, comprising the following steps:
(i) incubating human peripheral blood lymphocytes (PBL) with the antibody identified in step (d) as binding to at least one TCR Vα chain or binding to at least one TCR chain;
(ii) screening for cells that bind to the antibody by FACS sorting;
(iii) analysis of the TCR Vα chain repertoire or TCR Vβ chain repertoire of the cells that bind to the antibody of step (ii);
wherein a TCR Vα chain repertoire or TCR Vβ chain repertoire comprising different TCR Vα chains but less than all TCR Vα chains or at least two different TCR Vβ chains but less than all TCR Vβ chains indicates that the antibody binds to a fraction of TCR Vα chains comprising at least two different TCR Vα chains but less than all TCR Vα chains or that binds to a fraction of TCR Vβ chains comprising at least two different TCR Vβ chains but less than all TCR Vβ chains.

The invention claimed is:

1. A method for generating an antibody that binds to a cell surface protein of interest, the method comprising the following steps:
   (a) providing a non-human cell which does not express an endogenous form of the cell surface protein of interest, but expresses an exogenous form of the cell surface protein of interest comprising at least one human segment;
   (b) immunizing a non-human animal with the cell provided in step (a), wherein the non-human animal that is immunized in step (b) is of another species than the non-human cell provided in step (a);
   (c) generating antibody secreting hybridomas from the immunized non-human animal of step (b);
   (d) screening for an antibody that binds to the cell surface protein of interest by contacting the antibodies secreted by the hybridomas of step (c) with human cells which do not express the endogenous form of the cell surface protein of interest, but express an exogenous form of the cell surface protein of interest comprising at least one human segment,
   wherein the cell surface protein of interest is at least one T cell receptor (TCR) of interest; wherein the TCR is a native configuration TCR comprising a TCR α chain comprising a variable TCR α (TCR Vα) chain, a constant TCR α (TCR Cα) chain, a TCR α chain transmembrane (TCR TMα) domain, and a TCR α chain intracellular (TCR ICDα) domain; and a TCR β chain comprising a variable TCR β (TCR Vβ) chain, a constant TCR β (TCR Cβ) chain, a TCR β chain transmembrane (TCR TMβ) domain, and a TCR β chain intracellular (TCR ICDβ) domain.

2. The method according to claim 1, wherein in step (d), the antibodies secreted by the hybridomas of step (c) are contacted with a mixture of human cells which does not express the endogenous form of the cell surface protein of interest, said mixture of human cells comprising:
   (i) a first proportion of the mixture of human cells which expresses the cell surface protein of interest; and
   (ii) a second proportion of the mixture of human cells which does not express the cell surface protein of interest and which comprises a selection marker, wherein the selection marker is preferably a fluorescent marker;
wherein binding to the human cells in (i) and not to the human cells in (ii) indicates that the antibody is specifically binding to the cell surface protein of interest.

3. The method according to claim 1, wherein the non-human animal that is immunized in step (b) is a rat, and the non-human cell provided in step (a) is derived from a mouse cell line.

4. The method according to claim 1, wherein the cell provided in step (a) does not express an endogenous TCR α chain or an endogenous TCR β chain.

5. The method according to claim 4, wherein the cell provided in step (a) is derived from a cell line that does not express the endogenous TCR α chain or the endogenous TCR β chain, but stably expresses fluorescently tagged human CD3.

6. The method according to claim 5, wherein the human cells of step (d) are derived from a Jurkat cell line deficient of a TCR.

7. The method according to claim 6, wherein the exogenous TCR comprises a human TCR Vα chain and a human TCR Vβ chain.

8. The method according to claim 7, wherein the exogenous TCR comprises a constant mouse TCR Cβ chain and a constant mouse TCR Cβ chain.

9. The method of claim 5, wherein the cell line stably expresses fluorescently tagged CD3-GFP.

10. The method according to claim 4, wherein in step (d), the antibodies secreted by the hybridomas of step (c) are contacted with a mixture of human cells which does not express the endogenous form of the cell surface protein of interest, said mixture of human cells comprising:
    (i) a first proportion of the mixture of human cells which comprises the TCR having the TCR chains that are expressed by the non-human cell provided in step (a);
    (ii) a second proportion of the mixture of human cells which does not comprise a functional TCR but comprises a selection marker; wherein binding to the human cells in (i) and not to the human cells in (ii) indicates that the antibody binds to at least one TCR Vα chain or binds to at least one TCR Vβ chain.

11. The method according to claim 10, wherein the human cell of step (d) is derived from a Jurkat cell line deficient of a TCR.

12. The method according to claim 10, wherein the exogenous TCR comprises mouse TCR Cα and TCR Cβ chains.

13. The method according to claim 10, wherein the antibody binds to a fraction of TCR Vα chains comprising at least two different TCR Vα chains but less than all TCR Vα chains, or binds to a fraction of TCR Vβ chains comprising at least two different TCR Vβ chains but less than all TCR Vβ chains, wherein in step (d), the antibodies secreted by the hybridomas of step (c) are contacted with a mixture of human cells which does not express the endogenous form of the cell surface protein of interest, said mixture of human cells further comprising:
    (iii) a third proportion of the mixture of human cells which does not comprise a TCR having TCR chains that are expressed by the non-human cell provided in step (a), but comprises a TCR having TCR chains that are different than the TCR chains expressed by the non-human cell provided in step (a);

wherein the non-human animal that is immunized in step (b) is a rat and the non-human cell provided in step (a) is derived from a mouse cell line;

wherein binding to (i) and/or (iii) and not binding to (ii) identifies the antibody that binds to at least one TCR Vα chain or binds to at least one TCR Vβ chain; the method further comprising:

(e) identifying an antibody that binds to a fraction of TCR Vα chains comprising at least two different TCR Vβ chains but less than all TCR Vα chains, or that binds to a fraction of TCR Vβ chains comprising at least two different TCR Vβ chains but less than all TCR Vβ chains, comprising the following steps:
 (e1) incubating human peripheral blood lymphocytes (PBLs) with the antibody identified in step (d) as binding to at least one TCR Vα chain or binding to at least one TCR Vβ chain; (ii)
 (e2) screening for cells that bind to the antibody by FACS sorting;
 (e3) analyzing the TCR Vα chain repertoire or TCR VR chain repertoire of the cells of step (e2) that bind to the antibody of step (e);

wherein a TCR Vα chain repertoire or TCR Vβ chain repertoire comprising different TCR Vα chains but less than all TCR Vα chains or at least two different TCR Vβ chains but less than all TCR Vβ chains indicates that the antibody binds to a fraction of TCR Vα chains comprising at least two different TCR Vα chains but less than all TCR Vα chains, or binds to a fraction of TCR Vβ chains comprising at least two different TCR Vβ chains but less than all TCR Vβ chains.

14. The method according to claim 10, wherein the antibody binds to a fraction of TCR Vα chains comprising at least two different TCR Vα chains but less than all TCR Vα chains, or binds to a fraction of TCR Vβ chains comprising at least two different TCR Vβ chains but less than all TCR Vβ chains, wherein in step (d), the antibodies secreted by the hybridomas of step (c) are contacted with a mixture of human cells which does not express the endogenous form of the cell surface protein of interest, said mixture of human cells further comprising:

(iii) a third proportion of the mixture of human cells which does not comprise a TCR having TCR chains that are expressed by the non-human cell line provided in step (a), but comprises a TCR having TCR chains that are different than the TCR chains expressed by the non-human cell provided in step (a);

wherein the non-human animal immunized in step (b) is a rat and the non-human cell provided in step (a) is derived from a mouse cell line;

wherein binding to (i) and to (iii) and not binding to (ii) identifies the antibody that binds to at least two TCR Vα chains or binds to at least two TCR Vβ chains; the method further comprising;

(e) identifying an antibody that binds to a fraction of TCR Vα chains comprising at least two different TCR Vα chains but less than all TCR Vα chains or that binds to a fraction of TCR Vβ chains comprising at least two different TCR Vβ chains but less than all TCR Vβ chains, comprising the following steps:
 (e1) incubating human peripheral blood lymphocytes PBLs with the antibody identified in step (d) as binding to at least two TCR Vα chains or binding to at least two TCR Vβ chains;
 (e2) screening for cells that bind to the antibody by FACS sorting;
 (e3) analyzing the TCR Vα chain repertoire or TCR Vβ chain repertoire of the cells of step (e2) that bind to the antibody of step (e);

wherein a TCR Vα chain repertoire or TCR Vβ chain repertoire comprising different TCR Vα chains but less than all TCR Vα chains or at least two different TCR Vβ chains but less than all TCR Vβ chains indicates that the antibody binds to a fraction of TCR Vα chains comprising at least two different TCR Vα chains but less than all TCR Vα chains, or binds to a fraction of TCR Vβ chains comprising at least two different TCR Vβ chains but less than all TCR Vβ chains.

15. The method according to claim 4, wherein in step (d), the antibodies secreted by the hybridomas of step (c) are contacted with a mixture of human cells which does not express the endogenous form of the cell surface protein of interest, said mixture of human cells comprising:

(i) a first proportion of the mixture of human cells which comprises the TCR having the TCR chains that are expressed by the non-human cell provided in step (a), (ii) a second proportion of the mixture of human cells which does not comprise a TCR having TCR chains that are expressed by the non-human cell provided in step (a), but comprises a TCR having TCR chains that are different than the TCR chains expressed by the non-human cell provided in step (a), and (iii) a third proportion of the mixture of human cells which does not comprise a functional TCR but comprises a selection marker;

wherein binding to (i) and/or to (ii) and not binding to (iii) indicates that the antibody binds to at least one TCR Vα chain or binds to at least one TCR Vβ chain.

16. The method according to claim 15, wherein an antibody that binds to (i) and (ii) but not to (iii) indicates that the antibody recognizes at least two TCR chains, wherein binding to (i) and not to (ii) indicates that the antibody binds to at least one TCR Vα chain or at least one TCR Vβ chain, but does not bind to all TCR Vα chains or TCR Vβ chains.

17. The method of claim 1, wherein the antibody binds to a fraction of TCR Vα chains comprising at least two different Vα chains but less than all TCR Vα chains or binds to a fraction of TCR Vβ chains comprising at least two different TCR Vβ chains but less than all TCR Vβ chains.

* * * * *

SEQUENCE LISTING

```
<160> NUMBER OF SEQ ID NOS: 304

<210> SEQ ID NO 1
<211> LENGTH: 426
<212> TYPE: DNA
<213> ORGANISM: Homo sapiens

<400> SEQUENCE: 1
aacatccaga atccggaccc cgccgtgtac cagctgagag acagcaagag cagcgacaac        60
actgtgtgcc tgttcaccga cttcgactcc cagaccaacg tgtcccagag caaggacagc       120
gacgtgtaca tcaccgacaa gaccgtgctg gacatgcgga gcatggactt caagagcaac       180
agcgccgtgg cctggtccaa caagagcgat ttcgcctgcg ccaacgcctt caacaacagc       240
attatccccg aggacacatt cttcccaagc cccgagagca gctgcgacgt gaagctggtg       300
gaaaagagct tcgagacaga caccaacctg aatttccaga acctgagcgt gatcggcttc       360
```

```
agaatcctgc tgctgaaggt ggccggcttc aacctgctga tgaccctgcg gctgtggtcc    420
agctga                                                               426

<210> SEQ ID NO 2
<211> LENGTH: 426
<212> TYPE: DNA
<213> ORGANISM: Homo sapiens

<400> SEQUENCE: 2
aacatccaga atccggaccc cgccgtgtac cagctgagag acagcaagag cagcgacaag     60
agtgtgtgcc tgttcaccga cttcgactcc cagaccaacg tgtcccgaga caaggacagc    120
gacgtgtaca tcaccgacaa gaccgtgctg gacatgcgga gcatggactt caagagcaac    180
agcgccgtgg cctggtccaa caagagcgat ttcgcctgcg ccaacgcctt caacaacagc    240
attatccccg aggacacatt cttcccaagc cccgagagca gctgcgacgt gaagctggtg    300
gaaaagagct tcgagacaga caccaacctg aatttccaga acctgagcgt gatcggcttc    360
agaatcctgc tgctgaaggt ggccggcttc aacctgctga tgaccctgcg gctgtggtcc    420
agctga                                                               426

<210> SEQ ID NO 3
<211> LENGTH: 540
<212> TYPE: DNA
<213> ORGANISM: Homo sapiens

<400> SEQUENCE: 3
gaggatctga agaatgtttt ccccccggaa gtgaccgtgt cgaaccaag cgaagccgag      60 atatcccata cacagaaggc tacattggtg tgcctggcga ctggatttta cccagaccac    120
gtagaactga gctggtgggt gaacgggaag gaagtacatt ctggagtgtg cacagatccg    180
cagcctctca aagagcagcc agcactgaat gactcccgat actgcctttc ctcccgcctc    240
cgcgtgtcag ctacattctg gcagaatcca agaaatcatt ttagatgtca ggtgcagttc    300
tacggtctta gtgaaaacga cgagtggacc caggacaggg caaagccagt cacgcagatt    360
gtgtccgctg aagcctgggg cagggccgac tgcggcttca caagcgagtc ataccagcag    420
ggggtcctca gcgccacaat tttgtacgag atactgctgg gaaaggcaac cctctacgcg    480
gtgctggttt cagcccttgt cctgatggcc atggtcaagc gaaagactc tcgagggtaa    540

<210> SEQ ID NO 4
<211> LENGTH: 540
<212> TYPE: DNA
<213> ORGANISM: Homo sapiens

<400> SEQUENCE: 4
gaagatctga agaacgtgtt cccccagag gtgaccgtgt cgagcctag cgaggccgag       60 atcagccaca cccagaaagc caccctcgtg tgcctggcca ccggcttcta tcccgaccac    120
gtggaactgt cttggtgggt caacggcaaa gaggtgcaca cggcgtgtc caccgatccc    180 cagcctctga agaacagcc cgccctgaac gacagccggt actgcctgag cagcagactg    240
agagtgtccg ccaccttctg gcagaacccc cggaaccact tcagatgcca ggtgcagttc    300
tacggcctga gcgagaacga cgagtggacc caggacagag ccaagcccgt gacccagatc    360
gtgtctgccg aagcctgggg cagagccgat tgcggcttta ccagcgagag ctaccagcag    420
ggcgtgctga gcgccaccat cctgtacgag atcctgctgg gcaaggccac cctgtacgcc    480
gtgctggtgt ctgccctggt gctgatggct atggtcaagc ggaaggacag ccggggctga    540
```

<210> SEQ ID NO 5
<211> LENGTH: 540
<212> TYPE: DNA
<213> ORGANISM: Homo sapiens

<400> SEQUENCE: 5

```
gaagatctga agaacgtgtt ccccccagag gtggccgtgt tcgagcctag cgaggccgag      60
atcagccaca cccagaaagc caccctcgtg tgcctggcca ccggcttcta tcccgaccac     120
gtggaactgt cttggtgggt caacggcaaa gaggtgcaca cggcgtgtc caccgatccc      180
cagcctctga agaacagcc cgccctgaac gacagccggt actgcctgag cagcagactg     240
agagtgtccg ccaccttctg gcagaacccc cggaaccact tcagatgcca ggtgcagttc     300
tacggcctga gcgagaacga cgagtggacc caggacagag ccaagcccgt gacccagatc     360
gtgtctgccg aagcctgggg cagagccgat tgcggctta ccagcgagag ctaccagcag      420
ggcgtgctga cgccaccat cctgtacgag atcctgctgg gcaaggccac cctgtacgcc      480
gtgctggtgt ctgccctggt gctgatggct atggtcaagc ggaaggacag ccggggctga     540
```

<210> SEQ ID NO 6
<211> LENGTH: 414
<212> TYPE: DNA
<213> ORGANISM: Mus musculus

<400> SEQUENCE: 6

```
gacatccaga accccgagcc cgccgtgtac cagctgaagg accccagaag ccaggacagc      60
accctgtgcc tgttcaccga cttcgacagc cagatcaacg tgcccaagac catggaaagc     120
ggcaccttca tcaccgacaa acagtgctg gacatgaagg ccatggacag caagagcaac      180
ggcgccattg cctggtccaa ccagaccagc ttcacatgcc aggacatctt caaagagaca      240
aacgccacct accccagcag cgacgtgccc tgcgacgcca ccctgaccga aaagagcttc      300
gagacagaca tgaacctgaa tttccagaac ctgagcgtga tgggcctgcg gatcctgctg      360
ctgaaggtgg ccggcttcaa cctgctgatg accctgcggc tgtggagcag ctga           414
```

<210> SEQ ID NO 7
<211> LENGTH: 522
<212> TYPE: DNA
<213> ORGANISM: Mus musculus

<400> SEQUENCE: 7

```
gaagatctga ggaacgtgac ccccccaag gtgaccctgt tcgagcccag caaggccgag       60
atcgccaaca agcagaaagc caccctggtc tgcctggcca ggggcttctt ccccgaccac     120
gtggagctgt cttggtgggt gaacggcaaa gaggtgcaca cggagtcag taccgacccc      180
caggcctaca agagagcaa ctacagctac tgcctgagca gcaggctgag agtgagcgcc      240
accttctggc acaaccccg gaaccacttc cggtgccagg tgcagttcca cggcctgagc     300
gaagaggaca agtggcctga gggcagcccc aagcccgtga cccagaacat cagcgccgag      360
gcctggggca gagccgactg cggcatcacc agcgccagct accaccaggg cgtgctgtcc     420
gccaccatcc tgtacgagat cctgctggc aaggccaccc tgtacgccgt gctggtgtcc     480
ggcctggtgc tgatggccat ggtgaagaag aagaacagct ga                       522
```

<210> SEQ ID NO 8
<211> LENGTH: 315
<212> TYPE: DNA

<213> ORGANISM: Homo sapiens

<400> SEQUENCE: 8

```
atgtggggag cctttctgct gtacgtgtcc atgaagatgg gcggcacagc cggccagagc     60
ctggaacagc ctagcgaagt gaccgccgtg aaggcgcca tcgtgcagat caactgcacc    120
taccagacca gcggcttcta cggcctgagc tggtatcagc agcacgacgg cggagccccc    180
accttcctga gctacaacgc cctggacggc tggaagaga caggccggtt cagcagcttc    240
ctgagcagaa gcgacagcta cggctacctg ctgctgcagg aactgcagat gaaggacagc    300
gccagctact tctgc                                                    315
```

<210> SEQ ID NO 9
<211> LENGTH: 315
<212> TYPE: DNA
<213> ORGANISM: Homo sapiens

<400> SEQUENCE: 9

```
atgtggggag tgtttctgct gtacgtgtcc atgaagatgg gcggcaccac cggccagaac     60
atcgaccagc ccaccgagat gaccgccacc gagggcgcca tcgtgcagat caactgcacc    120
taccagacca gcggcttcaa cggcctgttc tggtatcagc agcacgccgg cgaggccccc    180
accttcctga gctacaacgt gctggacggc tggaagaga agggccggtt cagcagcttc    240
ctgagcagaa gcaagggcta cagctacctg ctgctgaaag aactgcagat gaaggacagc    300
gccagctacc tgtgc                                                    315
```

<210> SEQ ID NO 10
<211> LENGTH: 327
<212> TYPE: DNA
<213> ORGANISM: Homo sapiens

<400> SEQUENCE: 10

```
atggccctgc agagcaccct gggcgccgtg tggctgggcc tgctgctgaa cagcctgtgg     60
aaggtggccg agagcaagga ccaggtgttc cagcccagca ccgtggccag cagcgagggc    120
gccgtggtgg agatcttctg caaccacagc gttagcaacg cctacaactt cttctgtac    180
ctgcacttcc ccggctgcgc ccccgcctg ctggtgaagg cagcaagcc cagccagcag    240
ggccgctaca acatgaccta cgagcgcttc agcagcagcc tgctgatcct gcaggtgcgc    300
gaggccgacg ccgccgtgta ctactgc                                       327
```

<210> SEQ ID NO 11
<211> LENGTH: 330
<212> TYPE: DNA
<213> ORGANISM: Homo sapiens

<400> SEQUENCE: 11

```
atggcctctg cccctatcag catgctggcc atgctgttca ccctgagcgg cctgagagcc     60
cagagcgtgg cccagcccga ggatcaagtc aacgtggccg agggcaaccc cctgaccgtg    120
aagtgcacct acagcgtgtc cggcaacccc tacctgtttt ggtacgtgca gtaccccaac    180
cggggcctgc agttcctgct gaagtacatc accggcgaca acctggtgaa aggcagctac    240
ggcttcgagg ccgagttcaa caagagccag accagcttcc acctgaagaa acccagcgcc    300
ctggtgtccg acagcgccct gtacttctgc                                    330
```

<210> SEQ ID NO 12
<211> LENGTH: 315

<212> TYPE: DNA
<213> ORGANISM: Homo sapiens

<400> SEQUENCE: 12

```
atgcgccagg tggcccgcgt gatcgtgttc ctgaccctga gcaccctgag cctggccaag      60
accacccagc ccatcagcat ggacagctac gagggccagg aggtgaacat cacctgcagc     120
cacaacaaca tcgccaccaa cgactacatc acctggtacc agcagttccc cagccagggc     180
ccccgcttca tcatccaggg ctacaagacc aaggtgacca cgaggtggc cagcctgttc      240
atccccgccg accgcaagag cagcaccctg agcctgcccc gcgtgagcct gagcgacacc     300
gccgtgtact actgc                                                      315
```

<210> SEQ ID NO 13
<211> LENGTH: 330
<212> TYPE: DNA
<213> ORGANISM: Homo sapiens

<400> SEQUENCE: 13

```
atgaaaacct tcgccggctt cagcttcctg ttcctgtggc tgcagctgga ctgcatgagc      60
agaggcgagg acgtggaaca gagcctgttc ctgagcgtgc gcgagggcga cagcagcgtg     120
atcaactgca cctacaccga cagcagcagc acctacctgt actggtacaa gcaggaaccc     180
ggcgctggcc tgcagctgct gacctacatc ttcagcaaca tggacatgaa gcaggaccag     240
cggctgaccg tgctgctgaa caagaaggac aagcacctga gcctgcggat cgccgacacc     300
cagaccggcg acagcgccat ctactttgc                                       330
```

<210> SEQ ID NO 14
<211> LENGTH: 330
<212> TYPE: DNA
<213> ORGANISM: Homo sapiens

<400> SEQUENCE: 14

```
atggaatctt ttctgggcgg cgtgctgctg atcctgtggc tgcaggtcga ctgggtcaag      60
agccagaaga tcgagcagaa cagcgaggcc ctgaacatcc aggaaggcaa gaccgccacc     120
ctgacctgca actacaccaa ctacagcccc gcctacctgc agtggtacag acaggacccc     180
ggcagaggcc ccgtgttcct gctgctgatt cgcgagaacg agaaagagaa gcgcaaagag     240
cggctgaaag tcaccttcga caccaccctg aagcagagcc tgttccacat caccgccagc     300
cagcccgccg acagcgccac atatctgtgc                                      330
```

<210> SEQ ID NO 15
<211> LENGTH: 327
<212> TYPE: DNA
<213> ORGANISM: Homo sapiens

<400> SEQUENCE: 15

```
atggaaaaga tgcggaggcc cgtgctgatc atcttctgcc tgtgcctggg ctgggccaac      60
ggcgagaacc aggtggaaca gagcccccac tttctgggcc ccagcaggg ggatgtggcc      120
agcatgagct gcacctacag cgtgtcccgg ttcaacaacc tgcagtggta cagacagaac     180
accggcatgg gccccaaaca tctgctgagc atgtacagcg ccggctacga gaagcagaag     240
ggccggctga acgccacccct gctgaagaac ggcagcagcc tgtacatcac cgccgtgcag    300
cccgaggaca cgccaccta cttttgc                                          327
```

<210> SEQ ID NO 16

<211> LENGTH: 330
<212> TYPE: DNA
<213> ORGANISM: Homo sapiens

<400> SEQUENCE: 16

| atgctgctgc | tgctcatccc | cgtgctgggc | atgatcttcg | ccctgcggga | tgccagagcc | 60 |
| cagagcgtgt | cccagcacaa | ccaccacgtc | atcctgagcg | aggccgccag | cctggaactg | 120 |
| ggctgcaact | acagctacgg | cggcaccgtg | aacctgtttt | ggtacgtgca | gtaccccggc | 180 |
| cagcatctgc | agctgctgct | gaagtacttc | tccggcgacc | cctggtcaa | gggcatcaag | 240 |
| ggcttcgagg | ccgagttcat | caagagcaag | ttcagcttca | acctgcggaa | gcccagcgtg | 300 |
| cagtggtccg | ataccgccga | gtacttctgc | | | | 330 |

<210> SEQ ID NO 17
<211> LENGTH: 330
<212> TYPE: DNA
<213> ORGANISM: Homo sapiens

<400> SEQUENCE: 17

| atgctgctgc | tgctcgtgcc | cgtgctggaa | gtgatcttca | ccctgggcgg | caccagagcc | 60 |
| cagagcgtga | cccagctgga | cagccatgtg | tccgtgtccg | agggcacccc | cgtgctgctg | 120 |
| cggtgcaact | acagcagcag | ctacagcccc | agcctgtttt | ggtacgtgca | gcaccccaac | 180 |
| aagggcctgc | agctgctgct | gaagtacacc | agcgccgcca | cctggtcaa | gggcatcaac | 240 |
| ggcttcgagg | ccgagttcaa | gaagtccgag | acaagcttcc | acctgaccaa | gcccagcgcc | 300 |
| cacatgagcg | acgccgccga | gtacttctgc | | | | 330 |

<210> SEQ ID NO 18
<211> LENGTH: 330
<212> TYPE: DNA
<213> ORGANISM: Homo sapiens

<400> SEQUENCE: 18

| atgctgctgg | aactgatccc | cctgctgggc | atccatttcg | tgctgcggac | cgccagagcc | 60 |
| cagagcgtga | cccagcccga | catccacatc | accgtgtccg | agggcgccag | cctggaactg | 120 |
| cggtgcaact | acagctacgg | cgccacccc | tacctgtttt | ggtacgtgca | gagcccaggc | 180 |
| cagggcctgc | agctgctgct | gaagtacttc | tccggcgaca | cctggtgca | gggcatcaag | 240 |
| ggcttcgagg | ccgagttcaa | gcggagccag | agcagcttca | acctgcggaa | gccctccgtg | 300 |
| cattggagcg | acgccgccga | gtacttctgc | | | | 330 |

<210> SEQ ID NO 19
<211> LENGTH: 330
<212> TYPE: DNA
<213> ORGANISM: Homo sapiens

<400> SEQUENCE: 19

| atgctgctgc | tgctggtgcc | cgtgctggag | gtgatcttca | ccctgggcgg | cacccgcgcc | 60 |
| cagagcgtga | cccagctggg | cagccacgtg | agcgtgagcg | agggcgccct | ggtgctgctg | 120 |
| cgctgcaact | acagcagcag | cgtgcccccc | tacctgttct | ggtacgtgca | gtaccccaac | 180 |
| cagggcctgc | agctgctgct | gaagtacacc | agcgccgcca | ccctggtgaa | gggcatcaac | 240 |
| ggcttcgagg | ccgagttcaa | gaagagcgag | accagcttcc | acctgaccaa | gcccagcgcc | 300 |
| cacatgagcg | acgccgccga | gtacttctgc | | | | 330 |

<210> SEQ ID NO 20
<211> LENGTH: 330
<212> TYPE: DNA
<213> ORGANISM: Homo sapiens

<400> SEQUENCE: 20

| | | | | | |
|---|---|---|---|---|---|
| atgctgctgc | tgctcgtgcc | tgccttccag | gtcatcttca | ccctgggcgg | caccagagcc | 60 |
| cagagcgtga | cccagctgga | tagccaggtg | cccgtgttcg | aggaagcccc | cgtcgagctg | 120 |
| cggtgcaact | acagcagcag | cgtgtccgtg | tacctgtttt | ggtacgtgca | gtaccccaac | 180 |
| cagggcctgc | agctgctgct | gaagtacctg | agcggcagca | cctggtggga | atccatcaac | 240 |
| ggcttcgagg | ccgagttcaa | caagagccag | accagcttcc | acctgagaaa | gcccagcgtg | 300 |
| cacatcagcg | ataccgccga | gtacttctgc | | | | 330 |

<210> SEQ ID NO 21
<211> LENGTH: 327
<212> TYPE: DNA
<213> ORGANISM: Homo sapiens

<400> SEQUENCE: 21

| | | | | | |
|---|---|---|---|---|---|
| atgaattcta | gccctggccc | cgctatcgcc | ctgttcctga | tgttcggcgg | catcaacggc | 60 |
| gacagcgtgg | tgcagacaga | gggccaggtg | ctgcccagcg | agggcgacag | cctgatcgtg | 120 |
| aactgcagct | acgagacaac | ccagtacccc | agcctgtttt | ggtacgtgca | gtaccccggc | 180 |
| gagggccccc | agctgcacct | gaaagccatg | aaggccaacg | acaagggccg | gaacaagggc | 240 |
| ttcgaggcca | tgtaccggaa | agagacaacc | agcttccacc | tggaaaagga | cagcgtgcag | 300 |
| gaaagcgaca | gcgccgtcta | cttctgc | | | | 327 |

<210> SEQ ID NO 22
<211> LENGTH: 327
<212> TYPE: DNA
<213> ORGANISM: Homo sapiens

<400> SEQUENCE: 22

| | | | | | |
|---|---|---|---|---|---|
| atgaactaca | gccccggcct | ggtgagcctg | atcctgctgc | tgctgggccg | caccgcggc | 60 |
| aacagcgtga | cccagatgga | gggccccgtg | acctgagcg | aggaggcctt | cctgaccatc | 120 |
| aactgcacct | acaccgccac | cggctacccc | agcctgttct | ggtacgtgca | gtaccccggc | 180 |
| gagggcctgc | agctgctgct | gaaggccacc | aaggccgacg | acaagggcag | caacaagggc | 240 |
| ttcgaggcca | cctaccgcaa | ggagaccacc | agcttccacc | tggagaaggg | cagcgtgcag | 300 |
| gtgagcgaca | gcgccgtgta | cttctgc | | | | 327 |

<210> SEQ ID NO 23
<211> LENGTH: 333
<212> TYPE: DNA
<213> ORGANISM: Homo sapiens

<400> SEQUENCE: 23

| | | | | | |
|---|---|---|---|---|---|
| atgaagaagc | acctgaccac | ctttctggtc | atcctgtggc | tgtacttcta | ccggggcaac | 60 |
| ggcaagaacc | aggtggaaca | gagcccccag | agcctgatca | tcctggaagg | caagaactgc | 120 |
| accctgcagt | gcaactacac | cgtgtccccc | ttcagcaacc | tgcggtggta | caagcaggac | 180 |
| accggcagag | gccccgtgtc | cctgaccatc | atgaccttca | gcgagaacac | caagagcaac | 240 |
| ggccggtaca | ccgccaccct | ggacgccgac | acaaagcaga | gcagcctgca | catcaccgcc | 300 |
| agccagctga | gcgacagcgc | cagctacatc | tgc | | | 333 |

<210> SEQ ID NO 24
<211> LENGTH: 327
<212> TYPE: DNA
<213> ORGANISM: Homo sapiens

<400> SEQUENCE: 24

| | | |
|---|---|---|
| atgatcagcc tgagagtgct gctggtcatc ctgtggctgc agctgagctg ggtctggtcc | 60 |
| cagcggaaag aggtggaaca ggaccctggc cccttcaacg tgccagaggg cgccaccgtg | 120 |
| gccttcaact gcacctacag caacagcgcc agccagagct tcttctggta cagacaggac | 180 |
| tgccggaaag aacccaagct gctgatgagc gtgtacagca gcggcaacga ggacggccgg | 240 |
| ttcaccgccc agctgaacag agcctcccag tacatcagcc tgctgatccg ggacagcaag | 300 |
| ctgagcgaca gcgccaccta cctgtgc | 327 |

<210> SEQ ID NO 25
<211> LENGTH: 330
<212> TYPE: DNA
<213> ORGANISM: Homo sapiens

<400> SEQUENCE: 25

| | | |
|---|---|---|
| atgaagagcc tgcgcgtgct gctggtgatc ctgtggctgc agctgagctg ggtgtggagc | 60 |
| cagcagaagg aggtggagca gaacagcggc ccctgagcg tgcccgaggg cgccatcgcc | 120 |
| agcctgaact gcacctacag cgaccgcggc agccagagct tcttctggta ccgccagtac | 180 |
| agcggcaaga gccccgagct gatcatgttc atctacagca acggcgacaa ggaggacggc | 240 |
| cgcttcaccg cccagctgaa caaggccagc cagtacgtga cctgctgat ccgcgacagc | 300 |
| cagcccagcg acagcgccac ctacctgtgc | 330 |

<210> SEQ ID NO 26
<211> LENGTH: 333
<212> TYPE: DNA
<213> ORGANISM: Homo sapiens

<400> SEQUENCE: 26

| | | |
|---|---|---|
| atgatgaagt ccctgcgggt gctgctggtc atcctgtggc tgcagctgag ctgggtctgg | 60 |
| tcccagcaga aagaggtgga acaggaccct ggccccctga gcgtgccaga gggcgccatc | 120 |
| gtgtccctga actgcaccta cagcaacagc gccttccagt acttcatgtg gtacagacag | 180 |
| tacagccgga agggccccga gctgctgatg tacacctaca gctccggcaa caaagaggac | 240 |
| ggccggttca ccgcccaggt ggacaagagc agcaagtaca tcagcctgtt catccgggac | 300 |
| agccagccca gcgacagcgc cacctatctg tgc | 333 |

<210> SEQ ID NO 27
<211> LENGTH: 327
<212> TYPE: DNA
<213> ORGANISM: Homo sapiens

<400> SEQUENCE: 27

| | | |
|---|---|---|
| atgacctcta tccgggccgt gttcatcttc ctgtggctgc agctggacct ggtcaacggc | 60 |
| gagaacgtgg aacagcaccc cagcaccctg agcgtgcagg aaggcgacag cgccgtcatc | 120 |
| aagtgcacct acagcgactc cgccagcaac tacttcccct ggtacaagca ggaactgggc | 180 |
| aagggccccc agctgatcat cgacatccgg tccaacgtgg gcgagaagaa ggaccagcgg | 240 |
| atcgccgtga ccctgaacaa gaccgccaag cacttcagcc tgcacatcac cgagacacag | 300 |
| cccgaggact ccgccgtgta cttctgc | 327 |

```
<210> SEQ ID NO 28
<211> LENGTH: 330
<212> TYPE: DNA
<213> ORGANISM: Homo sapiens

<400> SEQUENCE: 28
atggctggaa tccgggccct gttcatgtac ctgtggctgc agctggactg ggtgtccaga      60
ggcgagagcg tgggcctgca tctgcccacc ctgagcgtgc aggaaggcga caacagcatc     120
atcaactgcg cctacagcaa cagcgccagc gactacttca tctggtacaa gcaggaaagc     180
ggcaagggcc cccagttcat catcgacatc cggtccaaca tggacaagcg cagggccag      240 cgcgtgaccg tgctgctgaa caagaccgtg aagcacctga gcctgcagat cgccgccacc     300
cagcctggcg atagcgccgt gtacttctgc                                      330

<210> SEQ ID NO 29
<211> LENGTH: 336
<212> TYPE: DNA
<213> ORGANISM: Homo sapiens

<400> SEQUENCE: 29
atgtctctga gcagcctgct gaaggtcgtg accgccagcc tgtggctggg ccctggaatc      60
gcccagaaga tcacccagac ccagcccggc atgttcgtgc aggaaaaaga ggccgtcacc     120
ctggactgca cctacgacac cagcgacccc agctacggcc tgttctggta caagcagccc     180
agcagcggcg agatgatctt cctgatctac cagggcagct acgaccagca gaacgccacc     240
gagggccggt acagcctgaa cttccagaag gcccggaagt ccgccaacct ggtcatcagc     300
gccagccagc tgggcgacag cgccatgtac ttttgc                               336

<210> SEQ ID NO 30
<211> LENGTH: 318
<212> TYPE: DNA
<213> ORGANISM: Homo sapiens

<400> SEQUENCE: 30
atgaagccta ccctgatcag cgtgctggtc atcatcttca tcctgcgggg caccagagcc      60
cagagagtga cccagcccga gaagctgctg agcgtgttca gggcgctcc cgtggaactg     120 aagtgcaact acagctacag cggcagcccc gagctgtttt ggtacgtgca gtacagccgg     180
cagcggctgc agctgctcct gcggcacatc agcagagaga gcatcaaggg cttcaccgcc     240
gacctgaaca agggcgagac aagcttccac ctgaagaagc ccttcgccca ggaagaggac     300
agcgccatgt actactgc                                                   318

<210> SEQ ID NO 31
<211> LENGTH: 327
<212> TYPE: DNA
<213> ORGANISM: Homo sapiens

<400> SEQUENCE: 31
atggagaccc tgctgggcgt gagcctggtg atcctgtggc tgcagctggc ccgcgtgaac      60
agccagcagg gcgaggagga ccccaggcc ctgagcatcc aggagggcga aacgccacc      120 atgaactgca gctacaagac cagcatcaac aacctgcagt ggtaccgcca gaacagcggc     180
aggggcctgg tgcacctgat cctgatccgc agcaacgagc gcgagaagca cagcggcagg     240
ctgcgcgtga ccctggacac cagcaagaag agcagcagcc tgctgatcac cgccagccgc     300
```

```
gccgccgaca ccgccagcta cttctgc                                327
```

<210> SEQ ID NO 32
<211> LENGTH: 324
<212> TYPE: DNA
<213> ORGANISM: Homo sapiens

<400> SEQUENCE: 32

```
atgctgagcg cctcttgtag cggcctggtc atcctgctga tcttccggcg gaccagcggc    60
gacagcgtga cccagactga gggccctgtg accctgcctg agagagccgc cctgaccctg   120
aactgcacct accagagcag ctacagcacc ttcctgtttt ggtacgtgca gtacctgaac   180
aaagagcccg agctgctgct gaagtccagc gagaaccagg aaaccgacag ccggggcttc   240
caggccagcc ccatcaagag cgacagcagc ttccacctgg aaaagcccag cgtgcagctg   300
agcgacagcg ccgtgtacta ctgc                                         324
```

<210> SEQ ID NO 33
<211> LENGTH: 336
<212> TYPE: DNA
<213> ORGANISM: Homo sapiens

<400> SEQUENCE: 33

```
atgctgaccg ccagcctgct gcgcgccgtg atcgccagca tctgcgtggt gagcagcatg    60
gcccagaagg tgacccaggc ccagaccgag atcagcgtgg tggagaagga ggacgtgacc   120
ctggactgcg tgtacgagac cgcgacacc acctactacc tgttctggta caagcagccc   180
cccagcggcg agctggtgtt cctgatccgc cgcaacagct cgacgagca gaacgagatc   240
agcggccgtt acagctggaa cttccagaag agcaccagca gcttcaactt caccatcacc   300
gccagccagg tggtggacag cgccgtgtac ttctgc                             336
```

<210> SEQ ID NO 34
<211> LENGTH: 327
<212> TYPE: DNA
<213> ORGANISM: Homo sapiens

<400> SEQUENCE: 34

```
atggaaaaga tgctggaatg cgccttcatc gtgctgtggc tgcagctggg ctggctgagc    60
ggcgaggacc aggtcacaca gagccccgag gccctgagac tgcaggaagg cgagagcagc   120
agcctgaact gcagctacac cgtgtccggc ctgcggggcc tgttctggta cagacaggac   180
cccggcaagg gccccgagtt cctgttcacc ctgtactctg ccggcgagga aaaagagaaa   240
gagcggctga aggccaccct gaccaagaaa gagagcttcc tgcacatcac cgccccccaag  300
cccgaggaca cgccaccta tctgtgc                                        327
```

<210> SEQ ID NO 35
<211> LENGTH: 327
<212> TYPE: DNA
<213> ORGANISM: Homo sapiens

<400> SEQUENCE: 35

```
atggagaccc tgctgggcct gctgatcctg tggctgcagc tgcagtgggt gagcagcaag    60
caggaggtga cccagatccc cgccgccctg agcgtgcccg agggcgagaa cctggtgctg   120
aactgcagct tcaccgacag cgccatctac aacctgcagt ggttccgcca ggaccccggc   180
aagggcctga ccagcctgct gctgatccag agcagccagc gcgagcagac cagcggccgc   240
ctgaacgcca gcctggacaa gagcagcggc cgcagcaccc tgtacatcgc cgccagccag   300
```

```
cccggcgaca gcgccaccta cctgtgc                                          327
```

<210> SEQ ID NO 36
<211> LENGTH: 321
<212> TYPE: DNA
<213> ORGANISM: Homo sapiens

<400> SEQUENCE: 36

```
atgaagagaa tcctgggcgc cctgctgggc ctgctgtctg cccaggtctg ctgtgtgcgg      60
ggcatccagg tggaacagag ccccctgac ctgatcctgc aggaaggcgc caacagcacc      120
ctgcggtgca acttcagcga cagcgtgaac aacctgcagt ggttccacca gaaccctgg      180
ggccagctga tcaacctgtt ctacatcccc agcggcacca gcagaacgg ccggctgagc      240
gccaccaccg tggccaccga gatacagc tgctgtaca tcagcagcag ccagaccacc        300
gacagcggcg tgtacttctg c                                                321
```

<210> SEQ ID NO 37
<211> LENGTH: 354
<212> TYPE: DNA
<213> ORGANISM: Homo sapiens

<400> SEQUENCE: 37

```
atggataaga tcctgggcgc cagcttcctg gtgctgtggc tgcagctgtg ctgggtgtcc      60
ggccagcaga aagagaagtc cgaccagcag caggtcaaac agagccccca gagcctgatc      120
gtgcagaagg gcggcatcag catcatcaac tgcgcctacg agaataccgc cttcgactac      180
ttcccctggt atcagcagtt ccccggcaag ggccctgccc tgctgatcgc catcagaccc      240
gacgtgtccg agaagaaaga gggccggttc accatcagct tcaacaagag cgccaagcag      300
ttcagcctgc acatcatgga cagccagccc ggcgacagcg ccacctactt ttgc            354
```

<210> SEQ ID NO 38
<211> LENGTH: 336
<212> TYPE: DNA
<213> ORGANISM: Homo sapiens

<400> SEQUENCE: 38

```
atggagaaga ccccctggc cgcccccctg ctgatcctgt ggttccacct ggactgcgtg       60
agcagcatcc tgaacgtgga gcagagcccc cagagcctgc acgtgcagga gggcgacagc     120
accaacttca cctgcagctt ccccagcagc aacttctacg ccctgcactg gtaccgctgg     180
gagaccgcca gagccccga ggccctgttc gtgatgaccc tgaacggcga cgagaagaag     240
aagggccgca tcagcgccac cctgaacacc aaggagggct acagctacct gtacatcaag     300
ggcagccagc ccgaggacag cgccacctac ctgtgc                                336
```

<210> SEQ ID NO 39
<211> LENGTH: 321
<212> TYPE: DNA
<213> ORGANISM: Homo sapiens

<400> SEQUENCE: 39

```
atgctgctga tcacctccat gctggtgctg tggatgcagc tgagccaggt caacggccag      60
caggtcatgc agatccccca gtaccagcat gtgcaggaag gcgaggactt caccacctac     120
tgcaacagca gcaccaccct gagcaacatc cagtggtaca gcagcggcc tggcggccat     180
cccgtgtttc tgatccagct ggtcaagtcc ggcgaagtga agaagcagaa gcggctgacc     240
```

```
ttccagttcg gcgaggccaa gaagaacagc agcctgcaca tcaccgccac ccagaccacc        300
gacgtgggca cctactttg c                                                   321

<210> SEQ ID NO 40
<211> LENGTH: 315
<212> TYPE: DNA
<213> ORGANISM: Homo sapiens

<400> SEQUENCE: 40
atgagactgg tggccagagt gaccgtgttc ctgaccttcg gcaccatcat cgacgccaag         60
accacccagc cccccagcat ggattgcgcc gaaggcagag ccgccaacct gccctgcaac        120
cacagcacca tcagcggcaa cgagtacgtg tactggtaca gacagatcca cagccagggc        180
ccccagtaca tcatccacgg cctgaagaac aacgagacaa cgagatggc cagcctgatc        240 atcaccgagg acagaaagag cagcaccctg atcctgcccc acgccaccct gagagacacc        300
gccgtgtact actgc                                                        315

<210> SEQ ID NO 41
<211> LENGTH: 315
<212> TYPE: DNA
<213> ORGANISM: Homo sapiens

<400> SEQUENCE: 41
atgaagctcg tgaccagcat caccgtgctg ctgagcctgg gcatcatggg cgacgccaag         60
accacccagc ccaacagcat ggaaagcaac gaagaggaac ccgtgcatct gccctgcaac        120
cacagcacca tcagcggcac cgactacatc cactggtaca gacagctgcc cagccagggc        180
cccgagtacg tgatccacgg cctgaccagc aacgtgaaca accggatggc ctccctggcc        240
attgccgagg acagaaagag cagcaccctg atcctgcacc gggccaccct gagagatgcc        300
gccgtgtact actgc                                                        315

<210> SEQ ID NO 42
<211> LENGTH: 321
<212> TYPE: DNA
<213> ORGANISM: Homo sapiens

<400> SEQUENCE: 42
atggtgctga agttcagcgt gtccatcctg tggatccagc tggcctgggt gtccacccag         60
ctgctggaac agagcccca gttcctgagc atccaggaag gcgagaacct gaccgtgtac        120
tgcaacagca gcagcgtgtt cagcagcctg cagtggtaca gacaggaacc cggcgagggc        180
cccgtgctgc tggtcacagt cgtgacaggc ggcgaagtga agaagctgaa gcggctgacc        240
ttccagttcg gcgacgcccg gaaggacagc tccctgcaca ttacagccgc ccagcccggc        300
gacaccggcc tgtatctgtg c                                                  321

<210> SEQ ID NO 43
<211> LENGTH: 348
<212> TYPE: DNA
<213> ORGANISM: Homo sapiens

<400> SEQUENCE: 43
atggctatgc tgctgggcgc cagcgtgctg atcctgtggc tgcagcccga ctgggtcaac         60
agccagcaga gaacgacga ccagcaggtc aaacagaaca gcccagcct gagcgtgcag        120 gaaggccgga tcagcatcct gaactgcgac tacaccaact ctatgttcga ctacttcctg        180
tggtacaaga agtaccccgc cgagggcccc accttcctga tcagcatcag cagcatcaag        240
```

```
gacaagaacg aggacggccg gttcaccgtg tttctgaaca agagcgccaa gcacctgagc        300
ctgcatatcg tgcccagcca gcccggcgac agcgccgtgt acttttgc                     348

<210> SEQ ID NO 44
<211> LENGTH: 327
<212> TYPE: DNA
<213> ORGANISM: Homo sapiens

<400> SEQUENCE: 44
atggaaaccc tgctgaaggt gctgagcggc accctgctgt ggcagctgac atgggtccga        60
agccagcagc ccgtgcagag ccctcaggcc gtgatcctga gaaaggcga ggacgccgtg         120 atcaactgca gcagcagcaa ggccctgtac agcgtgcact ggtacagaca gaagcacggc       180
gaggcccccg tgttcctgat gattctgctg aagggcggcg agcagaaggg ccacgagaag       240
atcagcgcca gcttcaacga aagaagcag cagagcagcc tgtacctgac cgccagccag        300
ctgagctaca gcggcaccta ctttttgc                                           327

<210> SEQ ID NO 45
<211> LENGTH: 327
<212> TYPE: DNA
<213> ORGANISM: Homo sapiens

<400> SEQUENCE: 45
atggagaccg tgctgcaggt gctgctgggc atcctgggct tccaggccgc ctgggtgagc        60
agccaggagc tggagcagag cccccagagc ctgatcgtgc aggagggcaa gaacctgacc       120
atcaactgca ccagcagcaa gaccctgtac ggcctgtact ggtacaagca gaagtacggc       180
gagggcctga tcttcctgat gatgctgcag aagggcggcg aggagaagag ccacgagaag       240
atcaccgcca agctggacga aagaagcag cagagcagcc tgcacatcac cgccagccag         300
cccagccacg ccggcatcta cctgtgc                                            327

<210> SEQ ID NO 46
<211> LENGTH: 321
<212> TYPE: DNA
<213> ORGANISM: Homo sapiens

<400> SEQUENCE: 46
atgctgctgg aacatctgct gatcatcctg tggatgcagc tgacctgggt gtccggccag        60
cagctgaacc agagccccca gagcatgttc atccaggaag gcgaggacgt cagcatgaac       120
tgcaccagca gcagcatctt caacacctgg ctgtggtaca gcaggaacc cggcgagggc         180 cccgtgctgc tgatcgccct gtataaggcc ggcgagctga ccagcaacgg ccggctgaca       240
gcccagttcg gcattacccg gaaggacagc ttcctgaaca tcagcgccag catccccagc       300
gacgtgggca tctactttg c                                                   321

<210> SEQ ID NO 47
<211> LENGTH: 330
<212> TYPE: DNA
<213> ORGANISM: Homo sapiens

<400> SEQUENCE: 47
atgatgaagt gtcccccaggc cctgctggcc atcttctggc tgctgctgag ctgggtgtcc        60
agcgaggaca aggtggtgca gagccccctg agcctggtgg tgcacgaggg cgataccgtg       120
accctgaact gcagctacga agtgaccaac ttccggtccc tgctgtggta caagcaggaa       180
```

```
aagaaggccc ccaccttcct gttcatgctg accagcagcg gcatcgagaa gaagtccggc    240
agactgagca gcatcctgga caagaaagag ctgtccagca tcctgaacat caccgccacc    300
cagaccggcg acagcgccat ctacctgtgc                                    330
```

<210> SEQ ID NO 48
<211> LENGTH: 336
<212> TYPE: DNA
<213> ORGANISM: Homo sapiens

<400> SEQUENCE: 48

```
atgaccagag tgtctctgct gtgggccgtg gtggtgtcca cctgtctgga aagcggcatg     60
gcccagaccg tgacccagag ccagcccgag atgagcgtgc aggaagccga cagtcacc     120 ctgagctgca cctacgacac cagcgagaac aactactacc tgttctggta caagcagccc   180
cccagccggc agatgatcct ggtcatccgg caggaagcct acaagcagca gaacgccacc   240
gagaacagat tcagcgtgaa cttccagaag gccgccaaga gcttcagcct gaagatcagc   300
gacagccagc tgggcgacac cgccatgtac ttttgc                             336
```

<210> SEQ ID NO 49
<211> LENGTH: 336
<212> TYPE: DNA
<213> ORGANISM: Homo sapiens

<400> SEQUENCE: 49

```
atggcctgtc ctggatttct gtgggccctg gtcatcagca cctgtctgga attcagcatg     60
gcccagaccg tgacccagag ccagcccgag atgagcgtgc aggaagccga cagtcacc     120 ctgagctgca cctacgacac cagcgagagc gactactacc tgttctggta caagcagccc   180
cccagccggc agatgatcct ggtcatccgg caggaagcct acaagcagca gaacgccacc   240
gagaacagat tcagcgtgaa cttccagaag gccgccaaga gcttcagcct gaagatcagc   300
gacagccagc tgggcgacgc cgccatgtac ttttgc                             336
```

<210> SEQ ID NO 50
<211> LENGTH: 321
<212> TYPE: DNA
<213> ORGANISM: Homo sapiens

<400> SEQUENCE: 50

```
atgaagaaac tgctggccat gatcctgtgg ctgcagctgg accggctgag cggcgagctg     60
aaggtggaac agaaccccct gttcctgagc atgcaggaag gcaagaacta caccatctac   120
tgcaactaca gcaccaccag cgaccggctg tactggtaca gacaggaccc cggcaagagc   180
ctggaaagcc tgttcgtgct gctgagcaac ggcgccgtga agcaggaagg ccggctgatg   240
gccagcctgg acaccaaggc cagactgagc accctgcaca tcacagccgc cgtgcacgac   300
ctgagcgcca cctactttg c                                              321
```

<210> SEQ ID NO 51
<211> LENGTH: 306
<212> TYPE: DNA
<213> ORGANISM: Homo sapiens

<400> SEQUENCE: 51

```
atgaacagca gcctggactt cctgatcctg attctgatgt tcggcggcac cagcagcaac     60
agcgtgaagc agaccggcca gatcaccgtg tccgagggcg ccagcgtgac catgaactgc   120
acctacacca gcaccggcta ccccacccctg ttttggtacg tggaataccc cagcaagccc   180
```

```
ctgcagctcc tgcagcggga aaccatggaa acagcaaga acttcggcgg aggcaacatc      240
aaggacaaga acagccccat cgtgaagtac agcgtccagg tgtccgacag cgccgtgtac      300
tactgc                                                                306
```

<210> SEQ ID NO 52
<211> LENGTH: 328
<212> TYPE: DNA
<213> ORGANISM: Homo sapiens

<400> SEQUENCE: 52

```
catggtcaag atccggcagt tcctgctggc catcctgtgg ctgcagctga gctgtgtgtc       60
cgccgccaag aacgaggtgg aacagagccc ccagaacctg accgcccagg aaggcgagtt      120
catcaccatc aactgcagct acagcgtggg catcagcgcc ctgcactggc tgcagcagca      180
tcccggcgga ggcatcgtgt ccctgttcat gctgagcagc ggcaagaaga agcacggccg      240
gctgatcgcc accatcaaca tccaggaaaa gcagcagcag ctgcacatca ccgccagcca      300
ccccagagac agcgccgtgt acatctgc                                        328
```

<210> SEQ ID NO 53
<211> LENGTH: 333
<212> TYPE: DNA
<213> ORGANISM: Homo sapiens

<400> SEQUENCE: 53

```
atggataccc tggctcgtgtg ctgggccatc ttcagcctgc tgaaggccgg cctgaccgag       60
cccgaagtga cccagacccc tagccaccag gtcacacaga tgggccagga agtgatcctg      120
cgctgcgtgc ccatcagcaa ccacctgtac ttctactggt acagacagat cctgggccag      180
aaagtggaat tcctggtgtc cttctacaac aacgagatca gcgagaagtc cgagatcttc      240
gacgaccagt tcagcgtgga acggcccgac ggcagcaact tcaccctgaa gatcagaagc      300
accaagctcg aggacagcgc catgtacttt tgc                                  333
```

<210> SEQ ID NO 54
<211> LENGTH: 330
<212> TYPE: DNA
<213> ORGANISM: Homo sapiens

<400> SEQUENCE: 54

```
atgggctgcc gcctgctgtg ctgcgtggtg ttctgcctgc tgcaggccgg cccccctggac       60 accgccgtga gccagacccc caagtacctg gtgacccaga tgggcaacga caagagcatc      120
aagtgcgagc agaacctggg ccacgacacc atgtactggt acaagcagga cagcaagaag      180
ttcctgaaga tcatgttcag ctacaacaac aaggagctga tcatcaacga gaccgtgccc      240
aaccgcttca gccccaagag ccccgacaag gcccacctga acctgcacat caacagcctg      300
gagctgggcg acagcgccgt gtacttctgc                                      330
```

<210> SEQ ID NO 55
<211> LENGTH: 330
<212> TYPE: DNA
<213> ORGANISM: Homo sapiens

<400> SEQUENCE: 55

```
atgggatgca gactgctgtg ctgcgccgtg ctgtgtctgc tgggcgccgt gcccatcgac       60
accgaagtga cccagacccc caagcacctg gtcatgggca tgaccaacaa gaaaagcctg      120
```

| | |
|---|---|
| aagtgcgagc agcacatggg ccaccgggcc atgtactggt acaagcagaa ggccaagaaa | 180 |
| cccccgagc tgatgttcgt gtacagctac gagaagctga gcatcaacga gagcgtgccc | 240 |
| agccggttca gccccgagtg ccccaatagc agcctgctga acctgcatct gcacgccctg | 300 |
| cagcccgagg acagcgccct gtatctgtgc | 330 |

<210> SEQ ID NO 56
<211> LENGTH: 330
<212> TYPE: DNA
<213> ORGANISM: Homo sapiens

<400> SEQUENCE: 56

| | |
|---|---|
| atgggatgta gactgctgtg ttgcgccgtg ctgtgtctgc tgggagccgt gcctatggaa | 60 |
| accggcgtga cccagacccc cagacatctc gtgatgggca tgaccaacaa gaaaagcctg | 120 |
| aagtgcgagc agcacctggg ccacaacgcc atgtactggt acaagcagag cgccaagaaa | 180 |
| cccctggaac tgatgttcgt gtacaacttc aaagagcaga ccgagaacaa cagcgtgccc | 240 |
| agcagattca gccccgagtg ccccaatagc agccacctgt tctgcatcct gcacaccctg | 300 |
| cagcccgagg acagcgccct gtatctgtgc | 330 |

<210> SEQ ID NO 57
<211> LENGTH: 339
<212> TYPE: DNA
<213> ORGANISM: Homo sapiens

<400> SEQUENCE: 57

| | |
|---|---|
| atgggatgca gactgctgtg ctgcgccgtg ctgtgcctgc tgggagctgg cgagctggtg | 60 |
| cccatggaaa ccggcgtgac ccagaccccc agacacctgg tcatgggcat gaccaacaag | 120 |
| aaaagcctga gtgcgagca gcacctgggc cacaacgcca tgtactggta caagcagagc | 180 |
| gccaagaaac ccctggaact gatgttcgtg tacagcctgg aagagagggt ggaaaacaac | 240 |
| agcgtgccca gccggttcag ccccgagtgc cccaatagca gccacctgtt tctgcatctg | 300 |
| cacacctcc agcccgagga cagcgccctg tatctgtgc | 339 |

<210> SEQ ID NO 58
<211> LENGTH: 330
<212> TYPE: DNA
<213> ORGANISM: Homo sapiens

<400> SEQUENCE: 58

| | |
|---|---|
| atgggaagca gactgctgtg ctgggtgctg ctgtgcctgc tgggagccgg acctgtgaag | 60 |
| gccggcgtga cccagacccc cagatacctg atcaagacca gaggccagca ggtcacactg | 120 |
| agctgcagcc ccatcagcgg ccacagaagc gtgtcctggt atcagcagac cccaggccag | 180 |
| ggcctgcagt tcctgttcga gtacttcagc gagacacagc ggaacaaggg caacttcccc | 240 |
| ggcagattca gcggcagaca gttcagcaac agccgcagcg agatgaacgt gtccaccctg | 300 |
| gaactgggcg acagcgccct gtatctgtgc | 330 |

<210> SEQ ID NO 59
<211> LENGTH: 330
<212> TYPE: DNA
<213> ORGANISM: Homo sapiens

<400> SEQUENCE: 59

| | |
|---|---|
| atgggacctg gactgctgtg ttgggtgctg ctgtgtctgc tgggagccgg cagtgtggaa | 60 |
| accggcgtga cacagagccc cacccacctg atcaagacca gaggccagca agtgaccctg | 120 |

```
cggtgcagct ctcagagcgg ccacaatacc gtgtcctggt atcagcaggc cctgggccag      180
ggaccccagt tcatcttcca gtactacaga gaggaagaga acggcagagg caacttccca      240
ccccggttta gcggcctgca gttccccaac tacagctccg agctgaacgt gaacgccctg      300
gaactggacg acagcgccct gtacctgtgc                                      330

<210> SEQ ID NO 60
<211> LENGTH: 330
<212> TYPE: DNA
<213> ORGANISM: Homo sapiens

<400> SEQUENCE: 60
atgggacctg gactgctgtg ttgggtgctg ctgtgtctgc tgggagccgg acctgtggat       60
gctggcgtga cacagagccc cacccacctg atcaagacca gaggccagca agtgaccctg      120
cggtgcagcc ctatcagcgg ccacaagagc gtgtcctggt atcagcaggt gctgggccag      180
ggcccccagt tcatcttcca gtactacgag aaagaggaac ggggcagagg caacttccccc     240 gacagattca gcgccagaca gttccccaac tacagctccg agctgaacgt gaacgccctg      300
ctgctgggcg atagcgccct gtatctgtgc                                      330

<210> SEQ ID NO 61
<211> LENGTH: 330
<212> TYPE: DNA
<213> ORGANISM: Homo sapiens

<400> SEQUENCE: 61
atgggacctg gactgctgtg ttgggccctg ctgtgcctgc tgggagccgg actggtggat       60
gccggcgtga cccagagccc cacccacctg atcaagacca gaggccagca ggtcacactg      120
cggtgcagcc ccaagagcgg ccacgacacc gtgtcctggt atcagcaggc cctcggccag      180
ggaccccagt tcatcttcca gtactacgag aagaggaac ggcagcgggg caacttccccc      240 gacagattca gcgccacca gttccccaac tacagcagcg agctgaacgt gaacgccctg       300
ctgctgggcg acagcgccct gtatctgtgc                                      330

<210> SEQ ID NO 62
<211> LENGTH: 330
<212> TYPE: DNA
<213> ORGANISM: Homo sapiens

<400> SEQUENCE: 62
atgggaccta gactgctgtt ttgggccctg ctgtgcctgc tgggcacagg acctgtggaa       60
gctggcgtga cccagagccc tacccacctg atcaagacca gaggccagca ggccaccctg      120
agatgcagcc ctatcagcgg ccacaccagc gtgtactggt atcagcaggc cctgggactg      180
ggcctgcagt tcctgctgtg gtacgacgag ggcgaggaac ggaaccgggg caacttccca      240
cccagattca gcggcagaca gttccccaac tacagcagcg agctgaacgt gaacgccctg      300
gaactggaag atagcgccct gtacctgtgc                                      330

<210> SEQ ID NO 63
<211> LENGTH: 330
<212> TYPE: DNA
<213> ORGANISM: Homo sapiens

<400> SEQUENCE: 63
atgtctatcg gcctgctgtg ctgcgtggcc ttcagcctgc tgtgggccag ccctgtgaat       60
```

```
gccggcgtga cccagacccc caagttccag gtgctgaaaa ccggccagag catgaccctg    120
cagtgcgccc aggacatgaa ccacaacagc atgtactggt acagacagga ccccggcatg    180
ggcctgcggc tgatctacta cagcgccagc gagggcacca ccgacaaggg cgaggtgccc    240
aacggctaca cgtgtcccg gctgaacaag agagagttca gcctgagact ggaaagcgcc     300
gctcccagcc agaccagcgt gtacttctgc                                    330
```

<210> SEQ ID NO 64
<211> LENGTH: 330
<212> TYPE: DNA
<213> ORGANISM: Homo sapiens

<400> SEQUENCE: 64

```
atgtctctgg gcctgctgtg ctgcggcgcc ttcagcctgc tgtgggccgg acctgtgaat    60
gccggcgtga cccagacccc caagttccgg gtgctgaaaa ccggccagag catgaccctg    120
ctgtgcgccc aggacatgaa ccacgagtac atgtattggt acagacagga ccccggcatg    180
ggcctgcggc tgatccacta ctctgtgggc gagggcacca ccgccaaggg cgaagtgccc    240
gacggctaca cgtgtcccg gctgaagaag cagaacttcc tgctgggcct ggaaagcgcc     300
gctcccagcc agaccagcgt gtacttctgc                                    330
```

<210> SEQ ID NO 65
<211> LENGTH: 330
<212> TYPE: DNA
<213> ORGANISM: Homo sapiens

<400> SEQUENCE: 65

```
atgagaatca gactgctgtg ctgcgtggcc ttcagcctgc tgtgggccgg acctgtgatc    60
gccggaatca cccaggcccc caccagccag attctggccg ctggcagacg gatgaccctg    120
cggtgtaccc aggacatgcg gcacaacgcc atgtactggt acagacagga cctgggcctg    180
ggcctgcggc tgatccacta cagcaatacc gccggcacca ccgcaaggg cgaggtgcca    240 gatggctaca cgtgtcccg ggccaacacc gacgacttcc cactgacact ggccagcgcc    300
gtgcccagcc agaccagcgt gtacttctgc                                    330
```

<210> SEQ ID NO 66
<211> LENGTH: 330
<212> TYPE: DNA
<213> ORGANISM: Homo sapiens

<400> SEQUENCE: 66

```
atgagcatcg gcctgctgtg ctgcgccgcc ctgagcctgc tgtgggccgg ccccgtgaac    60
gccggcgtga cccagacccc caagttccag gtgctgaaga ccggccagag catgaccctg    120
cagtgcgccc aggacatgaa ccacgagtac atgagctggt accgccagga ccccggcatg    180
ggcctgcgcc tgatccacta cagcgtgggc gccggcatca ccgaccaggg cgaggtgccc    240
aacggctaca cgtgagccg cagcaccacc gaggacttcc ccctgcgcct gctgagcgcc    300
gcccccagcc agaccagcgt gtacttctgc                                    330
```

<210> SEQ ID NO 67
<211> LENGTH: 330
<212> TYPE: DNA
<213> ORGANISM: Homo sapiens

<400> SEQUENCE: 67

```
atgtctatta gcctgctgtg ctgcgccgcc ttccccctgc tgtgggctgg acctgtgaat    60
```

```
gccggcgtga cccagacccc caagttccgg atcctgaaga tcggccagag catgaccctg      120
cagtgcaccc aggacatgaa ccacaactac atgtactggt acagacagga ccccggcatg      180
ggcctgaagc tgatctacta ctctgtggga gccggcatca ccgacaaggg cgaggtgccc      240
aatggctaca cgtgtccag aagcaccacc gaggacttcc ctctgcggct ggaactggcc       300
gctcctagcc agaccagcgt gtacttctgc                                        330
```

<210> SEQ ID NO 68
<211> LENGTH: 327
<212> TYPE: DNA
<213> ORGANISM: Homo sapiens

<400> SEQUENCE: 68

```
atgtctctgg gactgctgtg ctgcgccgcc ttctctctgc tgtgggccgg acctgtgaat      60
gccggcgtga cccagacccc caagttccac atcctgaaaa ccggccagag catgaccctg      120
cagtgcgccc aggacatgaa ccacggctac atgagctggt acagacagga ccccggcatg      180
ggcctgcggc tgatctacta ttctgccgcc gctggcacca ccgacaaaga ggtgccaaac      240
ggctacaacg tgtcccggct gaacaccgag gacttccac tgagactggt gtctgccgcc       300
cctagccaga ccagcgtgta cctgtgc                                           327
```

<210> SEQ ID NO 69
<211> LENGTH: 330
<212> TYPE: DNA
<213> ORGANISM: Homo sapiens

<400> SEQUENCE: 69

```
atgtctattg gcctgctgtg ctgcgtggcc ttcagtctgc tgtgggaggg ccctgtgaat      60
gccggcgtga cccagacccc caagttccac atcctgaaaa ccggccagag catgaccctg      120
cagtgcgccc aggacatgaa ccacggctac ctgagctggt acagacagga ccctggcatg      180
ggcctgcggc ggatccacta ttctgtggcc gctggcatca ccgacaaggg cgaagtgccc      240
gacggctaca cgtgtccag aagcaacacc gaggacttcc cactgcggct ggaatctgcc       300
gcccctagcc agaccagcgt gtacttctgc                                        330
```

<210> SEQ ID NO 70
<211> LENGTH: 333
<212> TYPE: DNA
<213> ORGANISM: Homo sapiens

<400> SEQUENCE: 70

```
atgggcaccc gcctgctgtt ctgggtggcc ttctgcctgc tgggcgccga ccacaccggc      60
gccggcgtga gccagagccc cagcaacaag gtaactgaga agggcaagga cgtggagctg      120
cgctgcgacc ccatcagcgg ccacaccgcc ctgtactggt accgccagag cctgggccag      180
ggcctggagt tcctgatcta cttccagggc aacagcgccc ccgacaagag cggcctgccc      240
agcgaccgct tcagcgccga gcgcaccggc ggcagcgtga gcaccctgac catccagcgc      300
acccagcagg aggacagcgc cgtgtacctg tgc                                    333
```

<210> SEQ ID NO 71
<211> LENGTH: 333
<212> TYPE: DNA
<213> ORGANISM: Homo sapiens

<400> SEQUENCE: 71

| | |
|---|---|
| atgggaacca gactgctgtg ctgggccgct ctgtgtctgc tgggcgccga tcatacaggc | 60 |
| gctggcgtgt cccagacccc cagcaacaaa gtgaccgaga agggcaaata cgtcgagctg | 120 |
| agatgcgacc ccatcagcgg ccacaccgcc ctgtactggt acagacagag cctgggccag | 180 |
| ggccccgagt tcctgatcta ttttcagggc accggcgctg cagacgacag cggcctgccc | 240 |
| aacgacagat tcttcgccgt gagacccgag ggcagcgtgt ccaccctgaa gatccagcgg | 300 |
| accgagaggg gcgacagcgc cgtgtatctg tgc | 333 |

<210> SEQ ID NO 72
<211> LENGTH: 333
<212> TYPE: DNA
<213> ORGANISM: Homo sapiens

<400> SEQUENCE: 72

| | |
|---|---|
| atgggaacaa gactgctgtg ctgggtggtg ctgggcttcc tgggcacaga tcatacaggc | 60 |
| gctggcgtgt cccagagccc cagatacaag gtggccaaga ggggcagaga tgtggccctg | 120 |
| agatgcgaca gcatcagcgg ccacgtgacc ctgtactggt acagacagac actgggccag | 180 |
| ggcagcgagg tgctgacata cagccagagc gacgcccagc gggacaagag cggcagacct | 240 |
| agcggcagat tttccgccga gaggcccgag agaagcgtgt ccaccctgaa gatccagcgg | 300 |
| accgagcagg gcgatagcgc cgtgtatctg tgc | 333 |

<210> SEQ ID NO 73
<211> LENGTH: 333
<212> TYPE: DNA
<213> ORGANISM: Homo sapiens

<400> SEQUENCE: 73

| | |
|---|---|
| atgggaacaa gctgctgtg ctgggtggtg ctgggcttcc tgggcaccga tcacacaggc | 60 |
| gctggcgtgt cccagagccc ccggtacaaa gtgaccaagc ggggccagga cgtggccctg | 120 |
| agatgcgacc ctatcagcgg ccatgtgtcc ctgtactggt acagacaggc actgggccag | 180 |
| ggacccgagt tcctgaccta cttcaactac gaggcccagc aggacaagag cggcctgccc | 240 |
| aacgacagat tcagcgccga gaggcccgag ggcagcatca gcaccctgac catccagcgg | 300 |
| accgagcagc gggacagcgc catgtacaga tgc | 333 |

<210> SEQ ID NO 74
<211> LENGTH: 333
<212> TYPE: DNA
<213> ORGANISM: Homo sapiens

<400> SEQUENCE: 74

| | |
|---|---|
| atgggaacat ctctgctgtg ctgggtggtg ctgggcttcc tgggcacaga tcatacaggc | 60 |
| gctggcgtgt cccagagccc ccggtacaaa gtgaccaaga ggggccagga cgtgaccctg | 120 |
| agatgcgacc ctatcagcag ccacgccacc ctgtactggt atcagcaggc cctgggacag | 180 |
| ggccccgagt tcctgaccta cttcaactac gaggcccagc ccgacaagag cggcctgccc | 240 |
| agcgatagat tttccgccga aagacccgag ggcagcatca gcaccctgac catccagaga | 300 |
| accgagcagc gggacagcgc catgtacaga tgc | 333 |

<210> SEQ ID NO 75
<211> LENGTH: 333
<212> TYPE: DNA
<213> ORGANISM: Homo sapiens

<400> SEQUENCE: 75

```
atgggaacaa gactgctgtg ctgggtggtg ctgggcttcc tgggcacaga tcatacaggc    60
gctggcgtgt cccagagccc cagatacaag gtggccaaga ggggccagga cgtggccctg   120
agatgcgatc ctatcagcgg ccacgtgtcc ctgttctggt atcagcaggc cctgggccag   180
ggacccgagt tcctgaccta cttccagaac gaggcccagc tggacaagag cggcctgccc   240
agcgatagat tcttcgccga aagacccgag ggcagcgtgt ccaccctgaa gatccagaga   300
acccagcagg aagatagcgc cgtgtacctg tgc                                333
```

<210> SEQ ID NO 76
<211> LENGTH: 333
<212> TYPE: DNA
<213> ORGANISM: Homo sapiens

<400> SEQUENCE: 76

```
atgggaacaa gcctgctgtg ctggatggcc ctgtgcctgc tgggagccga ccacgccgat    60
acaggcgtgt cccagaaccc ccggcacaag atcaccaagc ggggcagaa cgtgaccttc   120 agatgcgacc ccatcagcga gcacaaccgg ctgtactggt acagacagac cctgggccag   180
ggccccgagt tcctgaccta cttccagaac gaggcccagc tggaaaagag ccggctgctg   240
agcgacagat tcagcgccga gaggcccaag ggcagcttca gcaccctgga aatccagcgg   300
accgagcagg gcgacagcgc catgtatctg tgc                                333
```

<210> SEQ ID NO 77
<211> LENGTH: 330
<212> TYPE: DNA
<213> ORGANISM: Homo sapiens

<400> SEQUENCE: 77

```
atgggcttcc gcctgctgtg ctgcgtggcc ttctgcctgc tgggcgccgg ccccgtggac    60
agcggcgtga cccagacccc caagcacctg atcaccgcca ccggccagcg cgtgaccctg   120
cgctgcagcc cccgcagcgg cgacctgagc gtgtactggt accagcagag cctggaccag   180
ggcctgcagt tcctgatcca gtactacaac ggcgaggagc gcgccaaggg caacatcctg   240
gagcgcttca gcgcccagca gttccccgac ctgcacagcg agctgaacct gagcagcctg   300
gagctgggcg acagcgccct gtacttctgc                                    330
```

<210> SEQ ID NO 78
<211> LENGTH: 330
<212> TYPE: DNA
<213> ORGANISM: Homo sapiens

<400> SEQUENCE: 78

```
atgggcacca gactgttctt ctacgtggcc ctgtgcctgc tgtgggccgg acacagagat    60
gccgagatca cccagagccc cagacacaag atcaccgaga caggccggca ggtcacactg   120
gcctgccacc agacctggaa ccacaacaac atgttctggt acagacagga cctgggccac   180
ggcctgcggc tgatccacta cagctacggc gtgcaggaca ccaacaaggg cgaggtgtcc   240
gacggctaca gcgtgtccag aagcaacacc gaggacctgc ccctgaccct ggaaagcgcc   300
gccagcagcc agaccagcgt gtacttctgc                                    330
```

<210> SEQ ID NO 79
<211> LENGTH: 330
<212> TYPE: DNA
<213> ORGANISM: Homo sapiens

<400> SEQUENCE: 79

```
atgggaacca gactgttctt ctacgtggcc ctgtgcctgc tgtgggccgg acatagagat    60
gccggaatca cccagagccc ccggtacaag atcaccgaga caggcagaca agtgaccctg   120
atgtgccacc agacctggtc ccacagctac atgttctggt acagacagga cctgggccac   180
ggcctgcggc tgatctacta ttctgccgcc gctgacatca ccgacaaggg cgaagtgccc   240
gacggctacg tggtgtccag aagcaagacc gagaacttcc cactgaccct ggaaagcgcc   300
acccggtccc agaccagcgt gtacttttgc                                    330
```

<210> SEQ ID NO 80
<211> LENGTH: 330
<212> TYPE: DNA
<213> ORGANISM: Homo sapiens

<400> SEQUENCE: 80

```
atgggcacca gactgttctt ctacgtggcc ctgtgcctgc tgtggaccgg ccacatggac    60
gccggcatca cccagagccc cagacacaaa gtcaccgaga caggcacccc cgtgaccctg   120
agatgccacc agaccgagaa ccaccgctac atgtactggt acagacagga ccccggccac   180
ggcctgcggc tgatccacta cagctacggc gtgaaggaca ccgacaaggg cgaggtgtcc   240
gacggctaca gcgtgtccag aagcaagacc gaggacttcc tgctgaccct ggaaagcgcc   300
accagcagcc agaccagcgt gtacttctgc                                    330
```

<210> SEQ ID NO 81
<211> LENGTH: 333
<212> TYPE: DNA
<213> ORGANISM: Homo sapiens

<400> SEQUENCE: 81

```
atgagcacca gactgctgtg ctggatggcc ctgtgcctgc tgggcgccga gctgtctgaa    60
gccgaggtgg cccagagccc ccggtacaag atcaccgaga agtcccaggc cgtggccttt   120
tggtgcgacc ccatcagcgg ccacgccacc ctgtactggt acagacagat cctgggccag   180
ggccccgaac tgctggtgca gttccaggac gagagcgtgg tggacgacag ccagctgccc   240
aaggacagat tcagcgccga gcggctgaag ggcgtggaca gcaccctgaa gatccagccc   300
gccgagctgg gcgacagcgc catgtatctg tgc                                333
```

<210> SEQ ID NO 82
<211> LENGTH: 333
<212> TYPE: DNA
<213> ORGANISM: Homo sapiens

<400> SEQUENCE: 82

```
atgggaacca gactgctgtg ctgggccgct ctgtgtctgc tgggcgccga actgacagag    60
gctggcgtgg cacagagccc ccggtacaag atcatcgaga agcggcagag cgtggccttc   120
tggtgcaacc ccatcagcgg ccacgccacc ctgtactggt atcagcagat cctgggccag   180
ggccccaagc tgctgatcca gttccagaac aacggcgtgg tggacgacag ccagctgccc   240
aaggacagat tcagcgccga gcggctgaag ggcgtggaca gcaccctgaa gatccagccc   300
gccaagctgg aagatagcgc cgtgtatctg tgc                                333
```

<210> SEQ ID NO 83
<211> LENGTH: 333
<212> TYPE: DNA
<213> ORGANISM: Homo sapiens

<400> SEQUENCE: 83

```
atgggaacaa gactgctgtg ctgggtggcc ttctgcctgc tggtggaaga actgatcgag      60
gccggcgtgg tgcagagccc ccggtacaag atcatcgaga agaaacagcc cgtggccttt     120
tggtgcaacc ccatcagcgg ccacaacacc ctgtactggt atctgcagaa cctgggccag     180
ggccccgagc tgctgatcag atacgagaac gaggaagccg tggacgacag ccagctgccc     240
aaggacagat tcagcgccga gagactgaag ggcgtggaca gcaccctgaa gatccagcct     300
gccgagctgg gcgatagcgc cgtgtatctg tgc                                  333
```

<210> SEQ ID NO 84
<211> LENGTH: 333
<212> TYPE: DNA
<213> ORGANISM: Homo sapiens

<400> SEQUENCE: 84

```
atggacagct ggaccttctg ctgcgtgagc ctgtgcatcc tggtggccaa gcacaccgac      60
gccggcgtga tccagagccc ccgccacgag gttactgaga tgggccagga ggtgactctg     120
cgctgcaagc ccatcagcgg ccacaacagc ctgttctggt accgccagac catgatgcgc     180
ggcctggagc tgctgatcta cttcaacaac aacgtgccca tcgacgacag cggcatgccc     240
gaggaccgct tcagcgccaa gatgcccaac gccagcttca gcaccctgaa gatccagccc     300
agcgagcccc gcgacagcgc cgtgtacttc tgc                                  333
```

<210> SEQ ID NO 85
<211> LENGTH: 333
<212> TYPE: DNA
<213> ORGANISM: Homo sapiens

<400> SEQUENCE: 85

```
atgggatctt ggacactgtg ctgcgtgtcc ctgtgcatcc tggtggccaa gcacacagat      60
gccggcgtga tccagagccc cagacatgaa gtgaccgaga tgggccagga agtgaccctg     120
cgctgcaagc ctatcagcgg ccacgactac ctgttctggt acagacagac catgatgcgg     180
ggcctggaac tgctgatcta cttcaacaac aacgtgccca tcgacgacag cggcatgccc     240
gaggatagat tcagcgccaa gatgcccaac gccagcttca gcaccctgaa gatccagccc     300
agcgagccca gagacagcgc cgtgtacttt tgc                                  333
```

<210> SEQ ID NO 86
<211> LENGTH: 333
<212> TYPE: DNA
<213> ORGANISM: Homo sapiens

<400> SEQUENCE: 86

```
atggctacca gactgctgtg ctgcgtggtg ctgtgcctgc tgggcgagga actgatcgac      60
gccagagtga cccagacccc cagacacaaa gtcaccgaga tgggccagga agtgaccatg     120
cggtgccagc ccatcctggg ccacaacacc gtgttctggt acagacagac catgatgcag     180
ggcctggaac tgctggccta cttccggaac agagcccccc tggacgacag cggcatgccc     240
aaggacagat tcagcgccga gatgcccgac gccaccctgg ccacactgaa gatccagccc     300
agcgagccca gagacagcgc cgtgtacttc tgc                                  333
```

<210> SEQ ID NO 87
<211> LENGTH: 360
<212> TYPE: DNA

<213> ORGANISM: Homo sapiens

<400> SEQUENCE: 87

| atgctgtctc | cgacctgcc | tgacagcgcc | tggaacaccc | ggctgctgtg | ccatgtgatg | 60 |
| ctgtgcctgc | tgggcgccgt | gtctgtggcc | gctggcgtga | tccagagccc | agacacctg | 120 |
| atcaaagaga | agagagagac | agccaccctg | aagtgctacc | ccatcccccg | gcacgacacc | 180 |
| gtgtactggt | atcagcaggg | ccctggacag | gaccccagt | tcctgatcag | cttctacgag | 240 |
| aagatgcaga | gcgacaaggg | cagcatcccc | gacagattca | gcgcccagca | gttcagcgac | 300 |
| taccacagcg | agctgaacat | gagcagcctg | gaactgggcg | acagcgccct | gtacttctgc | 360 |

<210> SEQ ID NO 88
<211> LENGTH: 333
<212> TYPE: DNA
<213> ORGANISM: Homo sapiens

<400> SEQUENCE: 88

| atggtgagcc | gcctgctgag | cctggtgagc | ctgtgcctgc | tgggcgccaa | gcacatcgag | 60 |
| gccggcgtga | cccagttccc | cagccacagc | gtgatcgaga | agggccagac | cgtgaccctg | 120 |
| cgctgcgacc | ccatcagcgg | ccacgacaac | ctgtactggt | atcgccgcgt | gatgggcaag | 180 |
| gagatcaagt | tcctgctgca | cttcgtgaag | gagagcaagc | aggacgagag | cggcatgccc | 240 |
| aacaaccgct | tcctggccga | gcgcaccggc | ggcacctaca | gcaccctgaa | ggtgcagccc | 300 |
| gccgagctgg | aggacagcgg | cgtgtacttc | tgc | | | 333 |

<210> SEQ ID NO 89
<211> LENGTH: 330
<212> TYPE: DNA
<213> ORGANISM: Homo sapiens

<400> SEQUENCE: 89

| atgggacctg | gactgctgca | ctggatggcc | ctgtgcctgc | tgggcacagg | acacggcgac | 60 |
| gccatggtca | tccagaaccc | cagataccag | gtcacacagt | tcggcaagcc | cgtgaccctg | 120 |
| agctgcagcc | agaccctgaa | ccataacgtg | atgtactggt | atcagcagaa | gtccagccag | 180 |
| gcccccaagc | tgctgttcca | ctactacgac | aaggacttca | acaacgaggc | cgacaccccc | 240 |
| gacaacttcc | agagcagacg | gcccaatacc | agcttctgct | tcctggacat | cagaagccct | 300 |
| ggcctgggcg | acaccgccat | gtatctgtgc | | | | 330 |

<210> SEQ ID NO 90
<211> LENGTH: 333
<212> TYPE: DNA
<213> ORGANISM: Homo sapiens

<400> SEQUENCE: 90

| atgagcccca | tcttcacctg | tatcaccatc | ctgtgcctgc | tggccgctgg | cagccctggc | 60 |
| gaagaagtgg | cccagacccc | caagcacctc | gtcagaggcg | agggccagaa | ggccaagctg | 120 |
| tactgcgccc | ccatcaaggg | ccacagctac | gtgttctggt | atcagcaggt | cctgaagaac | 180 |
| gagttcaagt | tcctgatcag | cttccagaac | gagaacgtgt | cgacgagac | aggcatgccc | 240 |
| aaagagcggt | tcagcgccaa | gtgcctgccc | aacagcccct | gcagcctgga | aatccaggcc | 300 |
| accaagctgg | aagatagcgc | cgtgtacttc | tgc | | | 333 |

<210> SEQ ID NO 91
<211> LENGTH: 333

```
<212> TYPE: DNA
<213> ORGANISM: Homo sapiens

<400> SEQUENCE: 91
atggatacca gagtgctgtg ctgcgccgtg atctgcctgc tgggagccgg cctgtctaac    60
gccggcgtga tgcagaaccc ccggcatctc gtgcggcgga gaggcaggga agcccggctg   120
cgctgtagcc ccatgaaggg ccacagccat gtgtactggt acagacagct gcccgaagag   180
ggcctgaagt tcatggtgta cctgcagaaa gagaacatca tcgacgagag cggcatgccc   240
aaagagcggt tcagcgccga gttccccaaa gagggcccca gcatcctgag aatccagcag   300
gtcgtgcggg gcgatagcgc cgcctacttc tgc                                333

<210> SEQ ID NO 92
<211> LENGTH: 330
<212> TYPE: DNA
<213> ORGANISM: Homo sapiens

<400> SEQUENCE: 92
atgagcaatc aggtgctgtg ctgcgtggtg ctgtgttttc ctgggcgcca caccgtggac    60
ggcggcatca cccagagccc caagtacctg ttccggaaag agggccagaa cgtcaccctg   120
agctgcgagc agaacctgaa ccacgacgcc atgtactggt acagacagga ccccggccag   180
ggcctgcggc tgatctacta cagccagatc gtgaacgact ccagaagggg cgacattgcc   240
gagggctaca gcgtgtccag agagaagaaa gagtccttcc cactgaccgt gaccagcgcc   300
cagaagaacc caccgccttc ctacctgtgc                                    330

<210> SEQ ID NO 93
<211> LENGTH: 357
<212> TYPE: DNA
<213> ORGANISM: Homo sapiens

<400> SEQUENCE: 93
atgctgctgc tgctgctcct cctgggccct ggcatcagcc tgctgctgcc tggatctctg    60
gccggctctg gactgggcgc cgtggtgtct cagcacccca gctgggtcat ctgcaagagc   120
ggcaccagcg tgaagatcga gtgcagaagc ctggacttcc aggccaccac catgttctgg   180
tacagacagt tccccaagca gagcctgatg ctgatggcca ccagcaacga gggcagcaag   240
gccacctacg agcagggcgt ggaaaaggac aagttcctga tcaaccacgc cagcctgacc   300
ctgagcaccc tgaccgtgac aagcgcccac cccgaggaca gcagcttcta catctgc     357

<210> SEQ ID NO 94
<211> LENGTH: 330
<212> TYPE: DNA
<213> ORGANISM: Homo sapiens

<400> SEQUENCE: 94
atggctagcc tgctgttctt ctgcggcgcc ttctacctgc tgggcaccgg cagcatggac    60
gccgacgtga cccagacccc ccggaaccgg atcaccaaga ccggcaagcg gatcatgctg   120
gaatgcagcc agaccaaggg ccacgaccgg atgtactggt acagacagga ccccggcctg   180
ggcctgcggc tgatctacta cagcttcgac gtgaaggaca tcaacaaggg cgagatcagc   240
gacggctaca gcgtgtccag acaggcccag gctaagttca gcctgagcct ggaaagcgcc   300
atccccaacc agaccgccct gtacttctgc                                    330

<210> SEQ ID NO 95
```

```
<211> LENGTH: 330
<212> TYPE: DNA
<213> ORGANISM: Homo sapiens

<400> SEQUENCE: 95
atgaccatca gactgctgtg ctatatgggc ttctacttcc tgggagccgg cctgatggaa      60
gccgacatct accagacccc cagatacctg gtcatcggca ccggcaagaa aatcaccctg     120
gaatgcagcc agaccatggg ccacgacaag atgtactggt atcagcagga ccccggcatg     180
gaactgcacc tgatccacta cagctacggc gtgaacagca ccgagaaggg cgacctgagc     240
agcgagagca ccgtgtcccg gatccggacc gagcacttcc cactgaccct ggaaagcgcc     300
aggcccagcc acaccagcca gtacctgtgc                                      330

<210> SEQ ID NO 96
<211> LENGTH: 330
<212> TYPE: DNA
<213> ORGANISM: Homo sapiens

<400> SEQUENCE: 96
atgggacctc agctgctggg ctacgtggtg ctgtgcctgc tgggagccgg accctggaa       60 gcccaggtca cacagaaccc cagatacctg atcaccgtga ccggcaagaa actgaccgtg     120
acctgcagcc agaacatgaa ccacgagtac atgagctggt acagacagga ccccggcctg     180
ggcctgcggc agatctacta cagcatgaac gtggaagtga ccgacaaggg cgacgtgccc     240
gagggctaca aggtgtcccg gaaagagaag cggaacttcc cactgatcct ggaaagcccc     300
agccccaacc agaccagcct gtacttctgc                                      330

<210> SEQ ID NO 97
<211> LENGTH: 330
<212> TYPE: DNA
<213> ORGANISM: Homo sapiens

<400> SEQUENCE: 97
atgggaatca gactgctgtg ccgggtggcc ttctgcttcc tggccgtggg actggtggac      60
gtgaaagtga cccagagcag cagatacctg gtcaagcgga ccggcgagaa ggtgttcctg     120
gaatgcgtgc aggacatgga ccacgagaat atgttctggt acagacagga ccccggcctg     180
ggcctgcggc tgatctactt cagctacgac gtgaagatga ggaaaaaggg cgacatcccc     240
gagggctaca gcgtgtccag agagaagaaa gagcggttca gcctgatcct ggaaagcgcc     300
agcaccaacc agaccagcat gtatctgtgc                                      330

<210> SEQ ID NO 98
<211> LENGTH: 324
<212> TYPE: DNA
<213> ORGANISM: Homo sapiens

<400> SEQUENCE: 98
atgctgagcc tgctgctgct gctgctgggc ctgggcagcg tgttcagcgc cgtgatcagc      60
cagaagccca ccgcgacat ctgccagcgc ggcaccagcc tgaccatcca gtgccagtg      120 gacagccagg tgaccatgat gttctggtac cgccagcagc ccggcagag cctgaccctg     180 atcgccaccg ccaaccaggg cagcgaggcc acctacgaga gcggcttcgt gatcgacaag     240
ttccccatca gccgccccaa cctgaccttc agcaccctga ccgtgagcaa catgagcccc     300
gaggacagca gcatctacct gtgc                                            324
```

<210> SEQ ID NO 99
<211> LENGTH: 324
<212> TYPE: DNA
<213> ORGANISM: Homo sapiens

<400> SEQUENCE: 99

```
atgctgtgtt ctctgctggc cctgctgctg ggcaccttct tcggagtgcg gagccagacc      60
atccaccagt ggcctgccac cctggtgcag cctgtgggca gccctctgag cctggaatgc     120
accgtggaag gcaccagcaa ccccaacctg tactggtaca gacaggccgc tggcagaggc     180
ctgcagctgc tgttctacag cgtgggcatc ggccagatca gcagcgaggt gccccagaac     240
ctgagcgcca gcagacccca ggaccggcag ttcatcctga gcagcaagaa gctgctgctg     300
agcgacagcg gcttctacct gtgc                                             324
```

<210> SEQ ID NO 100
<211> LENGTH: 88
<212> TYPE: PRT
<213> ORGANISM: Homo sapiens

<400> SEQUENCE: 100

```
Gly Gln Ser Leu Glu Gln Pro Ser Glu Val Thr Ala Val Glu Gly Ala
1               5                   10                  15

Ile Val Gln Ile Asn Cys Thr Tyr Gln Thr Ser Gly Phe Tyr Gly Leu
                20                  25                  30

Ser Trp Tyr Gln Gln His Asp Gly Gly Ala Pro Thr Phe Leu Ser Tyr
            35                  40                  45

Asn Ala Leu Asp Gly Leu Glu Glu Thr Gly Arg Phe Ser Ser Phe Leu
        50                  55                  60

Ser Arg Ser Asp Ser Tyr Gly Tyr Leu Leu Leu Gln Glu Leu Gln Met
65                  70                  75                  80

Lys Asp Ser Ala Ser Tyr Phe Cys
                85
```

<210> SEQ ID NO 101
<211> LENGTH: 88
<212> TYPE: PRT
<213> ORGANISM: Homo sapiens

<400> SEQUENCE: 101

```
Gly Gln Asn Ile Asp Gln Pro Thr Glu Met Thr Ala Thr Glu Gly Ala
1               5                   10                  15

Ile Val Gln Ile Asn Cys Thr Tyr Gln Thr Ser Gly Phe Asn Gly Leu
                20                  25                  30

Phe Trp Tyr Gln Gln His Ala Gly Glu Ala Pro Thr Phe Leu Ser Tyr
            35                  40                  45

Asn Val Leu Asp Gly Leu Glu Glu Lys Gly Arg Phe Ser Ser Phe Leu
        50                  55                  60

Ser Arg Ser Lys Gly Tyr Ser Tyr Leu Leu Leu Lys Glu Leu Gln Met
65                  70                  75                  80

Lys Asp Ser Ala Ser Tyr Leu Cys
                85
```

<210> SEQ ID NO 102
<211> LENGTH: 84
<212> TYPE: PRT
<213> ORGANISM: Homo sapiens

<400> SEQUENCE: 102

-continued

Lys Asp Gln Val Phe Gln Pro Ser Thr Val Ala Ser Ser Glu Gly Ala
1               5                   10                  15

Val Val Glu Ile Phe Cys Asn His Ser Val Ser Asn Ala Tyr Asn Phe
            20                  25                  30

Phe Trp Tyr Leu His Phe Pro Gly Cys Ala Pro Arg Leu Leu Val Lys
        35                  40                  45

Gly Ser Lys Pro Ser Gln Gln Gly Arg Tyr Asn Met Thr Tyr Glu Arg
    50                  55                  60

Phe Ser Ser Ser Leu Leu Ile Leu Gln Val Arg Glu Ala Asp Ala Ala
65                  70                  75                  80

Val Tyr Tyr Cys

<210> SEQ ID NO 103
<211> LENGTH: 91
<212> TYPE: PRT
<213> ORGANISM: Homo sapiens

<400> SEQUENCE: 103

Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
            20                  25                  30

Leu Phe Trp Tyr Val Gln Tyr Pro Asn Arg Gly Leu Gln Phe Leu Leu
        35                  40                  45

Lys Tyr Ile Thr Gly Asp Asn Leu Val Lys Gly Ser Tyr Gly Phe Glu
    50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys
                85                  90

<210> SEQ ID NO 104
<211> LENGTH: 88
<212> TYPE: PRT
<213> ORGANISM: Homo sapiens

<400> SEQUENCE: 104

Leu Ala Lys Thr Thr Gln Pro Ile Ser Met Asp Ser Tyr Glu Gly Gln
1               5                   10                  15

Glu Val Asn Ile Thr Cys Ser His Asn Asn Ile Ala Thr Asn Asp Tyr
            20                  25                  30

Ile Thr Trp Tyr Gln Gln Phe Pro Ser Gln Gly Pro Arg Phe Ile Ile
        35                  40                  45

Gln Gly Tyr Lys Thr Lys Val Thr Asn Glu Val Ala Ser Leu Phe Ile
    50                  55                  60

Pro Ala Asp Arg Lys Ser Ser Thr Leu Ser Leu Pro Arg Val Ser Leu
65                  70                  75                  80

Ser Asp Thr Ala Val Tyr Tyr Cys
                85

<210> SEQ ID NO 105
<211> LENGTH: 89
<212> TYPE: PRT
<213> ORGANISM: Homo sapiens

<400> SEQUENCE: 105

Gly Glu Asp Val Glu Gln Ser Leu Phe Leu Ser Val Arg Glu Gly Asp
1               5                   10                  15

Ser Ser Val Ile Asn Cys Thr Tyr Thr Asp Ser Ser Ser Thr Tyr Leu
            20                  25                  30

Tyr Trp Tyr Lys Gln Glu Pro Gly Ala Gly Leu Gln Leu Leu Thr Tyr
            35                  40                  45

Ile Phe Ser Asn Met Asp Met Lys Gln Asp Gln Arg Leu Thr Val Leu
        50                  55                  60

Leu Asn Lys Lys Asp Lys His Leu Ser Leu Arg Ile Ala Asp Thr Gln
65                  70                  75                  80

Thr Gly Asp Ser Ala Ile Tyr Phe Cys
                85

<210> SEQ ID NO 106
<211> LENGTH: 90
<212> TYPE: PRT
<213> ORGANISM: Homo sapiens

<400> SEQUENCE: 106

Ser Gln Lys Ile Glu Gln Asn Ser Glu Ala Leu Asn Ile Gln Glu Gly
1               5                   10                  15

Lys Thr Ala Thr Leu Thr Cys Asn Tyr Thr Asn Tyr Ser Pro Ala Tyr
            20                  25                  30

Leu Gln Trp Tyr Arg Gln Asp Pro Gly Arg Gly Pro Val Phe Leu Leu
        35                  40                  45

Leu Ile Arg Glu Asn Glu Lys Glu Lys Arg Lys Glu Arg Leu Lys Val
    50                  55                  60

Thr Phe Asp Thr Thr Leu Lys Gln Ser Leu Phe His Ile Thr Ala Ser
65                  70                  75                  80

Gln Pro Ala Asp Ser Ala Thr Tyr Leu Cys
                85                  90

<210> SEQ ID NO 107
<211> LENGTH: 88
<212> TYPE: PRT
<213> ORGANISM: Homo sapiens

<400> SEQUENCE: 107

Glu Asn Gln Val Glu His Ser Pro His Phe Leu Gly Pro Gln Gln Gly
1               5                   10                  15

Asp Val Ala Ser Met Ser Cys Thr Tyr Ser Val Ser Arg Phe Asn Asn
            20                  25                  30

Leu Gln Trp Tyr Arg Gln Asn Thr Gly Met Gly Pro Lys His Leu Leu
        35                  40                  45

Ser Met Tyr Ser Ala Gly Tyr Glu Lys Gln Lys Gly Arg Leu Asn Ala
    50                  55                  60

Thr Leu Leu Lys Asn Gly Ser Ser Leu Tyr Ile Thr Ala Val Gln Pro
65                  70                  75                  80

Glu Asp Ser Ala Thr Tyr Phe Cys
                85

<210> SEQ ID NO 108
<211> LENGTH: 91
<212> TYPE: PRT
<213> ORGANISM: Homo sapiens

<400> SEQUENCE: 108

Ala Gln Ser Val Ser Gln His Asn His His Val Ile Leu Ser Glu Ala
1               5                   10                  15

```
Ala Ser Leu Glu Leu Gly Cys Asn Tyr Ser Tyr Gly Gly Thr Val Asn
            20                  25                  30

Leu Phe Trp Tyr Val Gln Tyr Pro Gly Gln His Leu Gln Leu Leu Leu
        35                  40                  45

Lys Tyr Phe Ser Gly Asp Pro Leu Val Lys Gly Ile Lys Gly Phe Glu
50                  55                  60

Ala Glu Phe Ile Lys Ser Lys Phe Ser Phe Asn Leu Arg Lys Pro Ser
65                  70                  75                  80

Val Gln Trp Ser Asp Thr Ala Glu Tyr Phe Cys
                85                  90

<210> SEQ ID NO 109
<211> LENGTH: 91
<212> TYPE: PRT
<213> ORGANISM: Homo sapiens

<400> SEQUENCE: 109

Ala Gln Ser Val Thr Gln Leu Asp Ser His Val Ser Val Ser Glu Gly
1               5                   10                  15

Thr Pro Val Leu Leu Arg Cys Asn Tyr Ser Ser Ser Tyr Ser Pro Ser
            20                  25                  30

Leu Phe Trp Tyr Val Gln His Pro Asn Lys Gly Leu Gln Leu Leu Leu
        35                  40                  45

Lys Tyr Thr Ser Ala Ala Thr Leu Val Lys Gly Ile Asn Gly Phe Glu
50                  55                  60

Ala Glu Phe Lys Lys Ser Glu Thr Ser Phe His Leu Thr Lys Pro Ser
65                  70                  75                  80

Ala His Met Ser Asp Ala Ala Glu Tyr Phe Cys
                85                  90

<210> SEQ ID NO 110
<211> LENGTH: 91
<212> TYPE: PRT
<213> ORGANISM: Homo sapiens

<400> SEQUENCE: 110

Ala Gln Ser Val Thr Gln Pro Asp Ile His Ile Thr Val Ser Glu Gly
1               5                   10                  15

Ala Ser Leu Glu Leu Arg Cys Asn Tyr Ser Tyr Gly Ala Thr Pro Tyr
            20                  25                  30

Leu Phe Trp Tyr Val Gln Ser Pro Gly Gln Gly Leu Gln Leu Leu Leu
        35                  40                  45

Lys Tyr Phe Ser Gly Asp Thr Leu Val Gln Gly Ile Lys Gly Phe Glu
50                  55                  60

Ala Glu Phe Lys Arg Ser Gln Ser Ser Phe Asn Leu Arg Lys Pro Ser
65                  70                  75                  80

Val His Trp Ser Asp Ala Ala Glu Tyr Phe Cys
                85                  90

<210> SEQ ID NO 111
<211> LENGTH: 91
<212> TYPE: PRT
<213> ORGANISM: Homo sapiens

<400> SEQUENCE: 111

Ala Gln Ser Val Thr Gln Leu Gly Ser His Val Ser Val Ser Glu Gly
1               5                   10                  15

Ala Leu Val Leu Leu Arg Cys Asn Tyr Ser Ser Ser Val Pro Pro Tyr
```

```
            20                  25                  30

Leu Phe Trp Tyr Val Gln Tyr Pro Asn Gln Gly Leu Gln Leu Leu Leu
            35                  40                  45

Lys Tyr Thr Ser Ala Ala Thr Leu Val Lys Gly Ile Asn Gly Phe Glu
 50                  55                  60

Ala Glu Phe Lys Lys Ser Glu Thr Ser Phe His Leu Thr Lys Pro Ser
 65                  70                  75                  80

Ala His Met Ser Asp Ala Ala Glu Tyr Phe Cys
                85                  90

<210> SEQ ID NO 112
<211> LENGTH: 91
<212> TYPE: PRT
<213> ORGANISM: Homo sapiens

<400> SEQUENCE: 112

Ala Gln Ser Val Thr Gln Leu Asp Ser Gln Val Pro Val Phe Glu Glu
 1               5                  10                  15

Ala Pro Val Glu Leu Arg Cys Asn Tyr Ser Ser Ser Val Ser Val Tyr
                20                  25                  30

Leu Phe Trp Tyr Val Gln Tyr Pro Asn Gln Gly Leu Gln Leu Leu Leu
            35                  40                  45

Lys Tyr Leu Ser Gly Ser Thr Leu Val Glu Ser Ile Asn Gly Phe Glu
 50                  55                  60

Ala Glu Phe Asn Lys Ser Gln Thr Ser Phe His Leu Arg Lys Pro Ser
 65                  70                  75                  80

Val His Ile Ser Asp Thr Ala Glu Tyr Phe Cys
                85                  90

<210> SEQ ID NO 113
<211> LENGTH: 90
<212> TYPE: PRT
<213> ORGANISM: Homo sapiens

<400> SEQUENCE: 113

Gly Asp Ser Val Val Gln Thr Glu Gly Gln Val Leu Pro Ser Glu Gly
 1               5                  10                  15

Asp Ser Leu Ile Val Asn Cys Ser Tyr Glu Thr Thr Gln Tyr Pro Ser
                20                  25                  30

Leu Phe Trp Tyr Val Gln Tyr Pro Gly Glu Gly Pro Gln Leu His Leu
            35                  40                  45

Lys Ala Met Lys Ala Asn Asp Lys Gly Arg Asn Lys Gly Phe Glu Ala
 50                  55                  60

Met Tyr Arg Lys Glu Thr Thr Ser Phe His Leu Glu Lys Asp Ser Val
 65                  70                  75                  80

Gln Glu Ser Asp Ser Ala Val Tyr Phe Cys
                85                  90

<210> SEQ ID NO 114
<211> LENGTH: 90
<212> TYPE: PRT
<213> ORGANISM: Homo sapiens

<400> SEQUENCE: 114

Gly Asn Ser Val Thr Gln Met Glu Gly Pro Val Thr Leu Ser Glu Glu
 1               5                  10                  15

Ala Phe Leu Thr Ile Asn Cys Thr Tyr Thr Ala Thr Gly Tyr Pro Ser
                20                  25                  30
```

```
Leu Phe Trp Tyr Val Gln Tyr Pro Gly Glu Gly Leu Gln Leu Leu Leu
            35                  40                  45

Lys Ala Thr Lys Ala Asp Asp Lys Gly Ser Asn Lys Gly Phe Glu Ala
 50                  55                  60

Thr Tyr Arg Lys Glu Thr Thr Ser Phe His Leu Glu Lys Gly Ser Val
 65                  70                  75                  80

Gln Val Ser Asp Ser Ala Val Tyr Phe Cys
                85                  90

<210> SEQ ID NO 115
<211> LENGTH: 90
<212> TYPE: PRT
<213> ORGANISM: Homo sapiens

<400> SEQUENCE: 115

Lys Asn Gln Val Glu Gln Ser Pro Gln Ser Leu Ile Ile Leu Glu Gly
 1               5                  10                  15

Lys Asn Cys Thr Leu Gln Cys Asn Tyr Thr Val Ser Pro Phe Ser Asn
                20                  25                  30

Leu Arg Trp Tyr Lys Gln Asp Thr Gly Arg Gly Pro Val Ser Leu Thr
            35                  40                  45

Ile Met Thr Phe Ser Glu Asn Thr Lys Ser Asn Gly Arg Tyr Thr Ala
 50                  55                  60

Thr Leu Asp Ala Asp Thr Lys Gln Ser Ser Leu His Ile Thr Ala Ser
 65                  70                  75                  80

Gln Leu Ser Asp Ser Ala Ser Tyr Ile Cys
                85                  90

<210> SEQ ID NO 116
<211> LENGTH: 88
<212> TYPE: PRT
<213> ORGANISM: Homo sapiens

<400> SEQUENCE: 116

Arg Lys Glu Val Glu Gln Asp Pro Gly Pro Phe Asn Val Pro Glu Gly
 1               5                  10                  15

Ala Thr Val Ala Phe Asn Cys Thr Tyr Ser Asn Ser Ala Ser Gln Ser
                20                  25                  30

Phe Phe Trp Tyr Arg Gln Asp Cys Arg Lys Glu Pro Lys Leu Leu Met
            35                  40                  45

Ser Val Tyr Ser Ser Gly Asn Glu Asp Gly Arg Phe Thr Ala Gln Leu
 50                  55                  60

Asn Arg Ala Ser Gln Tyr Ile Ser Leu Leu Ile Arg Asp Ser Lys Leu
 65                  70                  75                  80

Ser Asp Ser Ala Thr Tyr Leu Cys
                85

<210> SEQ ID NO 117
<211> LENGTH: 89
<212> TYPE: PRT
<213> ORGANISM: Homo sapiens

<400> SEQUENCE: 117

Gln Lys Glu Val Glu Gln Asn Ser Gly Pro Leu Ser Val Pro Glu Gly
 1               5                  10                  15

Ala Ile Ala Ser Leu Asn Cys Thr Tyr Ser Asp Arg Gly Ser Gln Ser
                20                  25                  30
```

Phe Phe Trp Tyr Arg Gln Tyr Ser Gly Lys Ser Pro Glu Leu Ile Met
            35                  40                  45

Phe Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys
                85

<210> SEQ ID NO 118
<211> LENGTH: 89
<212> TYPE: PRT
<213> ORGANISM: Homo sapiens

<400> SEQUENCE: 118

Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
            20                  25                  30

Phe Met Trp Tyr Arg Gln Tyr Ser Arg Lys Gly Pro Glu Leu Leu Met
            35                  40                  45

Tyr Thr Tyr Ser Ser Gly Asn Lys Glu Asp Gly Arg Phe Thr Ala Gln
    50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys
                85

<210> SEQ ID NO 119
<211> LENGTH: 90
<212> TYPE: PRT
<213> ORGANISM: Homo sapiens

<400> SEQUENCE: 119

Gly Glu Asn Val Glu Gln His Pro Ser Thr Leu Ser Val Gln Glu Gly
1               5                   10                  15

Asp Ser Ala Val Ile Lys Cys Thr Tyr Ser Asp Ser Ala Ser Asn Tyr
            20                  25                  30

Phe Pro Trp Tyr Lys Gln Glu Leu Gly Lys Gly Pro Gln Leu Ile Ile
            35                  40                  45

Asp Ile Arg Ser Asn Val Gly Glu Lys Lys Asp Gln Arg Ile Ala Val
    50                  55                  60

Thr Leu Asn Lys Thr Ala Lys His Phe Ser Leu His Ile Thr Glu Thr
65                  70                  75                  80

Gln Pro Glu Asp Ser Ala Val Tyr Phe Cys
                85                  90

<210> SEQ ID NO 120
<211> LENGTH: 90
<212> TYPE: PRT
<213> ORGANISM: Homo sapiens

<400> SEQUENCE: 120

Gly Glu Ser Val Gly Leu His Leu Pro Thr Leu Ser Val Gln Glu Gly
1               5                   10                  15

Asp Asn Ser Ile Ile Asn Cys Ala Tyr Ser Asn Ser Ala Ser Asp Tyr
            20                  25                  30

Phe Ile Trp Tyr Lys Gln Glu Ser Gly Lys Gly Pro Gln Phe Ile Ile

```
            35                  40                  45

Asp Ile Arg Ser Asn Met Asp Lys Arg Gln Gly Gln Arg Val Thr Val
        50                  55                  60

Leu Leu Asn Lys Thr Val Lys His Leu Ser Leu Gln Ile Ala Ala Thr
65                  70                  75                  80

Gln Pro Gly Asp Ser Ala Val Tyr Phe Cys
                85                  90

<210> SEQ ID NO 121
<211> LENGTH: 92
<212> TYPE: PRT
<213> ORGANISM: Homo sapiens

<400> SEQUENCE: 121

Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Pro Ser Tyr
                20                  25                  30

Gly Leu Phe Trp Tyr Lys Gln Pro Ser Ser Gly Glu Met Ile Phe Leu
            35                  40                  45

Ile Tyr Gln Gly Ser Tyr Asp Gln Gln Asn Ala Thr Glu Gly Arg Tyr
        50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys
                85                  90

<210> SEQ ID NO 122
<211> LENGTH: 87
<212> TYPE: PRT
<213> ORGANISM: Homo sapiens

<400> SEQUENCE: 122

Ala Gln Arg Val Thr Gln Pro Glu Lys Leu Leu Ser Val Phe Lys Gly
1               5                   10                  15

Ala Pro Val Glu Leu Lys Cys Asn Tyr Ser Tyr Ser Gly Ser Pro Glu
                20                  25                  30

Leu Phe Trp Tyr Val Gln Tyr Ser Arg Gln Arg Leu Gln Leu Leu Leu
            35                  40                  45

Arg His Ile Ser Arg Glu Ser Ile Lys Gly Phe Thr Ala Asp Leu Asn
        50                  55                  60

Lys Gly Glu Thr Ser Phe His Leu Lys Lys Pro Phe Ala Gln Glu Glu
65                  70                  75                  80

Asp Ser Ala Met Tyr Tyr Cys
                85

<210> SEQ ID NO 123
<211> LENGTH: 89
<212> TYPE: PRT
<213> ORGANISM: Homo sapiens

<400> SEQUENCE: 123

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
            35                  40                  45
```

```
Ile Arg Ser Asn Glu Arg Glu Lys His Ser Gly Arg Leu Arg Val Thr
 50                  55                  60

Leu Asp Thr Ser Lys Lys Ser Ser Leu Leu Ile Thr Ala Ser Arg
 65                  70                  75                  80

Ala Ala Asp Thr Ala Ser Tyr Phe Cys
                 85

<210> SEQ ID NO 124
<211> LENGTH: 89
<212> TYPE: PRT
<213> ORGANISM: Homo sapiens

<400> SEQUENCE: 124

Gly Asp Ser Val Thr Gln Thr Glu Gly Pro Val Thr Leu Pro Glu Arg
  1               5                  10                  15

Ala Ala Leu Thr Leu Asn Cys Thr Tyr Gln Ser Ser Tyr Ser Thr Phe
                 20                  25                  30

Leu Phe Trp Tyr Val Gln Tyr Leu Asn Lys Glu Pro Glu Leu Leu Leu
             35                  40                  45

Lys Ser Ser Glu Asn Gln Glu Thr Asp Ser Arg Gly Phe Gln Ala Ser
 50                  55                  60

Pro Ile Lys Ser Asp Ser Ser Phe His Leu Gly Lys Pro Ser Val Gln
 65                  70                  75                  80

Leu Ser Asp Ser Ala Val Tyr Tyr Cys
                 85

<210> SEQ ID NO 125
<211> LENGTH: 92
<212> TYPE: PRT
<213> ORGANISM: Homo sapiens

<400> SEQUENCE: 125

Ala Gln Lys Val Thr Gln Ala Gln Thr Glu Ile Ser Val Val Glu Lys
  1               5                  10                  15

Glu Asp Val Thr Leu Asp Cys Val Tyr Glu Thr Arg Asp Thr Thr Tyr
                 20                  25                  30

Tyr Leu Phe Trp Tyr Lys Gln Pro Pro Ser Gly Glu Leu Val Phe Leu
             35                  40                  45

Ile Arg Arg Asn Ser Phe Asp Glu Gln Asn Glu Ile Ser Gly Arg Tyr
 50                  55                  60

Ser Trp Asn Phe Gln Lys Ser Thr Ser Ser Phe Asn Phe Thr Ile Thr
 65                  70                  75                  80

Ala Ser Gln Val Val Asp Ser Ala Val Tyr Phe Cys
                 85                  90

<210> SEQ ID NO 126
<211> LENGTH: 88
<212> TYPE: PRT
<213> ORGANISM: Homo sapiens

<400> SEQUENCE: 126

Glu Asp Gln Val Thr Gln Ser Pro Glu Ala Leu Arg Leu Gln Glu Gly
  1               5                  10                  15

Glu Ser Ser Ser Leu Asn Cys Ser Tyr Thr Val Ser Gly Leu Arg Gly
                 20                  25                  30

Leu Phe Trp Tyr Arg Gln Asp Pro Gly Lys Gly Pro Glu Phe Leu Phe
             35                  40                  45
```

Thr Leu Tyr Ser Ala Gly Glu Lys Glu Lys Glu Arg Leu Lys Ala
        50                  55                  60

Thr Leu Thr Lys Lys Glu Ser Phe Leu His Ile Thr Ala Pro Lys Pro
 65                  70                  75                  80

Glu Asp Ser Ala Thr Tyr Leu Cys
                85

<210> SEQ ID NO 127
<211> LENGTH: 90
<212> TYPE: PRT
<213> ORGANISM: Homo sapiens

<400> SEQUENCE: 127

Lys Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys
                85                  90

<210> SEQ ID NO 128
<211> LENGTH: 87
<212> TYPE: PRT
<213> ORGANISM: Homo sapiens

<400> SEQUENCE: 128

Gly Ile Gln Val Glu Gln Ser Pro Pro Asp Leu Ile Leu Gln Glu Gly
 1               5                  10                  15

Ala Asn Ser Thr Leu Arg Cys Asn Phe Ser Asp Ser Val Asn Asn Leu
                20                  25                  30

Gln Trp Phe His Gln Asn Pro Trp Gly Gln Leu Ile Asn Leu Phe Tyr
            35                  40                  45

Ile Pro Ser Gly Thr Lys Gln Asn Gly Arg Leu Ser Ala Thr Thr Val
        50                  55                  60

Ala Thr Glu Arg Tyr Ser Leu Leu Tyr Ile Ser Ser Ser Gln Thr Thr
 65                  70                  75                  80

Asp Ser Gly Val Tyr Phe Cys
                85

<210> SEQ ID NO 129
<211> LENGTH: 90
<212> TYPE: PRT
<213> ORGANISM: Homo sapiens

<400> SEQUENCE: 129

Gln Gln Gln Val Lys Gln Ser Pro Gln Ser Leu Ile Val Gln Lys Gly
 1               5                  10                  15

Gly Ile Ser Ile Ile Asn Cys Ala Tyr Glu Asn Thr Ala Phe Asp Tyr
                20                  25                  30

Phe Pro Trp Tyr Gln Gln Phe Pro Gly Lys Gly Pro Ala Leu Leu Ile
            35                  40                  45

Ala Ile Arg Pro Asp Val Ser Glu Lys Lys Glu Gly Arg Phe Thr Ile

```
Ser Phe Asn Lys Ser Ala Lys Gln Phe Ser Leu His Ile Met Asp Ser
 65                  70                  75                  80

Gln Pro Gly Asp Ser Ala Thr Tyr Phe Cys
                 85                  90

<210> SEQ ID NO 130
<211> LENGTH: 90
<212> TYPE: PRT
<213> ORGANISM: Homo sapiens

<400> SEQUENCE: 130

Ile Leu Asn Val Glu Gln Ser Pro Gln Ser Leu His Val Gln Glu Gly
  1               5                  10                  15

Asp Ser Thr Asn Phe Thr Cys Ser Phe Pro Ser Ser Asn Phe Tyr Ala
                 20                  25                  30

Leu His Trp Tyr Arg Trp Glu Thr Ala Lys Ser Pro Glu Ala Leu Phe
             35                  40                  45

Val Met Thr Leu Asn Gly Asp Glu Lys Lys Gly Arg Ile Ser Ala
         50                  55                  60

Thr Leu Asn Thr Lys Glu Gly Tyr Ser Tyr Leu Tyr Ile Lys Gly Ser
 65                  70                  75                  80

Gln Pro Glu Asp Ser Ala Thr Tyr Leu Cys
                 85                  90

<210> SEQ ID NO 131
<211> LENGTH: 89
<212> TYPE: PRT
<213> ORGANISM: Homo sapiens

<400> SEQUENCE: 131

Gly Gln Gln Val Met Gln Ile Pro Gln Tyr Gln His Val Gln Glu Gly
  1               5                  10                  15

Glu Asp Phe Thr Thr Tyr Cys Asn Ser Ser Thr Thr Leu Ser Asn Ile
                 20                  25                  30

Gln Trp Tyr Lys Gln Arg Pro Gly Gly His Pro Val Phe Leu Ile Gln
             35                  40                  45

Leu Val Lys Ser Gly Glu Val Lys Lys Gln Lys Arg Leu Thr Phe Gln
         50                  55                  60

Phe Gly Glu Ala Lys Lys Asn Ser Ser Leu His Ile Thr Ala Thr Gln
 65                  70                  75                  80

Thr Thr Asp Val Gly Thr Tyr Phe Cys
                 85

<210> SEQ ID NO 132
<211> LENGTH: 88
<212> TYPE: PRT
<213> ORGANISM: Homo sapiens

<400> SEQUENCE: 132

Asp Ala Lys Thr Thr Gln Pro Pro Ser Met Asp Cys Ala Glu Gly Arg
  1               5                  10                  15

Ala Ala Asn Leu Pro Cys Asn His Ser Thr Ile Ser Gly Asn Glu Tyr
                 20                  25                  30

Val Tyr Trp Tyr Arg Gln Ile His Ser Gln Gly Pro Gln Tyr Ile Ile
             35                  40                  45

His Gly Leu Lys Asn Asn Glu Thr Asn Glu Met Ala Ser Leu Ile Ile
         50                  55                  60
```

```
Thr Glu Asp Arg Lys Ser Ser Thr Leu Ile Leu Pro His Ala Thr Leu
 65                  70                  75                  80

Arg Asp Thr Ala Val Tyr Tyr Cys
                85
```

<210> SEQ ID NO 133
<211> LENGTH: 88
<212> TYPE: PRT
<213> ORGANISM: Homo sapiens

<400> SEQUENCE: 133

```
Asp Ala Lys Thr Thr Gln Pro Asn Ser Met Glu Ser Asn Glu Glu
 1               5                  10                  15

Pro Val His Leu Pro Cys Asn His Ser Thr Ile Ser Gly Thr Asp Tyr
                20                  25                  30

Ile His Trp Tyr Arg Gln Leu Pro Ser Gln Gly Pro Glu Tyr Val Ile
            35                  40                  45

His Gly Leu Thr Ser Asn Val Asn Asn Arg Met Ala Ser Leu Ala Ile
        50                  55                  60

Ala Glu Asp Arg Lys Ser Ser Thr Leu Ile Leu His Arg Ala Thr Leu
 65                  70                  75                  80

Arg Asp Ala Ala Val Tyr Tyr Cys
                85
```

<210> SEQ ID NO 134
<211> LENGTH: 89
<212> TYPE: PRT
<213> ORGANISM: Homo sapiens

<400> SEQUENCE: 134

```
Thr Gln Leu Leu Glu Gln Ser Pro Gln Phe Leu Ser Ile Gln Glu Gly
 1               5                  10                  15

Glu Asn Leu Thr Val Tyr Cys Asn Ser Ser Ser Val Phe Ser Ser Leu
                20                  25                  30

Gln Trp Tyr Arg Gln Glu Pro Gly Glu Gly Pro Val Leu Leu Val Thr
            35                  40                  45

Val Val Thr Gly Gly Glu Val Lys Lys Leu Lys Arg Leu Thr Phe Gln
        50                  55                  60

Phe Gly Asp Ala Arg Lys Asp Ser Ser Leu His Ile Thr Ala Ala Gln
 65                  70                  75                  80

Pro Gly Asp Thr Gly Leu Tyr Leu Cys
                85
```

<210> SEQ ID NO 135
<211> LENGTH: 90
<212> TYPE: PRT
<213> ORGANISM: Homo sapiens

<400> SEQUENCE: 135

```
Asp Gln Gln Val Lys Gln Asn Ser Pro Ser Leu Ser Val Gln Glu Gly
 1               5                  10                  15

Arg Ile Ser Ile Leu Asn Cys Asp Tyr Thr Asn Ser Met Phe Asp Tyr
                20                  25                  30

Phe Leu Trp Tyr Lys Lys Tyr Pro Ala Glu Gly Pro Thr Phe Leu Ile
            35                  40                  45

Ser Ile Ser Ser Ile Lys Asp Lys Asn Glu Asp Gly Arg Phe Thr Val
        50                  55                  60
```

Phe Leu Asn Lys Ser Ala Lys His Leu Ser Leu His Ile Val Pro Ser
65                  70                  75                  80

Gln Pro Gly Asp Ser Ala Val Tyr Phe Cys
                85                  90

<210> SEQ ID NO 136
<211> LENGTH: 88
<212> TYPE: PRT
<213> ORGANISM: Homo sapiens

<400> SEQUENCE: 136

Gln Gln Pro Val Gln Ser Pro Gln Ala Val Ile Leu Arg Glu Gly Glu
1               5                   10                  15

Asp Ala Val Ile Asn Cys Ser Ser Lys Ala Leu Tyr Ser Val His
            20                  25                  30

Trp Tyr Arg Gln Lys His Gly Glu Ala Pro Val Phe Leu Met Ile Leu
            35                  40                  45

Leu Lys Gly Gly Glu Gln Lys Gly His Glu Lys Ile Ser Ala Ser Phe
        50                  55                  60

Asn Glu Lys Lys Gln Ser Ser Leu Tyr Leu Thr Ala Ser Gln Leu
65                  70                  75                  80

Ser Tyr Ser Gly Thr Tyr Phe Cys
                85

<210> SEQ ID NO 137
<211> LENGTH: 89
<212> TYPE: PRT
<213> ORGANISM: Homo sapiens

<400> SEQUENCE: 137

Ser Gln Glu Leu Glu Gln Ser Pro Gln Ser Leu Ile Val Gln Glu Gly
1               5                   10                  15

Lys Asn Leu Thr Ile Asn Cys Thr Ser Ser Lys Thr Leu Tyr Gly Leu
            20                  25                  30

Tyr Trp Tyr Lys Gln Lys Tyr Gly Glu Gly Leu Ile Phe Leu Met Met
            35                  40                  45

Leu Gln Lys Gly Gly Glu Glu Lys Ser His Glu Lys Ile Thr Ala Lys
        50                  55                  60

Leu Asp Glu Lys Lys Gln Gln Ser Ser Leu His Ile Thr Ala Ser Gln
65                  70                  75                  80

Pro Ser His Ala Gly Ile Tyr Leu Cys
                85

<210> SEQ ID NO 138
<211> LENGTH: 89
<212> TYPE: PRT
<213> ORGANISM: Homo sapiens

<400> SEQUENCE: 138

Gly Gln Gln Leu Asn Gln Ser Pro Gln Ser Met Phe Ile Gln Glu Gly
1               5                   10                  15

Glu Asp Val Ser Met Asn Cys Thr Ser Ser Ser Ile Phe Asn Thr Trp
            20                  25                  30

Leu Trp Tyr Lys Gln Glu Pro Gly Glu Gly Pro Val Leu Leu Ile Ala
            35                  40                  45

Leu Tyr Lys Ala Gly Glu Leu Thr Ser Asn Gly Arg Leu Thr Ala Gln
        50                  55                  60

Phe Gly Ile Thr Arg Lys Asp Ser Phe Leu Asn Ile Ser Ala Ser Ile

```
                65                  70                  75                  80

Pro Ser Asp Val Gly Ile Tyr Phe Cys
                85

<210> SEQ ID NO 139
<211> LENGTH: 89
<212> TYPE: PRT
<213> ORGANISM: Homo sapiens

<400> SEQUENCE: 139

Glu Asp Lys Val Val Gln Ser Pro Leu Ser Leu Val Val His Glu Gly
1               5                   10                  15

Asp Thr Val Thr Leu Asn Cys Ser Tyr Glu Val Thr Asn Phe Arg Ser
                20                  25                  30

Leu Leu Trp Tyr Lys Gln Glu Lys Lys Ala Pro Thr Phe Leu Phe Met
            35                  40                  45

Leu Thr Ser Ser Gly Ile Glu Lys Lys Ser Gly Arg Leu Ser Ser Ile
        50                  55                  60

Leu Asp Lys Lys Glu Leu Ser Ser Ile Leu Asn Ile Thr Ala Thr Gln
65                  70                  75                  80

Thr Gly Asp Ser Ala Ile Tyr Leu Cys
                85

<210> SEQ ID NO 140
<211> LENGTH: 92
<212> TYPE: PRT
<213> ORGANISM: Homo sapiens

<400> SEQUENCE: 140

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Asn Asn Tyr
                20                  25                  30

Tyr Leu Phe Trp Tyr Lys Gln Pro Pro Ser Arg Gln Met Ile Leu Val
            35                  40                  45

Ile Arg Gln Glu Ala Tyr Lys Gln Gln Asn Ala Thr Glu Asn Arg Phe
        50                  55                  60

Ser Val Asn Phe Gln Lys Ala Ala Lys Ser Phe Ser Leu Lys Ile Ser
65                  70                  75                  80

Asp Ser Gln Leu Gly Asp Thr Ala Met Tyr Phe Cys
                85                  90

<210> SEQ ID NO 141
<211> LENGTH: 92
<212> TYPE: PRT
<213> ORGANISM: Homo sapiens

<400> SEQUENCE: 141

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
                20                  25                  30

Tyr Leu Phe Trp Tyr Lys Gln Pro Pro Ser Arg Gln Met Ile Leu Val
            35                  40                  45

Ile Arg Gln Glu Ala Tyr Lys Gln Gln Asn Ala Thr Glu Asn Arg Phe
        50                  55                  60

Ser Val Asn Phe Gln Lys Ala Ala Lys Ser Phe Ser Leu Lys Ile Ser
65                  70                  75                  80
```

Asp Ser Gln Leu Gly Asp Ala Ala Met Tyr Phe Cys
            85                  90

<210> SEQ ID NO 142
<211> LENGTH: 89
<212> TYPE: PRT
<213> ORGANISM: Homo sapiens

<400> SEQUENCE: 142

Glu Leu Lys Val Glu Gln Asn Pro Leu Phe Leu Ser Met Gln Glu Gly
1               5                   10                  15

Lys Asn Tyr Thr Ile Tyr Cys Asn Tyr Ser Thr Thr Ser Asp Arg Leu
            20                  25                  30

Tyr Trp Tyr Arg Gln Asp Pro Gly Lys Ser Leu Glu Ser Leu Phe Val
        35                  40                  45

Leu Leu Ser Asn Gly Ala Val Lys Gln Glu Gly Arg Leu Met Ala Ser
    50                  55                  60

Leu Asp Thr Lys Ala Arg Leu Ser Thr Leu His Ile Thr Ala Ala Val
65                  70                  75                  80

His Asp Leu Ser Ala Thr Tyr Phe Cys
            85

<210> SEQ ID NO 143
<211> LENGTH: 84
<212> TYPE: PRT
<213> ORGANISM: Homo sapiens

<400> SEQUENCE: 143

Ser Asn Ser Val Lys Gln Thr Gly Gln Ile Thr Val Ser Glu Gly Ala
1               5                   10                  15

Ser Val Thr Met Asn Cys Thr Tyr Thr Ser Thr Gly Tyr Pro Thr Leu
            20                  25                  30

Phe Trp Tyr Val Glu Tyr Pro Ser Lys Pro Leu Gln Leu Leu Gln Arg
        35                  40                  45

Glu Thr Met Glu Asn Ser Lys Asn Phe Gly Gly Gly Asn Ile Lys Asp
    50                  55                  60

Lys Asn Ser Pro Ile Val Lys Tyr Ser Val Gln Val Ser Asp Ser Ala
65                  70                  75                  80

Val Tyr Tyr Cys

<210> SEQ ID NO 144
<211> LENGTH: 87
<212> TYPE: PRT
<213> ORGANISM: Homo sapiens

<400> SEQUENCE: 144

Lys Asn Glu Val Glu Gln Ser Pro Gln Asn Leu Thr Ala Gln Glu Gly
1               5                   10                  15

Glu Phe Ile Thr Ile Asn Cys Ser Tyr Ser Val Gly Ile Ser Ala Leu
            20                  25                  30

His Trp Leu Gln Gln His Pro Gly Gly Gly Ile Val Ser Leu Phe Met
        35                  40                  45

Leu Ser Ser Gly Lys Lys Lys His Gly Arg Leu Ile Ala Thr Ile Asn
    50                  55                  60

Ile Gln Glu Lys His Ser Ser Leu His Ile Thr Ala Ser His Pro Arg
65                  70                  75                  80

Asp Ser Ala Val Tyr Ile Cys

<210> SEQ ID NO 145
<211> LENGTH: 92
<212> TYPE: PRT
<213> ORGANISM: Homo sapiens

<400> SEQUENCE: 145

Glu Pro Glu Val Thr Gln Thr Pro Ser His Gln Val Thr Gln Met Gly
1               5                   10                  15

Gln Glu Val Ile Leu Arg Cys Val Pro Ile Ser Asn His Leu Tyr Phe
            20                  25                  30

Tyr Trp Tyr Arg Gln Ile Leu Gly Gln Lys Val Glu Phe Leu Val Ser
        35                  40                  45

Phe Tyr Asn Asn Glu Ile Ser Glu Lys Ser Glu Ile Phe Asp Asp Gln
    50                  55                  60

Phe Ser Val Glu Arg Pro Asp Gly Ser Asn Phe Thr Leu Lys Ile Arg
65                  70                  75                  80

Ser Thr Lys Leu Glu Asp Ser Ala Met Tyr Phe Cys
                85                  90

<210> SEQ ID NO 146
<211> LENGTH: 91
<212> TYPE: PRT
<213> ORGANISM: Homo sapiens

<400> SEQUENCE: 146

Asp Thr Ala Val Ser Gln Thr Pro Lys Tyr Leu Val Thr Gln Met Gly
1               5                   10                  15

Asn Asp Lys Ser Ile Lys Cys Glu Gln Asn Leu Gly His Asp Thr Met
            20                  25                  30

Tyr Trp Tyr Lys Gln Asp Ser Lys Lys Phe Leu Lys Ile Met Phe Ser
        35                  40                  45

Tyr Asn Asn Lys Glu Leu Ile Ile Asn Glu Thr Val Pro Asn Arg Phe
    50                  55                  60

Ser Pro Lys Ser Pro Asp Lys Ala His Leu Asn Leu His Ile Asn Ser
65                  70                  75                  80

Leu Glu Leu Gly Asp Ser Ala Val Tyr Phe Cys
                85                  90

<210> SEQ ID NO 147
<211> LENGTH: 91
<212> TYPE: PRT
<213> ORGANISM: Homo sapiens

<400> SEQUENCE: 147

Asp Thr Glu Val Thr Gln Thr Pro Lys His Leu Val Met Gly Met Thr
1               5                   10                  15

Asn Lys Lys Ser Leu Lys Cys Glu Gln His Met Gly His Arg Ala Met
            20                  25                  30

Tyr Trp Tyr Lys Gln Lys Ala Lys Lys Pro Pro Glu Leu Met Phe Val
        35                  40                  45

Tyr Ser Tyr Glu Lys Leu Ser Ile Asn Glu Ser Val Pro Ser Arg Phe
    50                  55                  60

Ser Pro Glu Cys Pro Asn Ser Ser Leu Leu Asn Leu His Leu His Ala
65                  70                  75                  80

Leu Gln Pro Glu Asp Ser Ala Leu Tyr Leu Cys
                85                  90

<210> SEQ ID NO 148
<211> LENGTH: 91
<212> TYPE: PRT
<213> ORGANISM: Homo sapiens

<400> SEQUENCE: 148

Glu Thr Gly Val Thr Gln Thr Pro Arg His Leu Val Met Gly Met Thr
1               5                   10                  15

Asn Lys Lys Ser Leu Lys Cys Glu Gln His Leu Gly His Asn Ala Met
            20                  25                  30

Tyr Trp Tyr Lys Gln Ser Ala Lys Lys Pro Leu Glu Leu Met Phe Val
        35                  40                  45

Tyr Asn Phe Lys Glu Gln Thr Glu Asn Asn Ser Val Pro Ser Arg Phe
    50                  55                  60

Ser Pro Glu Cys Pro Asn Ser Ser His Leu Phe Leu His Leu His Thr
65                  70                  75                  80

Leu Gln Pro Glu Asp Ser Ala Leu Tyr Leu Cys
                85                  90

<210> SEQ ID NO 149
<211> LENGTH: 91
<212> TYPE: PRT
<213> ORGANISM: Homo sapiens

<400> SEQUENCE: 149

Glu Thr Gly Val Thr Gln Thr Pro Arg His Leu Val Met Gly Met Thr
1               5                   10                  15

Asn Lys Lys Ser Leu Lys Cys Glu Gln His Leu Gly His Asn Ala Met
            20                  25                  30

Tyr Trp Tyr Lys Gln Ser Ala Lys Lys Pro Leu Glu Leu Met Phe Val
        35                  40                  45

Tyr Ser Leu Glu Glu Arg Val Glu Asn Asn Ser Val Pro Ser Arg Phe
    50                  55                  60

Ser Pro Glu Cys Pro Asn Ser Ser His Leu Phe Leu His Leu His Thr
65                  70                  75                  80

Leu Gln Pro Glu Asp Ser Ala Leu Tyr Leu Cys
                85                  90

<210> SEQ ID NO 150
<211> LENGTH: 91
<212> TYPE: PRT
<213> ORGANISM: Homo sapiens

<400> SEQUENCE: 150

Lys Ala Gly Val Thr Gln Thr Pro Arg Tyr Leu Ile Lys Thr Arg Gly
1               5                   10                  15

Gln Gln Val Thr Leu Ser Cys Ser Pro Ile Ser Gly His Arg Ser Val
            20                  25                  30

Ser Trp Tyr Gln Gln Thr Pro Gly Gln Gly Leu Gln Phe Leu Phe Glu
        35                  40                  45

Tyr Phe Ser Glu Thr Gln Arg Asn Lys Gly Asn Phe Pro Gly Arg Phe
    50                  55                  60

Ser Gly Arg Gln Phe Ser Asn Ser Arg Ser Glu Met Asn Val Ser Thr
65                  70                  75                  80

Leu Glu Leu Gly Asp Ser Ala Leu Tyr Leu Cys
                85                  90

<210> SEQ ID NO 151
<211> LENGTH: 91
<212> TYPE: PRT
<213> ORGANISM: Homo sapiens

<400> SEQUENCE: 151

Glu Thr Gly Val Thr Gln Ser Pro Thr His Leu Ile Lys Thr Arg Gly
1               5                   10                  15

Gln Gln Val Thr Leu Arg Cys Ser Ser Gln Ser Gly His Asn Thr Val
            20                  25                  30

Ser Trp Tyr Gln Gln Ala Leu Gly Gln Gly Pro Gln Phe Ile Phe Gln
        35                  40                  45

Tyr Tyr Arg Glu Glu Asn Gly Arg Gly Asn Phe Pro Pro Arg Phe
    50                  55                  60

Ser Gly Leu Gln Phe Pro Asn Tyr Ser Ser Glu Leu Asn Val Asn Ala
65                  70                  75                  80

Leu Glu Leu Asp Asp Ser Ala Leu Tyr Leu Cys
                85                  90

<210> SEQ ID NO 152
<211> LENGTH: 91
<212> TYPE: PRT
<213> ORGANISM: Homo sapiens

<400> SEQUENCE: 152

Asp Ala Gly Val Thr Gln Ser Pro Thr His Leu Ile Lys Thr Arg Gly
1               5                   10                  15

Gln Gln Val Thr Leu Arg Cys Ser Pro Ile Ser Gly His Lys Ser Val
            20                  25                  30

Ser Trp Tyr Gln Gln Val Leu Gly Gln Gly Pro Gln Phe Ile Phe Gln
        35                  40                  45

Tyr Tyr Glu Lys Glu Glu Arg Gly Arg Gly Asn Phe Pro Asp Arg Phe
    50                  55                  60

Ser Ala Arg Gln Phe Pro Asn Tyr Ser Ser Glu Leu Asn Val Asn Ala
65                  70                  75                  80

Leu Leu Leu Gly Asp Ser Ala Leu Tyr Leu Cys
                85                  90

<210> SEQ ID NO 153
<211> LENGTH: 91
<212> TYPE: PRT
<213> ORGANISM: Homo sapiens

<400> SEQUENCE: 153

Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys
                85                  90

```
<210> SEQ ID NO 154
<211> LENGTH: 91
<212> TYPE: PRT
<213> ORGANISM: Homo sapiens

<400> SEQUENCE: 154

Glu Ala Gly Val Thr Gln Ser Pro Thr His Leu Ile Lys Thr Arg Gly
1               5                   10                  15

Gln Gln Ala Thr Leu Arg Cys Ser Pro Ile Ser Gly His Thr Ser Val
            20                  25                  30

Tyr Trp Tyr Gln Gln Ala Leu Gly Leu Gly Leu Gln Phe Leu Leu Trp
        35                  40                  45

Tyr Asp Glu Gly Glu Glu Arg Asn Arg Gly Asn Phe Pro Pro Arg Phe
    50                  55                  60

Ser Gly Arg Gln Phe Pro Asn Tyr Ser Ser Glu Leu Asn Val Asn Ala
65                  70                  75                  80

Leu Glu Leu Glu Asp Ser Ala Leu Tyr Leu Cys
                85                  90

<210> SEQ ID NO 155
<211> LENGTH: 91
<212> TYPE: PRT
<213> ORGANISM: Homo sapiens

<400> SEQUENCE: 155

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Asn Ser Met
            20                  25                  30

Tyr Trp Tyr Arg Gln Asp Pro Gly Met Gly Leu Arg Leu Ile Tyr Tyr
        35                  40                  45

Ser Ala Ser Glu Gly Thr Thr Asp Lys Gly Glu Val Pro Asn Gly Tyr
    50                  55                  60

Asn Val Ser Arg Leu Asn Lys Arg Glu Phe Ser Leu Arg Leu Glu Ser
65                  70                  75                  80

Ala Ala Pro Ser Gln Thr Ser Val Tyr Phe Cys
                85                  90

<210> SEQ ID NO 156
<211> LENGTH: 91
<212> TYPE: PRT
<213> ORGANISM: Homo sapiens

<400> SEQUENCE: 156

Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Glu Tyr Met
            20                  25                  30

Tyr Trp Tyr Arg Gln Asp Pro Gly Met Gly Leu Arg Leu Ile His Tyr
        35                  40                  45

Ser Val Gly Glu Gly Thr Thr Ala Lys Gly Glu Val Pro Asp Gly Tyr
    50                  55                  60

Asn Val Ser Arg Leu Lys Lys Gln Asn Phe Leu Leu Gly Leu Glu Ser
65                  70                  75                  80

Ala Ala Pro Ser Gln Thr Ser Val Tyr Phe Cys
                85                  90

<210> SEQ ID NO 157
```

<211> LENGTH: 91
<212> TYPE: PRT
<213> ORGANISM: Homo sapiens

<400> SEQUENCE: 157

Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Thr Ala Gly Thr Thr Gly Lys Gly Glu Val Pro Asp Gly Tyr
50                  55                  60

Ser Val Ser Arg Ala Asn Thr Asp Asp Phe Pro Leu Thr Leu Ala Ser
65                  70                  75                  80

Ala Val Pro Ser Gln Thr Ser Val Tyr Phe Cys
                85                  90

<210> SEQ ID NO 158
<211> LENGTH: 91
<212> TYPE: PRT
<213> ORGANISM: Homo sapiens

<400> SEQUENCE: 158

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Gly Ala Gly Ile Thr Asp Gln Gly Glu Val Pro Asn Gly Tyr
50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys
                85                  90

<210> SEQ ID NO 159
<211> LENGTH: 91
<212> TYPE: PRT
<213> ORGANISM: Homo sapiens

<400> SEQUENCE: 159

Asn Ala Gly Val Thr Gln Thr Pro Lys Phe Arg Ile Leu Lys Ile Gly
1               5                   10                  15

Gln Ser Met Thr Leu Gln Cys Thr Gln Asp Met Asn His Asn Tyr Met
            20                  25                  30

Tyr Trp Tyr Arg Gln Asp Pro Gly Met Gly Leu Lys Leu Ile Tyr Tyr
        35                  40                  45

Ser Val Gly Ala Gly Ile Thr Asp Lys Gly Glu Val Pro Asn Gly Tyr
50                  55                  60

Asn Val Ser Arg Ser Thr Thr Glu Asp Phe Pro Leu Arg Leu Glu Leu
65                  70                  75                  80

Ala Ala Pro Ser Gln Thr Ser Val Tyr Phe Cys
                85                  90

<210> SEQ ID NO 160
<211> LENGTH: 90

<212> TYPE: PRT
<213> ORGANISM: Homo sapiens

<400> SEQUENCE: 160

Asn Ala Gly Val Thr Gln Thr Pro Lys Phe His Ile Leu Lys Thr Gly
1               5                   10                  15

Gln Ser Met Thr Leu Gln Cys Ala Gln Asp Met Asn His Gly Tyr Met
            20                  25                  30

Ser Trp Tyr Arg Gln Asp Pro Gly Met Gly Leu Arg Leu Ile Tyr Tyr
        35                  40                  45

Ser Ala Ala Gly Thr Thr Asp Lys Glu Val Pro Asn Gly Tyr Asn
    50                  55                  60

Val Ser Arg Leu Asn Thr Glu Asp Phe Pro Leu Arg Leu Val Ser Ala
65                  70                  75                  80

Ala Pro Ser Gln Thr Ser Val Tyr Leu Cys
            85                  90

<210> SEQ ID NO 161
<211> LENGTH: 91
<212> TYPE: PRT
<213> ORGANISM: Homo sapiens

<400> SEQUENCE: 161

Asn Ala Gly Val Thr Gln Thr Pro Lys Phe His Ile Leu Lys Thr Gly
1               5                   10                  15

Gln Ser Met Thr Leu Gln Cys Ala Gln Asp Met Asn His Gly Tyr Leu
            20                  25                  30

Ser Trp Tyr Arg Gln Asp Pro Gly Met Gly Leu Arg Ile His Tyr
        35                  40                  45

Ser Val Ala Ala Gly Ile Thr Asp Lys Gly Glu Val Pro Asp Gly Tyr
    50                  55                  60

Asn Val Ser Arg Ser Asn Thr Glu Asp Phe Pro Leu Arg Leu Glu Ser
65                  70                  75                  80

Ala Ala Pro Ser Gln Thr Ser Val Tyr Phe Cys
            85                  90

<210> SEQ ID NO 162
<211> LENGTH: 92
<212> TYPE: PRT
<213> ORGANISM: Homo sapiens

<400> SEQUENCE: 162

Gly Ala Gly Val Ser Gln Ser Pro Ser Asn Lys Val Thr Glu Lys Gly
1               5                   10                  15

Lys Asp Val Glu Leu Arg Cys Asp Pro Ile Ser Gly His Thr Ala Leu
            20                  25                  30

Tyr Trp Tyr Arg Gln Ser Leu Gly Gln Gly Leu Glu Phe Leu Ile Tyr
        35                  40                  45

Phe Gln Gly Asn Ser Ala Pro Asp Lys Ser Gly Leu Pro Ser Asp Arg
    50                  55                  60

Phe Ser Ala Glu Arg Thr Gly Gly Ser Val Ser Thr Leu Thr Ile Gln
65                  70                  75                  80

Arg Thr Gln Gln Glu Asp Ser Ala Val Tyr Leu Cys
            85                  90

<210> SEQ ID NO 163
<211> LENGTH: 92
<212> TYPE: PRT

<213> ORGANISM: Homo sapiens

<400> SEQUENCE: 163

Gly Ala Gly Val Ser Gln Thr Pro Ser Asn Lys Val Thr Glu Lys Gly
1               5                   10                  15

Lys Tyr Val Glu Leu Arg Cys Asp Pro Ile Ser Gly His Thr Ala Leu
                20                  25                  30

Tyr Trp Tyr Arg Gln Ser Leu Gly Gln Gly Pro Glu Phe Leu Ile Tyr
            35                  40                  45

Phe Gln Gly Thr Gly Ala Ala Asp Ser Gly Leu Pro Asn Asp Arg
        50                  55                  60

Phe Phe Ala Val Arg Pro Glu Gly Ser Val Ser Thr Leu Lys Ile Gln
65                  70                  75                  80

Arg Thr Glu Arg Gly Asp Ser Ala Val Tyr Leu Cys
                85                  90

<210> SEQ ID NO 164
<211> LENGTH: 92
<212> TYPE: PRT
<213> ORGANISM: Homo sapiens

<400> SEQUENCE: 164

Gly Ala Gly Val Ser Gln Ser Pro Arg Tyr Lys Val Ala Lys Arg Gly
1               5                   10                  15

Arg Asp Val Ala Leu Arg Cys Asp Ser Ile Ser Gly His Val Thr Leu
                20                  25                  30

Tyr Trp Tyr Arg Gln Thr Leu Gly Gln Gly Ser Glu Val Leu Thr Tyr
            35                  40                  45

Ser Gln Ser Asp Ala Gln Arg Asp Lys Ser Gly Arg Pro Ser Gly Arg
        50                  55                  60

Phe Ser Ala Glu Arg Pro Glu Arg Ser Val Ser Thr Leu Lys Ile Gln
65                  70                  75                  80

Arg Thr Glu Gln Gly Asp Ser Ala Val Tyr Leu Cys
                85                  90

<210> SEQ ID NO 165
<211> LENGTH: 92
<212> TYPE: PRT
<213> ORGANISM: Homo sapiens

<400> SEQUENCE: 165

Gly Ala Gly Val Ser Gln Ser Pro Arg Tyr Lys Val Thr Lys Arg Gly
1               5                   10                  15

Gln Asp Val Ala Leu Arg Cys Asp Pro Ile Ser Gly His Val Ser Leu
                20                  25                  30

Tyr Trp Tyr Arg Gln Ala Leu Gly Gln Gly Pro Glu Phe Leu Thr Tyr
            35                  40                  45

Phe Asn Tyr Glu Ala Gln Gln Asp Lys Ser Gly Leu Pro Asn Asp Arg
        50                  55                  60

Phe Ser Ala Glu Arg Pro Glu Gly Ser Ile Ser Thr Leu Thr Ile Gln
65                  70                  75                  80

Arg Thr Glu Gln Arg Asp Ser Ala Met Tyr Arg Cys
                85                  90

<210> SEQ ID NO 166
<211> LENGTH: 92
<212> TYPE: PRT
<213> ORGANISM: Homo sapiens

<400> SEQUENCE: 166

Gly Ala Gly Val Ser Gln Ser Pro Arg Tyr Lys Val Thr Lys Arg Gly
1               5                   10                  15

Gln Asp Val Thr Leu Arg Cys Asp Pro Ile Ser Ser His Ala Thr Leu
            20                  25                  30

Tyr Trp Tyr Gln Gln Ala Leu Gly Gln Gly Pro Glu Phe Leu Thr Tyr
        35                  40                  45

Phe Asn Tyr Glu Ala Gln Pro Asp Lys Ser Gly Leu Pro Ser Asp Arg
50                  55                  60

Phe Ser Ala Glu Arg Pro Glu Gly Ser Ile Ser Thr Leu Thr Ile Gln
65                  70                  75                  80

Arg Thr Glu Gln Arg Asp Ser Ala Met Tyr Arg Cys
                85                  90

<210> SEQ ID NO 167
<211> LENGTH: 92
<212> TYPE: PRT
<213> ORGANISM: Homo sapiens

<400> SEQUENCE: 167

Gly Ala Gly Val Ser Gln Ser Pro Arg Tyr Lys Val Ala Lys Arg Gly
1               5                   10                  15

Gln Asp Val Ala Leu Arg Cys Asp Pro Ile Ser Gly His Val Ser Leu
            20                  25                  30

Phe Trp Tyr Gln Gln Ala Leu Gly Gln Gly Pro Glu Phe Leu Thr Tyr
        35                  40                  45

Phe Gln Asn Glu Ala Gln Leu Asp Lys Ser Gly Leu Pro Ser Asp Arg
50                  55                  60

Phe Phe Ala Glu Arg Pro Glu Gly Ser Val Ser Thr Leu Lys Ile Gln
65                  70                  75                  80

Arg Thr Gln Gln Glu Asp Ser Ala Val Tyr Leu Cys
                85                  90

<210> SEQ ID NO 168
<211> LENGTH: 92
<212> TYPE: PRT
<213> ORGANISM: Homo sapiens

<400> SEQUENCE: 168

Asp Thr Gly Val Ser Gln Asn Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
        35                  40                  45

Phe Gln Asn Glu Ala Gln Leu Glu Lys Ser Arg Leu Leu Ser Asp Arg
50                  55                  60

Phe Ser Ala Glu Arg Pro Lys Gly Ser Phe Ser Thr Leu Glu Ile Gln
65                  70                  75                  80

Arg Thr Glu Gln Gly Asp Ser Ala Met Tyr Leu Cys
                85                  90

<210> SEQ ID NO 169
<211> LENGTH: 91
<212> TYPE: PRT
<213> ORGANISM: Homo sapiens

<400> SEQUENCE: 169

Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
            20                  25                  30

Tyr Trp Tyr Gln Gln Ser Leu Asp Gln Gly Leu Gln Phe Leu Ile Gln
        35                  40                  45

Tyr Tyr Asn Gly Glu Glu Arg Ala Lys Gly Asn Ile Leu Glu Arg Phe
    50                  55                  60

Ser Ala Gln Gln Phe Pro Asp Leu His Ser Glu Leu Asn Leu Ser Ser
65                  70                  75                  80

Leu Glu Leu Gly Asp Ser Ala Leu Tyr Phe Cys
                85                  90

<210> SEQ ID NO 170
<211> LENGTH: 91
<212> TYPE: PRT
<213> ORGANISM: Homo sapiens

<400> SEQUENCE: 170

Asp Ala Glu Ile Thr Gln Ser Pro Arg His Lys Ile Thr Glu Thr Gly
1               5                   10                  15

Arg Gln Val Thr Leu Ala Cys His Gln Thr Trp Asn His Asn Asn Met
            20                  25                  30

Phe Trp Tyr Arg Gln Asp Leu Gly His Gly Leu Arg Leu Ile His Tyr
        35                  40                  45

Ser Tyr Gly Val Gln Asp Thr Asn Lys Gly Glu Val Ser Asp Gly Tyr
    50                  55                  60

Ser Val Ser Arg Ser Asn Thr Glu Asp Leu Pro Leu Thr Leu Glu Ser
65                  70                  75                  80

Ala Ala Ser Ser Gln Thr Ser Val Tyr Phe Cys
                85                  90

<210> SEQ ID NO 171
<211> LENGTH: 91
<212> TYPE: PRT
<213> ORGANISM: Homo sapiens

<400> SEQUENCE: 171

Asp Ala Gly Ile Thr Gln Ser Pro Arg Tyr Lys Ile Thr Glu Thr Gly
1               5                   10                  15

Arg Gln Val Thr Leu Met Cys His Gln Thr Trp Ser His Ser Tyr Met
            20                  25                  30

Phe Trp Tyr Arg Gln Asp Leu Gly His Gly Leu Arg Leu Ile Tyr Tyr
        35                  40                  45

Ser Ala Ala Ala Asp Ile Thr Asp Lys Gly Glu Val Pro Asp Gly Tyr
    50                  55                  60

Val Val Ser Arg Ser Lys Thr Glu Asn Phe Pro Leu Thr Leu Glu Ser
65                  70                  75                  80

Ala Thr Arg Ser Gln Thr Ser Val Tyr Phe Cys
                85                  90

<210> SEQ ID NO 172
<211> LENGTH: 91
<212> TYPE: PRT
<213> ORGANISM: Homo sapiens

<400> SEQUENCE: 172

Asp Ala Gly Ile Thr Gln Ser Pro Arg His Lys Val Thr Glu Thr Gly
1               5                   10                  15

Thr Pro Val Thr Leu Arg Cys His Gln Thr Glu Asn His Arg Tyr Met
            20                  25                  30

Tyr Trp Tyr Arg Gln Asp Pro Gly His Gly Leu Arg Leu Ile His Tyr
        35                  40                  45

Ser Tyr Gly Val Lys Asp Thr Asp Lys Gly Glu Val Ser Asp Gly Tyr
50                  55                  60

Ser Val Ser Arg Ser Lys Thr Glu Asp Phe Leu Leu Thr Leu Glu Ser
65                  70                  75                  80

Ala Thr Ser Ser Gln Thr Ser Val Tyr Phe Cys
            85                  90

<210> SEQ ID NO 173
<211> LENGTH: 92
<212> TYPE: PRT
<213> ORGANISM: Homo sapiens

<400> SEQUENCE: 173

Glu Ala Glu Val Ala Gln Ser Pro Arg Tyr Lys Ile Thr Glu Lys Ser
1               5                   10                  15

Gln Ala Val Ala Phe Trp Cys Asp Pro Ile Ser Gly His Ala Thr Leu
            20                  25                  30

Tyr Trp Tyr Arg Gln Ile Leu Gly Gln Gly Pro Glu Leu Leu Val Gln
        35                  40                  45

Phe Gln Asp Glu Ser Val Val Asp Asp Ser Gln Leu Pro Lys Asp Arg
50                  55                  60

Phe Ser Ala Glu Arg Leu Lys Gly Val Asp Ser Thr Leu Lys Ile Gln
65                  70                  75                  80

Pro Ala Glu Leu Gly Asp Ser Ala Met Tyr Leu Cys
            85                  90

<210> SEQ ID NO 174
<211> LENGTH: 92
<212> TYPE: PRT
<213> ORGANISM: Homo sapiens

<400> SEQUENCE: 174

Glu Ala Gly Val Ala Gln Ser Pro Arg Tyr Lys Ile Ile Glu Lys Arg
1               5                   10                  15

Gln Ser Val Ala Phe Trp Cys Asn Pro Ile Ser Gly His Ala Thr Leu
            20                  25                  30

Tyr Trp Tyr Gln Gln Ile Leu Gly Gln Gly Pro Lys Leu Leu Ile Gln
        35                  40                  45

Phe Gln Asn Asn Gly Val Val Asp Asp Ser Gln Leu Pro Lys Asp Arg
50                  55                  60

Phe Ser Ala Glu Arg Leu Lys Gly Val Asp Ser Thr Leu Lys Ile Gln
65                  70                  75                  80

Pro Ala Lys Leu Glu Asp Ser Ala Val Tyr Leu Cys
            85                  90

<210> SEQ ID NO 175
<211> LENGTH: 92
<212> TYPE: PRT
<213> ORGANISM: Homo sapiens

<400> SEQUENCE: 175

-continued

Glu Ala Gly Val Val Gln Ser Pro Arg Tyr Lys Ile Ile Glu Lys Lys
1               5                   10                  15

Gln Pro Val Ala Phe Trp Cys Asn Pro Ile Ser Gly His Asn Thr Leu
            20                  25                  30

Tyr Trp Tyr Leu Gln Asn Leu Gly Gln Gly Pro Glu Leu Leu Ile Arg
        35                  40                  45

Tyr Glu Asn Glu Glu Ala Val Asp Asp Ser Gln Leu Pro Lys Asp Arg
    50                  55                  60

Phe Ser Ala Glu Arg Leu Lys Gly Val Asp Ser Thr Leu Lys Ile Gln
65                  70                  75                  80

Pro Ala Glu Leu Gly Asp Ser Ala Val Tyr Leu Cys
                85                  90

<210> SEQ ID NO 176
<211> LENGTH: 92
<212> TYPE: PRT
<213> ORGANISM: Homo sapiens

<400> SEQUENCE: 176

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asn Ser Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys
                85                  90

<210> SEQ ID NO 177
<211> LENGTH: 92
<212> TYPE: PRT
<213> ORGANISM: Homo sapiens

<400> SEQUENCE: 177

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asp Tyr Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys
                85                  90

<210> SEQ ID NO 178
<211> LENGTH: 92
<212> TYPE: PRT
<213> ORGANISM: Homo sapiens

<400> SEQUENCE: 178

Asp Ala Arg Val Thr Gln Thr Pro Arg His Lys Val Thr Glu Met Gly

-continued

```
                1               5                  10                  15
        Gln Glu Val Thr Met Arg Cys Gln Pro Ile Leu Gly His Asn Thr Val
                        20                  25                  30

Phe Trp Tyr Arg Gln Thr Met Met Gln Gly Leu Glu Leu Leu Ala Tyr
                        35                  40                  45

Phe Arg Asn Arg Ala Pro Leu Asp Asp Ser Gly Met Pro Lys Asp Arg
                        50                  55                  60

Phe Ser Ala Glu Met Pro Asp Ala Thr Leu Ala Thr Leu Lys Ile Gln
         65                 70                  75                  80

Pro Ser Glu Pro Arg Asp Ser Ala Val Tyr Phe Cys
                        85                  90
```

<210> SEQ ID NO 179
<211> LENGTH: 91
<212> TYPE: PRT
<213> ORGANISM: Homo sapiens

<400> SEQUENCE: 179

```
        Ala Ala Gly Val Ile Gln Ser Pro Arg His Leu Ile Lys Glu Lys Arg
         1                  5                  10                  15

Glu Thr Ala Thr Leu Lys Cys Tyr Pro Ile Pro Arg His Asp Thr Val
                        20                  25                  30

Tyr Trp Tyr Gln Gln Gly Pro Gly Gln Asp Pro Gln Phe Leu Ile Ser
                        35                  40                  45

Phe Tyr Glu Lys Met Gln Ser Asp Lys Gly Ser Ile Pro Asp Arg Phe
         50                 55                  60

Ser Ala Gln Gln Phe Ser Asp Tyr His Ser Glu Leu Asn Met Ser Ser
         65                 70                  75                  80

Leu Glu Leu Gly Asp Ser Ala Leu Tyr Phe Cys
                        85                  90
```

<210> SEQ ID NO 180
<211> LENGTH: 92
<212> TYPE: PRT
<213> ORGANISM: Homo sapiens

<400> SEQUENCE: 180

```
        Glu Ala Gly Val Thr Gln Phe Pro Ser His Ser Val Ile Glu Lys Gly
         1                  5                  10                  15

Gln Thr Val Thr Leu Arg Cys Asp Pro Ile Ser Gly His Asp Asn Leu
                        20                  25                  30

Tyr Trp Tyr Arg Arg Val Met Gly Lys Glu Ile Lys Phe Leu Leu His
                        35                  40                  45

Phe Val Lys Glu Ser Lys Gln Asp Glu Ser Gly Met Pro Asn Asn Arg
         50                 55                  60

Phe Leu Ala Glu Arg Thr Gly Gly Thr Tyr Ser Thr Leu Lys Val Gln
         65                 70                  75                  80

Pro Ala Glu Leu Glu Asp Ser Gly Val Tyr Phe Cys
                        85                  90
```

<210> SEQ ID NO 181
<211> LENGTH: 91
<212> TYPE: PRT
<213> ORGANISM: Homo sapiens

<400> SEQUENCE: 181

```
        Asp Ala Met Val Ile Gln Asn Pro Arg Tyr Gln Val Thr Gln Phe Gly
         1                  5                  10                  15
```

Lys Pro Val Thr Leu Ser Cys Ser Gln Thr Leu Asn His Asn Val Met
            20                  25                  30

Tyr Trp Tyr Gln Gln Lys Ser Ser Gln Ala Pro Lys Leu Leu Phe His
        35                  40                  45

Tyr Tyr Asp Lys Asp Phe Asn Asn Glu Ala Asp Thr Pro Asp Asn Phe
50                  55                  60

Gln Ser Arg Arg Pro Asn Thr Ser Phe Cys Phe Leu Asp Ile Arg Ser
65                  70                  75                  80

Pro Gly Leu Gly Asp Thr Ala Met Tyr Leu Cys
                85                  90

<210> SEQ ID NO 182
<211> LENGTH: 92
<212> TYPE: PRT
<213> ORGANISM: Homo sapiens

<400> SEQUENCE: 182

Gly Glu Glu Val Ala Gln Thr Pro Lys His Leu Val Arg Gly Glu Gly
1               5                   10                  15

Gln Lys Ala Lys Leu Tyr Cys Ala Pro Ile Lys Gly His Ser Tyr Val
            20                  25                  30

Phe Trp Tyr Gln Gln Val Leu Lys Asn Glu Phe Lys Phe Leu Ile Ser
        35                  40                  45

Phe Gln Asn Glu Asn Val Phe Asp Glu Thr Gly Met Pro Lys Glu Arg
50                  55                  60

Phe Ser Ala Lys Cys Leu Pro Asn Ser Pro Cys Ser Leu Glu Ile Gln
65                  70                  75                  80

Ala Thr Lys Leu Glu Asp Ser Ala Val Tyr Phe Cys
                85                  90

<210> SEQ ID NO 183
<211> LENGTH: 92
<212> TYPE: PRT
<213> ORGANISM: Homo sapiens

<400> SEQUENCE: 183

Asn Ala Gly Val Met Gln Asn Pro Arg His Leu Val Arg Arg Arg Gly
1               5                   10                  15

Gln Glu Ala Arg Leu Arg Cys Ser Pro Met Lys Gly His Ser His Val
            20                  25                  30

Tyr Trp Tyr Arg Gln Leu Pro Glu Glu Gly Leu Lys Phe Met Val Tyr
        35                  40                  45

Leu Gln Lys Glu Asn Ile Ile Asp Glu Ser Gly Met Pro Lys Glu Arg
50                  55                  60

Phe Ser Ala Glu Phe Pro Lys Glu Gly Pro Ser Ile Leu Arg Ile Gln
65                  70                  75                  80

Gln Val Val Arg Gly Asp Ser Ala Ala Tyr Phe Cys
                85                  90

<210> SEQ ID NO 184
<211> LENGTH: 91
<212> TYPE: PRT
<213> ORGANISM: Homo sapiens

<400> SEQUENCE: 184

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
         35                  40                  45

Ser Gln Ile Val Asn Asp Phe Gln Lys Gly Asp Ile Ala Glu Gly Tyr
 50                  55                  60

Ser Val Ser Arg Glu Lys Lys Glu Ser Phe Pro Leu Thr Val Thr Ser
 65                  70                  75                  80

Ala Gln Lys Asn Pro Thr Ala Phe Tyr Leu Cys
             85                  90

<210> SEQ ID NO 185
<211> LENGTH: 94
<212> TYPE: PRT
<213> ORGANISM: Homo sapiens

<400> SEQUENCE: 185

Gly Ala Val Val Ser Gln His Pro Ser Trp Val Ile Cys Lys Ser Gly
 1               5                  10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Leu Met Leu Met Ala
         35                  40                  45

Thr Ser Asn Glu Gly Ser Lys Ala Thr Tyr Glu Gln Gly Val Glu Lys
 50                  55                  60

Asp Lys Phe Leu Ile Asn His Ala Ser Leu Thr Leu Ser Thr Leu Thr
 65                  70                  75                  80

Val Thr Ser Ala His Pro Glu Asp Ser Ser Phe Tyr Ile Cys
             85                  90

<210> SEQ ID NO 186
<211> LENGTH: 91
<212> TYPE: PRT
<213> ORGANISM: Homo sapiens

<400> SEQUENCE: 186

Asp Ala Asp Val Thr Gln Thr Pro Arg Asn Arg Ile Thr Lys Thr Gly
 1               5                  10                  15

Lys Arg Ile Met Leu Glu Cys Ser Gln Thr Lys Gly His Asp Arg Met
            20                  25                  30

Tyr Trp Tyr Arg Gln Asp Pro Gly Leu Gly Leu Arg Leu Ile Tyr Tyr
         35                  40                  45

Ser Phe Asp Val Lys Asp Ile Asn Lys Gly Glu Ile Ser Asp Gly Tyr
 50                  55                  60

Ser Val Ser Arg Gln Ala Gln Ala Lys Phe Ser Leu Ser Leu Glu Ser
 65                  70                  75                  80

Ala Ile Pro Asn Gln Thr Ala Leu Tyr Phe Cys
             85                  90

<210> SEQ ID NO 187
<211> LENGTH: 91
<212> TYPE: PRT
<213> ORGANISM: Homo sapiens

<400> SEQUENCE: 187

Glu Ala Asp Ile Tyr Gln Thr Pro Arg Tyr Leu Val Ile Gly Thr Gly
 1               5                  10                  15

Lys Lys Ile Thr Leu Glu Cys Ser Gln Thr Met Gly His Asp Lys Met

-continued

```
                20                  25                  30

Tyr Trp Tyr Gln Gln Asp Pro Gly Met Glu Leu His Leu Ile His Tyr
             35                  40                  45

Ser Tyr Gly Val Asn Ser Thr Glu Lys Gly Asp Leu Ser Ser Glu Ser
 50                  55                  60

Thr Val Ser Arg Ile Arg Thr Glu His Phe Pro Leu Thr Leu Glu Ser
65                  70                  75                  80

Ala Arg Pro Ser His Thr Ser Gln Tyr Leu Cys
                 85                  90

<210> SEQ ID NO 188
<211> LENGTH: 91
<212> TYPE: PRT
<213> ORGANISM: Homo sapiens

<400> SEQUENCE: 188

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
                20                  25                  30

Ser Trp Tyr Arg Gln Asp Pro Gly Leu Gly Leu Arg Gln Ile Tyr Tyr
             35                  40                  45

Ser Met Asn Val Glu Val Thr Asp Lys Gly Asp Val Pro Glu Gly Tyr
 50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys
                 85                  90

<210> SEQ ID NO 189
<211> LENGTH: 91
<212> TYPE: PRT
<213> ORGANISM: Homo sapiens

<400> SEQUENCE: 189

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
             35                  40                  45

Ser Tyr Asp Val Lys Met Lys Glu Lys Gly Asp Ile Pro Glu Gly Tyr
 50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys
                 85                  90

<210> SEQ ID NO 190
<211> LENGTH: 93
<212> TYPE: PRT
<213> ORGANISM: Homo sapiens

<400> SEQUENCE: 190

Ser Ala Val Ile Ser Gln Lys Pro Ser Arg Asp Ile Cys Gln Arg Gly
1               5                   10                  15

Thr Ser Leu Thr Ile Gln Cys Gln Val Asp Ser Gln Val Thr Met Met
                20                  25                  30
```

```
Phe Trp Tyr Arg Gln Gln Pro Gly Gln Ser Leu Thr Leu Ile Ala Thr
        35                  40                  45

Ala Asn Gln Gly Ser Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys
                85                  90

<210> SEQ ID NO 191
<211> LENGTH: 91
<212> TYPE: PRT
<213> ORGANISM: Homo sapiens

<400> SEQUENCE: 191

Ser Gln Thr Ile His Gln Trp Pro Ala Thr Leu Val Gln Pro Val Gly
1               5                   10                  15

Ser Pro Leu Ser Leu Glu Cys Thr Val Glu Gly Thr Ser Asn Pro Asn
            20                  25                  30

Leu Tyr Trp Tyr Arg Gln Ala Ala Gly Arg Gly Leu Gln Leu Leu Phe
        35                  40                  45

Tyr Ser Val Gly Ile Gly Gln Ile Ser Ser Glu Val Pro Gln Asn Leu
    50                  55                  60

Ser Ala Ser Arg Pro Gln Asp Arg Gln Phe Ile Leu Ser Ser Lys Lys
65                  70                  75                  80

Leu Leu Leu Ser Asp Ser Gly Phe Tyr Leu Cys
                85                  90

<210> SEQ ID NO 192
<211> LENGTH: 27
<212> TYPE: DNA
<213> ORGANISM: Mus musculus

<400> SEQUENCE: 192
gcagccagcg acaactacca gctgatc                                           27

<210> SEQ ID NO 193
<211> LENGTH: 30
<212> TYPE: DNA
<213> ORGANISM: Mus musculus

<400> SEQUENCE: 193
gcaagcagcc gcgccaacta cgagcagtac                                        30

<210> SEQ ID NO 194
<211> LENGTH: 15
<212> TYPE: DNA
<213> ORGANISM: Artificial Sequence
<220> FEATURE:
<223> OTHER INFORMATION: synthetic

<400> SEQUENCE: 194
gcacacacgg caata                                                        15

<210> SEQ ID NO 195
<211> LENGTH: 15
<212> TYPE: DNA
<213> ORGANISM: Artificial Sequence
<220> FEATURE:
<223> OTHER INFORMATION: synthetic
```

<400> SEQUENCE: 195
gcacacacgg caata                                                        15

<210> SEQ ID NO 196
<211> LENGTH: 2703
<212> TYPE: DNA
<213> ORGANISM: Artificial Sequence
<220> FEATURE:
<223> OTHER INFORMATION: synthetic

<400> SEQUENCE: 196
tgatgcggta ttttctcctt acgcatctgt gcggtatttc acaccgcata tggtgcactc    60
tcagtacaat ctgctctgat gccgcatagt taagccagcc ccgacacccg ccaacacccg   120
ctgacgcgcc ctgacgggct tgtctgctcc cggcatccgc ttacagacaa gctgtgaccg   180
tctccgggag ctgcatgtgt cagaggtttt caccgtcatc accgaaacgc gcgagacgaa   240
agggcctcgt gatacgccta ttttataggt taatgtcat gataataatg gtttcttaga   300
cgtcaggtgg cacttttcgg ggaaatgtgc gcggaacccc tatttgttta ttttttctaaa   360 tacattcaaa tatgtatccg ctcatgagac aataaccctg ataaatgctt caataacatt   420
gaaaaaggaa gagtatgagt attcaacatt tccgtgtcgc ccttattccc ttttttgcgg   480
cattttgcct tcctgttttt gctcacccag aaacgctggt gaaagtaaaa gatgctgaag   540
atcagttggg tgcacgagtg ggttacatcg aactggatct caacagcggt aagatccttg   600
agagttttcg ccccgaagaa cgttttccaa tgatgagcac ttttaaagtt ctgctatgtg   660
gcgcggtatt atcccgtatt gacgccgggc aagagcaact cggtcgccgc atacactatt   720
ctcagaatga cttggttgag tactcaccag tcacagaaaa gcatcttacg gatggcatga   780
cagtaagaga attatgcagt gctgccataa ccatgagtga taacactgcg gccaacttac   840
ttctgacaac gatcggagga ccgaaggagc taaccgcttt tttgcacaac atgggggatc   900
atgtaactcg ccttgatcgt tgggaaccgg agctgaatga agccatacca aacgacgagc   960
gtgacaccac gatgcctgta gcaatgccaa caacgttgca caactatta actggcgaac  1020 tacttactct agcttcccgg caacaattaa tagactggat ggaggcggat aaagttgcag  1080
gaccacttct gcgctcggcc cttccggctg gctggtttat tgctgataaa tctggagccg  1140
gtgagcgtgg gtctcgcggt atcattgcag cactggggcc agatggtaag ccctcccgta  1200
tcgtagttat ctacacgacg gggagtcagg caactatgga tgaacgaaat agacagatcg  1260
ctgagatagg tgcctcactg attaagcatt ggtaactgtc agaccaagtt tactcatata  1320
tactttagat tgatttaaaa cttcattttt aatttaaaag gatctaggtg aagatccttt  1380
ttgataatct catgaccaaa atcccttaac gtgagttttc gttccactga gcgtcagacc  1440
ccgtagaaaa gatcaaagga tcttcttgag atcctttttt tctgcgcgta atctgctgct  1500
tgcaaacaaa aaaaccaccg ctaccagcgg tggtttgttt gccggatcaa gagctaccaa  1560
ctctttttcc gaaggtaact ggcttcagca gagcgcagat accaaatact gtccttctag  1620
tgtagccgta gttaggccac cacttcaaga actctgtagc accgcctaca tacctcgctc  1680
tgctaatcct gttaccagtg gctgctgcca gtggcgataa gtcgtgtctt accgggttgg  1740
actcaagacg atagttaccg gataaggcgc agcggtcggg ctgaacgggg ggttcgtgca  1800
cacagcccag cttggagcga acgacctaca ccgaactgag atacctacag cgtgagctat  1860
gagaaagcgc cacgcttccc gaagggagaa aggcggacag gtatccggta agcggcaggg  1920
tcggaacagg agagcgcacg agggagcttc caggggggaaa cgcctggtat ctttatagtc  1980

```
ctgtcgggtt tcgccacctc tgacttgagc gtcgattttt gtgatgctcg tcagggggc     2040 ggagcctatc gaaaaacgcc agcaacgcgg ccttttttacg gttcctggcc ttttgctggc   2100
cttttgctca catgttcttt cctgcgttat ccctgattc tgtggataac cgtattaccg     2160
cctttgagtg agctgatacc gctcgccgca gccgaacgac cgagcgcagc gagtcagtga    2220
gcgaggaagc ggaagagcgc ccaatacgca aaccgcctct ccccgcgcgt tggccgattc    2280
attaatgcag ctggcacgac aggtttcccg actcgaaagc gggcagtgag cgcaacgcaa    2340
ttaatgtgag ttagctcact cattaggcac cccaggcttt acactttatg cttccggctc    2400
gtatgttgtg tggaattgtg agcggataac aatttcacac aggaaacagc tatgaccatg    2460
attacgccaa gctctaatac gactcactat agggagacaa gcttgcatgc ctgcaggtcg    2520
actctagagg atccaccggt cgccaccggt accgagctcg aattcaaaaa aaaaaaaaaa    2580
aaaaaaaaaa aaaaaaaaaa aaaaaaaaaa aaaaaaaaaa aaaaaaaat aaaaaaaaaa     2640 aaaaaaaaaa aaaaaaaaaa aaaaaaaaaa aaaaaaaaaa aaaaaaaaaa aaaactagtg    2700
gcg                                                                  2703

<210> SEQ ID NO 197
<211> LENGTH: 3114
<212> TYPE: DNA
<213> ORGANISM: Artificial Sequence
<220> FEATURE:
<223> OTHER INFORMATION: synthetic

<400> SEQUENCE: 197
tgatgcggta ttttctcctt acgcatctgt gcggtatttc acaccgcata tggtgcactc      60
tcagtacaat ctgctctgat gccgcatagt taagccagcc ccgacacccg ccaacacccg     120
ctgacgcgcc ctgacgggct tgtctgctcc cggcatccgc ttacagacaa gctgtgaccg     180
tctccgggag ctgcatgtgt cagaggtttt caccgtcatc accgaaacgc gcgagacgaa     240
agggcctcgt gatacgccta ttttttatagg ttaatgtcat gataataatg gtttcttaga    300
cgtcaggtgg cacttttcgg ggaaatgtgc gcggaacccc tatttgttta ttttctaaa     360 tacattcaaa tatgtatccg ctcatgagac aataaccctg ataaatgctt caataacatt    420 gaaaaggaa gagtatgagt attcaacatt tccgtgtcgc ccttattccc ttttttgcgg     480
cattttgcct tcctgttttt gctcacccag aaacgctggt gaaagtaaaa gatgctgaag    540
atcagttggg tgcacgagtg ggttacatcg aactggatct caacagcggt aagatccttg    600
agagttttcg ccccgaagaa cgttttccaa tgatgagcac ttttaaagtt ctgctatgtg    660
gcgcggtatt atcccgtatt gacgccggc aagagcaact cggtcgccgc atacactatt     720
ctcagaatga cttggttgag tactcaccag tcacagaaaa gcatcttacg gatggcatga    780
cagtaagaga attatgcagt gctgccataa ccatgagtga taacactgcg gccaacttac    840
ttctgacaac gatcggagga ccgaaggagc taaccgcttt tttgcacaac atggggatc     900 atgtaactcg ccttgatcgt tgggaaccgg agctgaatga agccatacca aacgacgagc    960
gtgacaccac gatgcctgta gcaatgccaa caacgttgca caaactatta actggcgaac   1020
tacttactct agcttcccgg caacaattaa tagactggat ggaggcggat aaagttgcag    1080
gaccacttct gcgctcggcc cttccggctg gctggtttat tgctgataaa tctggagccg    1140
gtgagcgtgg gtctcgcggt atcattgcag cactggggcc agatggtaag ccctcccgta    1200
tcgtagttat ctacacgacg gggagtcagg caactatgga tgaacgaaat agacagatcg    1260
```

-continued

```
ctgagatagg tgcctcactg attaagcatt ggtaactgtc agaccaagtt tactcatata    1320
tactttagat tgatttaaaa cttcattttt aatttaaaag gatctaggtg aagatccttt    1380
ttgataatct catgaccaaa atcccttaac gtgagttttc gttccactga gcgtcagacc    1440
ccgtagaaaa gatcaaagga tcttcttgag atccttttttt tctgcgcgta atctgctgct    1500
tgcaaacaaa aaaaccaccg ctaccagcgg tggtttgttt gccggatcaa gagctaccaa    1560
ctcttttcc gaaggtaact ggcttcagca gagcgcagat accaaatact gtccttctag    1620
tgtagccgta gttaggccac cacttcaaga actctgtagc accgcctaca tacctcgctc    1680
tgctaatcct gttaccagtg gctgctgcca gtggcgataa gtcgtgtctt accgggttgg    1740
actcaagacg atagttaccg gataaggcgc agcggtcggg ctgaacgggg ggttcgtgca    1800
cacagcccag cttggagcga acgacctaca ccgaactgag atacctacag cgtgagctat    1860
gagaaagcgc cacgcttccc gaagggagaa aggcggacag gtatccggta agcggcaggg    1920
tcggaacagg agagcgcacg agggagcttc caggggggaaa cgcctggtat ctttatagtc    1980
ctgtcgggtt tcgccacctc tgacttgagc gtcgatttttt gtgatgctcg tcagggggggc    2040
ggagcctatc gaaaaacgcc agcaacgcgg cctttttacg gttcctggcc ttttgctggc    2100
cttttgctca catgttcttt cctgcgttat cccctgattc tgtggataac cgtattaccg    2160
cctttgagtg agctgatacc gctcgccgca gccgaacgac cgagcgcagc gagtcagtga    2220
gcgaggaagc ggaagagcgc ccaatacgca aaccgcctct ccccgcgcgt tggccgattc    2280
attaatgcag ctggcacgac aggtttcccg actcgaaagc gggcagtgag cgcaacgcaa    2340
ttaatgtgag ttagctcact cattaggcac cccaggcttt acactttatg cttccggctc    2400
gtatgttgtg tggaattgtg agcggataac aatttcacac aggaaacagc tatgaccatg    2460
attacgccaa gctctaatac gactcactat agggagacaa gcttgcatgc ctgcaggtcg    2520
actctagagg atccaccggt cgccaccatc cagaaccccg agcccgccgt gtaccagctg    2580
aaggacccca gaagccagga cagcaccctg tgcctgttca ccgacttcga cagccagatc    2640
aacgtgccca gaccatggaa agcggcacc ttcatcaccg acaagacagt gctggacatg    2700
aaggccatgg acagcaagag caacggcgcc attgcctggt ccaaccagac cagcttcaca    2760
tgccaggaca tcttcaaaga gacaaacgcc acctacccca gcagcgacgt gccctgcgac    2820
gccaccctga ccgagaagag cttcgagaca gacatgaacc tgaatttcca gaacctgagc    2880
gtgatgggcc tgcggatcct gctgctgaag gtggccggct tcaacctgct gatgaccctg    2940
cggctgtgga gcagctgagg taccgagctc gaattcaaaa aaaaaaaaaa aaaaaaaaaa    3000
aaaaaaaaaa aaaaaaaaaa aaaaaaaaaa aaaaaaaaaa taaaaaaaaa aaaaaaaaaa    3060
aaaaaaaaaa aaaaaaaaaa aaaaaaaaaa aaaaaaaaaa aaaaactagt ggcg          3114
```

<210> SEQ ID NO 198
<211> LENGTH: 3225
<212> TYPE: DNA
<213> ORGANISM: Artificial Sequence
<220> FEATURE:
<223> OTHER INFORMATION: synthetic

<400> SEQUENCE: 198

```
tgatgcggta ttttctcctt acgcatctgt gcggtatttc acaccgcata tggtgcactc     60
tcagtacaat ctgctctgat gccgcatagt taagccagcc ccgacacccg ccaacacccg    120
ctgacgcgcc ctgacgggct tgtctgctcc cggcatccgc ttacagacaa gctgtgaccg    180
tctccgggag ctgcatgtgt cagaggtttt caccgtcatc accgaaacgc gcgagacgaa    240
```

```
agggcctcgt gatacgccta ttttttatagg ttaatgtcat gataataatg gtttcttaga    300
cgtcaggtgg cacttttcgg ggaaatgtgc gcggaacccc tatttgttta ttttttctaaa   360
tacattcaaa tatgtatccg ctcatgagac aataaccctg ataaatgctt caataacatt    420
gaaaaaggaa gagtatgagt attcaacatt tccgtgtcgc ccttattccc ttttttgcgg    480
cattttgcct tcctgttttt gctcacccag aaacgctggt gaaagtaaaa gatgctgaag    540
atcagttggg tgcacgagtg ggttacatcg aactggatct caacagcggt aagatccttg    600
agagttttcg ccccgaagaa cgttttccaa tgatgagcac ttttaaagtt ctgctatgtg    660
gcgcggtatt atcccgtatt gacgccgggc aagagcaact cggtcgccgc atacactatt    720
ctcagaatga cttggttgag tactcaccag tcacagaaaa gcatcttacg gatggcatga    780
cagtaagaga attatgcagt gctgccataa ccatgagtga taacactgcg gccaacttac    840
ttctgacaac gatcggagga ccgaaggagc taaccgcttt tttgcacaac atggggatc    900
atgtaactcg ccttgatcgt tgggaaccgg agctgaatga agccatacca aacgacgagc    960
gtgacaccac gatgcctgta gcaatgccaa caacgttgca caaactatta actggcgaac   1020
tacttactct agcttcccgg caacaattaa tagactggat ggaggcggat aaagttgcag   1080
gaccacttct gcgctcggcc cttccggctg gctggtttat tgctgataaa tctggagccg   1140
gtgagcgtgg gtctcgcggt atcattgcag cactggggcc agatggtaag ccctcccgta   1200
tcgtagttat ctacacgacg gggagtcagg caactatgga tgaacgaaat agacagatcg   1260
ctgagatagg tgcctcactg attaagcatt ggtaactgtc agaccaagtt tactcatata   1320
tactttagat tgatttaaaa cttcattttt aatttaaaag gatctaggtg aagatccttt   1380
ttgataatct catgaccaaa atcccttaac gtgagttttc gttccactga gcgtcagacc   1440
ccgtagaaaa gatcaaagga tcttcttgag atcctttttt tctgcgcgta atctgctgct   1500
tgcaaacaaa aaaaccaccg ctaccagcgg tggtttgttt gccggatcaa gagctaccaa   1560
ctcttttttcc gaaggtaact ggcttcagca gagcgcagat accaaatact gtccttctag   1620
tgtagccgta gttaggccac cacttcaaga actctgtagc accgcctaca tacctcgctc   1680
tgctaatcct gttaccagtg gctgctgcca gtggcgataa gtcgtgtctt accgggttgg   1740
actcaagacg atagttaccg gataaggcgc agcggtcggg ctgaacgggg ggttcgtgca   1800
cacagcccag cttggagcga acgacctaca ccgaactgag atacctacag cgtgagctat   1860
gagaaagcgc cacgcttccc gaagggagaa aggcggacag gtatccggta agcggcaggg   1920
tcggaacagg agagcgcacg agggagcttc caggggggaaa cgcctggtat ctttatagtc   1980
ctgtcgggtt tcgccacctc tgacttgagc gtcgattttt gtgatgctcg tcagggggc    2040
ggagcctatc gaaaaacgcc agcaacgcgg ccttttttacg gttcctggcc ttttgctggc    2100
cttttgctca catgttcttt cctgcgttat cccctgattc tgtggataac cgtattaccg    2160
cctttgagtg agctgatacc gctcgccgca gccgaacgac cgagcgcagc gagtcagtga    2220
gcgaggaagc ggaagagcgc ccaatacgca aaccgcctct ccccgcgcgt tggccgattc    2280
attaatgcag ctggcacgac aggtttcccg actcgaaagc gggcagtgag cgcaacgcaa    2340
ttaatgtgag ttagctcact cattaggcac cccaggcttt acactttatg cttccggctc    2400
gtatgttgtg tggaattgtg agcggataac aatttcacac aggaaacagc tatgaccatg    2460
attacgccaa gctctaatac gactcactat agggagacaa gcttgcatgc ctgcaggtcg    2520
actctagagg atccaccggt cgccaccgaa gatctgagga acgtgacccc ccccaaggtg    2580
```

```
accctgttcg agcccagcaa ggccgagatc gccaacaagc agaaagccac cctggtctgc    2640
ctggccaggg gcttcttccc cgaccacgtg gagctgtctt ggtgggtgaa cggcaaagag    2700
gtgcacagcg gagtcagtac cgaccccag gcctacaaag agagcaacta cagctactgc    2760
ctgagcagca ggctgagagt gagcgccacc ttctggcaca accccggaa ccacttccgg     2820 tgccaggtgc agttccacgg cctgagcgaa gaggacaagt ggcctgaggg cagccccaag    2880
cccgtgaccc agaacatcag cgccgaggcc tggggcagag ccgactgcgg catcaccagc    2940
gccagctacc accagggcgt gctgtccgcc accatcctgt acgagatcct gctgggcaag    3000
gccaccctgt acgccgtgct ggtgtccggc ctggtgctga tggccatggt gaagaagaag    3060
aacagctgag gtaccgagct cgaattcaaa aaaaaaaaaa aaaaaaaaaa aaaaaaaaaa    3120
aaaaaaaaaa aaaaaaaaaa aaaaaaaaaa ataaaaaaaa aaaaaaaaaa aaaaaaaaaa    3180
aaaaaaaaaa aaaaaaaaaa aaaaaaaaaa aaaaaactag tggcg                   3225

<210> SEQ ID NO 199
<211> LENGTH: 3551
<212> TYPE: DNA
<213> ORGANISM: Artificial Sequence
<220> FEATURE:
<223> OTHER INFORMATION: synthetic

<400> SEQUENCE: 199
tgatgcggta ttttctcctt acgcatctgt gcggtatttc acaccgcata tggtgcactc      60
tcagtacaat ctgctctgat gccgcatagt taagccagcc ccgacacccg ccaacacccg     120
ctgacgcgcc ctgacgggct tgtctgctcc cggcatccgc ttacagacaa gctgtgaccg     180
tctccgggag ctgcatgtgt cagaggtttt caccgtcatc accgaaacgc gcgagacgaa     240
agggcctcgt gatacgccta ttttataggt taatgtcat gataataatg gtttcttaga     300
cgtcaggtgg cacttttcgg ggaaatgtgc gcggaacccc tatttgttta ttttttctaaa    360 tacattcaaa tatgtatccg ctcatgagac aataaccctg ataaatgctt caataacatt    420
gaaaaaggaa gagtatgagt attcaacatt tccgtgtcgc ccttattccc ttttttgcgg    480
cattttgcct tcctgttttt gctcacccag aaacgctggt gaaagtaaaa gatgctgaag    540
atcagttggg tgcacgagtg ggttacatcg aactggatct caacagcggt aagatccttg    600
agagttttcg ccccgaagaa cgttttccaa tgatgagcac ttttaaagtt ctgctatgtg    660
gcgcggtatt atcccgtatt gacgccgggc aagagcaact cggtcgccgc atacactatt    720
ctcagaatga cttggttgag tactcaccag tcacagaaaa gcatcttacg gatggcatga    780
cagtaagaga attatgcagt gctgccataa ccatgagtga taacactgcg gccaacttac    840
ttctgacaac gatcggagga ccgaaggagc taaccgcttt tttgcacaac atggggatc    900 atgtaactcg ccttgatcgt tgggaaccgg agctgaatga agccatacca aacgacgagc    960
gtgacaccac gatgcctgta gcaatgccaa caacgttgca caactatta actggcgaac   1020 tacttactct agcttcccgg caacaattaa tagactggat ggaggcggat aaagttgcag   1080
gaccacttct gcgctcggcc cttccggctg gctggtttat tgctgataaa tctggagccg   1140
gtgagcgtgg gtctcgcggt atcattgcag cactggggcc agatggtaag ccctcccgta   1200
tcgtagttat ctacacgacg gggagtcagg caactatgga tgaacgaaat agacagatcg   1260
ctgagatagg tgcctcactg attaagcatt ggtaactgtc agaccaagtt tactcatata   1320
tactttagat tgatttaaaa cttcatttt aatttaaaag gatctaggtg aagatccttt   1380
ttgataatct catgaccaaa atcccttaac gtgagttttc gttccactga gcgtcagacc   1440
```

```
ccgtagaaaa gatcaaagga tcttcttgag atccttttt tctgcgcgta atctgctgct     1500
tgcaaacaaa aaaaccaccg ctaccagcgg tggtttgttt gccggatcaa gagctaccaa     1560 ctcttttcc gaaggtaact ggcttcagca gagcgcagat accaaatact gtccttctag     1620
tgtagccgta gttaggccac cacttcaaga actctgtagc accgcctaca tacctcgctc     1680
tgctaatcct gttaccagtg gctgctgcca gtggcgataa gtcgtgtctt accgggttgg     1740
actcaagacg atagttaccg gataaggcgc agcggtcggg ctgaacgggg ggttcgtgca     1800
cacagcccag cttggagcga acgacctaca ccgaactgag atacctacag cgtgagctat     1860
gagaaagcgc cacgcttccc gaagggagaa aggcggacag gtatccggta agcggcaggg     1920
tcggaacagg agagcgcacg agggagcttc caggggggaaa cgcctggtat ctttatagtc     1980
ctgtcgggtt tcgccacctc tgacttgagc gtcgattttt gtgatgctcg tcagggggggc     2040 ggagcctatc gaaaacgcc agcaacgcgg ccttttacg gttcctggcc ttttgctggc     2100
cttttgctca catgttcttt cctgcgttat ccctgattc tgtggataac cgtattaccg     2160
cctttgagtg agctgatacc gctcgccgca gccgaacgac cgagcgcagc gagtcagtga     2220
gcgaggaagc ggaagagcgc ccaatacgca aaccgcctct ccccgcgcgt tggccgattc     2280
attaatgcag ctggcacgac aggtttcccg actcgaaagc gggcagtgag cgcaacgcaa     2340
ttaatgtgag ttagctcact cattaggcac cccaggcttt acactttatg cttccggctc     2400
gtatgttgtg tggaattgtg agcggataac aatttcacac aggaaacagc tatgaccatg     2460
attacgccaa gctctaatac gactcactat agggagacaa gcttgcatgc ctgctggtcg     2520
actctagagg atccaccggt cgccaccgcg gccgccatgg tgagaccacg tggagctgtc     2580
ttggtgggtg aacggcaaag aggtgcacag cggagtcagt accgaccccc aggcctacaa     2640
agagagcaac tacagctact gcctgagcag caggctgaga gtgagcgcca ccttctggca     2700 caaccccgg aaccacttcc ggtgccaggt gcagttccac ggcctgagcg aagaggacaa     2760
gtggcctgag ggcagcccca gcccgtgac ccagaacatc agcgccgagg cctggggcag     2820
agccgactgc ggcatcacca cgcgccagcta ccaccagggc gtgctgtccg ccaccatcct     2880
gtacgagatc ctgctgggca aggccaccct gtacgccgtg ctggtgtccg gcctggtgct     2940
gatggccatg gtgaagaaga gaacagcgg cagcggcgcc accaacttca gcctgctgaa     3000
gcaggccggc gacgtggagg aaaaccctgg gcctgcagga tgctgacgac agcaccctgt     3060
gcctgttcac cgacttcgac agccagatca acgtgcccaa gaccatggaa agcggcacct     3120
tcatcaccga caagacagtg ctggacatga aggccatgga cagcaagagc aacgcgcca     3180 ttgcctggtc caaccagacc agcttcacat gccaggacat cttcaaagag acaaacgcca     3240
cctaccccag cagcgacgtg ccctgcgacg ccaccctgac cgagaagagc ttcgagacag     3300
acatgaacct gaattccag aacctgagcg tgatgggcct gcggatcctg ctgctgaagg     3360
tggccggctt caacctgctg atgaccctgc ggctgtggag cagctgagaa ttcaaaaaaa     3420 aaaaaaaaa aaaaaaaaa aaaaaaaaa aaaaaaaaa aaaaaaaaa aaaaaaataa     3480 aaaaaaaaa aaaaaaaaa aaaaaaaaa aaaaaaaaa aaaaaaaaa aaaaaaaaa     3540 aactagtggc g                                                         3551

<210> SEQ ID NO 200
<211> LENGTH: 5477
<212> TYPE: DNA
<213> ORGANISM: Artificial Sequence
<220> FEATURE:
```

<223> OTHER INFORMATION: synthetic

<400> SEQUENCE: 200

```
tcaaggttag gaacagagag acagcagaat atgggccaaa caggatatct gtggtaagca        60
gttcctgccc cggctcaggg ccaagaacag ttggaacagc agaatatggg ccaaacagga       120
tatctgtggt aagcagttcc tgccccggct cagggccaag aacagatggt ccccagatgc       180
ggtcccgccc tcagcagttt ctagagaacc atcagatgtt tccagggtgc ccaaggacc        240
tgaaatgacc ctgtgcctta tttgaactaa ccaatcagtt cgcttctcgc ttctgttcgc       300
gcgcttctgc tccccgagct caataaaaga gcccacaacc cctcactcgg cgcgccagtc       360
ctccgataga ctgcgtcgcc cgggtacccg tattcccaat aaagcctctt gctgtttgca       420
tccgaatcgt ggactcgctg atccttggga gggtctcctc agattgattg actgcccacc       480
tcgggggtct ttcatttgga ggttccaccg agatttggag accctgccc agggaccacc        540
gaccccccg ccgggaggta agctggccag cggtcgtttc gtgtctgtct ctgtctttgt        600
gcgtgtttgt gccggcatct aatgtttgcg cctgcgtctg tactagttgg ctaactagat       660
ctgtatctgg cggtcccgcg gaagaactga cgagttcgta ttcccggccg cagcccctgg       720
gagacgtccc agcggcctcg ggggcccgtt ttgtggccca ttctgtatca gttaacctac       780
ccgagtcgga cttttggag ctccgccact gtccgagggg tacgtggctt tgttggggga       840
cgagagacag agacacttcc cgcccccgtc tgaattttg ctttcggttt tacgccgaaa        900
ccgcgccgcg cgtcttgtct gctgcagcat cgttctgtgt tgtctctgtc tgactgtgtt       960
tctgtatttg tctgaaaatt agctcgacaa agttaagtaa tagtccctct ctccaagctc      1020
acttacaggc ggccgcaccg gtcgccaccg gtaccgagct cgaattcgag catcttaccg      1080
ccatttattc ccatatttgt tctgttttc ttgatttggg tatacattta aatgttaata      1140
aaacaaaatg gtggggcaat catttacatt ttatgggata tgtaattact agttcaggtg      1200
tattgccaca agacaaacat gttaagaaac tttcccgtta tttacgctct gttcctgtta      1260
atcaacctct ggattacaaa atttgtgaaa gattgactga tattcttaac tatgttgctc      1320
cttttacgct gtgtggatat gctgctttaa tgcctctgta tcatgctatt gcttcccgta      1380
cggctttcgt tttctcctcc ttgtataaat cctggttgct gtctctttat gaggagttgt      1440
ggcccgttgt ccgtcaacgt ggcgtggtgt gctctgtgtt tgctgacgca accccccactg      1500
gctgggggcat tgccaccacc tgtcaactcc tttctgggac tttcgctttc ccctcccga      1560
tcgccacggc agaactcatc gccgcctgcc ttgcccgctg ctggacaggg gctaggttgc      1620
tgggcactga taattccgtg gtgttgtcgg ggaagctgac gtcctttcca tggctgctcg      1680
cctgtgttgc caactggatc ctgcgcggga cgtccttctg ctacgtccct tcggctctca      1740
atccagcgga cctcccttcc cgaggccttc tgccggttct gcggcctctc ccgcgtcttc      1800
gctttcggcc tccgacgagt cggatctccc tttgggccgc ctccccgcct gtttcgcctc      1860
ggcgtccggt ccgtgttgct tggtcgtcac ctgtgcagaa ttgcgaacca tggattccac      1920
cgtgaacttt gtctcctggc atgcaaatcg tcaacttggc atgccaagaa ttaattcgga      1980
tccaagctta ggcctgctcg ctttcttgct gtcccatttc tattaaaggt tcctttgttc      2040
cctaagtcca actactaaac tggggggatat tatgaagggc cttgagcatc tggattctgc      2100
ctagcgctaa gcttaacacg agccatagat agaataaaag attttattta gtctccagaa      2160
aaaggggggga atgaaagacc ccacctgtag gtttggcaag ctagcttaag taacgccatt      2220
ttgcaaggca tggaaaatac ataactgaga atagagaagt tcagatcaag gttaggaaca      2280
```

| | |
|---|---|
| gagagacagc agaatatggg ccaaacagga tatctgtggt aagcagttcc tgccccggct | 2340 |
| cagggccaag aacagttgga acagcagaat atgggccaaa caggatatct gtggtaagca | 2400 |
| gttcctgccc cggctcaggg ccaagaacag atggtcccca gatgcggtcc cgccctcagc | 2460 |
| agtttctaga gaaccatcag atgtttccag ggtgccccaa ggacctgaaa tgaccctgtg | 2520 |
| ccttatttga actaaccaat cagttcgctt ctcgcttctg ttcgcgcgct tctgctcccc | 2580 |
| gagctcaata aaagagccca caaccccctca ctcggcgcgc cagtcctccg atagactgcg | 2640 |
| tcgcccgggt acccgtgttc tcaataaacc ctcttgcagt tgcatccgac tcgtggtctc | 2700 |
| gctgttcctt gggagggtct cctctgagtg attgactgcc cacctcgggg gtctttcatt | 2760 |
| ctcgagcagc ttggcgtaat catggtcata gctgtttcct gtgtgaaatt gttatccgct | 2820 |
| cacaattcca cacaacatac gagccggaag cataaagtgt aaagcctggg gtgcctaatg | 2880 |
| agtgagctaa ctcacattaa ttgcgttgcg ctcactgccc gctttccagt cgggaaacct | 2940 |
| gtcgtgccag ctgcattaat gaatcggcca acgcgcgggg agaggcggtt tgcgtattgg | 3000 |
| gcgctcttcc gcttcctcgc tcactgactc gctgcgctcg gtcgttcggc tgcggcgagc | 3060 |
| ggtatcagct cactcaaagg cggtaatacg gttatccaca gaatcagggg ataacgcagg | 3120 |
| aaagaacatg tgagcaaaag gccagcaaaa ggccaggaac cgtaaaaagg ccgcgttgct | 3180 |
| ggcgtttttc cataggctcc gcccccctga cgagcatcac aaaaatcgac gctcaagtca | 3240 |
| gaggtggcga aacccgacag gactataaag ataccaggcg tttccccctg gaagctccct | 3300 |
| cgtgcgctct cctgttccga ccctgccgct taccggatac ctgtccgcct ttctcccttc | 3360 |
| gggaagcgtg gcgctttctc atagctcacg ctgtaggtat ctcagttcgg tgtaggtcgt | 3420 |
| tcgctccaag ctgggctgtg tgcacgaacc ccccgttcag cccgaccgct gcgccttatc | 3480 |
| cggtaactat cgtcttgagt ccaacccggt aagacacgac ttatcgccac tggcagcagc | 3540 |
| cactggtaac aggattagca gagcgaggta tgtaggcggt gctacagagt tcttgaagtg | 3600 |
| gtggcctaac tacggctaca ctagaagaac agtatttggt atctgcgctc tgctgaagcc | 3660 |
| agttaccttc ggaaaaagag ttggtagctc ttgatccggc aaacaaacca ccgctggtag | 3720 |
| cggtggtttt tttgtttgca agcagcagat tacgcgcaga aaaaaaggat ctcaagaaga | 3780 |
| tcctttgatc ttttctacgg ggtctgacgc tcagtggaac gaaaactcac gttaagggat | 3840 |
| tttggtcatg agattatcaa aaaggatctt cacctagatc cttttaaatt aaaaatgaag | 3900 |
| ttttaaatca atctaaagta tatatgagta aacttggtct gacagttacc aatgcttaat | 3960 |
| cagtgaggca cctatctcag cgatctgtct atttcgttca tccatagttg cctgactccc | 4020 |
| cgtcgtgtag ataactacga tacgggaggg cttaccatct ggccccagtg ctgcaatgat | 4080 |
| accgcgagac ccacgctcac cggctccaga tttatcagca ataaaccagc cagccggaag | 4140 |
| ggccgagcgc agaagtggtc ctgcaacttt atccgcctcc atccagtcta ttaattgttg | 4200 |
| ccgggaagct agagtaagta gttcgccagt taatagtttg cccaacgttg ttgccattgc | 4260 |
| tacaggcatc gtggtgtcac gctcgtcgtt tggtatggct tcattcagct ccggttccca | 4320 |
| acgatcaagg cgagttacat gatcccccat gttgtgcaaa aaagcggtta gctccttcgg | 4380 |
| tcctccgatc gttgtcagaa gtaagttggc cgcagtgtta tcactcatgg ttatggcagc | 4440 |
| actgcataat tctcttactg tcatgccatc cgtaagatgc ttttctgtga ctggtgagta | 4500 |
| ctcaaccaag tcattctgag aatagtgtat gcggcgaccg agttgctctt gcccggcgtc | 4560 |
| aatacgggat aataccgcgc cacatagcag aactttaaaa gtgctcatca ttggaaaacg | 4620 |

| | |
|---|---|
| ttcttcgggg cgaaaactct caaggatctt accgctgttg agatccagtt cgatgtaacc | 4680 |
| cactcgtgca cccaactgat cttcagcatc ttttactttc accagcgttt ctgggtgagc | 4740 |
| aaaaacagga aggcaaaatg ccgcaaaaaa gggaataagg gcgacacgga aatgttgaat | 4800 |
| actcatactc ttcctttttc aacattattg aagcatttat cagggttatt gtctcatgag | 4860 |
| cggatacata tttgaatgta tttagaaaaa taaacaaata ggggttccgc gcacatttcc | 4920 |
| ccgaaaagtg ccacctgacg tctaagaaac cattattatc atgacattaa cctataaaaa | 4980 |
| taggcgtatc acgaggccct tcgtctcgc gcgtttcggt gatgacggtg aaaacctctg | 5040 |
| acacatgcag ctcccggaga cggtcacagc ttgtctgtaa gcggatgccg ggagcagaca | 5100 |
| agcccgtcag ggcgcgtcag cgggtgttgg cgggtgtcgg gctggctta actatgcggc | 5160 |
| atcagagcag attgtactga gagtgcacca tatgcggtgt gaaataccgc acagatgcgt | 5220 |
| aaggagaaaa taccgcatca ggcgccattc gccattcagg ctgggcaact gttgggaagg | 5280 |
| gcgatcggtg cgggcctctt cgctattacg ccagctggcg aaaggggat gtgctgcaag | 5340 |
| gcgattaagt tgggtaacgc cagggttttc ccagtcacga cgttgtaaaa cgacggccag | 5400 |
| tgaattagta ctctagctta agtaacgcca ttttgcaagg catggaaaat acataactga | 5460 |
| gaatagagaa gttcaga | 5477 |

<210> SEQ ID NO 201
<211> LENGTH: 5888
<212> TYPE: DNA
<213> ORGANISM: Artificial Sequence
<220> FEATURE:
<223> OTHER INFORMATION: synthetic

<400> SEQUENCE: 201

| | |
|---|---|
| tcaaggttag gaacagagag acagcagaat atgggccaaa caggatatct gtggtaagca | 60 |
| gttcctgccc cggctcaggg ccaagaacag ttggaacagc agaatatggg ccaaacagga | 120 |
| tatctgtggt aagcagttcc tgccccggct cagggccaag aacagatggt ccccagatgc | 180 |
| ggtcccgccc tcagcagttt ctagagaacc atcagatgtt tccagggtgc cccaaggacc | 240 |
| tgaaatgacc ctgtgcctta tttgaactaa ccaatcagtt cgcttctcgc ttctgttcgc | 300 |
| gcgcttctgc tccccgagct caataaaaga gcccacaacc cctcactcgg cgcgccagtc | 360 |
| ctccgataga ctgcgtcgcc cgggtacccg tattcccaat aaagcctctt gctgtttgca | 420 |
| tccgaatcgt ggactcgctg atccttggga gggtctcctc agattgattg actgcccacc | 480 |
| tcggggtct ttcatttgga ggttccaccg agatttggag accctgcc agggaccacc | 540 |
| gaccccccg ccgggaggta agctggccag cggtcgtttc gtgtctgtct ctgtctttgt | 600 |
| gcgtgtttgt gccggcatct aatgtttgcg cctgcgtctg tactagttgg ctaactagat | 660 |
| ctgtatctgg cggtcccgcg gaagaactga cgagttcgta ttcccggccg cagcccctgg | 720 |
| gagacgtccc agcggcctcg ggggcccgtt ttgtggccca ttctgtatca gttaacctac | 780 |
| ccgagtcgga cttttggag ctccgccact gtccgagggg tacgtggctt tgttggggga | 840 |
| cgagagacag agacacttcc cgcccccgtc tgaatttttg ctttcggttt tacgccgaaa | 900 |
| ccgcgccgcg cgtcttgtct gctgcagcat cgttctgtgt tgtctctgtc tgactgtgtt | 960 |
| tctgtatttg tctgaaaatt agctcgacaa agttaagtaa tagtccctct ctccaagctc | 1020 |
| acttacaggc ggccgcaccg gtcgccacca tccagaaccc cgagcccgcc gtgtaccagc | 1080 |
| tgaaggaccc cagaagccag acagcaccc tgtgcctgtt caccgacttc gacagccaga | 1140 |
| tcaacgtgcc caagaccatg gaaagcggca cccttcatcac cgacaagaca gtgctggaca | 1200 |

```
tgaaggccat ggacagcaag agcaacggcg ccattgcctg gtccaaccag accagcttca   1260
catgccagga catcttcaaa gagacaaacg ccacctaccc cagcagcgac gtgccctgcg   1320
acgccaccct gaccgagaag agcttcgaga cagacatgaa cctgaatttc cagaacctga   1380
gcgtgatggg cctgcggatc ctgctgctga aggtggccgg cttcaacctg ctgatgaccc   1440
tgcggctgtg gagcagctga ggtaccgagc tcgaattcga gcatcttacc gccatttatt   1500
cccatatttg ttctgttttt cttgatttgg gtatacattt aaatgttaat aaaacaaaat   1560
ggtggggcaa tcatttacat tttatgggat atgtaattac tagttcaggt gtattgccac   1620
aagacaaaca tgttaagaaa ctttcccgtt atttacgctc tgttcctgtt aatcaacctc   1680
tggattacaa aatttgtgaa agattgactg atattcttaa ctatgttgct ccttttacgc   1740
tgtgtggata tgctgcttta atgcctctgt atcatgctat tgcttcccgt acggctttcg   1800
ttttctcctc cttgtataaa tcctggttgc tgtctcttta tgaggagttg tggcccgttg   1860
tccgtcaacg tggcgtggtg tgctctgtgt ttgctgacgc aaccccccact ggctggggca   1920 ttgccaccac ctgtcaactc ctttctggga ctttcgcttt ccccctcccg atcgccacgg   1980
cagaactcat cgccgcctgc cttgcccgct gctggacagg ggctaggttg ctgggcactg   2040
ataattccgt ggtgttgtcg gggaagctga cgtccttttcc atggctgctc gcctgtgttg   2100
ccaactggat cctgcgcggg acgtccttct gctacgtccc ttcggctctc aatccagcgg   2160
acctcccttc ccgaggcctt ctgccggttc tgcggcctct cccgcgtctt cgctttcggc   2220
ctccgacgag tcggatctcc ctttgggccg cctccccgcc tgtttcgcct cggcgtccgg   2280
tccgtgttgc ttggtcgtca cctgtgcaga attgcgaacc atggattcca ccgtgaactt   2340
tgtctcctgg catgcaaatc gtcaacttgg catgccaaga attaattcgg atccaagctt   2400
aggcctgctc gctttcttgc tgtcccattt ctattaaagg ttcctttgtt ccctaagtcc   2460
aactactaaa ctgggggata ttatgaaggg ccttgagcat ctggattctg cctagcgcta   2520
agcttaacac gagccataga tagaataaaa gatttatttt agtctccaga aaaggggggg   2580
aatgaaagac cccaccctgta ggtttggcaa gctagcttaa gtaacgccat tttgcaaggc   2640
atggaaaata cataactgag aatagagaag ttcagatcaa ggttaggaac agagagacag   2700
cagaatatgg gccaaacagg atatctgtgg taagcagttc ctgccccggc tcagggccaa   2760
gaacagttgg aacagcagaa tatgggccaa acaggatatc tgtggtaagc agttcctgcc   2820
ccggctcagg gccaagaaca gatggtcccc agatgcggtc ccgccctcag cagtttctag   2880
agaaccatca gatgtttcca gggtgcccca aggacctgaa atgaccctgt gccttatttg   2940
aactaaccaa tcagttcgct tctcgcttct gttcgcgcgc ttctgctccc cgagctcaat   3000
aaaagagccc acaaccctc actcggcgcg ccagtcctcc gatagactgc gtcgcccggg   3060
tacccgtgtt ctcaataaac cctcttgcag ttgcatccga ctcgtggtct cgctgttcct   3120
tgggagggtc tcctctgagt gattgactgc ccacctcggg ggtctttcat tctcgagcag   3180
cttggcgtaa tcatggtcat agctgtttcc tgtgtgaaat tgttatccgc tcacaattcc   3240
acacaacata cgagccggaa gcataaagtg taaagcctgg ggtgcctaat gagtgagcta   3300
actcacatta attgcgttgc gctcactgcc cgctttccag tcgggaaacc tgtcgtgcca   3360
gctgcattaa tgaatcggcc aacgcgcggg gagaggcggt ttgcgtattg ggcgctcttc   3420
cgcttcctcg ctcactgact cgctgcgctc ggtcgttcgg ctgcggcgag cggtatcagc   3480
tcactcaaag gcggtaatac ggttatccac agaatcaggg gataacgcag gaaagaacat   3540
```

```
gtgagcaaaa ggccagcaaa aggccaggaa ccgtaaaaag gccgcgttgc tggcgttttt    3600
ccataggctc cgccccctg  acgagcatca caaaaatcga cgctcaagtc agaggtggcg    3660
aaacccgaca ggactataaa gataccaggc gtttccccct ggaagctccc tcgtgcgctc    3720
tcctgttccg accctgccgc ttaccggata cctgtccgcc tttctccctt cgggaagcgt    3780
ggcgctttct catagctcac gctgtaggta tctcagttcg gtgtaggtcg ttcgctccaa    3840
gctgggctgt gtgcacgaac cccccgttca gcccgaccgc tgcgccttat ccggtaacta    3900
tcgtcttgag tccaacccgg taagacacga cttatcgcca ctggcagcag ccactggtaa    3960
caggattagc agagcgaggt atgtaggcgg tgctacagag ttcttgaagt ggtggcctaa    4020
ctacggctac actagaagaa cagtatttgg tatctgcgct ctgctgaagc cagttacctt    4080
cggaaaaaga gttggtagct cttgatccgg caaacaaacc accgctggta gcggtggttt    4140
ttttgtttgc aagcagcaga ttacgcgcag aaaaaaagga tctcaagaag atcctttgat    4200
cttttctacg gggtctgacg ctcagtggaa cgaaaactca cgttaaggga ttttggtcat    4260
gagattatca aaaaggatct tcacctagat ccttttaaat taaaaatgaa gttttaaatc    4320
aatctaaagt atatatgagt aaacttggtc tgacagttac caatgcttaa tcagtgaggc    4380
acctatctca gcgatctgtc tatttcgttc atccatagtt gcctgactcc ccgtcgtgta    4440
gataactacg atacgggagg gcttaccatc tggccccagt gctgcaatga taccgcgaga    4500
cccacgctca ccggctccag atttatcagc aataaaccag ccagccggaa gggccgagcg    4560
cagaagtggt cctgcaactt tatccgcctc catccagtct attaattgtt gccgggaagc    4620
tagagtaagt agttcgccag ttaatagttt gcccaacgtt gttgccattg ctacaggcat    4680
cgtggtgtca cgctcgtcgt ttggtatggc ttcattcagc tccggttccc aacgatcaag    4740
gcgagttaca tgatccccca tgttgtgcaa aaaagcggtt agctccttcg gtcctccgat    4800
cgttgtcaga agtaagttgg ccgcagtgtt atcactcatg gttatggcag cactgcataa    4860
ttctcttact gtcatgccat ccgtaagatg cttttctgtg actggtgagt actcaaccaa    4920
gtcattctga gaatagtgta tgcggcgacc gagttgctct tgcccggcgt caatacggga    4980
taataccgcg ccacatagca gaactttaaa agtgctcatc attggaaaac gttcttcggg    5040
gcgaaaactc tcaaggatct taccgctgtt gagatccagt tcgatgtaac ccactcgtgc    5100
acccaactga tcttcagcat cttttacttt caccagcgtt tctgggtgag caaaaacagg    5160
aaggcaaaat gccgcaaaaa agggaataag ggcgacacgg aaatgttgaa tactcatact    5220
cttccttttt caacattatt gaagcattta tcagggttat tgtctcatga gcggatacat    5280
atttgaatgt atttagaaaa ataaacaaat aggggttccg cgcacatttc cccgaaaagt    5340
gccacctgac gtctaagaaa ccattattat catgacatta acctataaaa ataggcgtat    5400
cacgaggccc tttcgtctcg cgcgtttcgg tgatgacggt gaaaacctct gacacatgca    5460
gctcccggag acggtcacag cttgtctgta agcggatgcc gggagcagac aagcccgtca    5520
gggcgcgtca gcgggtgttg gcgggtgtcg ggctggctt  aactatgcgg catcagagca    5580
gattgtactg agagtgcacc atatgcggtg tgaaataccg cacagatgcg taaggagaaa    5640
ataccgcatc aggcgccatt cgccattcag gctgggcaac tgtttgggaag ggcgatcggt    5700
gcgggcctct tcgctattac gccagctggc gaaagggggga tgtgctgcaa ggcgattaag    5760
ttgggtaacg ccagggtttt cccagtcacg acgttgtaaa acgacggcca gtgaattagt    5820
actctagctt aagtaacgcc attttgcaag gcatggaaaa tacataactg agaatagaga    5880
agttcaga                                                              5888
```

<210> SEQ ID NO 202
<211> LENGTH: 5999
<212> TYPE: DNA
<213> ORGANISM: Artificial Sequence
<220> FEATURE:
<223> OTHER INFORMATION: synthetic

<400> SEQUENCE: 202

| | | | | | |
|---|---|---|---|---|---|
| tcaaggttag | gaacagagag | acagcagaat | atgggccaaa | caggatatct | gtggtaagca | 60 |
| gttcctgccc | cggctcaggg | ccaagaacag | ttggaacagc | agaatatggg | ccaaacagga | 120 |
| tatctgtggt | aagcagttcc | tgccccggct | cagggccaag | aacagatggt | ccccagatgc | 180 |
| ggtcccgccc | tcagcagttt | ctagagaacc | atcagatgtt | tccagggtgc | cccaaggacc | 240 |
| tgaaatgacc | ctgtgcctta | tttgaactaa | ccaatcagtt | cgcttctcgc | ttctgttcgc | 300 |
| gcgcttctgc | tccccgagct | caataaaaga | gcccacaacc | cctcactcgg | cgcgccagtc | 360 |
| ctccgataga | ctgcgtcgcc | cgggtacccg | tattcccaat | aaagcctctt | gctgtttgca | 420 |
| tccgaatcgt | ggactcgctg | atccttggga | gggtctcctc | agattgattg | actgcccacc | 480 |
| tcggggtct | ttcatttgga | ggttccaccg | agatttggag | accctgccc | agggaccacc | 540 |
| gaccccccg | ccgggaggta | agctggccag | cggtcgtttc | gtgtctgtct | ctgtctttgt | 600 |
| gcgtgtttgt | gccggcatct | aatgtttgcg | cctgcgtctg | tactagttgg | ctaactagat | 660 |
| ctgtatctgg | cggtcccgcg | gaagaactga | cgagttcgta | ttcccggccg | cagcccctgg | 720 |
| gagacgtccc | agcggcctcg | ggggcccgtt | tgtggcccca | ttctgtatca | gttaacctac | 780 |
| ccgagtcgga | cttttggag | ctccgccact | gtccgagggg | tacgtggctt | tgttggggga | 840 |
| cgagagacag | agacacttcc | cgccccgtc | tgaatttttg | ctttcggttt | tacgccgaaa | 900 |
| ccgcgccgcg | cgtcttgtct | gctgcagcat | cgttctgtgt | tgtctctgtc | tgactgtgtt | 960 |
| tctgtatttg | tctgaaaatt | agctcgacaa | agttaagtaa | tagtccctct | ctccaagctc | 1020 |
| acttacaggc | ggccgcaccg | tcgccaccg | aagatctgag | gaacgtgacc | ccccccaagg | 1080 |
| tgaccctgtt | cgagcccagc | aaggccgaga | tcgccaacaa | gcagaaagcc | accctggtct | 1140 |
| gcctggccag | gggcttcttc | cccgaccacg | tggagctgtc | ttggtgggtg | aacggcaaag | 1200 |
| aggtgcacag | cggagtcagt | accgaccccc | aggcctacaa | agagagcaac | tacagctact | 1260 |
| gcctgagcag | caggctgaga | gtgagcgcca | ccttctggca | caaccccgg | aaccacttcc | 1320 |
| ggtgccaggt | gcagttccac | ggcctgagcg | aagaggacaa | gtggcctgag | gcagccccca | 1380 |
| agcccgtgac | ccagaacatc | agcgccgagg | cctgggcag | agccgactgc | ggcatcacca | 1440 |
| gcgccagcta | ccaccagggc | gtgctgtccg | ccaccatcct | gtacgagatc | ctgctgggca | 1500 |
| aggcacccct | gtacgccgtg | ctggtgtccg | gcctggtgct | gatggccatg | gtgaagaaga | 1560 |
| agaacagctg | aggtaccgag | ctcgaattcg | agcatcttac | cgccatttat | tcccatattt | 1620 |
| gttctgttt | tcttgatttg | ggtatacatt | taaatgttaa | taaaacaaaa | tggtggggca | 1680 |
| atcatttaca | ttttatggga | tatgtaatta | ctagttcagg | tgtattgcca | caagacaaac | 1740 |
| atgttaagaa | actttcccgt | tatttacgct | ctgttcctgt | taatcaacct | ctggattaca | 1800 |
| aaatttgtga | aagattgact | gatattctta | actatgttgc | tcctttacg | ctgtgtggat | 1860 |
| atgctgcttt | aatgcctctg | tatcatgcta | ttgcttcccg | tacggctttc | gttttctcct | 1920 |
| ccttgtataa | atcctggttg | ctgtctcttt | atgaggagtt | gtggcccgtt | gtccgtcaac | 1980 |
| gtggcgtggt | gtgctctgtg | tttgctgacg | caaccccac | tggctgggc | attgccacca | 2040 |

```
cctgtcaact cctttctggg actttcgctt tccccctccc gatcgccacg gcagaactca    2100
tcgccgcctg ccttgcccgc tgctggacag gggctaggtt gctgggcact gataattccg    2160
tggtgttgtc ggggaagctg acgtcctttc catggctgct cgcctgtgtt gccaactgga    2220
tcctgcgcgg gacgtccttc tgctacgtcc cttcggctct caatccagcg gacctccctt    2280
cccgaggcct tctgccggtt ctgcggcctc tcccgcgtct tcgctttcgg cctccgacga    2340
gtcggatctc cctttgggcc gcctcccgc ctgtttcgcc tcggcgtccg gtccgtgttg    2400
cttggtcgtc acctgtgcag aattgcgaac catggattcc accgtgaact tgtctcctg    2460 gcatgcaaat cgtcaacttg gcatgccaag aattaattcg gatccaagct taggcctgct    2520
cgctttcttg ctgtcccatt tctattaaag gttccttgt tccctaagtc caactactaa    2580
actgggggat attatgaagg gccttgagca tctggattct gcctagcgct aagcttaaca    2640
cgagccatag atagaataaa agattttatt tagtctccag aaaaaggggg gaatgaaaga    2700
ccccacctgt aggtttggca agctagctta agtaacgcca ttttgcaagg catggaaaat    2760
acataactga gaatagagaa gttcagatca aggttaggaa cagagagaca gcagaatatg    2820
ggccaaacag gatatctgtg gtaagcagtt cctgccccgg ctcagggcca agaacagttg    2880
gaacagcaga atatgggcca aacaggatat ctgtggtaag cagttcctgc cccggctcag    2940
ggccaagaac agatggtccc cagatgcggt cccgccctca gcagtttcta gagaaccatc    3000
agatgtttcc agggtgcccc aaggacctga aatgaccctg tgccttattt gaactaacca    3060
atcagttcgc ttctcgcttc tgttcgcgcg cttctgctcc ccgagctcaa taaaagagcc    3120
cacaacccct cactcggcgc gccagtcctc cgatagactg cgtcgcccgg gtacccgtgt    3180
tctcaataaa ccctcttgca gttgcatccg actcgtggtc tcgctgttcc ttgggagggt    3240
ctcctctgag tgattgactg cccacctcgg gggtctttca ttctcgagca gcttggcgta    3300
atcatggtca tagctgtttc ctgtgtgaaa ttgttatccg ctcacaattc cacacaacat    3360
acgagccgga agcataaagt gtaaagcctg gggtgcctaa tgagtgagct aactcacatt    3420
aattgcgttg cgctcactgc ccgctttcca gtcgggaaac ctgtcgtgcc agctgcatta    3480
atgaatcggc caacgcgcgg ggagaggcgg tttgcgtatt gggcgctctt ccgcttcctc    3540
gctcactgac tcgctgcgct cggtcgttcg gctgcggcga gcggtatcag ctcactcaaa    3600
ggcggtaata cggttatcca cagaatcagg ggataacgca ggaaagaaca tgtgagcaaa    3660
aggccagcaa aaggccagga accgtaaaaa ggccgcgttg ctggcgtttt tccataggct    3720
ccgcccccct gacgagcatc acaaaaatcg acgctcaagt cagaggtggc gaaacccgac    3780
aggactataa agataccagg cgtttccccc tggaagctcc ctcgtgcgct ctcctgttcc    3840
gaccctgccg cttaccggat acctgtccgc ctttctccct tcgggaagcg tggcgctttc    3900
tcatagctca cgctgtaggt atctcagttc ggtgtaggtc gttcgctcca agctgggctg    3960
tgtgcacgaa ccccccgttc agcccgaccg ctgcgcctta tccggtaact atcgtcttga    4020
gtccaacccg gtaagacacg acttatcgcc actggcagca gccactggta acaggattag    4080
cagagcgagg tatgtaggcg gtgctacaga gttcttgaag tggtggccta actacggcta    4140
cactagaaga acagtatttg gtatctgcgc tctgctgaag ccagttacct tcggaaaaag    4200
agttggtagc tcttgatccg gcaaacaaac caccgctggt agcggtggtt ttttgtttg    4260 caagcagcag attacgcgca gaaaaaaagg atctcaagaa gatcctttga tcttttctac    4320
ggggtctgac gctcagtgga acgaaaactc acgttaaggg attttggtca tgagattatc    4380
aaaaaggatc ttcacctaga tccttttaaa ttaaaaatga agttttaaat caatctaaag    4440
```

-continued

| | | |
|---|---|---|
| tatatatgag taaacttggt ctgacagtta ccaatgctta atcagtgagg cacctatctc | 4500 |
| agcgatctgt ctatttcgtt catccatagt tgcctgactc cccgtcgtgt agataactac | 4560 |
| gatacgggag ggcttaccat ctggccccag tgctgcaatg ataccgcgag acccacgctc | 4620 |
| accggctcca gatttatcag caataaacca gccagccgga agggccgagc gcagaagtgg | 4680 |
| tcctgcaact ttatccgcct ccatccagtc tattaattgt tgccgggaag ctagagtaag | 4740 |
| tagttcgcca gttaatagtt tgcccaacgt tgttgccatt gctacaggca tcgtggtgtc | 4800 |
| acgctcgtcg tttggtatgg cttcattcag ctccggttcc caacgatcaa ggcgagttac | 4860 |
| atgatccccc atgttgtgca aaaaagcggt tagctccttc ggtcctccga tcgttgtcag | 4920 |
| aagtaagttg gccgcagtgt tatcactcat ggttatggca gcactgcata attctcttac | 4980 |
| tgtcatgcca tccgtaagat gcttttctgt gactggtgag tactcaacca agtcattctg | 5040 |
| agaatagtgt atgcggcgac cgagttgctc ttgcccggcg tcaatacggg ataataccgc | 5100 |
| gccacatagc agaactttaa aagtgctcat cattggaaaa cgttcttcgg ggcgaaaact | 5160 |
| ctcaaggatc ttaccgctgt tgagatccag ttcgatgtaa cccactcgtg cacccaactg | 5220 |
| atcttcagca tcttttactt tcaccagcgt ttctgggtga gcaaaaacag gaaggcaaaa | 5280 |
| tgccgcaaaa aagggaataa gggcgacacg gaaatgttga atactcatac tcttcctttt | 5340 |
| tcaacattat tgaagcattt atcagggtta ttgtctcatg agcggataca tatttgaatg | 5400 |
| tatttagaaa aataaacaaa tagggggttcc gcgcacattt ccccgaaaag tgccacctga | 5460 |
| cgtctaagaa accattatta tcatgacatt aacctataaa aataggcgta tcacgaggcc | 5520 |
| ctttcgtctc gcgcgtttcg gtgatgacgg tgaaaacctc tgacacatgc agctcccgga | 5580 |
| gacggtcaca gcttgtctgt aagcggatgc cgggagcaga caagcccgtc agggcgcgtc | 5640 |
| agcgggtgtt ggcgggtgtc ggggctggct taactatgcg gcatcagagc agattgtact | 5700 |
| gagagtgcac catatgcggt gtgaaatacc gcacagatgc gtaaggagaa ataccgcat | 5760 |
| caggcgccat tcgccattca ggctgggcaa ctgttgggaa gggcgatcgg tgcgggcctc | 5820 |
| ttcgctatta cgccagctgg cgaaaggggg atgtgctgca aggcgattaa gttgggtaac | 5880 |
| gccagggttt tcccagtcac gacgttgtaa aacgacggcc agtgaattag tactctagct | 5940 |
| taagtaacgc cattttgcaa ggcatggaaa atacataact gagaatagag aagttcaga | 5999 |

<210> SEQ ID NO 203
<211> LENGTH: 6304
<212> TYPE: DNA
<213> ORGANISM: Artificial Sequence
<220> FEATURE:
<223> OTHER INFORMATION: synthetic

<400> SEQUENCE: 203

| | | |
|---|---|---|
| tcaaggttag gaacagagag acagcagaat atgggccaaa caggatatct gtggtaagca | 60 |
| gttcctgccc cggctcaggg ccaagaacag ttggaacagc agaatatggg ccaaacagga | 120 |
| tatctgtggt aagcagttcc tgccccggct cagggccaag aacagatggt ccccagatgc | 180 |
| ggtcccgccc tcagcagttt ctagagaacc atcagatgtt tccagggtgc cccaaggacc | 240 |
| tgaaatgacc ctgtgcctta tttgaactaa ccaatcagtt cgcttctcgc ttctgttcgc | 300 |
| gcgcttctgc tccccgagct caataaaaga gcccacaacc cctcactcgg cgcgccagtc | 360 |
| ctccgataga ctgcgtcgcc cgggtacccg tattcccaat aaagcctctt gctgtttgca | 420 |
| tccgaatcgt ggactcgctg atccttggga gggtctcctc agattgattg actgcccacc | 480 |

```
tcgggggtct ttcatttgga ggttccaccg agatttggag accccctgccc agggaccacc    540
gaccccccg  ccgggaggta agctggccag cggtcgtttc gtgtctgtct ctgtctttgt    600
gcgtgtttgt gccggcatct aatgtttgcg cctgcgtctg tactagttgg ctaactagat    660
ctgtatctgg cggtcccgcg gaagaactga cgagttcgta ttcccggccg cagcccctgg    720
gagacgtccc agcggcctcg ggggcccgtt ttgtggccca ttctgtatca gttaacctac    780
ccgagtcgga cttttggag  ctccgccact gtccgagggg tacgtggctt tgttggggga    840
cgagagacag agacacttcc cgccccgtc  tgaattttg  ctttcggttt tacgccgaaa    900
ccgcgccgcg cgtcttgtct gctgcagcat cgttctgtgt tgtctctgtc tgactgtgtt    960
tctgtatttg tctgaaaatt agctcgacaa agttaagtaa tagtccctct ctccaagctc   1020
acttacaggc ggccgccatg gtgagaccac gtggagctgt cttggtgggt gaacggcaaa   1080
gaggtgcaca gcggagtcag taccgacccc caggcctaca agagagcaa  ctacagctac   1140
tgcctgagca gcaggctgag agtgagcgcc accttctggc acaaccccg  gaaccacttc   1200
cggtgccagg tgcagttcca cggcctgagc gaagaggaca agtggcctga gggcagcccc   1260
aagcccgtga cccagaacat cagcgccgag gcctggggca gagccgactg cggcatcacc   1320
agcgccagct accaccaggg cgtgctgtcc gccaccatcc tgtacgagat cctgctgggc   1380
aaggccaccc tgtacgccgt gctggtgtcc ggcctggtgc tgatggccat ggtgaagaag   1440
aagaacagcg gcagcggcgc caccaacttc agcctgctga agcaggccgg cgacgtggag   1500
gaaaaccctg gcctgcagg  atgctgacga cagcaccctg tgcctgttca ccgacttcga   1560
cagccagatc aacgtgccca agaccatgga aagcggcacc ttcatcaccg acaagacagt   1620
gctggacatg aaggccatgg acagcaagag caacggcgcc attgcctggt ccaaccagac   1680
cagcttcaca tgccaggaca tcttcaaaga gacaaacgcc acctacccca gcagcgacgt   1740
gccctgcgac gccacccctga ccgagaagag cttcgagaca gacatgaacc tgaatttcca   1800
gaacctgagc gtgatgggcc tgcggatcct gctgctgaag gtggccggct tcaacctgct   1860
gatgacctg  cggctgtgga gcagctgaga attcgagcat cttaccgcca tttattccca   1920
tatttgttct gttttcttg  atttgggtat acatttaaat gttaataaaa caaaatggtg   1980
gggcaatcat ttacatttta tgggatatgt aattactagt tcaggtgtat tgccacaaga   2040
caaacatgtt aagaaacttt cccgttattt acgctctgtt cctgttaatc aacctctgga   2100
ttacaaaatt tgtgaaagat tgactgatat tcttaactat gttgctcctt ttacgctgtg   2160
tggatatgct gctttaatgc ctctgtatca tgctattgct tcccgtacgg ctttcgtttt   2220
ctcctccttg tataaatcct ggttgctgtc tctttatgag gagttgtggc ccgttgtccg   2280
tcaacgtggc gtggtgtgct ctgtgtttgc tgacgcaacc cccactggct ggggcattgc   2340
caccacctgt caactccttt ctgggacttt cgctttcccc ctcccgatcg ccacggcaga   2400
actcatcgcc gcctgccttg cccgctgctg acagggggct aggttgctgg cactgataa    2460
ttccgtggtg ttgtcgggga agctgacgtc ctttccatgg ctgctcgcct gtgttgccaa   2520
ctggatcctg cgcgggacgt ccttctgcta cgtcccttcg gctctcaatc cagcggacct   2580
cccttcccga ggccttctgc cggttctgcg gcctctcccg cgtcttcgct ttcggcctcc   2640
gacgagtcgg atctcccttt gggccgcctc cccgcctgtt tcgcctcggc gtccggtccg   2700
tgttgcttgg tcgtcacctg tgcagaattg cgaaccatgg attccaccgt gaactttgtc   2760
tcctggcatg caaatcgtca acttggcatg ccaagaatta attcggatcc aagcttaggc   2820
ctgctcgctt tcttgctgtc ccatttctat taaaggttcc tttgttccct aagtccaact   2880
```

```
actaaactgg gggatattat gaagggcctt gagcatctgg attctgccta gcgctaagct    2940
taacacgagc catagataga ataaaagatt ttatttagtc tccagaaaaa gggggggaatg   3000 aaagacccca cctgtaggtt tggcaagcta gcttaagtaa cgccattttg caaggcatgg    3060
aaaatacata actgagaata gagaagttca gatcaaggtt aggaacagag agacagcaga   3120
atatgggcca aacaggatat ctgtggtaag cagttcctgc cccggctcag ggccaagaac   3180
agttggaaca gcagaatatg ggccaaacag gatatctgtg gtaagcagtt cctgccccgg   3240
ctcagggcca agaacagatg gtccccagat gcggtcccgc cctcagcagt ttctagagaa   3300
ccatcagatg tttccagggt gccccaagga cctgaaatga ccctgtgcct tatttgaact   3360
aaccaatcag ttcgcttctc gcttctgttc gcgcgcttct gctccccgag ctcaataaaa   3420
gagcccacaa cccctcactc ggcgcgccag tcctccgata gactgcgtcg cccgggtacc   3480
cgtgttctca ataaaccctc ttgcagttgc atccgactcg tggtctcgct gttccttggg   3540
agggtctcct ctgagtgatt gactgcccac ctcgggggtc tttcattctc gagcagcttg   3600
gcgtaatcat ggtcatagct gtttcctgtg tgaaattgtt atccgctcac aattccacac   3660
aacatacgag ccggaagcat aaagtgtaaa gcctggggtg cctaatgagt gagctaactc   3720
acattaattg cgttgcgctc actgcccgct ttccagtcgg gaaacctgtc gtgccagctg   3780
cattaatgaa tcggccaacg cgcggggaga ggcggtttgc gtattgggcg ctcttccgct   3840
tcctcgctca ctgactcgct gcgctcggtc gttcggctgc ggcgagcggt atcagctcac   3900
tcaaaggcgg taatacggtt atccacagaa tcagggggata acgcaggaaa gaacatgtga   3960
gcaaaaggcc agcaaaaggc caggaaccgt aaaaaggccg cgttgctggc gtttttccat   4020
aggctccgcc cccctgacga gcatcacaaa aatcgacgct caagtcagag gtggcgaaac   4080
ccgacaggac tataaagata ccaggcgttt ccccctggaa gctccctcgt gcgctctcct   4140
gttccgaccc tgccgcttac cggatacctg tccgcctttc tcccttcggg aagcgtggcg   4200
ctttctcata gctcacgctg taggtatctc agttcggtgt aggtcgttcg ctccaagctg   4260
ggctgtgtgc acgaaccccc cgttcagccc gaccgctgcg ccttatccgg taactatcgt   4320
cttgagtcca acccggtaag acacgactta tcgccactgg cagcagccac tggtaacagg   4380
attagcagag cgaggtatgt aggcggtgct acagagttct tgaagtggtg cctaactac    4440 ggctacacta gaagaacagt atttggtatc tgcgctctgc tgaagccagt taccttcgga   4500
aaaagagttg gtagctcttg atccggcaaa caaaccaccg ctggtagcgg tggtttttt    4560 gtttgcaagc agcagattac gcgcagaaaa aaggatctc aagaagatcc tttgatcttt    4620
tctacggggt ctgacgctca gtggaacgaa aactcacgtt aagggatttt ggtcatgaga   4680
ttatcaaaaa ggatcttcac ctagatcctt ttaaattaaa aatgaagttt taaatcaatc   4740
taaagtatat atgagtaaac ttggtctgac agttaccaat gcttaatcag tgaggcacct   4800
atctcagcga tctgtctatt tcgttcatcc atagttgcct gactccccgt cgtgtagata   4860
actacgatac gggagggctt accatctggc cccagtgctg caatgatacc gcgagaccca   4920
cgctcaccgg ctccagattt atcagcaata aaccagccag ccggaagggc cgagcgcaga   4980
agtggtcctg caactttatc cgcctccatc cagtctatta attgttgccg ggaagctaga   5040
gtaagtagtt cgccagttaa tagtttgccc aacgttgttg ccattgctac aggcatcgtg   5100
gtgtcacgct cgtcgtttgg tatggcttca ttcagctccg gttcccaacg atcaaggcga   5160
gttacatgat cccccatgtt gtgcaaaaaa gcggttagct ccttcggtcc tccgatcgtt   5220
```

```
gtcagaagta agttggccgc agtgttatca ctcatggtta tggcagcact gcataattct    5280
cttactgtca tgccatccgt aagatgcttt tctgtgactg gtgagtactc aaccaagtca    5340
ttctgagaat agtgtatgcg gcgaccgagt tgctcttgcc cggcgtcaat acgggataat    5400
accgcgccac atagcagaac tttaaaagtg ctcatcattg gaaaacgttc ttcggggcga    5460
aaactctcaa ggatcttacc gctgttgaga tccagttcga tgtaacccac tcgtgcaccc    5520
aactgatctt cagcatcttt tactttcacc agcgtttctg ggtgagcaaa acaggaagg     5580 caaaatgccg caaaaaggg aataagggcg acacggaaat gttgaatact catactcttc     5640 cttttcaac attattgaag catttatcag ggttattgtc tcatgagcgg atacatattt     5700
gaatgtattt agaaaaataa acaaatagggg gttccgcgca catttccccg aaaagtgcca    5760
cctgacgtct aagaaaccat tattatcatg acattaacct ataaaaatag gcgtatcacg    5820
aggccctttc gtctcgcgcg tttcggtgat gacggtgaaa acctctgaca catgcagctc    5880
ccggagacgg tcacagcttg tctgtaagcg gatgccggga gcagacaagc ccgtcagggc    5940
gcgtcagcgg gtgttggcgg gtgtcggggc tggcttaact atgcggcatc agagcagatt    6000
gtactgagag tgcaccatat gcggtgtgaa ataccgcaca gatgcgtaag gagaaaatac    6060
cgcatcaggc gccattcgcc attcaggctg gcaactgtt gggaagggcg atcggtgcgg    6120
gcctcttcgc tattacgcca gctggcgaaa ggggatgtg ctgcaaggcg attaagttgg    6180
gtaacgccag ggttttccca gtcacgacgt tgtaaaacga cggccagtga attagtactc    6240
tagcttaagt aacgccattt tgcaaggcat ggaaaataca taactgagaa tagagaagtt    6300
caga                                                                 6304
```

<210> SEQ ID NO 204
<211> LENGTH: 6266
<212> TYPE: DNA
<213> ORGANISM: Artificial Sequence
<220> FEATURE:
<223> OTHER INFORMATION: synthetic

<400> SEQUENCE: 204

```
tcaaggttag gaacagagag acagcagaat atgggccaaa caggatatct gtggtaagca      60
gttcctgccc cggctcaggg ccaagaacag ttggaacagc agaatatggg ccaaacagga    120
tatctgtggt aagcagttcc tgccccggct cagggcaag aacagatggt ccccagatgc     180
ggtcccgccc tcagcagttt ctagagaacc atcagatgtt tccagggtgc cccaaggacc    240
tgaaatgacc ctgtgcctta tttgaactaa ccaatcagtt cgcttctcgc ttctgttcgc    300
gcgcttctgc tccccgagct caataaaaga gcccacaacc cctcactcgg cgcgccagtc    360
ctccgataga ctgcgtcgcc cgggtacccg tattcccaat aaagcctctt gctgtttgca    420
tccgaatcgt ggactcgctg atccttggga gggtctcctc agattgattg actgcccacc    480 tcggggggtct ttcatttgga ggttccaccg agatttggag accccctgccc agggaccacc    540 gacccccccg ccgggaggta agctggccag cgttcgtttc gtgtctgtct ctgtctttgt    600
gcgtgtttgt gccggcatct aatgtttgcg cctgcgtctg tactagttgg ctaactagat    660
ctgtatctgg cggtcccgcg gaagaactga cgagttcgta ttcccggccg cagcccctgg    720
gagacgtccc agcggcctcg ggggcccgtt ttgtggccca ttctgtatca gttaacctac    780
ccgagtcgga cttttttggag ctccgccact gtccgagggg tacgtggctt tgttgggga    840 cgagagacag agacacttcc cgcccccgtc tgaattttttg ctttcggttt tacgccgaaa    900
ccgcgccgcg cgtcttgtct gctgcagcat cgttctgtgt tgtctctgtc tgactgtgtt    960
```

```
tctgtatttg tctgaaaatt agctcgacaa agttaagtaa tagtccctct ctccaagctc   1020
acttacaggc ggccgcaccg gtcgccagca tgtggggagc ctttctgctg tacgtgtcca   1080
tgaagatggg cggcacagcc ggccagagcc tggaacagcc tagcgaagtg accgccgtgg   1140
aaggcgccat cgtgcagatc aactgcacct accagaccag cggcttctac ggcctgagct   1200
ggtatcagca gcacgacggc ggagccccca ccttcctgag ctacaacgcc ctggacggcc   1260
tggaagagac aggccggttc agcagcttcc tgagcagaag cgacagctac ggctacctgc   1320
tgctgcagga actgcagatg aaggacagcg ccagctactt ctgcgcagcc agcgacaact   1380
accagctgat ctggggcagc ggcaccaagc tgatcatcaa gcccgacatc cagaaccccg   1440
agcccgccgt gtaccagctg aaggacccca agccagga cagcaccctg tgcctgttca   1500
ccgacttcga cagccagatc aacgtgccca agaccatgga aagcggcacc ttcatcaccg   1560
acaagacagt gctggacatg aaggccatgg acagcaagag caacggcgcc attgcctggt   1620
ccaaccagac cagcttcaca tgccaggaca tcttcaaaga caaacgcc acctacccca    1680
gcagcgacgt gccctgcgac gccacctga ccgagaagag cttcgagaca gacatgaacc    1740
tgaatttcca gaacctgagc gtgatgggcc tgcggatcct gctgctgaag gtggccggct   1800
tcaacctgct gatgaccctg cggctgtgga gcagctgagg taccgagctc gaattcgagc   1860
atcttaccgc catttattcc catatttgtt ctgttttct tgatttgggt atacatttaa    1920
atgttaataa aacaaaatgg tggggcaatc atttacattt tatgggatat gtaattacta   1980
gttcaggtgt attgccacaa gacaaacatg ttaagaaact ttcccgttat ttacgctctg   2040
ttcctgttaa tcaacctctg gattacaaaa tttgtgaaag attgactgat attcttaact   2100
atgttgctcc ttttacgctg tgtggatatg ctgctttaat gcctctgtat catgctattg   2160
cttcccgtac ggctttcgtt ttctcctcct tgtataaatc ctggttgctg tctctttatg   2220
aggagttgtg gcccgttgtc cgtcaacgtg gcgtggtgtg ctctgtgttt gctgacgcaa   2280
cccccactgg ctggggcatt gccaccacct gtcaactcct ttctgggact ttcgctttcc   2340
ccctcccgat cgccacggca gaactcatcg ccgcctgcct tgcccgctgc tggacagggg   2400
ctaggttgct gggcactgat aattccgtgg tgttgtcggg gaagctgacg tccttcccat   2460
ggctgctcgc ctgtgttgcc aactggatcc tgcgcgggac gtccttctgc tacgtccctt   2520
cggctctcaa tccagcggac ctcccttccc gaggccttct gccggttctg cggcctctcc   2580
cgcgtcttcg ctttcggcct ccgacgagtc ggatctccct ttgggccgcc tccccgcctg   2640
tttcgcctcg gcgtccggtc cgtgttgctt ggtcgtcacc tgtgcagaat gcgaaccat   2700
ggattccacc gtgaactttg tctcctggca tgcaaatcgt caacttggca tgccaagaat   2760
taattcggat ccaagcttag gcctgctcgc tttcttgctg tcccatttct attaaaggtt   2820
cctttgttcc ctaagtccaa ctactaaact gggggatatt atgaagggcc ttgagcatct   2880
ggattctgcc tagcgctaag cttaacacga gccatagata gaataaaaga ttttatttag   2940
tctccagaaa aaggggggaa tgaaagaccc cacctgtagg tttggcaagc tagcttaagt   3000
aacgccattt tgcaaggcat ggaaaataca taactgagaa tagagaagtt cagatcaagg   3060
ttaggaacag agagacagca gaatatgggc caaacaggat atctgtggta agcagttcct   3120
gccccggctc agggccaaga acagttggaa cagcagaata tgggccaaac aggatatctg   3180
tggtaagcag ttcctgcccc ggctcagggc caagaacaga tggtcccag atgcggtccc   3240
gccctcagca gtttctagag aaccatcaga tgtttccagg gtgccccaag gacctgaaat   3300
```

```
gaccctgtgc cttatttgaa ctaaccaatc agttcgcttc tcgcttctgt tcgcgcgctt    3360
ctgctcccg  agctcaataa aagagcccac aaccccctcac tcggcgcgcc agtcctccga   3420
tagactgcgt cgcccgggta cccgtgttct caataaaccc tcttgcagtt gcatccgact    3480
cgtggtctcg ctgttccttg ggagggtctc ctctgagtga ttgactgccc acctcggggg    3540
tctttcattc tcgagcagct tggcgtaatc atggtcatag ctgtttcctg tgtgaaattg    3600
ttatccgctc acaattccac acaacatacg agccggaagc ataaagtgta aagcctgggg    3660
tgcctaatga gtgagctaac tcacattaat tgcgttgcgc tcactgcccg ctttccagtc    3720
gggaaacctg tcgtgccagc tgcattaatg aatcggccaa cgcgcgggga gaggcggttt    3780
gcgtattggg cgctcttccg cttcctcgct cactgactcg ctgcgctcgg tcgttcggct    3840
gcggcgagcg gtatcagctc actcaaaggc ggtaatacgg ttatccacag aatcaggggga   3900
taacgcagga aagaacatgt gagcaaaagg ccagcaaaag gccaggaacc gtaaaaaggc    3960
cgcgttgctg gcgttttttcc ataggctccg ccccccctgac gagcatcaca aaaatcgacg  4020
ctcaagtcag aggtggcgaa acccgacagg actataaaga taccaggcgt ttccccctgg    4080
aagctccctc gtgcgctctc ctgttccgac cctgccgctt accggatacc tgtccgcctt    4140
tctcccttcg ggaagcgtgg cgctttctca gctcacgc tgtaggtatc tcagttcggt     4200
gtaggtcgtt cgctccaagc tgggctgtgt gcacgaaccc cccgttcagc ccgaccgctg    4260
cgccttatcc ggtaactatc gtcttgagtc caacccggta agacacgact tatcgccact    4320
ggcagcagcc actggtaaca ggattagcag agcgaggtat gtaggcggtg ctacagagtt    4380
cttgaagtgg tggcctaact acggctacac tagaagaaca gtatttggta tctgcgctct    4440
gctgaagcca gttaccttcg gaaaaagagt tggtagctct tgatccggca acaaaccac    4500
cgctggtagc ggtggttttt ttgtttgcaa gcagcagatt acgcgcagaa aaaaaggatc   4560
tcaagaagat cctttgatct tttctacggg gtctgacgct cagtggaacg aaaactcacg   4620
ttaagggatt ttggtcatga gattatcaaa aaggatcttc acctagatcc ttttaaatta    4680
aaaatgaagt tttaaatcaa tctaaagtat atatgagtaa acttggtctg acagttacca   4740
atgcttaatc agtgaggcac ctatctcagc gatctgtcta tttcgttcat ccatagttgc    4800
ctgactcccc gtcgtgtaga taactacgat acgggagggc ttaccatctg gccccagtgc    4860
tgcaatgata ccgcgagacc cacgctcacc ggctccagat ttatcagcaa taaaccagcc    4920
agccggaagg gccgagcgca gaagtggtcc tgcaacttta tccgcctcca tccagtctat    4980
taattgttgc cgggaagcta gagtaagtag ttcgccagtt aatagtttgc caacgttgt     5040
tgccattgct acaggcatcg tggtgtcacg ctcgtcgttt ggtatggctt cattcagctc    5100
cggttcccaa cgatcaaggc gagttacatg atcccccatg ttgtgcaaaa aagcggttag    5160
ctccttcggt cctccgatcg ttgtcagaag taagttggcc gcagtgttat cactcatggt    5220
tatggcagca ctgcataatt ctcttactgt catgccatcc gtaagatgct tttctgtgac    5280
tggtgagtac tcaaccaagt cattctgaga atagtgtatg cggcgaccga gttgctcttg    5340
cccggcgtca atacgggata ataccgcgcc acatagcaga actttaaaag tgctcatcat    5400
tggaaaacgt tcttcgggc gaaaactctc aaggatctta ccgctgttga atccagttc    5460
gatgtaaccc actcgtgcac ccaactgatc ttcagcatct tttactttca ccagcgtttc    5520
tgggtgagca aaaacaggaa ggcaaaatgc cgcaaaaaag gaataagggg cgacacggaa    5580
atgttgaata ctcatactct ttccttttca acattattga agcatttatc agggttattg    5640
tctcatgagc ggatacatat ttgaatgtat ttagaaaaat aaacaaatag gggttccgcg    5700
```

| | |
|---|---|
| cacatttccc cgaaaagtgc cacctgacgt ctaagaaacc attattatca tgacattaac | 5760 |
| ctataaaaat aggcgtatca cgaggccctt tcgtctcgcg cgtttcggtg atgacggtga | 5820 |
| aaacctctga cacatgcagc tcccggagac ggtcacagct tgtctgtaag cggatgccgg | 5880 |
| gagcagacaa gcccgtcagg gcgcgtcagc gggtgttggc gggtgtcggg gctggcttaa | 5940 |
| ctatgcggca tcagagcaga ttgtactgag agtgcaccat atgcggtgtg aaataccgca | 6000 |
| cagatgcgta aggagaaaat accgcatcag gcgccattcg ccattcaggc tgggcaactg | 6060 |
| ttgggaaggg cgatcggtgc gggcctcttc gctattacgc cagctggcga aggggggatg | 6120 |
| tgctgcaagg cgattaagtt gggtaacgcc agggttttcc cagtcacgac gttgtaaaac | 6180 |
| gacggccagt gaattagtac tctagcttaa gtaacgccat tttgcaaggc atggaaaata | 6240 |
| cataactgag aatagagaag ttcaga | 6266 |

<210> SEQ ID NO 205
<211> LENGTH: 6392
<212> TYPE: DNA
<213> ORGANISM: Artificial Sequence
<220> FEATURE:
<223> OTHER INFORMATION: synthetic

<400> SEQUENCE: 205

| | |
|---|---|
| tcaaggttag gaacagagag acagcagaat atgggccaaa caggatatct gtggtaagca | 60 |
| gttcctgccc cggctcaggg ccaagaacag ttggaacagc agaatatggg ccaaacagga | 120 |
| tatctgtggt aagcagttcc tgccccggct cagggccaag aacagatggt ccccagatgc | 180 |
| ggtcccgccc tcagcagttt ctagagaacc atcagatgtt tccagggtgc cccaaggacc | 240 |
| tgaaatgacc ctgtgcctta tttgaactaa ccaatcagtt cgcttctcgc ttctgttcgc | 300 |
| gcgcttctgc tccccgagct caataaaaga gcccacaacc cctcactcgg cgcgccagtc | 360 |
| ctccgataga ctgcgtcgcc cgggtacccg tattcccaat aaagcctctt gctgtttgca | 420 |
| tccgaatcgt ggactcgctg atccttggga gggtctcctc agattgattg actgcccacc | 480 |
| tcggggggtct ttcatttgga ggttccaccg agatttggag accccctgccc agggaccacc | 540 |
| gacccccccg ccgggaggta agctggccag cggtcgtttc gtgtctgtct ctgtctttgt | 600 |
| gcgtgttttgt gccggcatct aatgtttgcg cctgcgtctg tactagttgg ctaactagat | 660 |
| ctgtatctgg cggtcccgcg gaagaactga cgagttcgta ttcccggccg cagcccctgg | 720 |
| gagacgtccc agcggcctcg ggggcccgtt ttgtggccca ttctgtatca gttaacctac | 780 |
| ccgagtcgga cttttttggag ctccgccact gtccgagggg tacgtggctt tgttggggga | 840 |
| cgagagacag agacacttcc cgccccgtc tgaattttg ctttcggttt tacgccgaaa | 900 |
| ccgcgccgcg cgtcttgtct gctgcagcat cgttctgtgt tgtctctgtc tgactgtgtt | 960 |
| tctgtatttg tctgaaaatt agctcgacaa agttaagtaa tagtccctct ctccaagctc | 1020 |
| acttacaggc ggccgcaccg tcgccacca tggatacctg gctcgtgtgc tgggccatct | 1080 |
| tcagcctgct gaaggccggc ctgaccgagc ccgaagtgac ccagacccct agccaccagg | 1140 |
| tcacacagat gggccaggaa gtgatcctgc gctgcgtgcc catcagcaac cacctgtact | 1200 |
| tctactggta cagacagatc ctgggccaga aagtggaatt cctggtgtcc ttctacaaca | 1260 |
| acgagatcag cgagaagtcc gagatcttcg acgaccagtt cagcgtggaa cggccccacg | 1320 |
| gcagcaactt cacccctgaag atcagaagca ccaagctcga ggacagcgcc atgtactttt | 1380 |
| gcgcaagcag ccgcgccaac tacgagcagt acttcggccc cggcacccgc ctgaccgtgc | 1440 |

-continued

```
tggaagatct gaggaacgtg accccccca aggtgaccct gttcgagccc agcaaggccg    1500
agatcgccaa caagcagaaa gccaccctgg tctgcctggc cagggcttc ttccccgacc    1560 acgtggagct gtcttggtgg gtgaacggca aagaggtgca cagcggagtc agtaccgacc   1620
cccaggccta caaagagagc aactacagct actgcctgag cagcaggctg agagtgagcg   1680
ccaccttctg gcacaacccc cggaaccact tccggtgcca ggtgcagttc cacggcctga   1740
gcgaagagga caagtggcct gagggcagcc ccaagcccgt gacccagaac atcagcgccg   1800
aggcctgggg cagagccgac tgcggcatca ccagcgccag ctaccaccag ggcgtgctgt   1860
ccgccaccat cctgtacgag atcctgctgg gcaaggccac cctgtacgcc gtgctggtgt   1920
ccggcctggt gctgatggcc atggtgaaga agaagaacag ctgaggtacc gagctcgaat   1980
tcgagcatct taccgccatt tattcccata tttgttctgt ttttcttgat ttgggtatac   2040
atttaaatgt taataaaaca aaatggtggg gcaatcattt acattttatg ggatatgtaa   2100
ttactagttc aggtgtattg ccacaagaca aacatgttaa gaaactttcc cgttatttac   2160
gctctgttcc tgttaatcaa cctctggatt acaaaatttg tgaaagattg actgatattc   2220
ttaactatgt tgctcctttt acgctgtgtg gatatgctgc tttaatgcct ctgtatcatg   2280
ctattgcttc ccgtacggct ttcgttttct cctccttgta taaatcctgg ttgctgtctc   2340
tttatgagga gttgtggccc gttgtccgtc aacgtggcgt ggtgtgctct gtgtttgctg   2400
acgcaacccc cactggctgg ggcattgcca ccacctgtca actccttcct gggactttcg   2460
ctttccccct cccgatcgcc acggcagaac tcatcgccgc ctgccttgcc cgctgctgga   2520
caggggctag gttgctgggc actgataatt ccgtggtgtt gtcggggaag ctgacgtcct   2580
ttccatggct gctcgcctgt gttgccaact ggatcctgcg cggacgtcc ttctgctacg    2640 tcccttcggc tctcaatcca gcggacctcc cttcccgagg ccttctgccg gttctgcggc   2700
ctctcccgcg tcttcgcttt cggcctccga cgagtcggat ctccctttgg ccgcctccc    2760 cgcctgtttc gcctcggcgt ccggtccgtg ttgcttggtc gtcacctgtg cagaattgcg   2820
aaccatggat tccaccgtga actttgtctc ctggcatgca aatcgtcaac ttggcatgcc   2880
aagaattaat tcggatccaa gcttaggcct gctcgctttc ttgctgtccc atttctatta   2940
aaggttcctt tgttccctaa gtccaactac taaactgggg gatattatga agggccttga   3000
gcatctggat tctgcctagc gctaagctta acacgagcca tagataagaat aaaagatttt   3060 atttagtctc cagaaaaagg ggggaatgaa agaccccacc tgtaggtttg gcaagctagc   3120
ttaagtaacg ccattttgca aggcatggaa aatacataac tgagaataga aagttcaga    3180 tcaaggttag gaacagagag acagcagaat atgggccaaa caggatatct gtggtaagca   3240
gttcctgccc cggctcaggg ccaagaacag ttggaacagc agaatatggg ccaaacagga   3300
tatctgtggt aagcagttcc tgccccggct cagggccaag aacagatggt ccccagatgc   3360
ggtcccgccc tcagcagttt ctagagaacc atcagatgtt tccagggtgc ccaaggacc    3420 tgaaatgacc ctgtgcctta tttgaactaa ccaatcagtt cgcttctcgc ttctgttcgc   3480
gcgcttctgc tccccgagct caataaaaga gcccacaacc cctcactcgg cgcgccagtc   3540
ctccgataga ctgcgtcgcc cgggtacccg tgttctcaat aaaccctctt gcagttgcat   3600
ccgactcgtg gtctcgctgt tccttgggag ggtctcctct gagtgattga ctgcccacct   3660
cgggggtctt tcattctcga gcagcttggc gtaatcatgg tcatagctgt ttcctgtgtg   3720
aaattgttat ccgctcacaa ttccacacaa catacgagcc ggaagcataa agtgtaaagc   3780
ctggggtgcc taatgagtga gctaactcac attaattgcg ttgcgctcac tgcccgcttt   3840
```

```
ccagtcggga aacctgtcgt gccagctgca ttaatgaatc ggccaacgcg cggggagagg    3900
cggtttgcgt attgggcgct cttccgcttc ctcgctcact gactcgctgc gctcggtcgt    3960
tcggctgcgg cgagcggtat cagctcactc aaaggcggta atacggttat ccacagaatc    4020
aggggataac gcaggaaaga acatgtgagc aaaaggccag caaaaggcca ggaaccgtaa    4080
aaaggccgcg ttgctggcgt ttttccatag gctccgcccc cctgacgagc atcacaaaaa    4140
tcgacgctca agtcagaggt ggcgaaaccc gacaggacta taaagatacc aggcgtttcc    4200
ccctggaagc tccctcgtgc gctctcctgt tccgaccctg ccgcttaccg gatacctgtc    4260
cgcctttctc ccttcgggaa gcgtggcgct ttctcatagc tcacgctgta ggtatctcag    4320
ttcggtgtag gtcgttcgct ccaagctggg ctgtgtgcac gaaccccccg ttcagcccga    4380
ccgctgcgcc ttatccggta actatcgtct tgagtccaac ccggtaagac acgacttatc    4440
gccactggca gcagccactg gtaacaggat tagcagagcg aggtatgtag gcggtgctac    4500
agagttcttg aagtggtggc ctaactacgg ctacactaga agaacagtat ttggtatctg    4560
cgctctgctg aagccagtta ccttcggaaa aagagttggt agctcttgat ccggcaaaca    4620
aaccaccgct ggtagcggtg gttttttgt ttgcaagcag cagattacgc gcagaaaaaa    4680
aggatctcaa gaagatcctt tgatcttttc tacggggtct gacgctcagt ggaacgaaaa    4740
ctcacgttaa gggattttgg tcatgagatt atcaaaaagg atcttcacct agatcctttt    4800
aaattaaaaa tgaagtttta aatcaatcta agtatatat gagtaaactt ggtctgacag    4860
ttaccaatgc ttaatcagtg aggcacctat ctcagcgatc tgtctatttc gttcatccat    4920
agttgcctga ctccccgtcg tgtagataac tacgatacgg gagggcttac catctggccc    4980
cagtgctgca atgataccgc gagacccacg ctcaccggct ccagatttat cagcaataaa    5040
ccagccagcc ggaagggccg agcgcagaag tggtcctgca actttatccg cctccatcca    5100
gtctattaat tgttgccggg aagctagagt aagtagttcg ccagttaata gtttgcccaa    5160
cgttgttgcc attgctacag gcatcgtggt gtcacgctcg tcgtttggta tggcttcatt    5220
cagctccggt tcccaacgat caaggcgagt tacatgatcc cccatgttgt gcaaaaaagc    5280
ggttagctcc ttcggtcctc cgatcgttgt cagaagtaag ttggccgcag tgttatcact    5340
catggttatg gcagcactgc ataattctct tactgtcatg ccatccgtaa gatgcttttc    5400
tgtgactggt gagtactcaa ccaagtcatt ctgagaataa tgtatgcggc gaccgagttg    5460
ctcttgcccg gcgtcaatac gggataatac cgcgccacat agcagaactt taaaagtgct    5520
catcattgga aaacgttctt cggggcgaaa actctcaagg atcttaccgc tgttgagatc    5580
cagttcgatg taacccactc gtgcacccaa ctgatcttca gcatctttta ctttcaccag    5640
cgtttctggg tgagcaaaaa caggaaggca aaatgccgca aaaaagggaa taagggcgac    5700
acggaaatgt tgaatactca tactcttcct ttttcaacat tattgaagca tttatcaggg    5760
ttattgtctc atgagcggat acatatttga atgtatttag aaaaataaac aaataggggt    5820
tccgcgcaca tttccccgaa aagtgccacc tgacgtctaa gaaaccatta ttatcatgac    5880
attaacctat aaaaataggc gtatcacgag gccctttcgt ctcgcgcgtt tcggtgatga    5940
cggtgaaaac ctctgacaca tgcagctccc ggagacggtc acagcttgtc tgtaagcgga    6000
tgccgggagc agacaagccc gtcagggcgc gtcagcgggt gttggcgggt gtcggggctg    6060
gcttaactat gcggcatcag agcagattgt actgagagtg caccatatgc ggtgtgaaat    6120
accgcacaga tgcgtaagga gaaaataccg catcaggcgc cattcgccat tcaggctggg    6180
```

-continued

| | |
|---|---|
| caactgttgg gaagggcgat cggtgcgggc ctcttcgcta ttacgccagc tggcgaaagg | 6240 |
| gggatgtgct gcaaggcgat taagttgggt aacgccaggg ttttcccagt cacgacgttg | 6300 |
| taaaacgacg gccagtgaat tagtactcta gcttaagtaa cgccattttg caaggcatgg | 6360 |
| aaaatacata actgagaata gagaagttca ga | 6392 |

<210> SEQ ID NO 206
<211> LENGTH: 3492
<212> TYPE: DNA
<213> ORGANISM: Artificial Sequence
<220> FEATURE:
<223> OTHER INFORMATION: synthetic

<400> SEQUENCE: 206

| | |
|---|---|
| tgatgcggta ttttctcctt acgcatctgt gcggtatttc acaccgcata tggtgcactc | 60 |
| tcagtacaat ctgctctgat gccgcatagt taagccagcc ccgacacccg ccaacacccg | 120 |
| ctgacgcgcc ctgacgggct tgtctgctcc cggcatccgc ttacagacaa gctgtgaccg | 180 |
| tctccgggag ctgcatgtgt cagaggtttt caccgtcatc accgaaacgc gcgagacgaa | 240 |
| agggcctcgt gatacgccta ttttataggt taatgtcat gataataatg gtttcttaga | 300 |
| cgtcaggtgg cacttttcgg ggaaatgtgc gcggaacccc tatttgttta ttttctaaa | 360 |
| tacattcaaa tatgtatccg ctcatgagac aataaccctg ataaatgctt caataacatt | 420 |
| gaaaaaggaa gagtatgagt attcaacatt tccgtgtcgc ccttattccc ttttttgcgg | 480 |
| cattttgcct tcctgttttt gctcacccag aaacgctggt gaaagtaaaa gatgctgaag | 540 |
| atcagttggg tgcacgagtg ggttacatcg aactggatct caacagcggt aagatccttg | 600 |
| agagttttcg ccccgaagaa cgttttccaa tgatgagcac ttttaaagtt ctgctatgtg | 660 |
| gcgcggtatt atcccgtatt gacgccgggc aagagcaact cggtcgccgc atacactatt | 720 |
| ctcagaatga cttggttgag tactcaccag tcacagaaaa gcatcttacg gatggcatga | 780 |
| cagtaagaga attatgcagt gctgccataa ccatgagtga taacactgcg gccaacttac | 840 |
| ttctgacaac gatcggagga ccgaaggagc taaccgcttt tttgcacaac atgggggatc | 900 |
| atgtaactcg ccttgatcgt tgggaaccgg agctgaatga agccatacca aacgacgagc | 960 |
| gtgacaccac gatgcctgta gcaatgccaa caacgttgca caaactatta actggcgaac | 1020 |
| tacttactct agcttcccgg caacaattaa tagactggat ggaggcggat aaagttgcag | 1080 |
| gaccacttct gcgctcggcc cttccggctg gctggtttat tgctgataaa tctggagccg | 1140 |
| gtgagcgtgg gtctcgcggt atcattgcag cactggggcc agatggtaag ccctcccgta | 1200 |
| tcgtagttat ctacacgacg gggagtcagg caactatgga tgaacgaaat agacagatcg | 1260 |
| ctgagatagg tgcctcactg attaagcatt ggtaactgtc agaccaagtt tactcatata | 1320 |
| tactttagat tgatttaaaa cttcattttt aatttaaaag gatctaggtg aagatccttt | 1380 |
| ttgataatct catgaccaaa atcccttaac gtgagttttc gttccactga gcgtcagacc | 1440 |
| ccgtagaaaa gatcaaagga tcttcttgag atccttttt tctgcgcgta atctgctgct | 1500 |
| tgcaaacaaa aaaaccaccg ctaccagcgg tggtttgttt gccggatcaa gagctaccaa | 1560 |
| ctctttttcc gaaggtaact ggcttcagca gagcgcagat accaaatact gtccttctag | 1620 |
| tgtagccgta gttaggccac cacttcaaga actctgtagc accgcctaca tacctcgctc | 1680 |
| tgctaatcct gttaccagtg gctgctgcca gtggcgataa gtcgtgtctt accgggttgg | 1740 |
| actcaagacg atagttaccg gataaggcgc agcggtcggg ctgaacgggg gttcgtgca | 1800 |
| cacagcccag cttggagcga acgacctaca ccgaactgag atacctacag cgtgagctat | 1860 |

```
gagaaagcgc cacgcttccc gaagggagaa aggcggacag gtatccggta agcggcaggg    1920
tcggaacagg agagcgcacg agggagcttc caggggaaa cgcctggtat ctttatagtc    1980
ctgtcgggtt tcgccacctc tgacttgagc gtcgattttt gtgatgctcg tcagggggc    2040 ggagcctatc gaaaaacgcc agcaacgcgg cctttttacg gttcctggcc ttttgctggc    2100
cttttgctca catgttcttt cctgcgttat ccctgattc tgtggataac cgtattaccg    2160
cctttgagtg agctgatacc gctcgccgca gccgaacgac cgagcgcagc gagtcagtga    2220
gcgaggaagc ggaagagcgc ccaatacgca aaccgcctct ccccgcgcgt tggccgattc    2280
attaatgcag ctggcacgac aggtttcccg actcgaaagc gggcagtgag cgcaacgcaa    2340
ttaatgtgag ttagctcact cattaggcac cccaggcttt acactttatg cttccggctc    2400
gtatgttgtg tggaattgtg agcggataac aatttcacac aggaaacagc tatgaccatg    2460
attacgccaa gctctaatac gactcactat agggagacaa gcttgcatgc ctgcaggtcg    2520
actctagaga tccaccggt cgccaccatg cgccaggtgg cccgcgtgat cgtgttcctg    2580
accctgagca ccctgagcct ggccaagacc acccagccca tcagcatgga cagctacgag    2640
ggccaggagg tgaacatcac ctgcagccac aacaacatcg ccaccaacga ctacatcacc    2700
tggtaccagc agttccccag ccagggcccc cgcttcatca tccagggcta caagaccaag    2760
gtgaccaacg aggtggccag cctgttcatc cccgccgacc gcaagagcag cacccctgagc    2820 ctgccccgcg tgagcctgag cgacaccgcc gtgtactact gcgcagccag cgacaactac    2880
cagctgatct ggggcagcgg caccaagctg atcatcaagc ccgacatcca gaaccccgag    2940
cccgccgtgt accagctgaa ggaccccaga agccaggaca gcaccctgtg cctgttcacc    3000
gacttcgaca ccagatcaa cgtgcccaag accatggaaa gcggcacctt catcaccgac    3060
aagacagtgc tggacatgaa ggccatggac agcaagagca acggcgccat tgcctggtcc    3120
aaccagacca gcttcacatg ccaggacatc ttcaaagaga caaacgccac ctacccagc    3180 agcgacgtgc cctgcgacgc caccctgacc gagaagagct tcgagacaga catgaacctg    3240
aatttccaga acctgagcgt gatgggcctg cggatcctgc tgctgaaggt ggccggcttc    3300
aacctgctga tgaccctgcg gctgtggagc agctgaggta ccgagctcga attcaaaaaa    3360
aaaaaaaaaa aaaaaaaaaa aaaaaaaaaa aaaaaaaaaa aaaaaaaaaa aaaaaaaata    3420
aaaaaaaaaa aaaaaaaaaa aaaaaaaaaa aaaaaaaaaa aaaaaaaaaa aaaaaaaaaa    3480
aaactagtgg cg                                                       3492
```

<210> SEQ ID NO 207
<211> LENGTH: 3615
<212> TYPE: DNA
<213> ORGANISM: Artificial Sequence
<220> FEATURE:
<223> OTHER INFORMATION: synthetic

<400> SEQUENCE: 207

```
tgatgcggta ttttctcctt acgcatctgt gcggtatttc acaccgcata tggtgcactc     60
tcagtacaat ctgctctgat gccgcatagt taagccagcc ccgacacccg ccaacacccg    120
ctgacgcgcc ctgacgggct tgtctgctcc cggcatccgc ttacagacaa gctgtgaccg    180
tctccgggag ctgcatgtgt cagaggtttt caccgtcatc accgaaacgc gcgagacgaa    240
agggcctcgt gatacgccta ttttataggt taatgtcat gataataatg gtttcttaga    300
cgtcaggtgg cacttttcgg ggaaatgtgc gcggaacccc tatttgttta ttttctaaa    360
```

```
tacattcaaa tatgtatccg ctcatgagac aataaccctg ataaatgctt caataacatt    420
gaaaaaggaa gagtatgagt attcaacatt tccgtgtcgc ccttattccc ttttttgcgg    480
cattttgcct tcctgttttt gctcacccag aaacgctggt gaaagtaaaa gatgctgaag    540
atcagttggg tgcacgagtg ggttacatcg aactggatct caacagcggt aagatccttg    600
agagttttcg ccccgaagaa cgttttccaa tgatgagcac ttttaaagtt ctgctatgtg    660
gcgcggtatt atcccgtatt gacgccgggc aagagcaact cggtcgccgc atacactatt    720
ctcagaatga cttggttgag tactcaccag tcacagaaaa gcatcttacg gatggcatga    780
cagtaagaga attatgcagt gctgccataa ccatgagtga taacactgcg gccaacttac    840
ttctgacaac gatcggagga ccgaaggagc taaccgcttt tttgcacaac atgggggatc    900
atgtaactcg ccttgatcgt tgggaaccgg agctgaatga agccatacca acgacgagc     960 gtgacaccac gatgcctgta gcaatgccaa caacgttgca caaactatta actggcgaac   1020
tacttactct agcttcccgg caacaattaa tagactggat ggaggcggat aaagttgcag   1080
gaccacttct gcgctcggcc cttccggctg gctggtttat tgctgataaa tctggagccg   1140
gtgagcgtgg gtctcgcggt atcattgcag cactggggcc agatggtaag ccctcccgta   1200
tcgtagttat ctacacgacg gggagtcagg caactatgga tgaacgaaat agacagatcg   1260
ctgagatagg tgcctcactg attaagcatt ggtaactgtc agaccaagtt tactcatata   1320
tactttagat tgatttaaaa cttcattttt aatttaaaag gatctaggtg aagatccttt   1380
ttgataatct catgaccaaa atcccttaac gtgagttttc gttccactga gcgtcagacc   1440
ccgtagaaaa gatcaaagga tcttcttgag atcctttttt tctgcgcgta atctgctgct   1500
tgcaaacaaa aaaaccaccg ctaccagcgg tggtttgttt gccggatcaa gagctaccaa   1560 ctcttttcc gaaggtaact ggcttcagca gagcgcagat accaaatact gtccttctag    1620
tgtagccgta gttaggccac cacttcaaga actctgtagc accgcctaca tacctcgctc   1680
tgctaatcct gttaccagtg gctgctgcca gtggcgataa gtcgtgtctt accgggttgg   1740
actcaagacg atagttaccg gataaggcgc agcggtcggg ctgaacgggg ggttcgtgca   1800
cacagcccag cttggagcga acgacctaca ccgaactgag atacctacag cgtgagctat   1860
gagaaagcgc cacgcttccc gaagggagaa aggcggacag gtatccggta agcggcaggg   1920
tcggaacagg agagcgcacg agggagcttc caggggggaaa cgcctggtat ctttatagtc   1980
ctgtcgggtt tcgccacctc tgacttgagc gtcgattttt gtgatgctcg tcaggggggc   2040
ggagcctatc gaaaaacgcc agcaacgcgg ccttttttacg gttcctggcc ttttgctggc   2100
cttttgctca catgttcttt cctgcgttat cccctgattc tgtggataac cgtattaccg   2160
cctttgagtg agctgatacc gctcgccgca gccgaacgac cgagcgcagc gagtcagtga   2220
gcgaggaagc ggaagagcgc ccaatacgca aaccgcctct ccccgcgcgt tggccgattc   2280
attaatgcag ctggcacgac aggtttcccg actcgaaagc gggcagtgag cgcaacgcaa   2340
ttaatgtgag ttagctcact cattaggcac cccaggcttt acactttatg cttccggctc   2400
gtatgttgtg tggaattgtg agcggataac aatttcacac aggaaacagc tatgaccatg   2460
attacgccaa gctctaatac gactcactat agggagacaa gcttgcatgc ctgcaggtcg   2520
actctagagg atccaccggt cgccaccatg gatgcagac tgctgtgctg cgccgtgctg   2580
tgtctgctgg gcgccgtgcc catcgacacc gaagtgaccc agacccccaa gcacctggtc   2640
atgggcatga ccaacaagaa aagcctgaag tgcgagcagc acatgggcca ccgggccatg   2700
tactggtaca agcagaaggc caagaaaccc cccgagctga tgttcgtgta cagctacgag   2760
```

```
aagctgagca tcaacgagag cgtgcccagc cggttcagcc ccgagtgccc caatagcagc   2820
ctgctgaacc tgcatctgca cgccctgcag cccgaggaca gcgccctgta tctgtgcgca   2880
agcagccgcg ccaactacga gcagtacttc ggccccggca cccgcctgac cgtgctggaa   2940
gatctgagga acgtgacccc ccccaaggtg accctgttcg agcccagcaa ggccgagatc   3000
gccaacaagc agaaagccac cctggtctgc ctggccaggg gcttcttccc cgaccacgtg   3060
gagctgtctt ggtgggtgaa cggcaaagag gtgcacagcg agtcagtac cgaccccag    3120 gcctacaaag agagcaacta cagctactgc ctgagcagca ggctgagagt gagcgccacc   3180
ttctggcaca ccccccggaa ccacttccgg tgccaggtgc agttccacgg cctgagcgaa   3240
gaggacaagt ggcctgaggg cagccccaag cccgtgaccc agaacatcag cgccgaggcc   3300
tggggcagag ccgactgcgg catcaccagc gccagctacc accagggcgt gctgtccgcc   3360
accatcctgt acgagatcct gctgggcaag gccaccctgt acgccgtgct ggtgtccggc   3420
ctggtgctga tggccatggt gaagaagaag aacagctgag gtaccgagct cgaattcaaa   3480
aaaaaaaaaa aaaaaaaaaa aaaaaaaaaa aaaaaaaaaa aaaaaaaaaa aaaaaaaaaa   3540
ataaaaaaaa aaaaaaaaaa aaaaaaaaaa aaaaaaaaaa aaaaaaaaaa aaaaaaaaaa   3600
aaaaaactag tggcg                                                   3615

<210> SEQ ID NO 208
<211> LENGTH: 6302
<212> TYPE: DNA
<213> ORGANISM: Artificial Sequence
<220> FEATURE:
<223> OTHER INFORMATION: synthetic

<400> SEQUENCE: 208
tcaaggttag gaacagagag acagcagaat atgggccaaa caggatatct gtggtaagca     60
gttcctgccc cggctcaggg ccaagaacag ttgaacagc agaatatggg ccaaacagga    120
tatctgtggt aagcagttcc tgccccggct cagggccaag aacagatggt ccccagatgc   180
ggtcccgccc tcagcagttt ctagagaacc atcagatgtt tccagggtgc ccaaggacc    240 tgaaatgacc ctgtgcctta tttgaactaa ccaatcagtt cgcttctcgc ttctgttcgc    300
gcgcttctgc tccccgagct caataaaaga gcccacaacc cctcactcgg cgcgccagtc    360
ctccgataga ctgcgtcgcc cgggtacccg tattcccaat aaagcctctt gctgtttgca    420
tccgaatcgt ggactcgctg atccttggga gggtctcctc agattgattg actgcccacc    480
tcgggggtct ttcatttgga ggttccaccg agatttggag acccctgccc agggaccacc    540
gacccccccg ccgggaggta agctggccag cggtcgtttc gtgtctgtct ctgtctttgt    600
gcgtgtttgt gccggcatct aatgtttgcg cctgcgtctg tactagttgg ctaactagat    660
ctgtatctgg cggtcccgcg gaagaactga cgagttcgta ttcccggccg cagcccctgg    720
gagacgtccc agcggcctcg ggggcccgtt ttgtggccca ttctgtatca gttaacctac    780
ccgagtcgga cttttggag ctccgccact gtccgagggg tacgtggctt tgttggggga    840
cgagagacag agacacttcc cgcccccgtc tgaattttg ctttcggttt tacgccgaaa    900
ccgcgccgcg cgtcttgtct gctgcagcat cgttctgtgt tgtctctgtc tgactgtgtt    960
tctgtatttg tctgaaaatt agctcgacaa agttaagtaa tagtccctct ctccaagctc   1020
acttacaggc ggccgcaccg gtcgccacca tgagcctgtc tagcctgctg aaggtcgtga   1080
ccgccagcct gtggctggga cctggaatcg cccagaagat cacccagacc cagcccggca   1140
```

```
tgttcgtgca ggaaaaagaa gccgtgaccc tggactgcac ctacgacacc agcgacccta    1200
gctacggcct gttctggtac aagcagccca gcagcggcga gatgatcttc ctgatctacc    1260
agggcagcta cgaccagcag aacgccaccg agggccggta cagcctgaac ttccagaagg    1320
cccggaagtc cgccaacctc gtgatcagcg ctagccagct gggcgacagc gccatgtact    1380
tttgcgcaat cagcaacacc ggcaaccagt tctacttcgg caccggcacc agcctgaccg    1440
tgatccccaa catccagaat ccggaccccg ccgtgtacca gctgagagac agcaagagca    1500
gcgacaacac tgtgtgcctg ttcaccgact tcgactccca gaccaacgtg tcccagagca    1560
aggacagcga cgtgtacatc accgacaaga ccgtgctgga catgcgggagc atggacttca    1620 agagcaacag cgccgtggcc tggtccaaca agagcgattt cgcctgcgcc aacgccttca    1680
acaacagcat tatccccgag gacacattct tcccaagccc cgagagcagc tgcgacgtga    1740
agctggtgga aaagagcttc gagacagaca ccaacctgaa tttccagaac ctgagcgtga    1800
tcggcttcag aatcctgctg ctgaaggtgg ccggcttcaa cctgctgatg acccctgcggc    1860 tgtggtccag ctgaacgcgt atcgatgaat tcgagcatct taccgccatt tattcccata    1920
tttgttctgt ttttcttgat ttgggtatac atttaaatgt taataaaaca aaatggtggg    1980
gcaatcattt acatttttatg ggatatgtaa ttactagttc aggtgtattg ccacaagaca    2040
aacatgttaa gaaactttcc cgttatttac gctctgttcc tgttaatcaa cctctggatt    2100
acaaaatttg tgaaagattg actgatattc ttaactatgt tgctcctttt acgctgtgtg    2160
gatatgctgc tttaatgcct ctgtatcatg ctattgcttc ccgtacggct ttcgttttct    2220
cctccttgta taaatcctgg ttgctgtctc tttatgagga gttgtggccc gttgtccgtc    2280
aacgtggcgt ggtgtgctct gtgtttgctg acgcaacccc cactggctgg ggcattgcca    2340
ccacctgtca actcctttct gggactttcg ctttccccct cccgatcgcc acggcagaac    2400
tcatcgccgc ctgccttgcc cgctgctgga caggggctag gttgctgggc actgataatt    2460
ccgtggtgtt gtcggggaag ctgacgtcct ttccatggct gctcgcctgt gttgccaact    2520
ggatcctgcg cgggacgtcc ttctgctacg tcccttcggc tctcaatcca gcggacctcc    2580
cttcccgagg ccttctgccg gttctgcggc ctctcccgcg tcttcgcttt cggcctccga    2640
cgagtcggat ctcccctttgg gccgcctccc cgcctgtttc gcctcggcgt ccggtccgtg    2700
ttgcttggtc gtcaccctgt cagaattgcg aaccatggat tccaccgtga actttgtctc    2760
ctggcatgca aatcgtcaac ttggcatgcc aagaattaat tcggatccaa gcttaggcct    2820
gctcgctttc ttgctgtccc atttctatta aaggttcctt tgttccctaa gtccaactac    2880
taaactgggg gatattatga agggccttga gcatctggat tctgcctagc gctaagctta    2940
acacgagcca tagatagaat aaaagatttt atttagtctc cagaaaaagg ggggaatgaa    3000 agacccccacc tgtaggtttg gcaagctagc ttaagtaacg ccattttgca aggcatggaa    3060
aatacataac tgagaataga aagttcaga tcaaggttag gaacagagag acagcagaat    3120
atgggccaaa caggatatct gtggtaagca gttcctgccc cggctcaggg ccaagaacag    3180
ttggaacagc agaatatggg ccaaacagga tatctgtggt aagcagttcc tgccccggct    3240
cagggccaag aacagatggt ccccagatgc ggtcccgccc tcagcagttt ctagagaacc    3300
atcagatgtt tccagggtgc cccaaggacc tgaaatgacc ctgtgcctta tttgaactaa    3360
ccaatcagtt cgcttctcgc ttctgttcgc gcgcttctgc tccccgagct caataaaaga    3420
gcccacaacc cctcactcgg cgcgccagtc ctccgataga ctgcgtcgcc cgggtacccg    3480
tgttctcaat aaaccctctt gcagttgcat ccgactcgtg gtctcgctgt tccttgggag    3540
```

```
ggtctcctct gagtgattga ctgcccacct cggggtctt tcattctcga gcagcttggc   3600
gtaatcatgg tcatagctgt ttcctgtgtg aaattgttat ccgctcacaa ttccacacaa   3660
catacgagcc ggaagcataa agtgtaaagc ctggggtgcc taatgagtga gctaactcac   3720
attaattgcg ttgcgctcac tgcccgcttt ccagtcggga aacctgtcgt gccagctgca   3780
ttaatgaatc ggccaacgcg cggggagagg cggtttgcgt attgggcgct cttccgcttc   3840
ctcgctcact gactcgctgc gctcggtcgt tcggctgcgg cgagcggtat cagctcactc   3900
aaaggcggta atacggttat ccacagaatc aggggataac gcaggaaaga acatgtgagc   3960
aaaaggccag caaaaggcca ggaaccgtaa aaaggccgcg ttgctggcgt ttttccatag   4020
gctccgcccc cctgacgagc atcacaaaaa tcgacgctca agtcagaggt ggcgaaaccc   4080
gacaggacta taaagatacc aggcgtttcc ccctggaagc tccctcgtgc gctctcctgt   4140
tccgaccctg ccgcttaccg gatacctgtc cgcctttctc ccttcgggaa gcgtggcgct   4200
ttctcatagc tcacgctgta ggtatctcag ttcggtgtag tcgttcgct ccaagctggg   4260 ctgtgtgcac gaacccccg ttcagcccga ccgctgcgcc ttatccggta actatcgtct   4320
tgagtccaac ccggtaagac acgacttatc gccactggca gcagccactg gtaacaggat   4380
tagcagagcg aggtatgtag gcggtgctac agagttcttg aagtggtggc ctaactacgg   4440
ctacactaga agaacagtat ttggtatctg cgctctgctg aagccagtta ccttcggaaa   4500
aagagttggt agctcttgat ccggcaaaca aaccaccgct ggtagcggtg gtttttttgt   4560
ttgcaagcag cagattacgc gcagaaaaaa aggatctcaa gaagatcctt tgatcttttc   4620 tacgggtct gacgctcagt ggaacgaaaa ctcacgttaa gggattttgg tcatgagatt   4680
atcaaaaagg atcttcacct agatcctttt aaattaaaaa tgaagtttta atcaatcta   4740 aagtatatat gagtaaactt ggtctgacag ttaccaatgc ttaatcagtg aggcacctat   4800
ctcagcgatc tgtctatttc gttcatccat agttgcctga ctccccgtcg tgtagataac   4860
tacgatacgg gagggcttac catctggccc cagtgctgca atgataccgc gagacccacg   4920
ctcaccggct ccagatttat cagcaataaa ccagccagcc ggaagggccg agcgcagaag   4980
tggtcctgca actttatccg cctccatcca gtctattaat tgttgccggg aagctagagt   5040
aagtagttcg ccagttaata gtttgcccaa cgttgttgcc attgctacag gcatcgtggt   5100
gtcacgctcg tcgtttggta tggcttcatt cagctccggt tcccaacgat caaggcgagt   5160
tacatgatcc cccatgttgt gcaaaaaagc ggttagctcc ttcggtcctc cgatcgttgt   5220
cagaagtaag ttggccgcag tgttatcact catggttatg gcagcactgc ataattctct   5280
tactgtcatg ccatccgtaa gatgcttttc tgtgactggt gagtactcaa ccaagtcatt   5340
ctgagaatag tgtatgcggc gaccgagttg ctcttgcccg gcgtcaatac gggataatac   5400
cgcgccacat agcagaactt taaaagtgct catcattgga aaacgttctt cggggcgaaa   5460
actctcaagg atcttaccgc tgttgagatc cagttcgatg taacccactc gtgcacccaa   5520
ctgatcttca gcatctttta ctttcaccag cgtttctggg tgagcaaaaa caggaaggca   5580
aaatgccgca aaaagggaa taagggcgac acggaaatgt tgaatactca tactcttcct   5640
ttttcaacat tattgaagca tttatcaggg ttattgtctc atgagcggat acatatttga   5700
atgtatttag aaaaataaac aaataggggt tccgcgcaca tttccccgaa aagtgccacc   5760
tgacgtctaa gaaaccatta ttatcatgac attaacctat aaaaataggc gtatcacgag   5820
gccctttcgt ctcgcgcgtt tcggtgatga cggtgaaaac ctctgacaca tgcagctccc   5880
```

| | |
|---|---:|
| ggagacggtc acagcttgtc tgtaagcgga tgccgggagc agacaagccc gtcagggcgc | 5940 |
| gtcagcgggt gttggcgggt gtcgggcctg gcttaactat gcggcatcag agcagattgt | 6000 |
| actgagagtg caccatatgc ggtgtgaaat accgcacaga tgcgtaagga gaaaataccg | 6060 |
| catcaggcgc cattcgccat tcaggctggg caactgttgg gaagggcgat cggtgcgggc | 6120 |
| ctcttcgcta ttacgccagc tggcgaaagg gggatgtgct gcaaggcgat taagttgggt | 6180 |
| aacgccaggg ttttcccagt cacgacgttg taaaacgacg gccagtgaat tagtactcta | 6240 |
| gcttaagtaa cgccattttg caaggcatgg aaaatacata actgagaata gagaagttca | 6300 |
| ga | 6302 |

<210> SEQ ID NO 209
<211> LENGTH: 6413
<212> TYPE: DNA
<213> ORGANISM: Artificial Sequence
<220> FEATURE:
<223> OTHER INFORMATION: synthetic

<400> SEQUENCE: 209

| | |
|---|---:|
| cacttacagg cggccgcacc ggtcgccacc atgggccctc agctgctggg atacgtggtg | 60 |
| ctgtgtctgc tgggagccgg acctctggaa gcccaagtga cccagaaccc cagatacctg | 120 |
| atcaccgtga ccggcaagaa actgaccgtg acctgcagcc agaacatgaa ccacgagtac | 180 |
| atgagctggt acagacagga ccccggcctg gcctgcgcc agatctacta cagcatgaac | 240 |
| gtggaagtga ccgacaaggg cgacgtgccc gagggctaca aggtgtcccg gaaagagaag | 300 |
| cggaacttcc cactgatcct ggaaagcccc agccccaacc agaccagcct gtacttctgc | 360 |
| gcaagcaaca acctggccag ctacaacgag cagttcttcg gccctggcac ccggctgacc | 420 |
| gtgctggaag atctgaagaa cgtgttcccc cagaggtga ccgtgttcga gcctagcgag | 480 |
| gccgagatca gccacaccca gaaagccacc ctcgtgtgcc tggccaccgg cttctatccc | 540 |
| gaccacgtga aactgtcttg gtgggtcaac ggcaaagagg tgcacagcgg cgtgtccacc | 600 |
| gatccccagc tctgaaaga cagccccgcc ctgaacgaca gccggtactg cctgagcagc | 660 |
| agactgagag tgtccgccac cttctggcag aaccccgga accacttcag atgccaggtg | 720 |
| cagttctacg gcctgagcga gaacgacgag tggacccagg acagagccaa gcccgtgacc | 780 |
| cagatcgtgt ctgccgaagc ctggggcaga gccgattgcg gctttaccag cgagagctac | 840 |
| cagcagggcg tgctgagcgc caccatcctg tacgagatcc tgctgggcaa ggccacccctg | 900 |
| tacgccgtgc tggtgtctgc cctggtgctg atggctatgg tcaagcggaa ggacagccgg | 960 |
| ggctgaacgc gtatcgatga attcgagcat cttaccgcca tttattccca tatttgttct | 1020 |
| gtttttcttg atttgggtat acatttaaat gttaataaaa caaatggtg gggcaatcat | 1080 |
| ttacatttta tgggatatgt aattactagt tcaggtgtat tgccacaaga caaacatgtt | 1140 |
| aagaaacttt cccgttattt acgctctgtt cctgttaatc aacctctgga ttacaaaatt | 1200 |
| tgtgaaagat tgactgatat tcttaactat gttgctcctt tacgctgtg tggatatgct | 1260 |
| gctttaatgc ctctgtatca tgctattgct tcccgtacgg cttttcgttt ctcctccttg | 1320 |
| tataaatcct ggttgctgtc tctttatgag gagttgtggc ccgttgtccg tcaacgtggc | 1380 |
| gtggtgtgct ctgtgtttgc tgacgcaacc cccactggct ggggcattgc caccacctgt | 1440 |
| caactccttt ctgggacttt cgctttcccc ctcccgatcg ccacggcaga actcatcgcc | 1500 |
| gcctgccttg cccgctgctg dacagggggct aggttgctgg cactgataa ttccgtggtg | 1560 |
| ttgtcgggga agctgacgtc ctttccatgg ctgctcgcct gtgttgccaa ctggatcctg | 1620 |

```
cgcgggacgt ccttctgcta cgtcccttcg gctctcaatc cagcggacct cccttcccga   1680
ggccttctgc cggttctgcg gcctctcccg cgtcttcgct ttcggcctcc gacgagtcgg   1740
atctcccttt gggccgcctc cccgcctgtt tcgcctcggc gtccggtccg tgttgcttgg   1800
tcgtcacctg tgcagaattg cgaaccatgg attccaccgt gaactttgtc tcctggcatg   1860
caaatcgtca acttggcatg ccaagaatta attcggatcc aagcttaggc ctgctcgctt   1920
tcttgctgtc ccatttctat taaaggttcc tttgttccct aagtccaact actaaactgg   1980
gggatattat gaagggcctt gagcatctgg attctgccta gcgctaagct taacacgagc   2040
catagataga ataaaagatt ttatttagtc tccagaaaaa gggggaatg aaagacccca    2100 cctgtaggtt tggcaagcta gcttaagtaa cgccattttg caaggcatgg aaaatacata   2160
actgagaata gagaagttca gatcaaggtt aggaacagag agacagcaga atatgggcca   2220
aacaggatat ctgtggtaag cagttcctgc cccggctcag ggccaagaac agttggaaca   2280
gcagaatatg ggccaaacag gatatctgtg gtaagcagtt cctgcccgg ctcagggcca    2340 agaacagatg gtccccagat gcggtcccgc cctcagcagt ttctagagaa ccatcagatg   2400
tttccagggt gccccaagga cctgaaatga ccctgtgcct tatttgaact aaccaatcag   2460
ttcgcttctc gcttctgttc gcgcgcttct gctccccgag ctcaataaaa gagcccacaa   2520
cccctcactc ggcgcgccag tcctccgata gactgcgtcg cccgggtacc cgtgttctca   2580
ataaaccctc ttgcagttgc atccgactcg tggtctcgct gttccttggg agggtctcct   2640
ctgagtgatt gactgcccac ctcggggtc tttcattctc gagcagcttg gcgtaatcat     2700
ggtcatagct gtttcctgtg tgaaattgtt atccgctcac aattccacac aacatacgag   2760
ccggaagcat aaagtgtaaa gcctggggtg cctaatgagt gagctaactc acattaattg   2820
cgttgcgctc actgcccgct ttccagtcgg gaaacctgtc gtgccagctg cattaatgaa   2880
tcggccaacg cgcggggaga ggcggtttgc gtattgggcg ctcttccgct tcctcgctca   2940
ctgactcgct gcgctcggtc gttcggctgc ggcgagcggt atcagctcac tcaaaggcgg   3000
taatacggtt atccacagaa tcaggggata acgcaggaaa gaacatgtga gcaaaaggcc   3060
agcaaaaggc caggaaccgt aaaaaggccg cgttgctggc gttttccat aggctccgcc    3120 cccctgacga gcatcacaaa aatcgacgct caagtcagag gtggcgaaac ccgacaggac   3180
tataaagata ccaggcgttt ccccctggaa gctccctcgt gcgctctcct gttccgaccc   3240
tgccgcttac cggatacctg tccgcctttc tcccttcggg aagcgtggcg ctttctcata   3300
gctcacgctg taggtatctc agttcggtgt aggtcgttcg ctccaagctg ggctgtgtgc   3360
acgaaccccc cgttcagccc gaccgctgcg ccttatccgg taactatcgt cttgagtcca   3420
acccggtaag acacgactta tcgccactgg cagcagccac tggtaacagg attagcagag   3480
cgaggtatgt aggcggtgct acagagttct tgaagtggtg cctaactac ggctacacta    3540 gaagaacagt atttggtatc tgcgctctgc tgaagccagt taccttcgga aaaagagttg   3600
gtagctcttg atccggcaaa caaaccaccg ctggtagcgg tggtttttt gtttgcaagc    3660 agcagattac gcgcagaaaa aaggatctc aagaagatcc tttgatcttt tctacggggt    3720
ctgacgctca gtggaacgaa aactcacgtt aagggatttt ggtcatgaga ttatcaaaaa   3780
ggatcttcac ctagatcctt ttaaattaaa aatgaagttt taaatcaatc taaagtatat   3840
atgagtaaac ttggtctgac agttaccaat gcttaatcag tgaggcacct atctcagcga   3900
tctgtctatt tcgttcatcc atagttgcct gactccccgt cgtgtagata actacgatac   3960
```

```
gggagggctt accatctggc cccagtgctg caatgatacc gcgagaccca cgctcaccgg    4020
ctccagattt atcagcaata aaccagccag ccggaagggc cgagcgcaga agtggtcctg    4080
caactttatc cgcctccatc cagtctatta attgttgccg ggaagctaga gtaagtagtt    4140
cgccagttaa tagtttgccc aacgttgttg ccattgctac aggcatcgtg gtgtcacgct    4200
cgtcgtttgg tatggcttca ttcagctccg gttcccaacg atcaaggcga gttacatgat    4260
cccccatgtt gtgcaaaaaa gcggttagct ccttcggtcc tccgatcgtt gtcagaagta    4320
agttggccgc agtgttatca ctcatggtta tggcagcact gcataattct cttactgtca    4380
tgccatccgt aagatgcttt tctgtgactg gtgagtactc aaccaagtca ttctgagaat    4440
agtgtatgcg gcgaccgagt tgctcttgcc cggcgtcaat acgggataat accgcgccac    4500
atagcagaac tttaaaagtg ctcatcattg gaaaacgttc ttcggggcga aaactctcaa    4560
ggatcttacc gctgttgaga tccagttcga tgtaacccac tcgtgcaccc aactgatctt    4620
cagcatcttt tactttcacc agcgtttctg ggtgagcaaa aacaggaagg caaaatgccg    4680
caaaaaaggg aataagggcg acacggaaat gttgaatact catactcttc cttttcaac    4740
attattgaag catttatcag ggttattgtc tcatgagcgg atacatattt gaatgtattt    4800
agaaaaataa acaaatagg gttccgcgca catttccccg aaaagtgcca cctgacgtct    4860
aagaaaccat tattatcatg acattaacct ataaaaatag gcgtatcacg aggccctttc    4920
gtctcgcgcg tttcggtgat gacggtgaaa acctctgaca catgcagctc ccggagacgg    4980
tcacagcttg tctgtaagcg gatgccggga gcagacaagc ccgtcagggc gcgtcagcgg    5040
gtgttggcgg gtgtcggggc tggcttaact atgcggcatc agagcagatt gtactgagag    5100
tgcaccatat gcggtgtgaa ataccgcaca gatgcgtaag gagaaaatac cgcatcaggc    5160
gccattcgcc attcaggctg gcaactgtt gggaagggcg atcggtgcgg gcctcttcgc    5220
tattacgcca gctggcgaaa ggggatgtg ctgcaaggcg attaagttgg gtaacgccag    5280
ggttttccca gtcacgacgt tgtaaaacga cggccagtga attagtactc tagcttaagt    5340
aacgccattt tgcaaggcat ggaaaataca taactgagaa tagagaagtt cagatcaagg    5400
ttaggaacag agagacagca gaatatgggc caaacaggat atctgtggta agcagttcct    5460
gccccggctc agggccaaga acagttggaa cagcagaata tgggccaaac aggatatctg    5520
tggtaagcag ttcctgcccc ggctcagggc caagaacaga tggtcccag atgcggtccc    5580
gccctcagca gtttctagag aaccatcaga tgtttccagg gtgccccaag gacctgaaat    5640
gaccctgtgc cttatttgaa ctaaccaatc agttcgcttc tcgcttctgt tcgcgcgctt    5700
ctgctccccg agctcaataa aagagcccac aaccccctcac tcggcgcgcc agtcctccga    5760
tagactgcgt cgcccgggta cccgtattcc aataaagcc tcttgctgtt tgcatccgaa    5820
tcgtggactc gctgatcctt gggagggtct cctcagattg attgactgcc cacctcgggg    5880
gtctttcatt tggaggttcc accgagattt ggagacccct gcccaggac caccgacccc    5940
cccgccggga ggtaagctgg ccagcggtcg tttcgtgtct gtctctgtct ttgtgcgtgt    6000
ttgtgccggc atctaatgtt tgcgcctgcg tctgtactag ttggctaact agatctgtat    6060
ctggcggtcc cgcggaagaa ctgacgagtt cgtattcccg gccgcagccc ctgggagacg    6120
tcccagcggc ctcgggggcc cgttttgtgg cccattctgt atcagttaac ctacccgagt    6180
cggactttt ggagctccgc cactgtccga ggggtacgtg ctttgttgg gggacgagag    6240
acagagacac ttcccgcccc cgtctgaatt tttgctttcg gttttacgcc gaaaccgcgc    6300
cgcgcgtctt gtctgctgca gcatcgttct gtgttgtctc tgtctgactg tgtttctgta    6360
```

```
tttgtctgaa aattagctcg acaaagttaa gtaatagtcc ctctctccaa gct        6413
```

<210> SEQ ID NO 210
<211> LENGTH: 561
<212> TYPE: DNA
<213> ORGANISM: Homo sapiens

<400> SEQUENCE: 210

```
atgtcacttt ctagcctgct gaaggtggtc acagcttcac tgtggctagg acctggcatt    60
gcccagaaga taactcaaac ccaaccagga atgttcgtgc aggaaaagga ggctgtgact   120
ctggactgca catatgacac cagtgatcca agttatggtc tattctggta caagcagccc   180
agcagtgggg aaatgatttt tcttatttat caggggtctt atgaccagca aaatgcaaca   240
gaaggtcgct actcattgaa tttccagaag gcaagaaaat ccgccaacct tgtcatctcc   300
gcttcacaac tgggggactc agcaatgtac ttctgtgcaa tttcgaacac cggtaaccag   360
ttctattttg gacagggac aagtttgacg gtcattccaa atatccagaa ccctgaccct   420
gccgtgtacc agctgagaga ctctaaatcc agtgacaagt ctgtctgcct attcaccgat   480
tttgattctc aaacaaatgt gtcacaaagt aaggattctg atgtgtatat cacagacaaa   540
actgtgctag acatagtcag g                                             561
```

<210> SEQ ID NO 211
<211> LENGTH: 598
<212> TYPE: DNA
<213> ORGANISM: Homo sapiens

<400> SEQUENCE: 211

```
atgggccccc agctccttgg ctatgtggtc ctttgccttc taggagcagg ccccctggaa    60
gcccaagtga cccagaaccc aagatacctc atcacagtga ctggaaagaa gttaacagtg   120
acttgttctc agaatatgaa ccatgagtat atgtcctggt atcgacaaga cccagggctg   180
ggcttaaggc agatctacta ttcaatgaat gttgaggtga ctgataaggg agatgttcct   240
gaagggtaca agtctctcg aaaagagaag aggaatttcc ccctgatcct ggagtcgccc   300
agccccaacc agacctctct gtacttctgt gccagcaata acttagcctc ctacaatgag   360
cagttcttcg gccagggac acggctcacc gtgctagagg acctgaaaaa cgtgttccca   420
cccgaggtcg ctgtgtttga gccatcagaa gcagagatct cccacaccca aaaggccaca   480
ctggtgtgcc tggccacagg cttctacccc gaccacgtgg agctgagctg gtgggtgaat   540
gggaaggagg tgcacagtgg ggtcagcaca gacccgcagc ccctcaagag cagcgctt     598
```

<210> SEQ ID NO 212
<211> LENGTH: 11
<212> TYPE: PRT
<213> ORGANISM: Rattus norvegicus

<400> SEQUENCE: 212

Gln Ser Val Ser Ile Ser Arg His Asn Leu Ile
1               5                   10

<210> SEQ ID NO 213

<400> SEQUENCE: 213

000

<210> SEQ ID NO 214

```
<211> LENGTH: 7
<212> TYPE: PRT
<213> ORGANISM: Rattus norvegicus

<400> SEQUENCE: 214

Gln Gln Ser Gly Glu Ser Pro
1               5

<210> SEQ ID NO 215
<211> LENGTH: 8
<212> TYPE: PRT
<213> ORGANISM: Rattus norvegicus

<400> SEQUENCE: 215

Gly Tyr Thr Phe Thr Glu Asn Tyr
1               5

<210> SEQ ID NO 216
<211> LENGTH: 8
<212> TYPE: PRT
<213> ORGANISM: Rattus norvegicus

<400> SEQUENCE: 216

Ile Asp Pro Glu Asp Gly Thr Thr
1               5

<210> SEQ ID NO 217
<211> LENGTH: 8
<212> TYPE: PRT
<213> ORGANISM: Rattus norvegicus

<400> SEQUENCE: 217

Ala Arg Gly Val Gly Ser Gly Asp
1               5

<210> SEQ ID NO 218
<211> LENGTH: 99
<212> TYPE: PRT
<213> ORGANISM: Rattus norvegicus

<400> SEQUENCE: 218

Leu Ser Leu Gly Gln Arg Ala Thr Ile Ser Cys Arg Ala Ser Gln Ser
1               5                   10                  15

Val Ser Ile Ser Arg His Asn Leu Ile His Trp Tyr Gln Gln Lys Pro
            20                  25                  30

Gly Gln Gln Pro Lys Leu Leu Ile Tyr Arg Ala Ser Asn Leu Ala Ser
        35                  40                  45

Gly Ile Pro Ala Arg Phe Ser Gly Ser Gly Ser Gly Thr Asp Phe Thr
    50                  55                  60

Leu Thr Ile Asn Pro Val Gln Ala Asp Asp Val Ala Thr Tyr Tyr Cys
65                  70                  75                  80

Gln Gln Ser Gly Glu Ser Pro Arg Thr Phe Gly Gly Gly Thr Lys Leu
                85                  90                  95

Glu Leu Lys

<210> SEQ ID NO 219
<211> LENGTH: 108
<212> TYPE: PRT
<213> ORGANISM: Rattus norvegicus

<400> SEQUENCE: 219

Gly Arg Gly Arg Ala Gln Ser Val Val Val Gln Ala Ser Gly Tyr Thr
```

```
            1               5                  10                 15
Phe Thr Glu Asn Tyr Ile Tyr Trp Val Lys Gln Arg Pro Lys Gln Gly
                20                  25                 30

Leu Glu Leu Ile Gly Arg Ile Asp Pro Glu Asp Gly Thr Thr Asp Tyr
            35                  40                 45

Val Glu Lys Phe Lys Asn Lys Ala Thr Leu Thr Val Asp Thr Ser Ser
        50                  55                 60

Lys Thr Ala Tyr Met Gln Leu Ser Ser Leu Thr Ser Glu Asp Thr Ala
65                  70                  75                 80

Ser Tyr Phe Cys Ala Arg Gly Val Gly Ser Gly Asp Tyr Val Met Asp
                85                  90                 95

Ala Trp Gly Gln Gly Ala Ser Val Thr Val Ser Ser
                100                 105

<210> SEQ ID NO 220
<211> LENGTH: 114
<212> TYPE: PRT
<213> ORGANISM: Rattus norvegicus

<400> SEQUENCE: 220

Leu Ser Leu Gly Gln Arg Ala Thr Ile Ser Cys Arg Ala Ser Gln Ser
1               5                  10                 15

Val Ser Ile Ser Arg His Asn Leu Ile His Trp Tyr Gln Gln Lys Pro
                20                  25                 30

Gly Gln Gln Pro Lys Leu Leu Ile Tyr Arg Ala Ser Asn Leu Ala Ser
            35                  40                 45

Gly Ile Pro Ala Arg Phe Ser Gly Ser Gly Ser Gly Thr Asp Phe Thr
        50                  55                 60

Leu Thr Ile Asn Pro Val Gln Ala Asp Asp Val Ala Thr Tyr Tyr Cys
65                  70                  75                 80

Gln Gln Ser Gly Glu Ser Pro Arg Thr Phe Gly Gly Gly Thr Lys Leu
                85                  90                 95

Glu Leu Lys Arg Ala Asp Ala Ala Pro Thr Val Pro His Leu Pro Gln
                100                 105                110

Leu Cys

<210> SEQ ID NO 221
<211> LENGTH: 360
<212> TYPE: PRT
<213> ORGANISM: Rattus norvegicus

<400> SEQUENCE: 221

Gly Arg Gly Arg Ala Gln Ser Val Val Gln Ala Ser Gly Tyr Thr
1               5                  10                 15

Phe Thr Glu Asn Tyr Ile Tyr Trp Val Lys Gln Arg Pro Lys Gln Gly
                20                  25                 30

Leu Glu Leu Ile Gly Arg Ile Asp Pro Glu Asp Gly Thr Thr Asp Tyr
            35                  40                 45

Val Glu Lys Phe Lys Asn Lys Ala Thr Leu Thr Val Asp Thr Ser Ser
        50                  55                 60

Lys Thr Ala Tyr Met Gln Leu Ser Ser Leu Thr Ser Glu Asp Thr Ala
65                  70                  75                 80

Ser Tyr Phe Cys Ala Arg Gly Val Gly Ser Gly Asp Tyr Val Met Asp
                85                  90                 95

Ala Trp Gly Gln Gly Ala Ser Val Thr Val Ser Ser Ala Glu Thr Thr
                100                 105                110
```

Ala Pro Ser Val Tyr Pro Leu Ala Pro Gly Thr Ala Leu Lys Ser Asn
            115                 120                 125

Ser Met Val Thr Leu Gly Cys Leu Val Lys Gly Tyr Phe Pro Glu Pro
    130                 135                 140

Val Thr Val Thr Trp Asn Ser Gly Ala Leu Ser Ser Gly Val His Thr
145                 150                 155                 160

Phe Pro Ala Val Leu Gln Ser Gly Leu Tyr Thr Leu Thr Ser Ser Val
                165                 170                 175

Thr Val Pro Ser Ser Thr Trp Ser Ser Gln Ala Val Thr Cys Asn Val
            180                 185                 190

Thr His Pro Ala Ser Ser Thr Lys Val Asp Lys Ile Val Pro Arg
        195                 200                 205

Glu Cys Asn Pro Cys Gly Cys Thr Gly Ser Glu Val Ser Ser Val Phe
    210                 215                 220

Ile Phe Pro Pro Lys Thr Lys Asp Val Leu Thr Ile Thr Leu Thr Pro
225                 230                 235                 240

Lys Val Thr Cys Val Val Asp Ile Ser Gln Asn Asp Pro Glu Val
                245                 250                 255

Arg Phe Ser Trp Phe Ile Asp Asp Val Lys Val His Thr Ala Gln Thr
            260                 265                 270

His Ala Pro Glu Lys Gln Ser Asn Ser Thr Leu Arg Ser Val Ser Glu
        275                 280                 285

Leu Pro Ile Val His Arg Asp Trp Leu Asn Gly Lys Thr Phe Lys Cys
    290                 295                 300

Lys Val Asn Ser Gly Ala Phe Pro Ala Pro Ile Glu Lys Ala Ser Pro
305                 310                 315                 320

Asn Pro Ser Thr Pro Arg Gly Pro Gln Tyr Thr Pro Cys Ala Ser Gln
                325                 330                 335

Arg Asp Asp Pro Glu Ser Val Ser Ile Thr Ala Cys Lys Ala Ser Ile
            340                 345                 350

Pro Arg His Leu Tyr Gly Val Arg
        355                 360

<210> SEQ ID NO 222
<211> LENGTH: 423
<212> TYPE: DNA
<213> ORGANISM: Rattus norvegicus

<400> SEQUENCE: 222
gagatgctgt ctctagggca gagggccaca atctcctgta gggccagcca aagtgtcagt    60
atatctagac ataatcttat acactggtac caacagaaac caggacagca acccaaactc   120
ctcatctacc gtgcatccaa tctagcatct gggatccctg ccaggttcag tggcagtggg   180
tctgggacag acttcaccct caccatcaat cctgtgcagg ctgatgatgt tgcaacctat   240
tactgtcagc agagtgggga gtctcctcgg acgttcggtg gaggcaccaa gctggaattg   300
aaaagggctg atgctgcacc aactgtaccc atcttcccc aactctgctg acagtaatag   360
gttgcaacat ctcgcctgca caggattgat tgtgagggtg aagtctgttc catacctact   420
gtg                                                                 423

<210> SEQ ID NO 223
<211> LENGTH: 1107
<212> TYPE: DNA
<213> ORGANISM: Rattus norvegicus

<400> SEQUENCE: 223

```
gcggtcgagg tcgggctcag tcagttgtcg tgcaggcttc tggctatacc tttacagaaa      60
attatatata ctgggtgaag cagaggccta acagggcct ggaattaata ggaaggattg     120
atcctgaaga cggtactact gattatgttg agaagttcaa aaacaaggcc acactgacag     180
tagatacatc gtccaagaca gcctacatgc aactcagcag cctgacatct gaggacacag     240
catcctatttt ttgtgccaga ggtgtggggt ccggggacta tgttatggat gcctggggtc     300
aaggagcttc agtcactgtc tcctcagctg aaacaacagc cccatctgtc tatccactgg     360
ctcctggaac tgctctcaaa agtaactcca tggtgaccct gggatgcctg gtcaagggct     420
atttccctga gccagtcacc gtgacctgga actctggagc cctgtccagc ggtgtgcaca     480
ccttcccagc tgtcctgcag tctggactct acactctcac cagctcagtg actgtaccct     540
ccagcacctg gtccagccag gccgtcacct gcaacgtaac ccacccggcc agcagcacca     600
aggtggacaa gaaaattgtg ccaagggaat gcaatccttg tggatgtaca ggctcagaag     660
tatcatctgt cttcatcttc cccccaaaga ccaaagatgt gctcaccatc actctgactc     720
caaaggtcac gtgtgttgtg gtagacatta gccagaatga tcccgaggtc cggttcagct     780
ggtttataga tgacgtgaaa gtccacacag ctcagactca tgccccggag aagcagtcca     840
acagcacttt acgctcagtc agtgaactcc ccatcgtgca ccgggactgg ctcaatggca     900
agacgttcaa atgcaaagtc aacagtggag cattccctgc ccccatcgag aaagcatctc     960
caaacccgag cacaccacga ggtccacagt atacaccatg cgcctccag agagatgacc    1020
cagagtcagt cagtatcact gcatgtaaag cttctatccc cagacattta tacggagtga    1080
gatgacgggc agccacagaa actacag                                       1107
```

<210> SEQ ID NO 224
<211> LENGTH: 218
<212> TYPE: PRT
<213> ORGANISM: Artificial Sequence
<220> FEATURE:
<223> OTHER INFORMATION: humanized light chain

<400> SEQUENCE: 224

```
Glu Ile Val Leu Thr Gln Ser Pro Ala Thr Leu Ser Leu Ser Pro Gly
 1               5                  10                  15

Gln Arg Ala Thr Ile Ser Cys Arg Ala Ser Gln Ser Val Ser Ile Ser
                20                  25                  30

Arg His Asn Leu Ile His Trp Tyr Gln Gln Lys Pro Gly Gln Ala Pro
            35                  40                  45

Arg Leu Leu Ile Tyr Arg Ala Ser Asn Arg Ala Thr Gly Ile Pro Ala
        50                  55                  60

Arg Phe Ser Gly Ser Gly Ser Gly Thr Asp Phe Thr Leu Thr Ile Asn
 65                  70                  75                  80

Pro Val Gln Ala Glu Asp Phe Ala Val Tyr Tyr Cys Gln Gln Ser Gly
                85                  90                  95

Glu Ser Pro Arg Thr Phe Gly Gly Gly Thr Lys Leu Glu Leu Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160
```

```
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 225
<211> LENGTH: 444
<212> TYPE: PRT
<213> ORGANISM: Artificial Sequence
<220> FEATURE:
<223> OTHER INFORMATION: humanized heavy chain

<400> SEQUENCE: 225

Glu Val Gln Leu Val Gln Ser Gly Ala Glu Val Lys Lys Pro Gly Arg
1               5                   10                  15

Thr Val Lys Ile Val Cys Gln Ala Ser Gly Tyr Thr Phe Thr Glu Asn
            20                  25                  30

Tyr Ile Tyr Trp Val Gln Gln Ala Pro Gly Lys Gly Leu Glu Trp Met
        35                  40                  45

Gly Arg Ile Asp Pro Glu Asp Gly Thr Thr Asp Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Phe Cys
                85                  90                  95

Ala Arg Gly Val Gly Ser Gly Asp Tyr Val Met Asp Ala Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300
```

```
Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
            325                 330                 335

Lys Thr Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 226
<211> LENGTH: 10
<212> TYPE: PRT
<213> ORGANISM: Rattus norvegicus

<400> SEQUENCE: 226

Gln Ser Val Ser Ile Ser Gly Ile Asn Leu
1               5                   10

<210> SEQ ID NO 227

<400> SEQUENCE: 227

000

<210> SEQ ID NO 228
<211> LENGTH: 10
<212> TYPE: PRT
<213> ORGANISM: Rattus norvegicus

<400> SEQUENCE: 228

Cys Gln Gln Ser Trp Glu Ser Pro Arg Thr
1               5                   10

<210> SEQ ID NO 229
<211> LENGTH: 8
<212> TYPE: PRT
<213> ORGANISM: Rattus norvegicus

<400> SEQUENCE: 229

Gly Tyr Thr Phe Thr Ala Tyr Tyr
1               5

<210> SEQ ID NO 230
<211> LENGTH: 8
<212> TYPE: PRT
<213> ORGANISM: Rattus norvegicus

<400> SEQUENCE: 230

Ile Asp Pro Glu Asp Gly Ser Thr
1               5
```

<210> SEQ ID NO 231
<211> LENGTH: 7
<212> TYPE: PRT
<213> ORGANISM: Rattus norvegicus

<400> SEQUENCE: 231

Cys Ala Arg Gly Asn Ser Asp
1               5

<210> SEQ ID NO 232
<211> LENGTH: 100
<212> TYPE: PRT
<213> ORGANISM: Rattus norvegicus

<400> SEQUENCE: 232

Leu Cys Leu Arg Gln Arg Ala Thr Ile Ser Cys Arg Ala Ser Gln Ser
1               5                   10                  15

Val Ser Ile Ser Gly Ile Asn Leu Met His Trp Tyr Gln Gln Arg Pro
            20                  25                  30

Gly Gln Gln Pro Lys Leu Leu Ile Tyr Arg Ala Ser Ser Leu Ala Ser
        35                  40                  45

Gly Ile Pro Ala Arg Phe Ser Gly Arg Gly Ser Gly Thr Asp Phe Thr
    50                  55                  60

Leu Thr Ile Asp Pro Val Gln Ala Asp Asp Ile Ala Ala Tyr Phe Cys
65                  70                  75                  80

Gln Gln Ser Trp Glu Ser Pro Arg Thr Phe Gly Gly Gly Thr Gln Leu
                85                  90                  95

Glu Leu Lys Arg
            100

<210> SEQ ID NO 233
<211> LENGTH: 109
<212> TYPE: PRT
<213> ORGANISM: Rattus norvegicus

<400> SEQUENCE: 233

Asp Trp Asn Ser Arg Thr Gly Leu Ser Gln Val Ser Cys Lys Ala Ser
1               5                   10                  15

Gly Tyr Thr Phe Thr Ala Tyr Tyr Ile Ser Trp Val Lys Gln Arg Pro
            20                  25                  30

Lys Gln Gly Leu Glu Leu Ile Gly Arg Ile Asp Pro Glu Asp Gly Ser
        35                  40                  45

Thr Asp Tyr Val Glu Lys Phe Lys Ile Lys Ala Thr Leu Thr Ala Asp
    50                  55                  60

Thr Ser Ser Asn Thr Ala Tyr Met Gln Phe Ser Ser Leu Thr Phe Glu
65                  70                  75                  80

Asp Thr Ala Thr Tyr Phe Cys Ala Arg Gly Asn Ser Asp Tyr Val Met
                85                  90                  95

Asp Ala Trp Gly Gln Gly Ala Ser Val Thr Val Ser Ser
            100                 105

<210> SEQ ID NO 234
<211> LENGTH: 107
<212> TYPE: PRT
<213> ORGANISM: Rattus norvegicus

<400> SEQUENCE: 234

Leu Cys Leu Arg Gln Arg Ala Thr Ile Ser Cys Arg Ala Ser Gln Ser
1               5                   10                  15

Val Ser Ile Ser Gly Ile Asn Leu Met His Trp Tyr Gln Gln Arg Pro
            20                  25                  30

Gly Gln Gln Pro Lys Leu Leu Ile Tyr Arg Ala Ser Ser Leu Ala Ser
        35                  40                  45

Gly Ile Pro Ala Arg Phe Ser Gly Arg Gly Ser Gly Thr Asp Phe Thr
    50                  55                  60

Leu Thr Ile Asp Pro Val Gln Ala Asp Asp Ile Ala Ala Tyr Phe Cys
65                  70                  75                  80

Gln Gln Ser Trp Glu Ser Pro Arg Thr Phe Gly Gly Gly Thr Gln Leu
                85                  90                  95

Glu Leu Lys Arg Ala Asp Ala Ala Pro Thr Val
            100                 105

<210> SEQ ID NO 235
<211> LENGTH: 407
<212> TYPE: PRT
<213> ORGANISM: Rattus norvegicus

<400> SEQUENCE: 235

Asp Trp Asn Ser Arg Thr Gly Leu Ser Gln Val Ser Cys Lys Ala Ser
1               5                   10                  15

Gly Tyr Thr Phe Thr Ala Tyr Tyr Ile Ser Trp Val Lys Gln Arg Pro
            20                  25                  30

Lys Gln Gly Leu Glu Leu Ile Gly Arg Ile Asp Pro Glu Asp Gly Ser
        35                  40                  45

Thr Asp Tyr Val Glu Lys Phe Lys Ile Lys Ala Thr Leu Thr Ala Asp
    50                  55                  60

Thr Ser Ser Asn Thr Ala Tyr Met Gln Phe Ser Ser Leu Thr Phe Glu
65                  70                  75                  80

Asp Thr Ala Thr Tyr Phe Cys Ala Arg Gly Asn Ser Asp Tyr Val Met
                85                  90                  95

Asp Ala Trp Gly Gln Gly Ala Ser Val Thr Val Ser Ser Ala Glu Thr
            100                 105                 110

Thr Ala Pro Ser Val Tyr Pro Leu Ala Pro Gly Thr Ala Leu Lys Ser
        115                 120                 125

Asn Ser Met Val Thr Leu Gly Cys Leu Val Lys Gly Tyr Phe Pro Glu
    130                 135                 140

Pro Val Thr Val Thr Trp Asn Ser Gly Ala Leu Ser Ser Gly Val His
145                 150                 155                 160

Thr Phe Pro Ala Val Leu Gln Ser Gly Leu Tyr Thr Leu Thr Ser Ser
                165                 170                 175

Val Thr Val Pro Ser Ser Thr Trp Ser Ser Gln Ala Val Thr Cys Asn
            180                 185                 190

Val Ala His Pro Ala Ser Ser Thr Lys Val Asp Lys Lys Ile Val Pro
        195                 200                 205

Arg Glu Cys Asn Pro Cys Gly Cys Thr Gly Ser Glu Val Ser Ser Val
    210                 215                 220

Phe Ile Phe Pro Pro Lys Thr Lys Asp Val Leu Thr Ile Thr Leu Thr
225                 230                 235                 240

Pro Lys Val Thr Cys Val Val Asp Ile Ser Gln Asn Asp Pro Glu
                245                 250                 255

Val Arg Phe Ser Trp Phe Ile Asp Asp Val Glu Val His Thr Ala Gln
            260                 265                 270

Thr His Ala Pro Glu Lys Gln Ser Asn Ser Thr Leu Arg Ser Val Ser

```
              275                 280                 285
Glu Leu Pro Ile Val His Arg Asp Trp Leu Asn Gly Lys Thr Phe Lys
    290                 295                 300

Cys Lys Val Asn Ser Gly Ala Phe Pro Ala Pro Ile Glu Lys Ser Ile
305                 310                 315                 320

Ser Lys Pro Glu Gly Thr Pro Arg Gly Pro Gln Val Tyr Thr Met Ala
                325                 330                 335

Pro Pro Lys Glu Glu Met Thr Gln Ser Gln Val Ser Ile Thr Cys Met
            340                 345                 350

Val Lys Gly Phe Tyr Pro Pro Asp Ile Tyr Thr Glu Trp Lys Met Asn
        355                 360                 365

Gly Gln Pro Gln Glu Asn Tyr Lys Asn Thr Pro Pro Thr Met Asp Thr
    370                 375                 380

Asp Gly Ser Tyr Phe Leu Tyr Ser Lys Leu Asn Val Lys Glu Thr
385                 390                 395                 400

Cys Ser Arg Lys His Leu Arg
            405
```

<210> SEQ ID NO 236
<211> LENGTH: 746
<212> TYPE: DNA
<213> ORGANISM: Rattus norvegicus

<400> SEQUENCE: 236

```
gcatgctgtg tctcaggcag agggccacca tctcctgtag ggccagccag agtgtcagta    60
tatctggcat taatttgatg cactggtacc aacagagacc aggacagcaa cccaaactcc   120
tcatctatcg tgcatccagc ctagcatctg ggatccctgc caggttcagt ggccgtgggt   180
ctgggacaga cttcaccctc accatcgatc tgtgcaggc tgatgatatt gcagcctatt    240
tctgtcagca gagttgggag tctcctcgga cgttcggtgg aggcacccag ctggaattga   300
aacgggctga tgctgcacca actgtaccca tcttccacaa ttgtcggatc tttggggacg   360
gggggatttt gggatcctct agcccaccaa gcgtcttccg tgcacgctcc cggggggatat  420
gacttatatc tcccgcccct agacctggat gtgagatagc tgattcgaat ctgacaccaa   480
ggtgtatagc gggaattttg tgccgatgga gatgctttac ttttttggcg tcgtcgcgat   540
ggaaacggac agagctaaca gcctctattt tagttcacca catagtagtg aaaccatacc   600
ggcgcaacag tatcgcatga tactcagatg ataacgctct ggaccctcta attactctac   660
gattactgct attctatcat caggaggggt gaaggtccgg tatatcgaag tcggttttcc   720
atctctcgcc tctctgcgat tgtcat                                         746
```

<210> SEQ ID NO 237
<211> LENGTH: 1221
<212> TYPE: DNA
<213> ORGANISM: Rattus norvegicus

<400> SEQUENCE: 237

```
gactggaatt cgaggacggg gctcagtcaa gtgtcgtgca aggcttctgg ctataccttt    60
acagcatact atatatcctg ggtgaagcag aggcctaaac agggcctgga attaatagga   120
aggattgatc ctgaagacgg tagtactgat tatgttgaga agttcaaaat caaggccaca   180
ctgactgcag atacatcgtc caacacagcc tacatgcaat tcagcagcct gacatctgag   240
gacacagcaa cctatttctg tgctagaggg aattcggact acgttatgga tgcctggggt   300
caaggagctt cagtcactgt ctcctcagct gaaacaacag ccccatctgt ctatccactg   360
```

```
gctcctggaa ctgctctcaa aagtaactcc atggtgaccc tgggatgcct ggtcaagggc      420
tatttccctg agccagtcac cgtgacctgg aactctggag ccctgtccag cggtgtgcac      480
accttcccag ctgtcctgca gtctggactc tacactctca ccagctcagt gactgtaccc      540
tccagcacct ggtccagcca ggccgtcacc tgcaacgtag cccacccggc cagcagcacc      600
aaggtggaca agaaaattgt gccaagggaa tgcaatcctt gtggatgtac aggctcagaa      660
gtatcatctg tcttcatctt cccccccaaag accaaagatg tgctcaccat cactctgact      720
cctaaggtca cgtgtgttgt ggtagacatt agccagaatg atcccgaggt ccggttcagc      780
tggtttatag atgacgtgga agtccacaca gctcagactc atgccccgga gaagcagtcc      840
aacagcactt tacgctcagt cagtgaactc cccatcgtgc accgggactg gctcaatggc      900
aagacgttca atgcaaagt caacagtgga gcattccctg cccccatcga gaaaagcatc      960
tccaaacccg aaggcacacc acgaggtcca caggtataca ccatggcgcc tcccaaggaa     1020
gagatgaccc agagtcaagt cagtatcacc tgcatggtaa aaggcttcta tcccccagac     1080
atttatacgg agtggaagat gaacgggcag ccacaggaaa actacaagaa cactccacct     1140
acgatggaca cagatgggag ttacttcctc tacagcaagc tcaatgtaaa gaaagaaaca     1200
tgcagcagga aacacttaag g                                              1221
```

<210> SEQ ID NO 238
<211> LENGTH: 5
<212> TYPE: PRT
<213> ORGANISM: Artificial Sequence
<220> FEATURE:
<223> OTHER INFORMATION: synthetic

<400> SEQUENCE: 238

Gly Gly Gly Gly Ser
1               5

<210> SEQ ID NO 239
<211> LENGTH: 75
<212> TYPE: DNA
<213> ORGANISM: Artificial Sequence
<220> FEATURE:
<223> OTHER INFORMATION: synthetic

<400> SEQUENCE: 239

```
gcaatcagca acaccggcaa ccagttctac ttcggcaccg gcaccagcct gaccgtgatc       60
cccaacatcc agaat                                                       75
```

<210> SEQ ID NO 240
<211> LENGTH: 79
<212> TYPE: DNA
<213> ORGANISM: Artificial Sequence
<220> FEATURE:
<223> OTHER INFORMATION: synthetic

<400> SEQUENCE: 240

```
ccggattctg gatgttgggg atcacggtca ggctggtgcc ggtgccgaag tagaactggt       60
tgccggtgtt gctgattgc                                                   79
```

<210> SEQ ID NO 241
<211> LENGTH: 96
<212> TYPE: DNA
<213> ORGANISM: Artificial Sequence
<220> FEATURE:
<223> OTHER INFORMATION: synthetic

<400> SEQUENCE: 241
gcaagcaaca acctggccag ctacaacgag cagttcttcg gccctggcac ccggctgacc    60
gtgctggaag atctgaagaa cgtgttcccc ccagag                              96

<210> SEQ ID NO 242
<211> LENGTH: 101
<212> TYPE: DNA
<213> ORGANISM: Artificial Sequence
<220> FEATURE:
<223> OTHER INFORMATION: synthetic

<400> SEQUENCE: 242
gtcacctctg gggggaacac gttcttcaga tcttccagca cggtcagccg ggtgccaggg    60
ccgaagaact gctcgttgta gctggccagg ttgttgcttg c                       101

<210> SEQ ID NO 243
<211> LENGTH: 30
<212> TYPE: DNA
<213> ORGANISM: Homo sapiens

<400> SEQUENCE: 243
gcaatttcga acaccggtaa ccagttctat                                     30

<210> SEQ ID NO 244
<211> LENGTH: 36
<212> TYPE: DNA
<213> ORGANISM: Homo sapiens

<400> SEQUENCE: 244
gccagcaata acttagcctc ctacaatgag cagttc                              36

<210> SEQ ID NO 245
<211> LENGTH: 10
<212> TYPE: PRT
<213> ORGANISM: Homo sapiens

<400> SEQUENCE: 245

Ala Ile Ser Asn Thr Gly Asn Gln Phe Tyr
1               5                   10

<210> SEQ ID NO 246
<211> LENGTH: 12
<212> TYPE: PRT
<213> ORGANISM: Homo sapiens

<400> SEQUENCE: 246

Ala Ser Asn Asn Leu Ala Ser Tyr Asn Glu Gln Phe
1               5                   10

<210> SEQ ID NO 247
<211> LENGTH: 825
<212> TYPE: DNA
<213> ORGANISM: Artificial Sequence
<220> FEATURE:
<223> OTHER INFORMATION: synthetic

<400> SEQUENCE: 247
atgagcctgt ctagcctgct gaaggtcgtg accgccagcc tgtggctggg acctggaatc    60
gcccagaaga tcacccagac ccagcccggc atgttcgtgc aggaaaaaga agccgtgacc   120
ctggactgca cctacgacac cagcgaccct agctacggcc tgttctggta caagcagccc   180
agcagcggcg agatgatctt cctgatctac cagggcagct acgaccagca gaacgccacc    240
gagggccggt acagcctgaa cttccagaag gcccggaagt ccgccaacct cgtgatcagc    300
gctagccagc tgggcgacag cgccatgtac ttttgcgcaa tcagcaacac cggcaaccag    360
ttctacttcg gcaccggcac cagcctgacc gtgatcccca acatccagaa tccggacccc    420
gccgtgtacc agctgagaga cagcaagagc agcgacaaca ctgtgtgcct gttcaccgac    480
ttcgactccc agaccaacgt gtcccagagc aaggacagcg acgtgtacat caccgacaag    540
accgtgctgg acatgcggag catggacttc aagagcaaca gcgccgtggc ctggtccaac    600
aagagcgatt tcgcctgcgc caacgccttc aacaacagca ttatccccga ggacacattc    660
ttcccaagcc ccgagagcag ctgcgacgtg aagctggtgg aaaagagctt cgagacagac    720
accaacctga atttccagaa cctgagcgtg atcggcttca gaatcctgct gctgaaggtg    780
gccggcttca acctgctgat gaccctgcgg ctgtggtcca gctga    825

<210> SEQ ID NO 248
<211> LENGTH: 936
<212> TYPE: DNA
<213> ORGANISM: Artificial Sequence
<220> FEATURE:
<223> OTHER INFORMATION: synthetic

<400> SEQUENCE: 248
atgggccctc agctgctggg atacgtggtg ctgtgtctgc tgggagccgg acctctggaa     60
gcccaagtga cccagaaccc cagataccty atcaccgtga ccggcaagaa actgaccgtg    120
acctgcagcc agaacatgaa ccacgagtac atgagctggt acagacagga ccccggcctg    180
ggcctgcggc agatctacta cagcatgaac gtggaagtga ccgacaaggg cgacgtgccc    240
gagggctaca aggtgtcccg gaaagagaag cggaacttcc cactgatcct ggaaagcccc    300
agccccaacc agaccagcct gtacttctgc gcaagcaaca acctggccag ctacaacgag    360
cagttcttcg gccctggcac ccggctgacc gtgctggaag atctgaagaa cgtgttcccc    420
ccagaggtga ccgtgttcga gcctagcgag gccgagatca gccacaccca gaaagccacc    480
ctcgtgtgcc tggccaccgg cttctatccc gaccacgtgg aactgtcttg gtgggtcaac    540
ggcaaagagg tgcacagcgg cgtgtccacc gatccccagc ctctgaaaga cagcccgcc    600 ctgaacgaca ccggctactg cctgagcagc agactgagag tgtccgccac cttctggcag    660
aacccccgga ccacttcag atgccaggtg cagttctacg gcctgagcga aaacgacgag    720
tggacccagg acagagccaa gcccgtgacc cagatcgtgt ctgccgaagc tggggcaga    780 gccgattgcg gctttaccag cgagagctac cagcagggcg tgctgagcgc caccatcctg    840
tacgagatcc tgctgggcaa ggccacctg tacgccgtgc tggtgtctgc cctggtgctg    900
atggctatgg tcaagcggaa ggacagccgg ggctga    936

<210> SEQ ID NO 249
<211> LENGTH: 274
<212> TYPE: PRT
<213> ORGANISM: Homo sapiens

<400> SEQUENCE: 249

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser

```
            35                  40                  45
Asp Pro Ser Tyr Gly Leu Phe Trp Tyr Lys Gln Pro Ser Ser Gly Glu
 50                  55                  60

Met Ile Phe Leu Ile Tyr Gln Gly Ser Tyr Asp Gln Gln Asn Ala Thr
 65                  70                  75                  80

Glu Gly Arg Tyr Ser Leu Asn Phe Gln Lys Ala Arg Lys Ser Ala Asn
                 85                  90                  95

Leu Val Ile Ser Ala Ser Gln Leu Gly Asp Ser Ala Met Tyr Phe Cys
            100                 105                 110

Ala Ile Ser Asn Thr Gly Asn Gln Phe Tyr Phe Gly Thr Gly Thr Ser
            115                 120                 125

Leu Thr Val Ile Pro Asn Ile Gln Asn Pro Asp Pro Ala Val Tyr Gln
130                 135                 140

Leu Arg Asp Ser Lys Ser Ser Asp Asn Thr Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
            195                 200                 205

Ala Phe Asn Asn Ser Ile Ile Pro Glu Asp Thr Phe Phe Pro Ser Pro
210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 250
<211> LENGTH: 311
<212> TYPE: PRT
<213> ORGANISM: Homo sapiens

<400> SEQUENCE: 250

Met Gly Pro Gln Leu Gly Tyr Val Val Leu Cys Leu Leu Gly Ala
 1               5                  10                  15

Gly Pro Leu Glu Ala Gln Val Thr Gln Asn Pro Arg Tyr Leu Ile Thr
                 20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Leu Gly Leu Arg Gln
 50                  55                  60

Ile Tyr Tyr Ser Met Asn Val Glu Val Thr Asp Lys Gly Asp Val Pro
 65                  70                  75                  80

Glu Gly Tyr Lys Val Ser Arg Lys Glu Lys Arg Asn Phe Pro Leu Ile
                 85                  90                  95

Leu Glu Ser Pro Ser Pro Asn Gln Thr Ser Leu Tyr Phe Cys Ala Ser
            100                 105                 110

Asn Asn Leu Ala Ser Tyr Asn Glu Gln Phe Phe Gly Pro Gly Thr Arg
            115                 120                 125

Leu Thr Val Leu Glu Asp Leu Lys Asn Val Phe Pro Pro Glu Val Thr
```

```
                    130                 135                 140
Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 251
<211> LENGTH: 3551
<212> TYPE: DNA
<213> ORGANISM: Artificial Sequence
<220> FEATURE:
<223> OTHER INFORMATION: synthetic

<400> SEQUENCE: 251
acaagcttgc atgcctgcag gtcgactcta gaggatccac cggtcgccac catgagcctg      60
tctagcctgc tgaaggtcgt gaccgccagc ctgtggctgg acctggaat cgcccagaag      120 atcacccaga cccagcccgg catgttcgtg caggaaaaag aagccgtgac cctggactgc      180
acctacgaca ccagcgaccc tagctacggc ctgttctggt acaagcagcc cagcagcggc      240
gagatgatct tcctgatcta ccagggcagc tacgaccagc agaacgccac cgagggccgg      300
tacagcctga acttccagaa ggcccggaag tccgccaacc tcgtgatcag cgctagccag      360
ctgggcgaca gcgccatgta cttttgcgca atcagcaaca ccggcaacca gttctacttc      420
ggcaccggca ccagcctgac cgtgatcccc aacatccaga atccggaccc cgccgtgtac      480
cagctgagag acagcaagag cagcgacaac actgtgtgcc tgttcaccga cttcgactcc      540
cagaccaacg tgtcccagag caaggacagc gacgtgtaca tcaccgacaa gaccgtgctg      600
gacatgcgga gcatggactt caagagcaac agcgccgtgg cctggtccaa caagagcgat      660
ttcgcctgcg ccaacgcctt caacaacagc attatccccg aggacacatt cttcccaagc      720
cccgagagca gctgcgacgt gaagctggtg gaaagagagct tcgagacaga caccaacctg      780
aatttccaga acctgagcgt gatcggcttc agaatcctgc tgctgaaggt ggccggcttc      840
aacctgctga tgaccctgcg gctgtggtcc agctgaacgc gtatcgatga attccacgct      900
agccacgata tcaattcaaa aaaaaaaaaa aaaaaaaaaa aaaaaaaaaa aaaaaaaaaa      960
aaaaaaaaaa aaaaaaaaaa ataaaaaaaa aaaaaaaaaa aaaaaaaaaa aaaaaaaaaa     1020
```

```
aaaaaaaaaa aaaaaaaaa aaaaaactag tggcgtgatg cggtattttc tccttacgca    1080
tctgtgcggt atttcacacc gcatatggtg cactctcagt acaatctgct ctgatgccgc    1140
atagttaagc cagccccgac acccgccaac acccgctgac gcgccctgac gggcttgtct    1200
gctcccggca tccgcttaca gacaagctgt gaccgtctcc gggagctgca tgtgtcagag    1260
gttttcaccg tcatcaccga aacgcgcgag acgaaagggc ctcgtgatac gcctattttt    1320
ataggttaat gtcatgataa taatggtttc ttagacgtca ggtggcactt ttcggggaaa    1380
tgtgcgcgga acccctattt gtttattttt ctaaatacat tcaaatatgt atccgctcat    1440
gagacaataa ccctgataaa tgcttcaata cattgaaaa aggaagagta tgagtattca    1500
acatttccgt gtcgccctta ttcccttttt tgcggcattt tgccttcctg tttttgctca    1560
cccagaaacg ctggtgaaag taaaagatgc tgaagatcag ttgggtgcac gagtgggtta    1620
catcgaactg gatctcaaca gcggtaagat ccttgagagt tttcgccccg aagaacgttt    1680
tccaatgatg agcactttta aagttctgct atgtggcgcg gtattatccc gtattgacgc    1740
cgggcaagag caactcggtc gccgcataca ctattctcag aatgacttgg ttgagtactc    1800
accagtcaca gaaaagcatc ttacggatgg catgacagta agagaattat gcagtgctgc    1860
cataaccatg agtgataaca ctgcggccaa cttacttctg acaacgatcg gaggaccgaa    1920
ggagctaacc gcttttttgc acaacatggg ggatcatgta actcgccttg atcgttggga    1980
accggagctg aatgaagcca taccaaacga cgagcgtgac accacgatgc ctgtagcaat    2040
gccaacaacg ttgcacaaac tattaactgg cgaactactt actctagctt cccggcaaca    2100
attaatagac tggatggagg cggataaagt tgcaggacca cttctgcgct cggcccttcc    2160
ggctggctgg tttattgctg ataaatctgg agccggtgag cgtgggtctc gcggtatcat    2220
tgcagcactg gggccagatg gtaagccctc ccgtatcgta gttatctaca cgacggggag    2280
tcaggcaact atggatgaac gaaatagaca gatcgctgag ataggtgcct cactgattaa    2340
gcattggtaa ctgtcagacc aagtttactc atatatactt tagattgatt taaaacttca    2400
tttttaattt aaaaggatct aggtgaagat cctttttgat aatctcatga ccaaaatccc    2460
ttaacgtgag ttttcgttcc actgagcgtc agaccccgta gaaaagatca aaggatcttc    2520
ttgagatcct ttttttctgc gcgtaatctg ctgcttgcaa acaaaaaaac caccgctacc    2580
agcggtggtt tgtttgccgg atcaagagct accaactctt tttccgaagg taactggctt    2640
cagcagagcg cagataccaa atactgtcct tctagtgtag ccgtagttag gccaccactt    2700
caagaactct gtagcaccgc ctacatacct cgctctgcta atcctgttac cagtggctgc    2760
tgccagtggc gataagtcgt gtcttaccgg gttggactca agacgatagt taccggataa    2820
ggcgcagcgg tcgggctgaa cggggggttc gtgcacacag cccagcttgg agcgaacgac    2880
ctacaccgaa ctgagatacc tacagcgtga gctatgagaa agcgccacgc ttcccgaagg    2940
gagaaaggcg gacaggtatc cggtaagcgg cagggtcgga acaggagagc gcacgaggga    3000
gcttccaggg ggaaacgcct ggtatcttta tagtcctgtc gggtttcgcc acctctgact    3060
tgagcgtcga ttttgtgat gctcgtcagg gggcggagc ctatcgaaaa cgccagcaa    3120 cgcggccttt ttacggttcc tggccttttg ctggcctttt gctcacatgt tctttcctgc    3180
gttatcccct gattctgtgg ataaccgtat taccgccttt gagtgagctg ataccgctcg    3240
ccgcagccga acgaccgagc gcagcgagtc agtgagcgag gaagcggaag agcgcccaat    3300
acgcaaaccg cctctccccg cgcgttggcc gattcattaa tgcagctggc acgacaggtt    3360
tcccgactcg aaagcgggca gtgagcgcaa cgcaattaat gtgagttagc tcactcatta    3420
```

```
ggcacccccag gctttacact ttatgcttcc ggctcgtatg ttgtgtggaa ttgtgagcgg    3480
ataacaattt cacacaggaa acagctatga ccatgattac gccaagctct aatacgactc    3540 actatagggag                                                          3551
```

<210> SEQ ID NO 252
<211> LENGTH: 3662
<212> TYPE: DNA
<213> ORGANISM: Artificial Sequence
<220> FEATURE:
<223> OTHER INFORMATION: synthetic

<400> SEQUENCE: 252

```
acaagcttgc atgcctgcag gtcgactcta gaggatccac cggtcgccac catgggccct      60
cagctgctgg atacgtggt gctgtgtctg ctgggagccg acctctgga agcccaagtg      120 acccagaacc ccagatacct gatcaccgtg accggcaaga actgaccgt gacctgcagc      180 cagaacatga ccacgagta catgagctgg tacagacagg accccggcct gggcctgcgg      240
cagatctact acagcatgaa cgtggaagtg accgacaagg gcgacgtgcc cgagggctac      300
aaggtgtccc ggaaagagaa gcggaacttc ccactgatcc tggaaagccc cagccccaac      360
cagaccagcc tgtacttctg cgcaagcaac aacctggcca gctacaacga gcagttcttc      420
ggccctggca cccggctgac cgtgctggaa gatctgaaga acgtgttccc cccagaggtg      480
accgtgttcg agcctagcga ggccgagatc agccacaccc agaaagccac cctcgtgtgc      540
ctggccaccg gcttctatcc cgaccacgtg gaactgtctt ggtgggtcaa cggcaaagag      600
gtgcacagcg gcgtgtccac cgatccccag cctctgaaag aacagcccgc cctgaacgac      660
agccggtact gcctgagcag cagactgaga gtgtccgcca ccttctggca gaaccccgg      720 aaccacttca gatgccaggt gcagttctac ggcctgagcg agaacgacga gtggaccag      780 gacagagcca gccccgtgac ccagatcgtg tctgccgaag cctggggcag agccgattgc      840
ggctttacca gcgagagcta ccagcagggc gtgctgagcg ccaccatcct gtacgagatc      900
ctgctgggca aggccaccct gtacgccgtg ctggtgtctg ccctggtgct gatggctatg      960
gtcaagcgga aggacagccg gggctgaacg cgtatcgatg aattccacgc tagccacgat     1020
atcaattcaa aaaaaaaaaa aaaaaaaaaa aaaaaaaaaa aaaaaaaaaa              1080
aaaaaaaaaa aataaaaaaa aaaaaaaaaa aaaaaaaaa aaaaaaaaaa aaaaaaaaaa     1140
aaaaaaaaaa aaaaaaacta gtggcgtgat gcggtatttt ctccttacgc atctgtgcgg     1200
tatttcacac cgcatatggt gcactctcag tacaatctgc tctgatgccg catagttaag     1260
ccagccccga cacccgccaa caccccgctga cgcgccctga cgggcttgtc tgctcccggc     1320
atccgcttac agacaagctg tgaccgtctc cgggagctgc atgtgtcaga ggttttcacc     1380
gtcatcaccg aaacgcgcga cgcgaaggg cctcgtgata cgcctatttt tataggttaa     1440
tgtcatgata ataatggttt cttagacgtc aggtggcact tttcggggaa atgtgcgcgg     1500
aacccctatt tgtttatttt tctaaataca ttcaaatatg tatccgctca tgagacaata     1560
accctgataa atgcttcaat aacattgaaa aaggaagagt atgagtattc aacatttccg     1620
tgtcgcccct attcccttttt tgcggcatt ttgccttcct gttttgtgtc acccagaaac     1680
gctggtgaaa gtaaaagatg ctgaagatca gttgggtgca cgagtgggtt acatcgaact     1740
ggatctcaac agcggtaaga tccttgagag ttttcgcccc gaagaacgtt ttccaatgat     1800
gagcactttt aaagttctgc tatgtggcgc ggtattatcc cgtattgacg ccgggcaaga     1860
```

```
gcaactcggt cgccgcatac actattctca gaatgacttg gttgagtact caccagtcac    1920
agaaaagcat cttacggatg gcatgacagt aagagaatta tgcagtgctg ccataaccat    1980
gagtgataac actgcggcca acttactict gacaacgatc ggaggaccga aggagctaac    2040
cgctttttg cacaacatgg gggatcatgt aactcgcctt gatcgttggg aaccggagct     2100
gaatgaagcc ataccaaacg acgagcgtga caccacgatg cctgtagcaa tgccaacaac    2160
gttgcacaaa ctattaactg gcgaactact tactctagct tcccggcaac aattaataga    2220
ctggatggag gcggataaag ttgcaggacc acttctgcgc tcggcccttc cggctggctg    2280
gtttattgct gataaatctg gagccggtga gcgtgggtct cgcggtatca ttgcagcact    2340
ggggccagat ggtaagccct cccgtatcgt agttatctac acgacgggga gtcaggcaac    2400
tatggatgaa cgaaatagac agatcgctga gataggtgcc tcactgatta agcattggta    2460
actgtcagac caagtttact catatatact ttagattgat ttaaaacttc attttaatt    2520
taaaaggatc taggtgaaga tccttttga taatctcatg accaaaatcc cttaacgtga    2580
gttttcgttc cactgagcgt cagacccgt agaaaagatc aaaggatctt cttgagatcc    2640
ttttttctg cgcgtaatct gctgcttgca acaaaaaaa ccaccgctac cagcggtggt      2700
ttgtttgccg gatcaagagc taccaactct ttttccgaag gtaactggct tcagcagagc    2760
gcagatacca atactgtcc ttctagtgta gccgtagtta ggccaccact tcaagaactc     2820
tgtagcaccg cctacatacc tcgctctgct aatcctgtta ccagtggctg ctgccagtgg    2880
cgataagtcg tgtcttaccg ggttggactc aagacgatag ttaccggata aggcgcagcg    2940
gtcgggctga acgggggt cgtgcacaca gcccagcttg gagcgaacga cctacaccga      3000
actgagatac ctacagcgtg agctatgaga aagcgccacg cttcccgaag ggagaaaggc    3060
ggacaggtat ccggtaagcg gcagggtcgg aacaggagag cgcacgaggg agcttccagg    3120
gggaaacgcc tggtatcttt atagtcctgt cgggtttcgc cacctctgac ttgagcgtcg    3180
attttgtga tgctcgtcag ggggcggag cctatcgaaa aacgccagca acgcggcctt      3240
tttacggttc ctggccttt gctggccttt tgctcacatg ttctttcctg cgttatcccc     3300
tgattctgtg gataaccgta ttaccgcctt tgagtgagct gataccgctc gccgcagccg    3360
aacgaccgag cgcagcgagt cagtgagcga ggaagcggaa gagcgcccaa tacgcaaacc    3420
gcctctcccc gcgcgttggc cgattcatta atgcagctgg cacgacaggt ttcccgactc    3480
gaaagcgggc agtgagcgca acgcaattaa tgtgagttag ctcactcatt aggcacccca    3540
ggctttacac tttatgcttc cggctcgtat gttgtgtgga attgtgagcg gataacaatt    3600
tcacacagga aacagctatg accatgatta cgccaagctc taatacgact cactataggg    3660
ag                                                                    3662
```

<210> SEQ ID NO 253
<211> LENGTH: 10
<212> TYPE: PRT
<213> ORGANISM: Artificial Sequence
<220> FEATURE:
<223> OTHER INFORMATION: humanized version

<400> SEQUENCE: 253

Gln Ser Val Ser Ile Ser Gly Ile Asn Leu
1               5                   10

<210> SEQ ID NO 254
<211> LENGTH: 10
<212> TYPE: PRT

```
<213> ORGANISM: Artificial Sequence
<220> FEATURE:
<223> OTHER INFORMATION: humanized version

<400> SEQUENCE: 254

Cys Gln Gln Ser Trp Glu Ser Pro Arg Thr
1               5                   10

<210> SEQ ID NO 255
<211> LENGTH: 8
<212> TYPE: PRT
<213> ORGANISM: Artificial Sequence
<220> FEATURE:
<223> OTHER INFORMATION: humanized version

<400> SEQUENCE: 255

Gly Tyr Thr Phe Thr Ala Tyr Tyr
1               5

<210> SEQ ID NO 256
<211> LENGTH: 7
<212> TYPE: PRT
<213> ORGANISM: Artificial Sequence
<220> FEATURE:
<223> OTHER INFORMATION: humanized version

<400> SEQUENCE: 256

Asp Pro Glu Asp Gly Ser Thr
1               5

<210> SEQ ID NO 257
<211> LENGTH: 12
<212> TYPE: PRT
<213> ORGANISM: Artificial Sequence
<220> FEATURE:
<223> OTHER INFORMATION: humanized version

<400> SEQUENCE: 257

Cys Ala Arg Gly Asn Ser Asp Tyr Gly Met Asp Val
1               5                   10

<210> SEQ ID NO 258
<211> LENGTH: 111
<212> TYPE: PRT
<213> ORGANISM: Artificial Sequence
<220> FEATURE:
<223> OTHER INFORMATION: humanized version

<400> SEQUENCE: 258

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ile Ser
            20                  25                  30

Gly Ile Asn Leu Leu Ser Trp Tyr Gln Gln Lys Pro Gly Gln Ala Pro
        35                  40                  45

Arg Leu Leu Ile Tyr Arg Ala Ser Thr Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Val Gln Ala Glu Asp Ile Ala Val Tyr Tyr Cys Gln Gln Ser Trp
                85                  90                  95

Glu Ser Pro Arg Thr Phe Gly Gly Gly Thr Lys Leu Glu Ile Lys
            100                 105                 110
```

<210> SEQ ID NO 259
<211> LENGTH: 118
<212> TYPE: PRT
<213> ORGANISM: Artificial Sequence
<220> FEATURE:
<223> OTHER INFORMATION: humanized version

<400> SEQUENCE: 259

```
Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Thr Ala Tyr
            20                  25                  30

Tyr Met His Trp Val Gln Ala Pro Gly Lys Gly Leu Glu Trp Met
        35                  40                  45

Gly Arg Ile Asp Pro Glu Asp Gly Ser Thr Ile Tyr Ala Glu Lys Phe
    50                  55                  60

Gln Gly Arg Val Thr Leu Thr Ala Asp Thr Ser Thr Asp Thr Ala Tyr
65                  70                  75                  80

Met Glu Leu Ser Ser Leu Arg Ser Glu Asp Thr Ala Val Tyr Phe Cys
                85                  90                  95

Ala Arg Gly Asn Ser Asp Tyr Gly Met Asp Val Trp Gly Gln Gly Thr
            100                 105                 110

Thr Val Thr Val Ser Ser
        115
```

<210> SEQ ID NO 260
<211> LENGTH: 218
<212> TYPE: PRT
<213> ORGANISM: Artificial Sequence
<220> FEATURE:
<223> OTHER INFORMATION: humanized version

<400> SEQUENCE: 260

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ile Ser
            20                  25                  30

Gly Ile Asn Leu Leu Ser Trp Tyr Gln Gln Lys Pro Gly Gln Ala Pro
        35                  40                  45

Arg Leu Leu Ile Tyr Arg Ala Ser Thr Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Val Gln Ala Glu Asp Ile Ala Val Tyr Tyr Cys Gln Gln Ser Trp
                85                  90                  95

Glu Ser Pro Arg Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 261
<211> LENGTH: 448
<212> TYPE: PRT
<213> ORGANISM: Artificial Sequence
<220> FEATURE:
<223> OTHER INFORMATION: humanized version

<400> SEQUENCE: 261

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Thr Ala Tyr
            20                  25                  30

Tyr Met His Trp Val Gln Gln Ala Pro Gly Lys Gly Leu Glu Trp Met
        35                  40                  45

Gly Arg Ile Asp Pro Glu Asp Gly Ser Thr Ile Tyr Ala Glu Lys Phe
    50                  55                  60

Gln Gly Arg Val Thr Leu Thr Ala Asp Thr Ser Thr Asp Thr Ala Tyr
65                  70                  75                  80

Met Glu Leu Ser Ser Leu Arg Ser Glu Asp Thr Ala Val Tyr Phe Cys
                85                  90                  95

Ala Arg Gly Asn Ser Asp Tyr Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Ala Gly Pro Asp
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Glu Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 262
<211> LENGTH: 238
<212> TYPE: PRT
<213> ORGANISM: Artificial Sequence
<220> FEATURE:
<223> OTHER INFORMATION: humanized version

<400> SEQUENCE: 262

Met Tyr Arg Met Gln Leu Leu Ser Cys Ile Ala Leu Ser Leu Ala Leu
1               5                   10                  15

Val Thr Asn Ser Glu Ile Val Met Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ile Ser Gly Ile Asn Leu Leu Ser Trp Tyr Gln Gln Lys Pro
        50                  55                  60

Gly Gln Ala Pro Arg Leu Leu Ile Tyr Arg Ala Ser Thr Arg Ala Thr
65                  70                  75                  80

Gly Ile Pro Ala Arg Phe Ser Gly Ser Gly Ser Gly Thr Asp Phe Thr
                85                  90                  95

Leu Thr Ile Ser Ser Val Gln Ala Glu Asp Ile Ala Val Tyr Tyr Cys
            100                 105                 110

Gln Gln Ser Trp Glu Ser Pro Arg Thr Phe Gly Gly Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 263

```
<211> LENGTH: 468
<212> TYPE: PRT
<213> ORGANISM: Artificial Sequence
<220> FEATURE:
<223> OTHER INFORMATION: humanized version

<400> SEQUENCE: 263
```

| | | | | | | | | | | | | | | | |
|---|---|---|---|---|---|---|---|---|---|---|---|---|---|---|---|
| Met | Tyr | Arg | Met | Gln | Leu | Leu | Ser | Cys | Ile | Ala | Leu | Ser | Leu | Ala | Leu |
| 1 | | | | 5 | | | | | 10 | | | | | 15 | |
| Val | Thr | Asn | Ser | Glu | Val | Gln | Leu | Val | Gln | Ser | Gly | Ala | Glu | Val | Lys |
| | | | 20 | | | | | 25 | | | | | 30 | | |
| Lys | Pro | Gly | Ala | Thr | Val | Lys | Ile | Ser | Cys | Lys | Ala | Ser | Gly | Tyr | Thr |
| | | | 35 | | | | | 40 | | | | | 45 | | |
| Phe | Thr | Ala | Tyr | Tyr | Met | His | Trp | Val | Gln | Gln | Ala | Pro | Gly | Lys | Gly |
| | 50 | | | | | 55 | | | | | 60 | | | | |
| Leu | Glu | Trp | Met | Gly | Arg | Ile | Asp | Pro | Glu | Asp | Gly | Ser | Thr | Ile | Tyr |
| 65 | | | | | 70 | | | | | 75 | | | | | 80 |
| Ala | Glu | Lys | Phe | Gln | Gly | Arg | Val | Thr | Leu | Thr | Ala | Asp | Thr | Ser | Thr |
| | | | | 85 | | | | | 90 | | | | | 95 | |
| Asp | Thr | Ala | Tyr | Met | Glu | Leu | Ser | Ser | Leu | Arg | Ser | Glu | Asp | Thr | Ala |
| | | | 100 | | | | | 105 | | | | | 110 | | |
| Val | Tyr | Phe | Cys | Ala | Arg | Gly | Asn | Ser | Asp | Tyr | Gly | Met | Asp | Val | Trp |
| | | | 115 | | | | | 120 | | | | | 125 | | |
| Gly | Gln | Gly | Thr | Thr | Val | Thr | Val | Ser | Ser | Ala | Ser | Thr | Lys | Gly | Pro |
| | 130 | | | | | 135 | | | | | 140 | | | | |
| Ser | Val | Phe | Pro | Leu | Ala | Pro | Ser | Ser | Lys | Ser | Thr | Ser | Gly | Gly | Thr |
| 145 | | | | | 150 | | | | | 155 | | | | | 160 |
| Ala | Ala | Leu | Gly | Cys | Leu | Val | Lys | Asp | Tyr | Phe | Pro | Glu | Pro | Val | Thr |
| | | | | 165 | | | | | 170 | | | | | 175 | |
| Val | Ser | Trp | Asn | Ser | Gly | Ala | Leu | Thr | Ser | Gly | Val | His | Thr | Phe | Pro |
| | | | 180 | | | | | 185 | | | | | 190 | | |
| Ala | Val | Leu | Gln | Ser | Ser | Gly | Leu | Tyr | Ser | Leu | Ser | Ser | Val | Val | Thr |
| | | | 195 | | | | | 200 | | | | | 205 | | |
| Val | Pro | Ser | Ser | Ser | Leu | Gly | Thr | Gln | Thr | Tyr | Ile | Cys | Asn | Val | Asn |
| | 210 | | | | | 215 | | | | | 220 | | | | |
| His | Lys | Pro | Ser | Asn | Thr | Lys | Val | Asp | Lys | Lys | Val | Glu | Pro | Lys | Ser |
| 225 | | | | | 230 | | | | | 235 | | | | | 240 |
| Cys | Asp | Lys | Thr | His | Thr | Cys | Pro | Pro | Cys | Pro | Ala | Pro | Glu | Leu | Leu |
| | | | | 245 | | | | | 250 | | | | | 255 | |
| Ala | Gly | Pro | Asp | Val | Phe | Leu | Phe | Pro | Pro | Lys | Pro | Lys | Asp | Thr | Leu |
| | | | 260 | | | | | 265 | | | | | 270 | | |
| Met | Ile | Ser | Arg | Thr | Pro | Glu | Val | Thr | Cys | Val | Val | Val | Asp | Val | Ser |
| | | | 275 | | | | | 280 | | | | | 285 | | |
| His | Glu | Asp | Pro | Glu | Val | Lys | Phe | Asn | Trp | Tyr | Val | Asp | Gly | Val | Glu |
| | 290 | | | | | 295 | | | | | 300 | | | | |
| Val | His | Asn | Ala | Lys | Thr | Lys | Pro | Arg | Glu | Glu | Gln | Tyr | Asn | Ser | Thr |
| 305 | | | | | 310 | | | | | 315 | | | | | 320 |
| Tyr | Arg | Val | Val | Ser | Val | Leu | Thr | Val | Leu | His | Gln | Asp | Trp | Leu | Asn |
| | | | | 325 | | | | | 330 | | | | | 335 | |
| Gly | Lys | Glu | Tyr | Lys | Cys | Lys | Val | Ser | Asn | Lys | Ala | Leu | Pro | Ala | Pro |
| | | | 340 | | | | | 345 | | | | | 350 | | |
| Ile | Glu | Lys | Thr | Glu | Ser | Lys | Ala | Lys | Gly | Gln | Pro | Arg | Glu | Pro | Gln |
| | | | 355 | | | | | 360 | | | | | 365 | | |
| Val | Tyr | Thr | Leu | Pro | Pro | Ser | Arg | Glu | Glu | Met | Thr | Lys | Asn | Gln | Val |
| | 370 | | | | | 375 | | | | | 380 | | | | |

```
Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 264
<211> LENGTH: 657
<212> TYPE: DNA
<213> ORGANISM: Artificial Sequence
<220> FEATURE:
<223> OTHER INFORMATION: humanized version

<400> SEQUENCE: 264
gaaattgtga tgacccagag cccggcgacc ctgagcctga gcccgggcga acgcgcgacc      60
ctgagctgcc gcgcgagcca gagcgtgagc attagcggca ttaacctgct gagctggtat     120
cagcagaaac cgggccaggc gccgcgcctg ctgatttatc gcgcgagcac ccgcgcgacc     180
ggcattccgg cgcgctttag cggcagcggc agcggcaccg attttaccct gaccattagc     240
agcgtgcagg cggaagatat tgcggtgtat tattgccagc agagctggga aagcccgcgc     300
acctttggcg gcggcaccaa actggaaatt aaaaggacag tggccgctcc cagcgtgttc     360
atcttcccac ctagcgacga acagctgaag tctggcaccg cctccgtcgt gtgcctgctg     420
aacaacttct acccccgcga ggccaaggtg cagtggaaag tggacaatgc cctgcagtcc     480
ggcaacagcc aggaaagcgt gaccgagcag gactccaagg atagcaccta cagcctgagc     540
agcacccctg cactgagcaa ggccgactac gagaagcaca aggtgtacgc ctgtgaagtg     600
acccaccagg gcctgtccag cccagtgacc aagagcttca ccggggcga gtgctga        657

<210> SEQ ID NO 265
<211> LENGTH: 1347
<212> TYPE: DNA
<213> ORGANISM: Artificial Sequence
<220> FEATURE:
<223> OTHER INFORMATION: humanized version

<400> SEQUENCE: 265
gaagtgcagc tggtgcagag cggcgcggaa gtgaaaaaac cgggcgcgac cgtgaaaatt      60
agctgcaaag cgagcggcta cacctttacc gcgtattata tgcattgggt gcagcaggcg     120
ccgggcaaag cctggaatg gatgggccgc attgatccgg aagatggcag caccatttat     180
gcggaaaaat tcagggccg cgtgacctg accgcggata ccagcaccga taccgcgtat     240
atggaactga gcagcctgcg cagcgaagat accgcggtgt attttgcgc gcgcggcaac     300 agcgattatg gcatggatgt gtggggccag ggcaccaccg tgaccgtgag cagcgcctct     360
acaaagggcc cctccgtgtt ccctctggcc cctagcagca gagcacatc tggcggaaca     420 gccgccctgg gctgcctcgt gaaggactac tttcccgagc ccgtgaccgt gtcctggaac     480
agcggagcac tgacaagcgg cgtgcacacc tttccagccg tgctgcagtc tagcggcctg     540
```

```
tacagcctgt cctccgtcgt gactgtgccc agcagctctc tgggcaccca gacctacatc    600
tgcaacgtga accacaagcc cagcaacacc aaggtggaca agaaggtgga acccaagagc    660
tgcgacaaga cccacacctg tcccccttgt cctgccccg  aactgctggc tggccctgac    720
gtgttcctgt tcccccaaa  gcccaaggat accctgatga tcagccggac ccccgaagtg    780
acctgcgtgg tggtggatgt gtcccacgag gaccctgaag tgaagttcaa ttggtacgtg    840
gacggcgtgg aagtgcacaa cgccaagacc aagcctagag aggaacagta caacagcacc    900
taccgggtgg tgtccgtgct gacagtgctg caccaggact ggctgaacgg caaagagtac    960
aagtgcaagg tgtccaacaa ggccctgcct gcccccatcg agaaaaccga gtctaaggcc   1020
aagggacagc cccgcgagcc ccaggtgtac acactgcctc caagccggga gagatgacc    1080 aagaaccagg tgtccctgac ctgtctcgtg aaaggcttct accccctcga tatcgccgtg   1140
gaatgggaga gcaacggcca gcccgagaac aactacaaga ccaccccccc tgtgctggac   1200
agcgacggct cattcttcct gtactccaag ctgaccgtgg acaagtcccg gtggcagcag   1260
ggcaacgtgt tcagctgctc cgtgatgcac gaggccctgc acaaccacta cacccagaag   1320
tccctgtccc tgagccccgg caaatac                                       1347
```

<210> SEQ ID NO 266
<211> LENGTH: 10
<212> TYPE: PRT
<213> ORGANISM: Artificial Sequence
<220> FEATURE:
<223> OTHER INFORMATION: chimeric version

<400> SEQUENCE: 266

Gln Ser Val Ser Ile Ser Gly Ile Asn Leu
1               5                   10

<210> SEQ ID NO 267
<211> LENGTH: 10
<212> TYPE: PRT
<213> ORGANISM: Artificial Sequence
<220> FEATURE:
<223> OTHER INFORMATION: chimeric version

<400> SEQUENCE: 267

Cys Gln Gln Ser Trp Glu Ser Pro Arg Thr
1               5                   10

<210> SEQ ID NO 268
<211> LENGTH: 8
<212> TYPE: PRT
<213> ORGANISM: Artificial Sequence
<220> FEATURE:
<223> OTHER INFORMATION: chimeric version

<400> SEQUENCE: 268

Gly Tyr Thr Phe Thr Ala Tyr Tyr
1               5

<210> SEQ ID NO 269
<211> LENGTH: 8
<212> TYPE: PRT
<213> ORGANISM: Artificial Sequence
<220> FEATURE:
<223> OTHER INFORMATION: chimeric version

<400> SEQUENCE: 269

Ile Asp Pro Glu Asp Gly Ser Thr
1               5

```
<210> SEQ ID NO 270
<211> LENGTH: 12
<212> TYPE: PRT
<213> ORGANISM: Artificial Sequence
<220> FEATURE:
<223> OTHER INFORMATION: chimeric version

<400> SEQUENCE: 270

Cys Ala Arg Gly Asn Ser Asp Tyr Val Met Asp Ala
1               5                   10

<210> SEQ ID NO 271
<211> LENGTH: 110
<212> TYPE: PRT
<213> ORGANISM: Artificial Sequence
<220> FEATURE:
<223> OTHER INFORMATION: chimeric version

<400> SEQUENCE: 271

Asp Ile Val Leu Thr Gln Ser Pro Val Leu Ala Val Ser Leu Gly Gln
1               5                   10                  15

Arg Ala Thr Ile Ser Cys Arg Ala Ser Gln Ser Val Ser Ile Ser Gly
            20                  25                  30

Ile Asn Leu Met His Trp Tyr Gln Gln Arg Pro Gly Gln Gln Pro Lys
        35                  40                  45

Leu Leu Ile Tyr Arg Ala Ser Ser Leu Ala Ser Gly Ile Pro Ala Arg
    50                  55                  60

Phe Ser Gly Arg Gly Ser Gly Thr Asp Phe Thr Leu Thr Ile Asp Pro
65                  70                  75                  80

Val Gln Ala Asp Asp Ile Ala Ala Tyr Phe Cys Gln Gln Ser Trp Glu
                85                  90                  95

Ser Pro Arg Thr Phe Gly Gly Gly Thr Gln Leu Glu Leu Lys
            100                 105                 110

<210> SEQ ID NO 272
<211> LENGTH: 118
<212> TYPE: PRT
<213> ORGANISM: Artificial Sequence
<220> FEATURE:
<223> OTHER INFORMATION: chimeric version

<400> SEQUENCE: 272

Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Thr Phe Thr Ala Tyr
            20                  25                  30

Tyr Ile Ser Trp Val Lys Gln Arg Pro Lys Gln Gly Leu Glu Leu Ile
        35                  40                  45

Gly Arg Ile Asp Pro Glu Asp Gly Ser Thr Asp Tyr Val Glu Lys Phe
    50                  55                  60

Lys Ile Lys Ala Thr Leu Thr Ala Asp Thr Ser Asn Thr Ala Tyr
65                  70                  75                  80

Met Gln Phe Ser Ser Leu Thr Ser Glu Asp Thr Ala Thr Tyr Phe Cys
                85                  90                  95

Ala Arg Gly Asn Ser Asp Tyr Val Met Asp Ala Trp Gly Gln Gly Ala
            100                 105                 110

Ser Val Thr Val Ser Ser
            115
```

<210> SEQ ID NO 273
<211> LENGTH: 217
<212> TYPE: PRT
<213> ORGANISM: Artificial Sequence
<220> FEATURE:
<223> OTHER INFORMATION: chimeric version

<400> SEQUENCE: 273

```
Asp Ile Val Leu Thr Gln Ser Pro Val Leu Ala Val Ser Leu Gly Gln
1               5                   10                  15

Arg Ala Thr Ile Ser Cys Arg Ala Ser Gln Ser Val Ser Ile Ser Gly
            20                  25                  30

Ile Asn Leu Met His Trp Tyr Gln Gln Arg Pro Gly Gln Gln Pro Lys
        35                  40                  45

Leu Leu Ile Tyr Arg Ala Ser Ser Leu Ala Ser Gly Ile Pro Ala Arg
    50                  55                  60

Phe Ser Gly Arg Gly Ser Gly Thr Asp Phe Thr Leu Thr Ile Asp Pro
65                  70                  75                  80

Val Gln Ala Asp Asp Ile Ala Ala Tyr Phe Cys Gln Gln Ser Trp Glu
                85                  90                  95

Ser Pro Arg Thr Phe Gly Gly Gly Thr Gln Leu Glu Leu Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 274
<211> LENGTH: 448
<212> TYPE: PRT
<213> ORGANISM: Artificial Sequence
<220> FEATURE:
<223> OTHER INFORMATION: chimeric version

<400> SEQUENCE: 274

```
Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Thr Phe Thr Ala Tyr
            20                  25                  30

Tyr Ile Ser Trp Val Lys Gln Arg Pro Lys Gln Gly Leu Glu Leu Ile
        35                  40                  45

Gly Arg Ile Asp Pro Glu Asp Gly Ser Thr Asp Tyr Val Glu Lys Phe
    50                  55                  60

Lys Ile Lys Ala Thr Leu Thr Ala Asp Thr Ser Ser Asn Thr Ala Tyr
65                  70                  75                  80

Met Gln Phe Ser Ser Leu Thr Ser Glu Asp Thr Ala Thr Tyr Phe Cys
                85                  90                  95
```

```
Ala Arg Gly Asn Ser Asp Tyr Val Met Asp Ala Trp Gly Gln Gly Ala
            100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Ala Gly Pro Asp
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Glu Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 275
<211> LENGTH: 237
<212> TYPE: PRT
<213> ORGANISM: Artificial Sequence
<220> FEATURE:
<223> OTHER INFORMATION: chimeric version

<400> SEQUENCE: 275

Met Tyr Arg Met Gln Leu Leu Ser Cys Ile Ala Leu Ser Leu Ala Leu
1               5                   10                  15
```

```
Val Thr Asn Ser Asp Ile Val Leu Thr Gln Ser Pro Val Leu Ala Val
            20                  25                  30

Ser Leu Gly Gln Arg Ala Thr Ile Ser Cys Arg Ala Ser Gln Ser Val
        35                  40                  45

Ser Ile Ser Gly Ile Asn Leu Met His Trp Tyr Gln Gln Arg Pro Gly
    50                  55                  60

Gln Gln Pro Lys Leu Leu Ile Tyr Arg Ala Ser Ser Leu Ala Ser Gly
65                  70                  75                  80

Ile Pro Ala Arg Phe Ser Gly Arg Gly Ser Gly Thr Asp Phe Thr Leu
                85                  90                  95

Thr Ile Asp Pro Val Gln Ala Asp Ile Ala Ala Tyr Phe Cys Gln
            100                 105                 110

Gln Ser Trp Glu Ser Pro Arg Thr Phe Gly Gly Gly Thr Gln Leu Glu
        115                 120                 125

Leu Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 276
<211> LENGTH: 468
<212> TYPE: PRT
<213> ORGANISM: Artificial Sequence
<220> FEATURE:
<223> OTHER INFORMATION: chimeric version

<400> SEQUENCE: 276

Met Tyr Arg Met Gln Leu Leu Ser Cys Ile Ala Leu Ser Leu Ala Leu
1               5                   10                  15

Val Thr Asn Ser Glu Val Gln Leu Gln Gln Ser Gly Pro Glu Leu Gln
            20                  25                  30

Arg Pro Gly Ala Ser Val Lys Leu Ser Cys Lys Ala Ser Gly Tyr Thr
        35                  40                  45

Phe Thr Ala Tyr Tyr Ile Ser Trp Val Lys Gln Arg Pro Lys Gln Gly
    50                  55                  60

Leu Glu Leu Ile Gly Arg Ile Asp Pro Glu Asp Gly Ser Thr Asp Tyr
65                  70                  75                  80

Val Glu Lys Phe Lys Ile Lys Ala Thr Leu Thr Ala Asp Thr Ser Ser
                85                  90                  95

Asn Thr Ala Tyr Met Gln Phe Ser Leu Thr Ser Glu Asp Thr Ala
            100                 105                 110

Thr Tyr Phe Cys Ala Arg Gly Asn Ser Asp Tyr Val Met Asp Ala Trp
        115                 120                 125

Gly Gln Gly Ala Ser Val Thr Val Ser Ser Ala Ser Thr Lys Gly Pro
130                 135                 140
```

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Ala Gly Pro Asp Val Phe Leu Phe Pro Pro Lys Pro Lys Asp Thr Leu
            260                 265                 270

Met Ile Ser Arg Thr Pro Glu Val Thr Cys Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Glu Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 277
<211> LENGTH: 654
<212> TYPE: DNA
<213> ORGANISM: Artificial Sequence
<220> FEATURE:
<223> OTHER INFORMATION: chimeric version

<400> SEQUENCE: 277
gacatcgtgc tgacccagag ccccgtgctg gctgtgtctc tgggacagag agccaccatc    60
agctgtcggg cctctcagag cgtgtccatc agcggcatca acctgatgca ctggtatcag   120
cagcgccctg gccagcagcc caagctgctg atctacagag ccagctccct ggcctctggc   180

```
atccccgcca gattttctgg cagaggctcc ggcaccgact ttaccctgac catcgaccct    240
gtgcaggccg acgatattgc cgcctacttc tgccagcaga gctgggagag ccccagaacc    300
tttggcggcg aacccagct ggaactgaag aggacagtgg ccgctcccag cgtgttcatc     360
ttcccaccta cgacgaaca gctgaagtct ggcaccgcct ccgtcgtgtg cctgctgaac     420
aacttctacc ccgcgaggc caaggtgcag tggaaagtgg acaatgccct gcagtccggc     480
aacagccagg aaagcgtgac cgagcaggac tccaaggata gcacctacag cctgagcagc    540 acccctgacac tgagcaaggc cgactacgag aagcacaagg tgtacgcctg tgaagtgacc    600
caccagggcc tgtccagccc agtgaccaag agcttcaacc ggggcgagtg ctga           654
```

<210> SEQ ID NO 278
<211> LENGTH: 1347
<212> TYPE: DNA
<213> ORGANISM: Artificial Sequence
<220> FEATURE:
<223> OTHER INFORMATION: chimeric version

<400> SEQUENCE: 278

```
gaagtgcagc tgcagcagag cggccctgag ctgcagaggc ctggcgcttc tgtgaagctg     60
tcctgcaagg ccagcggcta caccttcacc gcctactaca tcagctgggt caagcagcgg    120
cccaagcagg gcctggaact gatcggcaga atcgaccccg aggacggcag caccgactac    180
gtggaaaagt tcaagatcaa ggccaccctg accgccgaca ccagcagcaa taccgcctac    240
atgcagttca gcagcctgac cagcgaggac accgccacct actttgcgc cagaggcaac    300 agcgattacg tgatggacgc ctggggacag ggcgccagcg tgacagtgtc tagcgcctct    360
acaaagggcc cctccgtgtt ccctctggcc cctagcagca gagcacatc tggcggaaca    420 gccgccctgg gctgcctcgt gaaggactac tttcccgagc ccgtgaccgt gtcctggaac    480
agcggagcac tgacaagcgg cgtgcacacc tttccagccg tgctgcagtc tagcggcctg    540
tacagcctgt cctccgtcgt gactgtgccc agcagctctc tgggcaccca gacctacatc    600
tgcaacgtga accacaagcc cagcaacacc aaggtggaca gaaggtgga acccaagagc    660 tgcgacaaga cccacacctg tccccttgt cctgcccccg aactgctggc tggccctgac    720
gtgttcctgt ccccccaaa gcccaaggat accctgatga tcagccggac ccccgaagtg    780
acctgcgtgt ggtggatgt gtcccacgag gaccctgaag tgaagttcaa ttggtacgtg    840
gacggcgtgg aagtgcacaa cgccaagacc aagcctagag aggaacagta caacagcacc    900
taccgggtgg tgtccgtgct gacagtgctg caccaggact ggctgaacgg caaagagtac    960
aagtgcaagg tgtccaacaa ggccctgcct gcccccatcg agaaaaccga gtctaaggcc    1020
aagggacagc cccgcgagcc ccaggtgtac acactgcctc caagccggga agagatgacc    1080
aagaaccagg tgtccctgac ctgtctcgtg aaaggcttct acccctccga tatcgccgtg    1140
gaatgggaga gcaacggcca gcccgagaac aactacaaga ccaccccccc tgtgctggac    1200
agcgacggct cattcttcct gtactccaag ctgaccgtgg acaagtcccg gtggcagcag    1260
ggcaacgtgt tcagctgctc cgtgatgcac gaggccctgc acaaccacta cacccagaag    1320
tccctgtccc tgagccccgg caaatac                                        1347
```

<210> SEQ ID NO 279
<211> LENGTH: 11
<212> TYPE: PRT
<213> ORGANISM: Artificial Sequence
<220> FEATURE:

```
<223> OTHER INFORMATION: chimeric version

<400> SEQUENCE: 279

Gln Ser Val Ser Ile Ser Arg His Asn Leu Ile
1               5                   10

<210> SEQ ID NO 280
<211> LENGTH: 10
<212> TYPE: PRT
<213> ORGANISM: Artificial Sequence
<220> FEATURE:
<223> OTHER INFORMATION: chimeric version

<400> SEQUENCE: 280

Cys Gln Gln Ser Gly Glu Ser Pro Arg Thr
1               5                   10

<210> SEQ ID NO 281
<211> LENGTH: 8
<212> TYPE: PRT
<213> ORGANISM: Artificial Sequence
<220> FEATURE:
<223> OTHER INFORMATION: chimeric version

<400> SEQUENCE: 281

Gly Tyr Thr Phe Thr Glu Asn Tyr
1               5

<210> SEQ ID NO 282
<211> LENGTH: 8
<212> TYPE: PRT
<213> ORGANISM: Artificial Sequence
<220> FEATURE:
<223> OTHER INFORMATION: chimeric version

<400> SEQUENCE: 282

Ile Asp Pro Glu Asp Gly Thr Thr
1               5

<210> SEQ ID NO 283
<211> LENGTH: 14
<212> TYPE: PRT
<213> ORGANISM: Artificial Sequence
<220> FEATURE:
<223> OTHER INFORMATION: chimeric version

<400> SEQUENCE: 283

Cys Ala Arg Gly Val Gly Ser Gly Asp Tyr Val Met Asp Ala
1               5                   10

<210> SEQ ID NO 284
<211> LENGTH: 110
<212> TYPE: PRT
<213> ORGANISM: Artificial Sequence
<220> FEATURE:
<223> OTHER INFORMATION: chimeric version

<400> SEQUENCE: 284

Asp Ile Val Leu Thr Gln Ser Pro Ala Leu Ala Val Ser Leu Gly Gln
1               5                   10                  15

Arg Ala Thr Ile Ser Cys Arg Ala Ser Gln Ser Val Ser Ile Ser Arg
                20                  25                  30

His Asn Leu Ile His Trp Tyr Gln Gln Lys Pro Gly Gln Gln Pro Lys
            35                  40                  45

Leu Leu Ile Tyr Arg Ala Ser Asn Leu Ala Ser Gly Ile Pro Ala Arg
```

```
                    50                  55                  60

Phe Ser Gly Ser Gly Ser Gly Thr Asp Phe Thr Leu Thr Ile Asn Pro
 65                  70                  75                  80

Val Gln Ala Asp Asp Val Ala Thr Tyr Tyr Cys Gln Gln Ser Gly Glu
                     85                  90                  95

Ser Pro Arg Thr Phe Gly Gly Gly Thr Lys Leu Glu Leu Lys
                100                 105                 110

<210> SEQ ID NO 285
<211> LENGTH: 120
<212> TYPE: PRT
<213> ORGANISM: Artificial Sequence
<220> FEATURE:
<223> OTHER INFORMATION: chimeric version

<400> SEQUENCE: 285

Glu Val Gln Leu Gln Gln Ser Gly Pro Glu Leu Gln Arg Pro Gly Arg
  1               5                  10                  15

Ala Gln Ser Val Val Cys Gln Ala Ser Gly Tyr Thr Phe Thr Glu Asn
                 20                  25                  30

Tyr Ile Tyr Trp Val Lys Gln Arg Pro Lys Gln Gly Leu Glu Leu Ile
             35                  40                  45

Gly Arg Ile Asp Pro Glu Asp Gly Thr Thr Asp Tyr Val Glu Lys Phe
         50                  55                  60

Lys Asn Lys Ala Thr Leu Thr Val Asp Thr Ser Ser Lys Thr Ala Tyr
 65                  70                  75                  80

Met Gln Leu Ser Ser Leu Thr Ser Glu Asp Thr Ala Ser Tyr Phe Cys
                 85                  90                  95

Ala Arg Gly Val Gly Ser Gly Asp Tyr Val Met Asp Ala Trp Gly Gln
                100                 105                 110

Gly Ala Ser Val Thr Val Ser Ser
                115                 120

<210> SEQ ID NO 286
<211> LENGTH: 217
<212> TYPE: PRT
<213> ORGANISM: Artificial Sequence
<220> FEATURE:
<223> OTHER INFORMATION: chimeric version

<400> SEQUENCE: 286

Asp Ile Val Leu Thr Gln Ser Pro Ala Leu Ala Val Ser Leu Gly Gln
  1               5                  10                  15

Arg Ala Thr Ile Ser Cys Arg Ala Ser Gln Ser Val Ser Ile Ser Arg
                 20                  25                  30

His Asn Leu Ile His Trp Tyr Gln Gln Lys Pro Gly Gln Gln Pro Lys
             35                  40                  45

Leu Leu Ile Tyr Arg Ala Ser Asn Leu Ala Ser Gly Ile Pro Ala Arg
         50                  55                  60

Phe Ser Gly Ser Gly Ser Gly Thr Asp Phe Thr Leu Thr Ile Asn Pro
 65                  70                  75                  80

Val Gln Ala Asp Asp Val Ala Thr Tyr Tyr Cys Gln Gln Ser Gly Glu
                 85                  90                  95

Ser Pro Arg Thr Phe Gly Gly Gly Thr Lys Leu Glu Leu Lys Arg Thr
                100                 105                 110

Val Ala Ala Pro Ser Val Phe Ile Phe Pro Pro Ser Asp Glu Gln Leu
            115                 120                 125
```

```
Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 287
<211> LENGTH: 450
<212> TYPE: PRT
<213> ORGANISM: Artificial Sequence
<220> FEATURE:
<223> OTHER INFORMATION: chimeric version

<400> SEQUENCE: 287

Glu Val Gln Leu Gln Gln Ser Gly Pro Glu Leu Gln Arg Pro Gly Arg
1               5                   10                  15

Ala Gln Ser Val Val Cys Gln Ala Ser Gly Tyr Thr Phe Thr Glu Asn
            20                  25                  30

Tyr Ile Tyr Trp Val Lys Gln Arg Pro Lys Gln Gly Leu Glu Leu Ile
        35                  40                  45

Gly Arg Ile Asp Pro Glu Asp Gly Thr Thr Asp Tyr Val Glu Lys Phe
    50                  55                  60

Lys Asn Lys Ala Thr Leu Thr Val Asp Thr Ser Ser Lys Thr Ala Tyr
65                  70                  75                  80

Met Gln Leu Ser Ser Leu Thr Ser Glu Asp Thr Ala Ser Tyr Phe Cys
                85                  90                  95

Ala Arg Gly Val Gly Ser Gly Asp Tyr Val Met Asp Ala Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Ala Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Glu Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 288
<211> LENGTH: 237
<212> TYPE: PRT
<213> ORGANISM: Artificial Sequence
<220> FEATURE:
<223> OTHER INFORMATION: chimeric version

<400> SEQUENCE: 288

Met Tyr Arg Met Gln Leu Leu Ser Cys Ile Ala Leu Ser Leu Ala Leu
1               5                   10                  15

Val Thr Asn Ser Asp Ile Val Leu Thr Gln Ser Pro Ala Leu Ala Val
            20                  25                  30

Ser Leu Gly Gln Arg Ala Thr Ile Ser Cys Arg Ala Ser Gln Ser Val
        35                  40                  45

Ser Ile Ser Arg His Asn Leu Ile His Trp Tyr Gln Gln Lys Pro Gly
    50                  55                  60

Gln Gln Pro Lys Leu Leu Ile Tyr Arg Ala Ser Asn Leu Ala Ser Gly
65                  70                  75                  80

Ile Pro Ala Arg Phe Ser Gly Ser Gly Ser Gly Thr Asp Phe Thr Leu
                85                  90                  95

Thr Ile Asn Pro Val Gln Ala Asp Asp Val Ala Thr Tyr Tyr Cys Gln
            100                 105                 110

Gln Ser Gly Glu Ser Pro Arg Thr Phe Gly Gly Gly Thr Lys Leu Glu
        115                 120                 125

Leu Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175
```

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 289
<211> LENGTH: 470
<212> TYPE: PRT
<213> ORGANISM: Artificial Sequence
<220> FEATURE:
<223> OTHER INFORMATION: chimeric version

<400> SEQUENCE: 289

Met Tyr Arg Met Gln Leu Leu Ser Cys Ile Ala Leu Ser Leu Ala Leu
1               5                   10                  15

Val Thr Asn Ser Glu Val Gln Leu Gln Gln Ser Gly Pro Glu Leu Gln
            20                  25                  30

Arg Pro Gly Arg Ala Gln Ser Val Val Cys Gln Ala Ser Gly Tyr Thr
        35                  40                  45

Phe Thr Glu Asn Tyr Ile Tyr Trp Val Lys Gln Arg Pro Lys Gln Gly
    50                  55                  60

Leu Glu Leu Ile Gly Arg Ile Asp Pro Glu Asp Gly Thr Thr Asp Tyr
65                  70                  75                  80

Val Glu Lys Phe Lys Asn Lys Ala Thr Leu Thr Val Asp Thr Ser Ser
                85                  90                  95

Lys Thr Ala Tyr Met Gln Leu Ser Ser Leu Thr Ser Glu Asp Thr Ala
            100                 105                 110

Ser Tyr Phe Cys Ala Arg Gly Val Gly Ser Gly Asp Tyr Val Met Asp
        115                 120                 125

Ala Trp Gly Gln Gly Ala Ser Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Ala Gly Pro Asp Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
        340                 345                 350

Ala Pro Ile Glu Lys Thr Glu Ser Lys Ala Lys Gly Gln Pro Arg Glu
            355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
        420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 290
<211> LENGTH: 654
<212> TYPE: DNA
<213> ORGANISM: Artificial Sequence
<220> FEATURE:
<223> OTHER INFORMATION: chimeric version

<400> SEQUENCE: 290
gatattgtgc tgacccagag cccggcgctg gcggtgagcc tgggccagcg cgcgaccatt      60
agctgccgcg cgagccagag cgtgagcatt agccgccata acctgattca ttggtatcag     120
cagaaaccgg gccagcagcc gaaactgctg atttatcgcg cgagcaacct ggcgagcggc     180
attccggcgc gctttagcgg cagcggcagc ggcaccgatt ttaccctgac cattaacccg     240
gtgcaggcgg atgatgtggg gacctattat tgccagcaga gcggcgaaag cccgcgcacc     300
tttggcggcg gcaccaaact ggaactgaaa cgtacggtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg ttag     654

<210> SEQ ID NO 291
<211> LENGTH: 1353
<212> TYPE: DNA
<213> ORGANISM: Artificial Sequence
<220> FEATURE:
<223> OTHER INFORMATION: chimeric version

<400> SEQUENCE: 291
gaagtgcagc tgcagcagag cggcccggaa ctgcagcgcc cgggccgcgc gcagagcgtg      60
gtgtgccagg cgagcggcta tacctttacc gaaaactata tttattgggt gaaacagcgc     120

| | |
|---|---|
| ccgaaacagg gcctggaact gattggccgc attgatccgg aagatggcac caccgattat | 180 |
| gtggaaaaat ttaaaaacaa agcgaccctg accgtggata ccagcagcaa aaccgcgtat | 240 |
| atgcagctga gcagcctgac cagcgaagat accgcgagct attttgcgc gcgcggcgtg | 300 |
| ggcagcggcg attatgtgat ggatgcgtgg ggccagggcg cgagcgtgac cgtgagcagc | 360 |
| gctagcacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagaa agttgagccc | 660 |
| aaatcttgtg acaaaactca cacatgccca ccgtgcccag cacctgaact cctggcggga | 720 |
| ccggacgtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccgaatcc | 1020 |
| aaagccaaag gcagccccg agaaccacag gtgtacaccc tgcccccatc ccgggaggag | 1080 |
| atgaccaaga accaggtcag cctgacctgc ctggtcaaag gcttctatcc agcgacatc | 1140 |
| gccgtggagt gggagagcaa tgggcagccg gagaacaact acaagaccac gcctcccgtg | 1200 |
| ctggactccg acggctcctt cttcctctac agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggtaaa tga | 1353 |

<210> SEQ ID NO 292
<211> LENGTH: 11
<212> TYPE: PRT
<213> ORGANISM: Artificial Sequence
<220> FEATURE:
<223> OTHER INFORMATION: humanized version

<400> SEQUENCE: 292

Gln Ser Val Ser Ile Ser Arg His Asn Leu Ile
1               5                   10

<210> SEQ ID NO 293
<211> LENGTH: 10
<212> TYPE: PRT
<213> ORGANISM: Artificial Sequence
<220> FEATURE:
<223> OTHER INFORMATION: humanized version

<400> SEQUENCE: 293

Cys Gln Gln Ser Gly Glu Ser Pro Arg Thr
1               5                   10

<210> SEQ ID NO 294
<211> LENGTH: 8
<212> TYPE: PRT
<213> ORGANISM: Artificial Sequence
<220> FEATURE:
<223> OTHER INFORMATION: humanized version

<400> SEQUENCE: 294

Gly Tyr Thr Phe Thr Glu Asn Tyr

```
<210> SEQ ID NO 295
<211> LENGTH: 8
<212> TYPE: PRT
<213> ORGANISM: Artificial Sequence
<220> FEATURE:
<223> OTHER INFORMATION: humanized version

<400> SEQUENCE: 295

Ile Asp Pro Glu Asp Gly Thr Thr
1               5

<210> SEQ ID NO 296
<211> LENGTH: 14
<212> TYPE: PRT
<213> ORGANISM: Artificial Sequence
<220> FEATURE:
<223> OTHER INFORMATION: humanized version

<400> SEQUENCE: 296

Cys Ala Arg Gly Val Gly Ser Gly Asp Tyr Val Met Asp Ala
1               5                   10

<210> SEQ ID NO 297
<211> LENGTH: 111
<212> TYPE: PRT
<213> ORGANISM: Artificial Sequence
<220> FEATURE:
<223> OTHER INFORMATION: humanized version

<400> SEQUENCE: 297

Glu Ile Val Leu Thr Gln Ser Pro Ala Thr Leu Ser Leu Ser Pro Gly
1               5                   10                  15

Gln Arg Ala Thr Ile Ser Cys Arg Ala Ser Gln Ser Val Ser Ile Ser
            20                  25                  30

Arg His Asn Leu Ile His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
    50                  55                  60

Arg Phe Ser Gly Ser Gly Ser Gly Thr Asp Phe Thr Leu Thr Ile Asn
65                  70                  75                  80

Pro Val Gln Ala Glu Asp Phe Ala Val Tyr Tyr Cys Gln Gln Ser Gly
                85                  90                  95

Glu Ser Pro Arg Thr Phe Gly Gly Gly Thr Lys Leu Glu Leu Lys
            100                 105                 110

<210> SEQ ID NO 298
<211> LENGTH: 120
<212> TYPE: PRT
<213> ORGANISM: Artificial Sequence
<220> FEATURE:
<223> OTHER INFORMATION: humanized version

<400> SEQUENCE: 298

Glu Val Gln Leu Val Gln Ser Gly Ala Glu Val Lys Lys Pro Gly Arg
1               5                   10                  15

Thr Val Lys Ile Val Cys Gln Ala Ser Gly Tyr Thr Phe Thr Glu Asn
            20                  25                  30

Tyr Ile Tyr Trp Val Gln Gln Ala Pro Gly Lys Gly Leu Glu Trp Met
        35                  40                  45

Gly Arg Ile Asp Pro Glu Asp Gly Thr Thr Asp Tyr Ala Glu Lys Phe
```

```
                 50                  55                  60
Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Phe Cys
                 85                  90                  95

Ala Arg Gly Val Gly Ser Gly Asp Tyr Val Met Asp Ala Trp Gly Gln
                100                 105                 110

Gly Ala Ser Val Thr Val Ser Ser
            115                 120

<210> SEQ ID NO 299
<211> LENGTH: 218
<212> TYPE: PRT
<213> ORGANISM: Artificial Sequence
<220> FEATURE:
<223> OTHER INFORMATION: humanized version

<400> SEQUENCE: 299

Glu Ile Val Leu Thr Gln Ser Pro Ala Thr Leu Ser Leu Ser Pro Gly
 1               5                  10                  15

Gln Arg Ala Thr Ile Ser Cys Arg Ala Ser Gln Ser Val Ser Ile Ser
                20                  25                  30

Arg His Asn Leu Ile His Trp Tyr Gln Gln Lys Pro Gly Gln Ala Pro
            35                  40                  45

Arg Leu Leu Ile Tyr Arg Ala Ser Asn Arg Ala Thr Gly Ile Pro Ala
        50                  55                  60

Arg Phe Ser Gly Ser Gly Ser Gly Thr Asp Phe Thr Leu Thr Ile Asn
 65                  70                  75                  80

Pro Val Gln Ala Glu Asp Phe Ala Val Tyr Tyr Cys Gln Gln Ser Gly
                 85                  90                  95

Glu Ser Pro Arg Thr Phe Gly Gly Gly Thr Lys Leu Glu Leu Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 300
<211> LENGTH: 450
<212> TYPE: PRT
<213> ORGANISM: Artificial Sequence
<220> FEATURE:
<223> OTHER INFORMATION: humanized version

<400> SEQUENCE: 300

Glu Val Gln Leu Val Gln Ser Gly Ala Glu Val Lys Lys Pro Gly Arg
 1               5                  10                  15
```

```
Thr Val Lys Ile Val Cys Gln Ala Ser Gly Tyr Thr Phe Thr Glu Asn
             20                  25                  30

Tyr Ile Tyr Trp Val Gln Gln Ala Pro Gly Lys Gly Leu Glu Trp Met
         35                  40                  45

Gly Arg Ile Asp Pro Glu Asp Gly Thr Thr Asp Tyr Ala Glu Lys Phe
 50                  55                  60

Gln Gly Arg Val Thr Ile Thr Ala Asp Thr Ser Thr Asp Thr Ala Tyr
65                   70                  75                  80

Met Glu Leu Ser Ser Leu Arg Ser Glu Asp Thr Ala Val Tyr Phe Cys
                 85                  90                  95

Ala Arg Gly Val Gly Ser Gly Asp Tyr Val Met Asp Ala Trp Gly Gln
                100                 105                 110

Gly Ala Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Ala Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Glu Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
            435                 440                 445

Gly Lys
    450

<210> SEQ ID NO 301
<211> LENGTH: 238
<212> TYPE: PRT
<213> ORGANISM: Artificial Sequence
<220> FEATURE:
<223> OTHER INFORMATION: humanized version

<400> SEQUENCE: 301

Met Tyr Arg Met Gln Leu Leu Ser Cys Ile Ala Leu Ser Leu Ala Leu
1               5                   10                  15

Val Thr Asn Ser Glu Ile Val Leu Thr Gln Ser Pro Ala Thr Leu Ser
            20                  25                  30

Leu Ser Pro Gly Gln Arg Ala Thr Ile Ser Cys Arg Ala Ser Gln Ser
        35                  40                  45

Val Ser Ile Ser Arg His Asn Leu Ile His Trp Tyr Gln Gln Lys Pro
50                  55                  60

Gly Gln Ala Pro Arg Leu Leu Ile Tyr Arg Ala Ser Asn Arg Ala Thr
65                  70                  75                  80

Gly Ile Pro Ala Arg Phe Ser Gly Ser Gly Ser Gly Thr Asp Phe Thr
                85                  90                  95

Leu Thr Ile Asn Pro Val Gln Ala Glu Asp Phe Ala Val Tyr Tyr Cys
            100                 105                 110

Gln Gln Ser Gly Glu Ser Pro Arg Thr Phe Gly Gly Gly Thr Lys Leu
        115                 120                 125

Glu Leu Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 302
<211> LENGTH: 470
<212> TYPE: PRT
<213> ORGANISM: Artificial Sequence
<220> FEATURE:
<223> OTHER INFORMATION: humanized version

<400> SEQUENCE: 302

Met Tyr Arg Met Gln Leu Leu Ser Cys Ile Ala Leu Ser Leu Ala Leu
1               5                   10                  15

Val Thr Asn Ser Glu Val Gln Leu Val Gln Ser Gly Ala Glu Val Lys
            20                  25                  30
```

Lys Pro Gly Arg Thr Val Lys Ile Val Cys Gln Ala Ser Gly Tyr Thr
35                  40                  45

Phe Thr Glu Asn Tyr Ile Tyr Trp Val Gln Ala Pro Gly Lys Gly
    50                  55                  60

Leu Glu Trp Met Gly Arg Ile Asp Pro Glu Asp Gly Thr Thr Asp Tyr
65                  70                  75                  80

Ala Glu Lys Phe Gln Gly Arg Val Thr Ile Thr Ala Asp Thr Ser Thr
                85                  90                  95

Asp Thr Ala Tyr Met Glu Leu Ser Ser Leu Arg Ser Glu Asp Thr Ala
                100                 105                 110

Val Tyr Phe Cys Ala Arg Gly Val Gly Ser Gly Asp Tyr Val Met Asp
            115                 120                 125

Ala Trp Gly Gln Gly Ala Ser Val Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
        210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Ala Gly Pro Asp Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Glu Ser Lys Ala Lys Gly Gln Pro Arg Glu
            355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 303
<211> LENGTH: 657
<212> TYPE: DNA
<213> ORGANISM: Artificial Sequence
<220> FEATURE:
<223> OTHER INFORMATION: humanized version

<400> SEQUENCE: 303
gaaattgtgc tgacccagag cccggcgacc ctgagcctga gcccgggcca gcgcgcgacc     60
attagctgcc gcgcgagcca gagcgtgagc attagccgcc ataacctgat tcattggtat    120
cagcagaaac cgggccaggc gccgcgcctg ctgatttatc gcgcgagcaa ccgcgcgacc    180
ggcattccgg cgcgctttag cggcagcggc agcggcaccg attttaccct gaccattaac    240
ccggtgcagg cggaagattt tgcggtgtat tattgccagc agagcggcga aagcccgcgc    300
acctttggcg gcggcaccaa actggaactg aaacgtacgg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc     600 acccatcagg gcctgagctc gcccgtcaca aagagcttca caggggaga gtgttag       657

<210> SEQ ID NO 304
<211> LENGTH: 1353
<212> TYPE: DNA
<213> ORGANISM: Artificial Sequence
<220> FEATURE:
<223> OTHER INFORMATION: humanized version

<400> SEQUENCE: 304
gaagtgcagc tggtgcagag cggcgcggaa gtgaaaaaac cgggccgcac cgtgaaaatt     60
gtgtgccagg cgagcggcta cctttacc gaaaactata tttattgggt gcagcaggcg    120
ccgggcaaag cctggaatg gatgggccgc attgatccgg aagatggcac caccgattat    180
gcggaaaaat ttcagggccg cgtgaccatt accgcggata ccagcaccga taccgcgtat    240
atggaactga gcagcctgcg cagcgaagat accgcggtgt attttgcgc gcgcggcgtg    300 ggcagcggcg attatgtgat ggatgcgtgg ggccagggcg cgagcgtgac cgtgagcagc    360
gctagcacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctggcggga    720
ccggacgtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960

```
gagtacaagt gcaaggtctc caacaaagcc ctcccagccc ccatcgagaa aaccgaatcc    1020
aaagccaaag ggcagccccg agaaccacag gtgtacaccc tgcccccatc ccgggaggag    1080
atgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tga                                1353
```